US011530274B2

(12) United States Patent
Nolan-Stevaux et al.

(10) Patent No.: US 11,530,274 B2
(45) Date of Patent: Dec. 20, 2022

(54) ANTI-STEAP1 ANTIGEN-BINDING PROTEIN

(71) Applicants: AMGEN INC., Thousand Oaks, CA (US); XENCOR, INC., Monrovia, CA (US)

(72) Inventors: Olivier Nolan-Stevaux, Millbrae, CA (US); Cong Li, Palo Alto, CA (US); Christopher M. Murawsky, Roberts Creek (CA); Benjamin M. Alba, South San Francisco, CA (US); Neeraj Jagdish Agrawal, Thousand Oaks, CA (US); Kevin Graham, Thousand Oaks, CA (US); Jennitte LeAnn Stevens, Thousand Oaks, CA (US); Gregory Moore, Azusa, CA (US)

(73) Assignees: AMGEN INC., Thousand Oaks, CA (US); XENCOR, INC., Monrovia, CA (US)

( * ) Notice: Subject to any disclaimer, the term of this patent is extended or adjusted under 35 U.S.C. 154(b) by 74 days.

(21) Appl. No.: 16/634,571

(22) PCT Filed: Jul. 2, 2019

(86) PCT No.: PCT/US2019/040296
§ 371 (c)(1),
(2) Date: Jan. 27, 2020

(87) PCT Pub. No.: WO2020/010079
PCT Pub. Date: Jan. 9, 2020

(65) Prior Publication Data
US 2021/0179731 A1   Jun. 17, 2021

Related U.S. Application Data

(60) Provisional application No. 62/800,259, filed on Feb. 1, 2019, provisional application No. 62/693,216, filed on Jul. 2, 2018.

(51) Int. Cl.
C07K 16/30 (2006.01)
A61P 35/00 (2006.01)
C07K 16/28 (2006.01)
A61K 39/00 (2006.01)

(52) U.S. Cl.
CPC .......... *C07K 16/3069* (2013.01); *A61P 35/00* (2018.01); *C07K 16/2809* (2013.01); *C07K 16/2818* (2013.01); *A61K 2039/505* (2013.01); *C07K 2317/24* (2013.01); *C07K 2317/31* (2013.01); *C07K 2317/34* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,691,016 A | 9/1972 | Patel |
| 3,773,919 A | 11/1973 | Boswell et al. |
| 3,969,287 A | 7/1976 | Jaworek et al. |
| 4,169,888 A | 10/1979 | Hanka et al. |
| 4,179,337 A | 12/1979 | Davis et al. |
| 4,195,128 A | 3/1980 | Gribnau et al. |
| 4,229,537 A | 10/1980 | Hodgins et al. |
| 4,247,642 A | 1/1981 | Hirohara et al. |
| 4,256,746 A | 3/1981 | Miyashita et al. |
| 4,294,757 A | 10/1981 | Asai |
| 4,301,144 A | 11/1981 | Iwashita et al. |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,330,440 A | 5/1982 | Ayers et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,880,935 A | 11/1989 | Thorpe |
| 4,923,990 A | 5/1990 | Nakano et al. |
| 4,970,198 A | 11/1990 | Lee et al. |
| 5,053,394 A | 10/1991 | Ellestad et al. |

(Continued)

FOREIGN PATENT DOCUMENTS

| | | |
|---|---|---|
| EP | 0425235 A2 | 5/1991 |
| EP | 1391213 A1 | 2/2004 |

(Continued)

OTHER PUBLICATIONS

Umana et al., Engineered glycoforms of an antineuroblastoma IgG1 with optimized antibody-dependent cellular cytotoxic activity, Nat. Biotechnol., 17:176-180 (1999).
Verhoeyen et al., Reshaping human antibodies: grafting an antilysozyme activity, Science, 239:1534-1536 (1988).
Wang et al., Expanding the genetic code, Chem., 1-11 (2002).
Whitlow et al., An improved linker for single-chain Fv with reduced aggregation and enhanced proteolytic stability, Protein Engineering, 6(8):989-995 (1993).
Williams et al., "ImmunoPET helps predicting the efficacy of antibody-drug conjugates targeting TENB2 and STEAP1", Oncotarget, vol. 7, No. 18, May 3, 2016, XP055622544.
Woyke et al., In vitro activities and postantifungal effects of the potent dolastatin 10 derivative auristatin PHE, Antimicrob. Agents Chemother., 44(12):3580-3584 (2001).

(Continued)

*Primary Examiner* — Nelson B Moseley, II
(74) *Attorney, Agent, or Firm* — Marshall, Gerstein & Borun LLP

(57) ABSTRACT

The disclosure provides novel antigen-binding proteins that bind STEAP1 and methods of use.

72 Claims, 48 Drawing Sheets
Specification includes a Sequence Listing.

(56) References Cited

U.S. PATENT DOCUMENTS

| | | |
|---|---|---|
| 5,084,468 A | 1/1992 | Saito et al. |
| 5,101,038 A | 3/1992 | Nakano et al. |
| 5,122,368 A | 6/1992 | Greenfield et al. |
| 5,187,186 A | 2/1993 | Kanda et al. |
| 5,208,020 A | 5/1993 | Chari et al. |
| 5,225,539 A | 7/1993 | Winter |
| 5,264,586 A | 11/1993 | Nicolaou et al. |
| 5,384,412 A | 1/1995 | Nicolaou et al. |
| 5,416,064 A | 5/1995 | Chari et al. |
| 5,475,092 A | 12/1995 | Chari et al. |
| 5,530,101 A | 6/1996 | Queen et al. |
| 5,545,806 A | 8/1996 | Lonberg et al. |
| 5,550,246 A | 8/1996 | Nicolaou et al. |
| 5,569,825 A | 10/1996 | Lonberg et al. |
| 5,585,089 A | 12/1996 | Queen et al. |
| 5,585,499 A | 12/1996 | Chari et al. |
| 5,635,483 A | 6/1997 | Pettit et al. |
| 5,641,780 A | 6/1997 | Amishiro et al. |
| 5,663,149 A | 9/1997 | Pettit et al. |
| 5,693,761 A | 12/1997 | Queen et al. |
| 5,693,762 A | 12/1997 | Queen et al. |
| 5,703,080 A | 12/1997 | Nakakura et al. |
| 5,712,374 A | 1/1998 | Kuntsmann et al. |
| 5,714,352 A | 2/1998 | Jakobobits et al. |
| 5,714,586 A | 2/1998 | Kunstmann et al. |
| 5,739,116 A | 4/1998 | Hamann et al. |
| 5,767,237 A | 6/1998 | Sakakibara et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,814,318 A | 9/1998 | Lonberg et al. |
| 5,821,337 A | 10/1998 | Carter et al. |
| 5,824,805 A | 10/1998 | King et al. |
| 5,846,545 A | 12/1998 | Chari et al. |
| 5,859,205 A | 1/1999 | Adair et al. |
| 5,869,619 A | 2/1999 | Studnicka |
| 5,877,296 A | 3/1999 | Hamann et al. |
| 6,054,297 A | 4/2000 | Carter et al. |
| 6,124,431 A | 9/2000 | Sakakibara et al. |
| 6,180,370 B1 | 1/2001 | Queen et al. |
| 6,214,345 B1 | 4/2001 | Firestone et al. |
| 6,407,213 B1 | 6/2002 | Carter et al. |
| 6,441,163 B1 | 8/2002 | Chari et al. |
| 6,586,207 B2 | 7/2003 | Tirrell et al. |
| 6,602,684 B1 | 8/2003 | Umana et al. |
| 6,884,869 B2 | 4/2005 | Senter et al. |
| 6,989,452 B2 | 1/2006 | Ng et al. |
| 7,053,186 B2 | 5/2006 | Afar et al. |
| 7,087,600 B2 | 8/2006 | Ng et al. |
| 7,129,261 B2 | 10/2006 | Ng et al. |
| 7,276,497 B2 | 10/2007 | Chari et al. |
| 7,303,749 B1 | 12/2007 | Chari |
| 7,319,006 B2 | 1/2008 | Afar et al. |
| 7,368,565 B2 | 5/2008 | Chari et al. |
| 7,494,646 B2 | 2/2009 | Jakobovits et al. |
| 7,498,302 B2 | 3/2009 | Ng et al. |
| 7,507,420 B2 | 3/2009 | Ng et al. |
| 7,517,903 B2 | 4/2009 | Chen et al. |
| 7,521,541 B2 | 4/2009 | Eigenbrot et al. |
| 7,601,354 B2 | 10/2009 | Chari |
| 7,635,472 B2 | 12/2009 | Kufer et al. |
| 7,691,962 B2 | 4/2010 | Boyd et al. |
| 7,727,533 B2 | 6/2010 | Afar et al. |
| 7,872,106 B2 | 1/2011 | Paszty et al. |
| 8,008,442 B2 | 8/2011 | Jakobovits et al. |
| 8,216,805 B2 | 7/2012 | Carter et al. |
| 8,414,898 B2 | 4/2013 | Afar et al. |
| 8,436,147 B2 | 5/2013 | Dennis et al. |
| 8,771,966 B2 | 7/2014 | Dennis et al. |
| 8,889,847 B2 | 11/2014 | Dennis et al. |
| 9,023,605 B2 | 5/2015 | Jakobovits et al. |
| 9,546,202 B2 | 1/2017 | Felber et al. |
| 9,546,203 B2 | 1/2017 | Kannan |
| 9,593,167 B2 | 3/2017 | Dennis et al. |
| 9,617,346 B2 | 4/2017 | Jakobovits et al. |
| 9,632,091 B2 | 4/2017 | Atwal et al. |
| 9,822,186 B2 | 11/2017 | Bernett et al. |
| 10,202,452 B2 | 2/2019 | Tan et al. |
| 2002/0103345 A1 | 8/2002 | Zhu |
| 2002/0197266 A1 | 12/2002 | Debinski |
| 2003/0003097 A1 | 1/2003 | Reff et al. |
| 2003/0039649 A1 | 2/2003 | Foote |
| 2003/0157108 A1 | 8/2003 | Presta |
| 2004/0214988 A1 | 10/2004 | Tirrell et al. |
| 2004/0253232 A1 | 12/2004 | Jakobovits et al. |
| 2005/0114037 A1 | 5/2005 | Desjarlais et al. |
| 2005/0238648 A1 | 10/2005 | Jacobs et al. |
| 2005/0238649 A1 | 10/2005 | Doronina et al. |
| 2006/0008883 A1 | 1/2006 | Lazar et al. |
| 2006/0024298 A1 | 2/2006 | Lazar et al. |
| 2006/0024317 A1 | 2/2006 | Boyd et al. |
| 2006/0073150 A1* | 4/2006 | Faris ............... A61K 51/1045 424/155.1 |
| 2006/0074008 A1 | 4/2006 | Senter et al. |
| 2006/0121032 A1 | 6/2006 | Dahiyat et al. |
| 2006/0235208 A1 | 10/2006 | Lazar et al. |
| 2007/0148170 A1 | 6/2007 | Desjarlais et al. |
| 2008/0305105 A1 | 12/2008 | Kufer et al. |
| 2009/0004109 A1* | 1/2009 | Jacobovits ........... A61K 51/106 424/139.1 |
| 2009/0163699 A1 | 6/2009 | Chamberlain et al. |
| 2009/0317869 A1 | 12/2009 | Alley et al. |
| 2012/0028304 A1 | 2/2012 | Dahiyat et al. |
| 2012/0149876 A1 | 6/2012 | Von et al. |
| 2013/0205756 A1 | 8/2013 | Levin et al. |
| 2014/0178905 A1 | 6/2014 | Walker et al. |
| 2014/0288275 A1 | 9/2014 | Moore et al. |
| 2014/0370013 A1 | 12/2014 | Desjarlais et al. |
| 2015/0284475 A1 | 10/2015 | Zhou et al. |
| 2016/0090426 A1 | 3/2016 | Zhou et al. |
| 2016/0145339 A1 | 5/2016 | Zhou et al. |
| 2017/0096496 A1 | 4/2017 | Sleeman et al. |
| 2017/0342155 A1 | 11/2017 | King et al. |
| 2018/0209982 A1 | 7/2018 | Kabbarah et al. |
| 2021/0047407 A1* | 2/2021 | Christian ........... C07K 16/2896 |

FOREIGN PATENT DOCUMENTS

| | | |
|---|---|---|
| WO | 1987/05330 A1 | 9/1987 |
| WO | 1992/11018 A1 | 7/1992 |
| WO | 1993/21232 A1 | 10/1993 |
| WO | 1998/48032 A2 | 10/1998 |
| WO | 1999/54440 A1 | 10/1999 |
| WO | 2000/61739 A1 | 10/2000 |
| WO | 2001/24763 A2 | 4/2001 |
| WO | 2001/29246 A1 | 4/2001 |
| WO | 2002/16368 A1 | 2/2002 |
| WO | 2002/30954 A1 | 4/2002 |
| WO | 2002/31140 A1 | 4/2002 |
| WO | 2002/83180 A1 | 10/2002 |
| WO | 2002/88172 A2 | 11/2002 |
| WO | 2002/98883 A1 | 12/2002 |
| WO | 2003/022995 A2 | 3/2003 |
| WO | 2003/73238 A2 | 9/2003 |
| WO | 2004/010957 A2 | 2/2004 |
| WO | 2004/043493 A1 | 5/2004 |
| WO | 2004/099249 A2 | 11/2004 |
| WO | 2004/106380 A2 | 12/2004 |
| WO | 2005/035727 A2 | 4/2005 |
| WO | 2005/040220 A1 | 5/2005 |
| WO | 2005/061547 A2 | 7/2005 |
| WO | 2005/074524 A2 | 8/2005 |
| WO | 2005/112919 A2 | 12/2005 |
| WO | 2005/113601 A2 | 12/2005 |
| WO | 2006/020258 A2 | 2/2006 |
| WO | 2006/034488 A2 | 3/2006 |
| WO | 2006/110476 A2 | 10/2006 |
| WO | 2007/018431 A2 | 2/2007 |
| WO | 2007/059404 A2 | 5/2007 |
| WO | 2007/089149 A2 | 8/2007 |
| WO | 2008/052187 A2 | 5/2008 |
| WO | 2009/017394 A1 | 2/2009 |

(56) References Cited

FOREIGN PATENT DOCUMENTS

| WO | 2009/032782 A2 | 3/2009 |
|---|---|---|
| WO | 2010/062171 A2 | 6/2010 |
| WO | 2011/153346 A1 | 12/2011 |
| WO | 2011/156328 A1 | 12/2011 |
| WO | 2012/131555 A2 | 10/2012 |
| WO | 2013/082249 A2 | 6/2013 |
| WO | 2013/093809 A1 | 6/2013 |
| WO | 2014/165818 A2 | 10/2014 |
| WO | 2015/112909 A1 | 7/2015 |
| WO | 2016/040856 A2 | 3/2016 |
| WO | 2016/172160 A1 | 10/2016 |
| WO | 2016/179003 A1 | 11/2016 |
| WO | 2017/053856 A1 | 3/2017 |
| WO | 2017/091656 A1 | 6/2017 |
| WO | 2017/147368 A1 | 8/2017 |
| WO | 2017/218707 A2 | 12/2017 |
| WO | WO-2018/184966 A1 | 10/2018 |
| WO | 2019/157340 A1 | 8/2019 |
| WO | WO-2020/018695 A1 | 1/2020 |

OTHER PUBLICATIONS

Wu et al., Humanization of a murine monoclonal antibody by simultaneous optimization of framework and CDR residues, J. Mol. Biol., 294:151-162 (1999).

Wu et al., Simultaneous targeting of multiple disease mediators by a dual-variable-domain immunoglobulin, Nat. Biotechnol., 25(11):1290-1297 (2007).

Yu et al., The biosynthetic gene cluster of the maytansinoid anti-tumor agent ansamitocin from Actinosynnema pretiosum, Proc. Natl. Acad. Sci. USA, 99:7968-7973 (2002).

Zuo et al., An efficient route to the production of an IgG-like bispecific antibody, Protein Eng., 13(5):361-367 (2000).

Vered Kunik et al., "Structural consensus among antibodies defines the antigen binding site", PLoS Computational Biology, vol. 8, No. 2, p. e1002388 (Feb. 23, 2012).

Aplin et al., Preparation, properties, and applications of carbohydrate conjugates of proteins and lipids, CRC Crit. Rev. Biochem., 10:259-306 (1981).

Atwell et al., Stable heterodimers from remodeling the domain interface of a homodimer using a phage display library, J. Mol. Biol., 270:26-35 (1997).

Baca et al., Antibody humanization using monovalent phage display, J. Biol. Chem., 272(16):10678-10684 (1997).

Bird et al., Single-chain antigen-binding proteins, Science, 242:423-426 (1988).

Bruhl et al., Depletion of CCR5-expressing cells with bispecific antibodies and chemokine toxins: a new slialegy in the treatment of chronic inflammatory diseases and HIV, Immunol., 166,2420-2426 (2001).

Carter et al., Antibody-drug conjugates for cancer therapy, Cancer J., 14:154-69 (2008).

Carter et al., Humanization of an anti-p185HER2 antibody for human cancer therapy, Proc Natl Acad Sci U S A., 89:4285-9 (1992).

Chames et al., Bispecific antibodies for cancer therapy: the light at the end of the tunnel?, Mabs., 1(6):1-9 (2009).

Chand et al., A competitive ELISA for detection of group specific antibody to bluetongue virus using anti-core antibody, Biologicals, 46:168-171 (2017).

Chari et al., Immunoconjugates containing novel maytansinoids: promising anticancer drugs, Cancer Research, 52:127-131 (1992).

Chatenoud et al., CD3-specific antibodies: a portal to the treatment of autoimmunity, Nature Reviews Immunology, 7:622-632 (2007).

Chin et al., Addition of a photocrosslinking amino acid to the genetic code of Escherichiacoli, PICAS United States of America, 99:11020-11024 (2002).

Chin et al., Addition of p-azido-L-phenylalanine to the genetic code of Escherichia coli, Journal of the American Chemical Society, 124:9026-9027 (2002).

Chin et al., In vivo photocrosslinking with unnatural amino Acid mutagenesis, Chem. Bio. Chem, 3:1135-1137 (2002).

Chothia et al., Canonical structures for the hypervariable regions of immunoglobulins, J. Mol. Biol., 196:901-917 (1987).

Chothia et al., Conformations of immunoglobulin hypervariable regions, Nature, 342: 877-883 (1989).

Creighton, T, Proteins: Structure and Molecular Properties, W. H. Freeman & Co., San Francisco, 79-86 (1983).

Davies et al., Expression of GnTIII in a recombinant anti-CD20 CHO production cell line: Expression of antibodies with altered glycoforms leads to an increase in ADCC through higher affinity for FC gamma RIII, Biotechnol Bioeng, 74:288-294 (2001).

De Pascalis et al., Grafting of "abbreviated" complementarity-determining regions containing specificity-determining residues essential for ligand contact to engineer a less immunogenic humanized monoclonal antibody, J. Immunol., 169:3076-3084 (2002).

Doronina et al., Development of potent monoclonal antibody auristatin conjugates for cancer therapy, Nat. Biotechnol., 21:778-784 (2003).

Dubowchik et al., Receptor-mediated and enzyme-dependent targeting of cytotoxic anticancer drugs, Pharm. Therapeutics, 83:67-123 (1999).

Ducry et al., Antibody-drug conjugates: linking cytotoxic payloads to monoclonal antibodies, Bioconjugate Chem., 21:5-13 (2010).

Duskin et al., Relationship of the structure and biological activity of the natural homologues of tunicamycin, J. Biol. Chem., 257:3105-9 (1982).

Edelman et al., The covalent structure of an entire gammaG immunoglobulin molecule, Proc. Natl. Acad. Sci. USA., 63:78-85 (1969).

Edge et al., Deglycosylation of glycoproteins by trifluoromethanesulfonic acid, Anal. Biochem., 118:131-7 (1981).

Gluzman, SV40-transformed simian cells support the replication of early SV40 mutants, Cell, 23:175-82 (1981).

Goolia et al., Validation of a competitive ELISA and a virus neutralization test for the detection and confirmation of antibodies to Senecavirus A in swine sera, J. Vet. Diagn. Invest., 29:250-253 (2017).

Gorman et al., Reshaping a therapeutic CD4 antibody, Proc. Natl. Acad. Sci. USA., 88:4181-4185 (1991).

Gunasekaran et al., Enhancing antibody Fc heterodimer formation through electrostatic steering effects: applications to bispecific molecules and monovalent IgG, J. Biol. Chem., 285:19637-46 (2010).

Hakimuddin et al., A chemical method for the deglycosylation of proteins, Arch. Biochem. Biophys., 259:52-57 (1987).

Haskard et al., The production of human monoclonal autoantibodies from patients with rheumatoid arthritis by the EBV-hybridoma technique, J. Immunol. Methods, 74:361-67 (1984).

He et al., Humanization and pharmacokinetics of a monoclonal antibody with specificity for both E- and P-selectin, J. Immunol., 160: 1029-1035 (1998).

Hinman et al., Preparation and characterization of monoclonal antibody conjugates of the calicheamicins: a novel and potent family of antitumor antibiotics, Cancer Research 53:3336-3342 (1993).

Holliger et al., Engineered antibody fragments and the rise of single domains, Nature Biotechnology, 23:1126-1136 (2005).

Huse et al., Generation of a large combinatorial library of the immunoglobulin repertoire in phage lambda, Science, 246:1275-81 (1989).

Huston et al., Protein engineering of antibody binding sites: recovery of specific activity in an anti-digoxin single-chain Fv analogue produced in Escherichia coli, Proc. Natl. Acad. Sci. USA., 85:5879-83 (1988).

Igawa et al., Reduced elimination of IgG antibodies by engineering the variable region, PEDS., 23:385-392 (2010).

International Search Report and Written Opinion, PCT App. No. PCT/US2019/040296, dated Feb. 10, 2020, 17 pages.

Jefferis et al., Interaction sites on human IgG—Fc for FcgammaR: current models, Immunol Lett., 82:57-65 (2002).

Johnson et al., Anti-tumor activity of CC49-doxorubicin immunoconjugates, Anticancer Res., 15:1387-93 (1995).

(56) References Cited

OTHER PUBLICATIONS

Jones et al., Replacing the complementarity-determining regions in a human antibody with those from a mouse, Nature, 321:522-525 (1986).
Kabat et al., Sequences of proteins of immunological interest, 5th Ed. Public Health Service, National Institutes of Health, Bethesda, Md. (1991).
Kipriyanov et al., Bispecific tandem diabody for tumor therapy with improved antigen binding and pharmacokinetics, J. Mol. Biol., 293:41-56 (1999).
Kirkland et al., Analysis of the fine specificity and cross-reactivity of monoclonal anti-lipid A antibodies, J. Immunol., 137:3614-3619 (1986).
Kontermann, Dual targeting strategies with bispecific antibodies, Mabs., 4:182-97 (2012).
Korndorfer et al., Crystallographic analysis of an "Anticalin" with tailored specificity for fluorescein reveals high structural plasticity of the lipocalin loop region, Proteins: Structure, Function, and bioinformatics, 53(1):121-129 (2003).
Krauss et al., Specificity grafting of human antibody frameworks selected from a phage display library: generation of a highly stable humanized anti-CD22 single-chain Fv fragment, Protein Engineering, 16:753-759 (2003).
Kufer et al., Construction and biological activity of a recombinant bispecific single-chain antibody designed for therapy of minimal residual colorectal cancer, Cancer Immunol. Immunother., 45:193-197 (1997).
Kuhns et al., Deconstructing the form and function of the TCR/CD3 complex, Immunity, 24:133-139 (2006).
Lau et al., Conjugation of doxorubicin to monoclonal anti-carcinoembryonic antigen antibody via novel thiol-directed cross-linking reagents, Bioorg-MedChem., 3:1299-1304 (1995).
Lau et al., Novel doxorubicin-monoclonal anti-carcinoembryonic antigen antibody immunoconjugate activity in vitro, Bioorg-Med-Chem., 3:1305-12 (1995).
Lefranc et al., IMGT unique numbering for immunoglobulin and T cell receptor variable domains and Ig superfamily V-like domains, Dev. Comp. Immunol., 27:55-77 (2003).
Liu et al., Development of competitive ELISA for the detection of bovine serum albumin using single-chain variable fragments, Anal. Biochem., 525:89-91 (2017).
Liu et al., Eradication of large colon tumor xenografts by targeted delivery of maytansinoids, Proc. Natl. Acad Sci. USA, 93:8618-8623 (1996).
Lode et al., Targeted therapy with a novel enediyene antibiotic calicheamicin theta(I)1 effectively suppresses growth and dissemination of liver metastases in a syngeneic model of murine neuroblastoma, Cancer Res., 58:2925-2928 (1998).
Loffler et al., A recombinant bispecific single-chain antibody, CD19 x CD3, induces rapid and high lymphoma-directed cytotoxicity by unstimulated T lymphocytes, Blood, 95:2098-2103 (2000).
Lu et al., A fully human recombinant IgG-like bispecific antibody to both the epidermal growth factor receptor and the insulin-like growth factor receptor for enhanced antitumor activity, J. Biol. Chem., 280:19665-19672 (2005).
Mack et al., A small bispecific antibody construct expressed as a functional single-chain molecule with high tumor cell cytotoxicity, PNAS., 92:7021-7025 (1995).
Mack et al., Biologic properties of a bispecific single-chain antibody directed against 17-1A (EpCAM) and CD3: tumor cell-dependent T cell stimulation and cytotoxic activity, J. Immunol., 158:3965-3970 (1997).
Mandler et al., Immunoconjugates of geldanamycin and anti-HER2 monoclonal antibodies: antiproliferative activity on human breast carcinoma cell lines, J. Nat. Cancer Inst., 92:1573-1581 (2000).
Mandler et al., Modifications in synthesis strategy improve the yield and efficacy of geldanamycin-herceptin immunoconjugates. Bioconjugate Chem., 13:786-791 (2002).
Mandler et al., Synthesis and evaluation of antiproliferative activity of a geldanamycin-Herceptin immunoconjugate, Bioorganic & Med. Chem. Letters, 10:1025-1028 (2000).
Mcmahan et al., A novel IL-1 receptor, cloned from B cells by mammalian expression, is expressed in many cell types, EMBO J., 10:2821-32 (1991).
Merchant et al., An efficient route to human bispecific IgG, Nature Biotech., 16:677-81 (1998).
Michaelson et al., Anti-tumor activity of stability-engineered IgG-like bispecific antibodies targeting TRAIL-R2 and LTbetaR, Mabs, 1:128-141 (2009).
Morel et al., Monoclonal antibodies to bovine serum albumin: affinity and specificity determinations, Molec. Immunol., 25:7-15 (1988).
Neville et al., Enhancement of immunotoxin efficacy by acid-cleavable cross-linking agents utilizing diphtheria toxin and toxin mutants, Biol. Chem., 264:14653-14661 (1989).
O'Connor et al., Humanization of an antibody against human protein C and calcium-dependence involving framework residues, Protein Eng., 11:321-8 (1998).
Padlan et al., Identification of specificity-determining residues in antibodies, FASEB. J., 9:133-39 (1995).
Perruche et al., Lethal effect of CD3-specific antibody in mice deficient in TGF-beta1 by uncontrolled flu-like syndrome, J. Immunol., 183:953-61 (2009).
Pettit et al., Antineoplastic agents 365. Dolastatin 10 SAR probes, Anti-Cancer Drug Design, 13:243-277 (1998).
Pettit et al., Dolastatins 24: synthesis of (−)-dolastatin 10. X-Ray molecular structure of N,N-dimethylvalyl-valyl-dolaisoleuine tert-butyl ester, J. Chem. Soc. Perkin Trans., 1:859-863 (1996).
Pettit et al., Specific activities of dolastatin 10 and peptide derivatives against Cryptococcus neoformans, Antimicrob. Agents Chemother, 42:2961-2965 (1998).
Pettit et al., The Dolastatins; 18: Stereospecific Synthesis of Dolaproine, Synthesis, 1996:719-725 (1996).
Presta et al., Humanization of an anti-vascular endothelial growth factor monoclonal antibody for the therapy of solid tumors and other disorders, Cancer Res., 57:4593-9 (1997).
Queen et al., A humanized antibody that binds to the interleukin 2 receptor, Proc. Natl. Acad. Sci. USA, 86:10029-33 (1989).
Rader et al., A phage display approach for rapid antibody humanization: designed combinatorial V gene libraries, Proc. Natl. Acad. Sci. USA, 95:8910-8915 (1998).
Reiter et al., Engineering antibody Fv fragments for cancer detection and therapy: disulfide-stabilized Fv fragments, Nature Biotech., 14:1239-1245 (1996).
Ridgway et al., 'Knobs-into-holes' engineering of antibody CH3 domains for heavy chain heterodimerization, Protein Eng., 9(7):617-621 (1996).
Riechmann et al., Reshaping human antibodies for therapy, Nature, 332:323-329 (1988).
Roder et al., The EBV-hybridoma technique, Methods Enzymol., 121:140-67 (1986).
Roguska et al., Humanization of murine monoclonal antibodies through variable domain resurfacing, Proc. Natl. Acad. Sci. USA, 91:969-973 (1994).
Roque et al., Antibodies and genetically engineered related molecules: production and purification, Biotechnol. Prog., 20:639-654 (2004).
Rosok et al., A combinatorial library strategy for the rapid humanization of anticarcinoma BR96 Fab, J. Biol. Chem., 271(37):22611-22618 (1996).
Sambrook et al., Molecular cloning: A laboratory manual, 3rd ed., Cold Spring Harbor Laboratory Press, Cold Spring Harbor, N.Y. (2001).
Schier et al., Isolation of picomolar affinity anti-c-erbB-2 single-chain Fv by molecular evolution of the complementarity determining regions in the center of the antibody binding site, J. Mol. Biol., 263:551-67 (1996).
Senter et al, Proceedings of the american association for cancer research, Abstract No. 623, presented, 45 (2004).
Senter, Potent antibody drug conjugates for cancer therapy, Curr. Opin. Chem. Biol., 13:235-244 (2009).

(56) References Cited

OTHER PUBLICATIONS

Shen et al., Single variable domain-IgG fusion. A novel recombinant approach to Fc domain-containing bispecific antibodies, J. Biol. Chem., 281(16):10706-10714 (2006).

Shields et al., Lack of fucose on human IgG1 N-linked oligosaccharide improves binding to human Fcgamma RIII and antibody-dependent cellular toxicity, J. Biol. Chem., 277:26733-26740 (2002).

Shimamoto et al., Peptibodies: A flexible alternative format to antibodies, Mabs., 4(5):586-591 (2012).

Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chem., 278:3466-3473 (2003).

Spiess et al., Alternative molecular formats and therapeutic applications for bispecific antibodies, Mol. Immunol., 67(2 Pt A):95-106 (2015).

Stahli et al., Distinction of epitopes by monoclonal antibodies, Methods Enzymol., 9:242-253 (1983).

Tamura et al., Production of Antibodies against Multi pass Membrane Proteins Expressed in Human Tumor Cells Using Dendritic Cell Immunization, Journal of Biomedicine and Biotechnology, 60:6568-9 (2009).

Tamura et al., Structural correlates of an anticarcinoma antibody: identification of specificity-determining residues (SDRs) and development of a minimally immunogenic antibody variant by retention of SDRs only, J. Immunol., 164:1432-41 (2000).

Tan et al., "Superhumanized" antibodies: reduction of immunogenic potential by complementarity-determining region grafting with human germline sequences: application to an anti-CD28, J. Immunol., 169:1119-1125 (2002).

Thorpe et al., New coupling agents for the synthesis of immunotoxins containing a hindered disulfide bond with improved stability in vivo, Cancer Res., 47:5924-5931 (1987).

Thotakura et al., Enzymatic Deglycosylation of Glycoproteins, Meth. Enzymol., 138:350 (1987).

Tsurushita et al., Humanization of monoclonal antibodies, Molecular Biology of B Cells, 533-545 (2004).

* cited by examiner

FIGURE 1

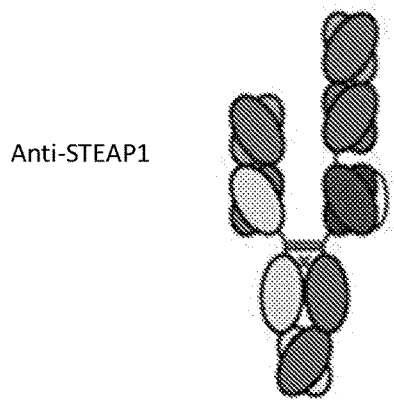

Anti-STEAP1

FIGURE 2

MQSGTHWRVLGLCLLSVGVWGQDGNEEMGGITQTPYKVSISGTTVILTCPQYPGSEILWQHNDKNIGGDE
DDKNIGSDEDHLSLKEFSELEQSGYYVCYPRGSKPEDANFYLYLRARVCENCMEMDVMSVATIVIVDICITGG
LLLLVYYWSKNRKAKAKPVTRGAGAGGRQRGQNKERPPPVPNPDYEPIRKGQRDLYSGLNQRRI (SEQ ID NO: 1)

FIGURE 3

MESRKDITNQEELWKMKPRRNLEEDDYLHKDTGETSMLKRPVLLHLHQTAHADEFDCPSE
LQHTQELFPQWHLPIKIAAIIASLTFLYTLL<u>REVIHPLATSHQQYFYKIPILVINKVL</u>PM
VSITLLALVYLPGVIAAIVQLHNGTKYKKFPHWLDKWMLTRKQFGLLSFFFAVLHAIYSL
SYPM<u>RRSYRYKLLNWAYQQVQQNKEDAWIEHDVWRME</u>IYVSLGIVGLAILALLAVTSIPS
VSDSLTWREFHYIQSKLGIVSLLLGTIHALIFAWNKWI<u>DIKQFVWYTPPT</u>FMIAVFLPIV
VLIFKSILFLPCLRKKILKIRHGWEDVTKINKTEICSQL (SEQ ID NO: 2)

FIGURE 4A

| Monomer 1 | Monomer 2 |
|---|---|
| F405A | T394F |
| S364D | Y349K |
| S364E | L368K |
| S364E | Y349K |
| S364F | K370G |
| S364H | Y349K |
| S364H | Y349T |
| S364Y | K370G |
| T411K | K370E |
| V397S/F405A | T394F |
| K370R/T411K | K370E/T411E |
| L351E/S364D | Y349K/L351K |
| L351E/S364E | Y349K/L351K |
| L351E/T366D | L351K/T366K |
| P395T/V397S/F405A | T394F |
| S364D/K370G | S364Y/K370R |
| S364D/T394F | Y349K/F405A |
| S364E/F405A | Y349K/T394F |
| S364E/F405S | Y349K/T394Y |
| S364E/T411E | Y349K/D401K |
| S364H/D401K | Y349T/T411E |
| S364H/F405A | Y349T/T394F |
| S364H/T394F | Y349T/F405A |
| Y349C/S364E | Y349K/S354C |
| L351E/S364D/F405A | Y349K/L351K/T394F |
| L351K/S364H/D401K | Y349T/L351E/T411E |
| S364E/T411E/F405A | Y349K/T394F/D401K |
| S364H/D401K/F405A | Y349T/T394F/T411E |
| S364H/F405A/T411E | Y349T/T394F/D401K |

FIGURE 4B

| Monomer 1 | Monomer 2 |
|---|---|
| K370E/T411D | T411K |
| L368E/K409E | L368K |
| Y349T/T394F/S354C | S364H/F405A/Y349C |
| T411E | D401K |
| T411E | D401R/T411R |
| Q347E/K360E | Q347R |
| L368E | S364K |
| L368E/K370S | S364K |
| L368E/K370T | S364K |
| L368E/D401R | S364K |
| L368E/D401N | S364K |
| L368E | E357S/S364K |
| L368E | S364K/K409E |
| L368E | S364K/K409V |
| L368D | S364K |
| L368D/K370S | S364K |
| L368D/K370S | S364K/E357L |
| L368D/K370S | S364K/E357Q |
| T411E/K360E/Q362E | D401K |
| K370S | S364K |
| L368E/K370S | S364K/E357Q |
| K370S | S364K/E357Q |
| T411E/K360D | D401K |
| T411E/K360E | D401K |
| T411E/Q362E | D401K |
| T411E/N390D | D401K |
| T411E | D401K/Q347K |
| T411E | D401K/Q347R |
| T411E/K360D/Q362E | D401K |

FIGURE 4C

| Monomer 1 | Monomer 2 |
|---|---|
| T411E/K360E/N390D | D401K |
| T411E/Q362E/N390D | D401K |
| T411E/Q347R | D401K/K360D |
| T411E/Q347R | D401K/K360E |
| T411E/K360 | D401K/Q347K |
| T411E/K360D | D401K/Q347R |
| T411E/K360E | D401K/Q347K |
| T411E/K360E | D401K/Q347R |
| T411E/S364K | D401K/K370S |
| T411E/K370S | D401K/S364K |
| Q347E | E357Q |
| Q347E | E357Q/Q362K |
| K360D/Q362E | Q347R |
| K360D/Q362E | D401K |
| K360D/Q362E | Q347R/D401K |
| K360E/Q362E | Q347R |
| K360E/Q362E | D401K |
| K360E/Q362E | Q347R/D401K |
| Q362E/N390D | D401K |
| Q347E/K360D | D401N |
| K360D | Q347R/N390K |
| K360D | N390K/D401N |
| K360E | Y349H |
| K370S/Q347E | S364K |
| K370S/E357L | S364K |
| K370S/E357Q | S364K |
| K370S/Q347E/E357L | S364K |
| K370S/Q347E/E357Q | S364K |

FIGURE 4D

| Monomer 1 | Monomer 2 |
|---|---|
| L368D/K370S/Q347E | S364K |
| L368D/K370S/E357L | S364K |
| L368D/K370S/E357Q | S364K |
| L368D/K370S/Q347E/E357L | S364K |
| L368D/K370S/Q347E/E357Q | S364K |
| L368E/K370S/Q347E | S364K |
| L368E/K370S/E357L | S364K |
| L368E/K370S/E357Q | S364K |
| L368E/K370S/Q347E/E357L | S364K |
| L368E/K370S/Q347E/E357Q | S364K |
| L368D/K370T/Q347E | S364K |
| L368D/K370T/E357L | S364K |
| L368D/K370T/E357Q | S364K |
| L368D/K370T/Q347E/E357L | S364K |
| L368D/K370T/Q347E/E357Q | S364K |
| L368E/K370T/Q347E | S364K |
| L368E/K370T/E357L | S364K |
| L368E/K370T/E357Q | S364K |
| L368E/K370T/Q347E/E357L | S364K |
| L368E/K370T/Q347E/E357Q | S364K |
| T411E/Q362E | D401K/T411K |
| T411E/N390D | D401K/T411K |
| T411E/Q362E | D401R/T411R |
| T411E/N390D | D401R/T411R |
| Y407T | T366Y |
| F405A | T394W |
| T366Y/F405A | T394W/Y407T |
| Y407A | T366W |
| T366S/L368A/Y407V | T366W |
| T366S/L368A/Y407V/Y349C | T366W/S354C |

FIGURE 4E

| Monomer 1 | Monomer 2 |
|---|---|
| K392D/K409D | E356K/D399K |
| K370D/K392D/K409D | E356K/E357K/D399K |
| I199T/N203D/K247Q/R355Q/N384S/K392N/V397M/Q419E/K447_ | Q196K/I199T/P217R/P228R/N276K |
| I199T/N203D/K247Q/R355Q/N384S/K392N/V397M/Q419E/K447_ | Q196K/I199T/N276K |
| N384S/K392N/V397M/Q419E | N276K |
| D221E/P228E/L368E | D221R/P228R/K409R |
| C220E/P228E/L368E | C220R/E224R/P228R/K409R |
| F405L | K409R |
| T366I/K392M/T394W | F405A/Y407V |
| T366V/K409F | L351Y/Y407A |
| T366A/K392E/K409F/T411E | D399R/S400R/Y407A |
| L351K | L351E |
| I199T/N203D/K247Q/R355Q/Q419E/K447_ | Q196K/I199T/P217R/P228R/N276K |
| I199T/N203D/K247Q/R355Q/Q419E/K447_ | Q196K/I199T/N276K |
| I199T N203D K274Q R355Q N384S K392N V397M Q419E DEL447 | |
| N208D Q295E N384D Q418E N421D | |
| N208D Q295E Q418E N421D | |
| Q196K I199T P217R P228R N276K | |
| Q196K I199T N276K | |
| E269Q E272Q E283Q E357Q | |
| E269Q E272Q E283Q | |
| E269Q E272Q | |
| E269Q E283Q | |
| E272Q E283Q | |
| E269Q | |

FIGURE 5 pI variants

| Variant constant region | Substitutions |
|---|---|
| pI_ISO(-) | I199T N203D K274Q R355Q N384S K392N V397M Q419E DEL447 |
| pI_(-)_isosteric_A | N208D Q295E N384D Q418E N421D |
| pI_(-)_isosteric_B | N208D Q295E Q418E N421D |
| pI_ISO(+RR) | Q196K I199T P217R P228R N276K |
| pI_ISO(+) | Q196K I199T N276K |
| pI_(+)_isosteric_A | E269Q E272Q E283Q E357Q |
| pI_(+)_isosteric_B | E269Q E272Q E283Q |
| pI_(+)_isosteric_E269Q/E272Q | E269Q E272Q |
| pI_(+)_isosteric_E269Q/E283Q | E269Q E283Q |
| pI_(+)_isosteric_E272Q/E283Q | E272Q E283Q |
| pI_(+)_isosteric_E269Q | E269Q |

FIGURE 6

Ablation variants

| Variant | Variant(s), cont. |
|---|---|
| G236R | P329K |
| S239G | A330L |
| S239K | A330S/P331S |
| S239Q | I332K |
| S239R | I332R |
| V266D | V266D/A327Q |
| S267K | V266D/P329K |
| S267R | S267R/A327Q |
| H268K | S267R/P329K |
| E269R | G236R/L328R |
| 299R | E233P/L234V/L235A/G236del/S239K |
| 299K | E233P/L234V/L235A/G236del/S267K |
| K322A | E233P/L234V/L235A/G236del/S239K/A327G |
| A327G | E233P/L234V/L235A/G236del/S267K/A327G |
| A327L | E233P/L234V/L235A/G236del |
| A327N | S239K/S267K |
| A327Q | 267K/P329K |
| L328E | |
| L328R | |
| P329A | |
| P329H | |

FIGURE 7 scFv monomer (+)

Heterodimerization skew variants
S364K/E357Q

Optional scFv charged linker including
but not limited to (GKPGS)₄

FcKO
E233P/L234V/L235A/G236del/S267K

± 428L/434S for FcRn scFv of anti-CD3

Fab monomer (-)

Heterodimerization skew variants L368D/K370S

Isosteric pI substitutions
N208D/Q295E/N384D/Q418E/N421D

FcKO E233P/L234V/L235A/G236del/S267K

± 428L/434S for FcRn

Fv sequences for anti-STEAP1 scFv monomer

Heterodimerization skew variants
S364K/E357Q

Optional scFv charged linker including,
but not limited to (GKPGS)₄

FcKO
E233P/L234V/L235A/G236del/S267K

± 428L/434S for FcRn (optional)

scFv of anti-CD3

Fab monomer

Heterodimerization skew variants L368D/K370S pI substitutions I199T N203D K274Q R355Q Q419E K447del FcKO E233P/L234V/L235A/G236del/S267K ± 428L/434S for FcRn (optional)

scFv of anti- STEAP1

FIGURE 8A

Positive charged scFv linkers

| Name | Sequence | Length | Charge | SEQ ID NO: |
|---|---|---|---|---|
| Gly-Ser 15 | GGGGSGGGGSGGGGS | 15 | 0 | 143 |
| Whitlow linker | GSTSGSGKPGSGEGSTKG | 18 | +1 | 144 |
| 6paxA_1 (+A) | IRPRAIGGSKPRVA | 14 | +4 | 145 |
| +B | GKGGSGKGGSGKGGS | 15 | +3 | 146 |
| +C | GGKGSGGKGSGGKGS | 15 | +3 | 147 |
| +D | GGGKSGGGKSGGGKS | 15 | +3 | 148 |
| +E | GKGKSGKGKSGKGKS | 15 | +6 | 149 |
| +F | GGGKSGGKGSGKGGS | 15 | +3 | 150 |
| +G | GKPGSGKPGSGKPGS | 15 | +3 | 151 |
| +H | GKPGSGKPGSGKPGSGKPGS | 20 | +4 | 152 |
| +I | GKGKSGKGKSGKGKSGKGKS | 20 | +8 | 153 |

Negative charged scFv linkers

| Name | Sequence | Length | Charge | SEQ ID NO: |
|---|---|---|---|---|
| Gly-Ser 15 | GGGGSGGGGSGGGGSGGGGS | 20 | 0 | 154 |
| 3hsc_2 (-A) | STAGDTHLGGEDFD | 14 | -4 | 155 |
| -B | GEGGSGEGGSGEGGS | 15 | -3 | 156 |
| -C | GGEGSGGEGSGGEGS | 15 | -3 | 157 |
| -D | GGGESGGGESGGGES | 15 | -3 | 158 |
| -E | GEGESGEGESGEGES | 15 | -6 | 159 |
| -F | GGGESGGEGSGEGGS | 15 | -3 | 160 |
| -G | GEGESGEGESGEGESGEGES | 20 | -8 | 161 |

FIGURE 8B scFv Linkers

GGGGSGGGGSGGGGS            (SEQ ID NO: 162)

GGGGSGGGGSGGGGSGGGGS       (SEQ ID NO: 163)

GSTSGSGKPGSGEGSTKG         (SEQ ID NO: 164)

PRGASKSGSASQTGSAPGS        (SEQ ID NO: 165)

GTAAAGAGAAGGAAAGAAG        (SEQ ID NO: 166)

GTSGSSGSGSGGSGSGGGG        (SEQ ID NO: 167)

GKPGSGKPGSGKPGSGKPGS       (SEQ IS NO: 168)

<u>Useful domain linkers</u>

| | |
|---|---|
| KTHTCPPCP ("half hinge") | SEQ ID NO:210 |
| EPKSSDKTHTCPPCP ("full hinge C220S variant") | SEQ ID NO:211 |
| GGGGSGGGGSKTHTCPPCP ("flex half hinge") | SEQ ID NO:212 |
| GKPGSGKPGSKTHTCPPCP ("charged half hinge1") | SEQ ID NO:213 |
| GKPGSKTHTCPPCP ("charged half hinge2") | SEQ ID NO:214 |

FIGURE 9

| XENP | Heterodimer-skewing variant, Chain 1 | Heterodimer-skewing variant, Chain 2 | Heterodimer Yield (%) | CH3 Tm (°C) |
|---|---|---|---|---|
| 12757 | none | none | 52.7 | 83.1 |
| 12758 | L368D/K370S | S364K | 94.4 | 76.6 |
| 12759 | L368D/K370S | S364K/E357L | 90.2 | 77.2 |
| 12760 | L368D/K370S | S364K/E357Q | 95.2 | 77.5 |
| 12761 | T411E/K360E/Q362E | D401K | 85.6 | 80.6 |
| 12496 | L368E/K370S | S364K | 91.5 | n.d. |
| 12511 | K370S | S364K | 59.9 | n.d. |
| 12840 | L368E/K370S | S364K/E357Q | 59.5 | n.d. |
| 12841 | K370S | S364K/E357Q | 90.4 | n.d. |
| 12894 | L368E/K370S | S364K | 41.0 | n.d. |
| 12895 | K370S | S364K | 49.3 | n.d. |
| 12896 | L368E/K370S | S364K/E357Q | 73.9 | n.d. |
| 12901 | K370S | S364K/E357Q | 87.9 | n.d. |

FIGURE 10A

| VH ID | VL ID | VH Substitutions | VL Substitutions |
|---|---|---|---|
| H1 | L1.4 | | |
| H1.30 | L1.47 | N30S/N100D | Q42K/A43S/L75I/E85D/L95H |
| H1.33 | L1.47 | N30S/N100D/A101D | Q42K/A43S/L75I/E85D/L95H |
| H1.31 | L1.47 | N30S/N35S/N100D | Q42K/A43S/L75I/E85D/L95H |
| H1.32 | L1.47 | N30S/Y52CA/N100D | Q42K/A43S/L75I/E85D/L95H |
| H1.88 | L1.47 | N30S/N100P | Q42K/A43S/L75I/E85D/L95H |
| H1.89 | L1.47 | N30S/N100D/S100AE | Q42K/A43S/L75I/E85D/L95H |
| H1.90 | L1.47 | N30S/N100D/S100AP | Q42K/A43S/L75I/E85D/L95H |
| H1.91 | L1.47 | N30S/Y52CA/N100D | Q42K/A43S/L75I/E85D/L95H |
| H1.92 | L1.47 | N30S/Y58A/N100D | Q42K/A43S/L75I/E85D/L95H |
| H1.93 | L1.47 | N30S/N100E | Q42K/A43S/L75I/E85D/L95H |
| H1.94 | L1.47 | N30S/N100Q | Q42K/A43S/L75I/E85D/L95H |
| H1.96 | L1.47 | N30S/N100D/S100AN | Q42K/A43S/L75I/E85D/L95H |
| H1.97 | L1.47 | N30S/N100D/S100AQ | Q42K/A43S/L75I/E85D/L95H |
| H1.98 | L1.47 | N30S/Y52CA/N100D/A101D | Q42K/A43S/L75I/E85D/L95H |
| H1.99 | L1.47 | N30S/Y58A/N100D/A101D | Q42K/A43S/L75I/E85D/L95H |
| H1.100 | L1.47 | N30S/N100A/A101D | Q42K/A43S/L75I/E85D/L95H |
| H1.101 | L1.47 | N30S/N100Q/A101D | Q42K/A43S/L75I/E85D/L95H |
| H1.102 | L1.47 | N30S/N100D/S100AE/A101D | Q42K/A43S/L75I/E85D/L95H |
| H1.103 | L1.47 | N30S/N100D/S100AN/A101D | Q42K/A43S/L75I/E85D/L95H |
| H1.104 | L1.47 | N30S/N100D/S100AP/A101D | Q42K/A43S/L75I/E85D/L95H |
| H1.105 | L1.47 | N30S/N100D/S100AQ/A101D | Q42K/A43S/L75I/E85D/L95H |

FIGURE 10B

| VH ID | VL ID | VH Substitutions | VL Substitutions |
|---|---|---|---|
| H1.106 | L1.47 | N30S/Y52CA/Y58A/N100D | Q42K/A43S/L75I/E85D/L95H |
| H1.107 | L1.47 | N30S/Y52CA/Y58A/N100A | Q42K/A43S/L75I/E85D/L95H |
| H1.108 | L1.47 | N30S/Y52CA/Y58A/N100Q | Q42K/A43S/L75I/E85D/L95H |
| H1.109 | L1.47 | N30S/Y52CA/Y58A/N100D/A101D | Q42K/A43S/L75I/E85D/L95H |

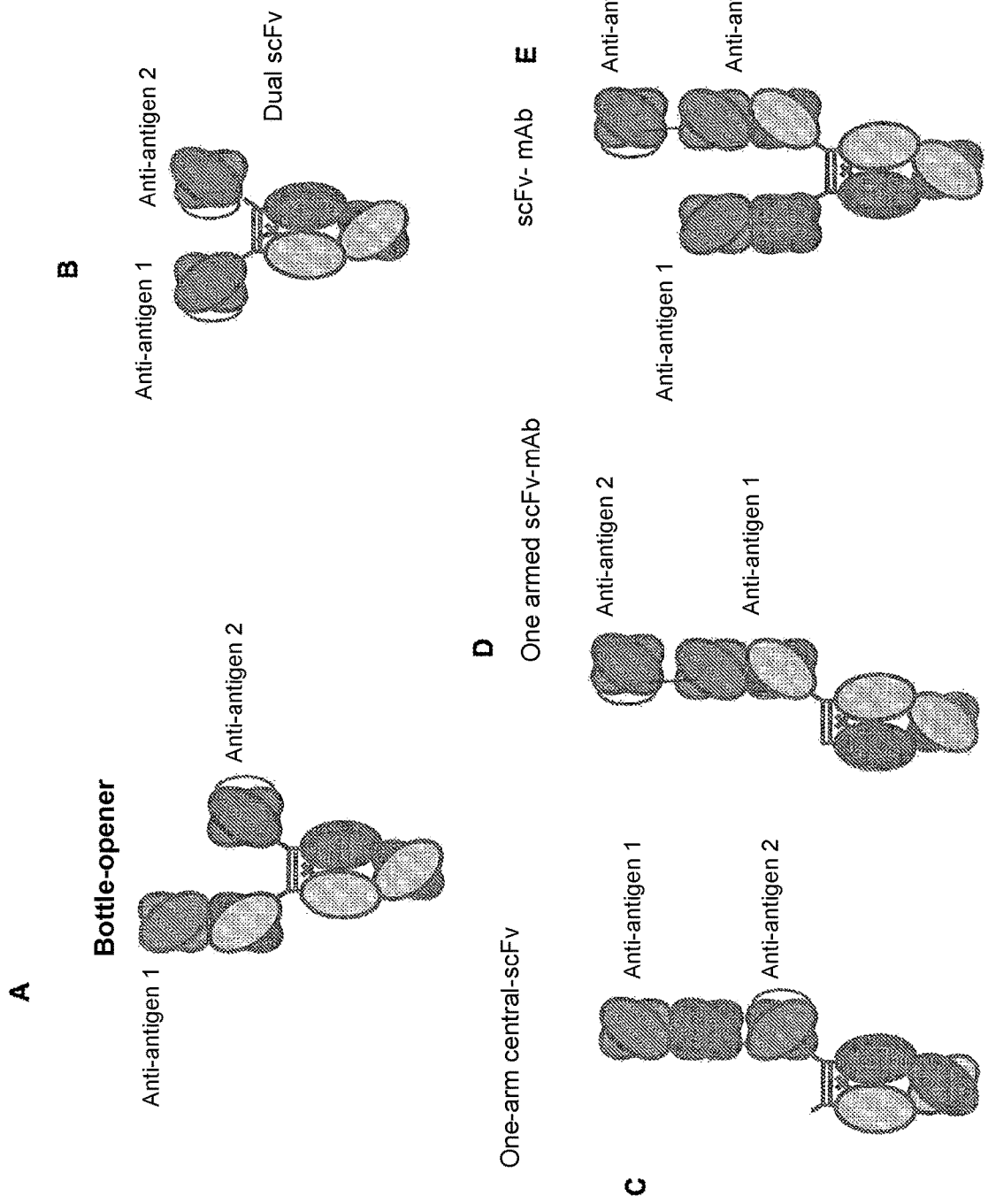
FIGURE 18A-E

FIGURE 18F-I
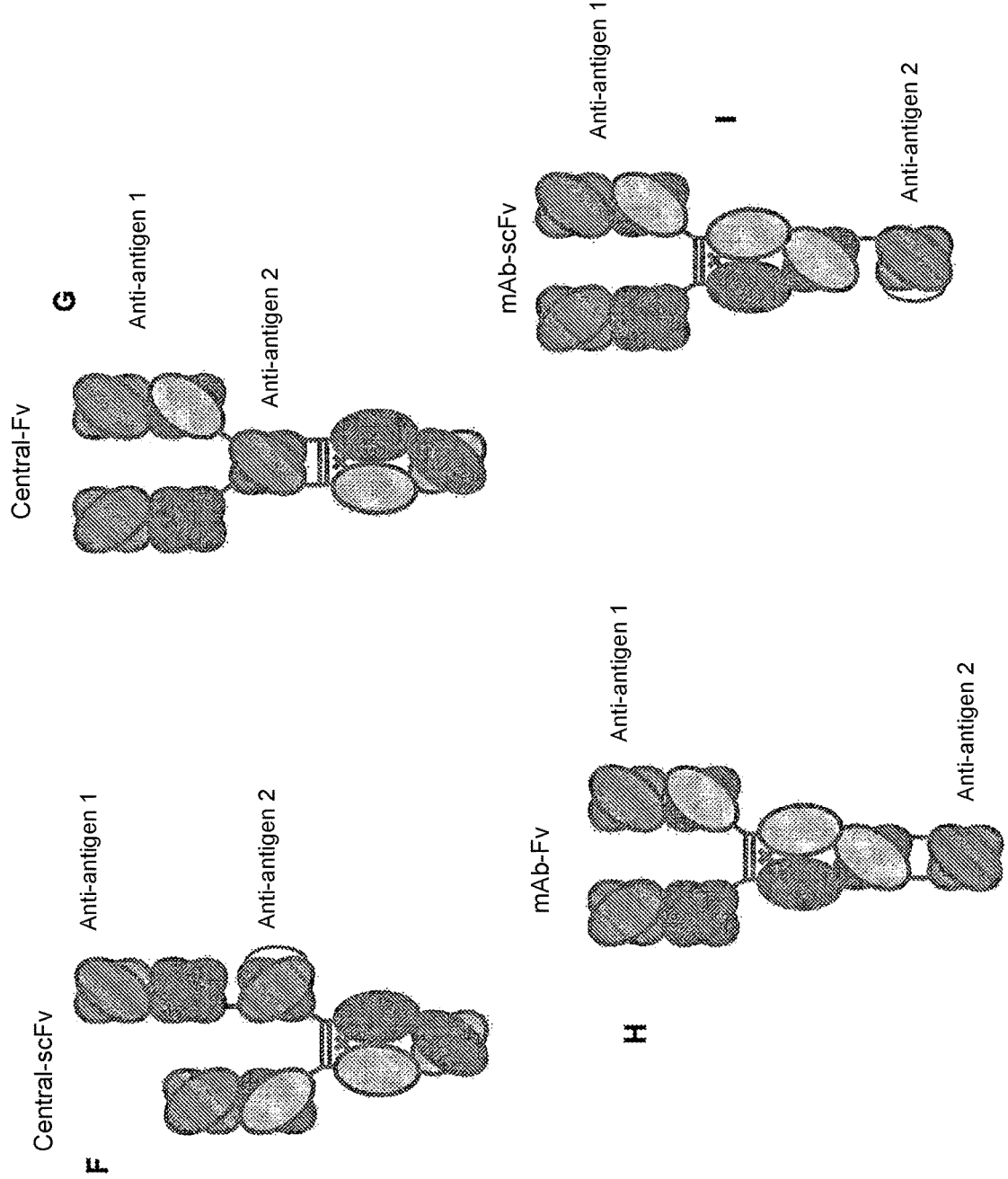

FIGURE 19

| SEQ ID NO: | Description | Sequence |
|---|---|---|
| 1. | CD3 epsilon chain human | MQSGTHWRVLGLCLLSVGVWGQDGNEEMGGITQTPYKVSISGTTVILTCPQYPGSEILWQHNDKNIGGDEDDKNI GSDEDHLSLKEFSELEQSGYYVCYPRGSKPEDANFYLYLRARVCENCMEMDVMSVATIVIVDICITGGLLLLVYYWSK NRKAKAKPVTRGAGAGGRQRGQNKERPPPVPNPDYEPIRKGQRDLYSGLNQRRI |
| 2. | STEAP-1 – human | MESRKDITNQEELWKMKPRRNLEEDDYLHKDTGETSMLKRPVLLHLHQTAHADEFDCPSE LQHTQELFPQWHLPIKIAAIIASLTFLYTLLREVIHPLATSHQQYFYKIPILVINKVLPM VSITLLALVLYLPGVIAAIVQLHNGTKYKKFPHWLDKWMLTRKQFGLLSFFFAVLHAIYSL SYPMRRSYRYKLLNWAYQQVQQNKEDAWIEHDVWRMEIYVSLGIVGLAILALLAVTSIPS VSDSLTWREFHYIQSKLGIVSLLLGTIHALIFAWNKWIDIKQFVWYTPPTFMIAVFLPIV VLIFKSILFLPCLRKKILKIRHGWEDVTKINKTEICSQL |
| 3. | Ab-A HC variable | QVQLQQSGAEMMKPGASVKISCKATGYTFSTYWIEWVKQRPGHGLEWIGEILPGSGNTDFNEKFKGKATFTADTS SDTAYMHLSSLTSEDSAVYYCTRWGYYGTRGYFNVWGAGSTVTVSS |
| 4. | Ab-A HCDR1 | TYWIE |
| 5. | Ab-A HCDR2 | EILPGSGNTDFNEKFKG |
| 6. | Ab-A HCDR3 | WGYYGTRGYFNV |
| 7. | Ab-A LC variable | QIVLTQSPAIMSASPGEKVTITCSASSSVSYMHWFQQKPGTSPKLWIYSTSNLASGVPARFSGSGSGTSYSLTISRME AEDAATYCQQRRSFPYTFGGGTKLEIK |
| 8. | Ab-A LCDR1 | SASSSVSYMH |
| 9. | Ab-A LCDR2 | STSNLAS |
| 10. | Ab-A LCDR3 | QQRRSFPYT |
| 11. | Ab-A1/A2 (N67Q) Xmab²⁺¹ LCDR1 | RASSSVSYMH |

FIGURE 19 Cont.

| | | |
|---|---|---|
| 12. | Ab-A1/A2(N67Q) Xmab²⁺¹ LCDR2 | STSNLAS |
| 13. | Ab-A1/A2 (N67Q) Xmab²⁺¹ LCDR3 | QQRRSFPYT |
| 14. | Ab-A1/A2 (N67Q) Xmab²⁺¹ HCDR1 | TYWIE |
| 15. | Ab-A1 Xmab²⁺¹ HCDR2 | EILPGSGNTDFNEKFQG |
| 16. | Ab-A1/A2 (N67Q) Xmab²⁺¹ HCDR3 | WGYYGTRGYFNV |
| 17. | Ab-A1/A2 (N67Q) Xmab²⁺¹ light chain | MGWSCIILFLVATATGVHSEIVLTQSPATLSLSPGERATLSCRASSSVSYMHWFQQKPGQAPRLLIYSTSNLASGIPAR FSGSGSGTDYTLTISSLEPEDFAVYYCQQRRSFPYTFGQGTKLEIKRTVAAPSVFIFPPSDEQLKSGTASVVCLLNNFYP REAKVQWKVDNALQSGNSQESVTEQDSKDSTYSLSSTLTLSKADYEKHKVYACEVTHQGLSSPVTKSFNRGEC |
| 18. | Ab-A1 Xmab²⁺¹ heavy chain | MGWSCIILFLVATATGVHSQVQLVQSGAEVKKPGASVKVSCKASGYTFSTYWIEWVRQAPGQRLEWMGEILPGSG NTDFNEKFQGRVTFTADTSSDTAYMELSSLRSEDTAVYYCTRWGYYGTRGYFNVWGQGTLVTVSSASTKGPSVFPL APSSKSTSGGTAALGCLVKDYFPEPVTVSWNSGALTSGVHTFPAVLQSSGLYSLSSVVTVPSSSLGTQTYICNVNHKPS DTKVDKKVEPKSCDKTHTCPPCPAPPVAGPSVFLFPPKPKDTLMISRTPEVTCVVVDVKHEDPEVKFNWYVDGVEV HNAKTKPREEEYNSTYRVVSVLTVLHQDWLNGKEYKCKVSNKALPAPIEKTISKAKGQPREPQVYTLPPSREEMTKN QVSLTCDVSGFYPSDIAVEWESDGQPENNYKTTPPVLDSDGSFFLYSKLTVDKSRWEQGDVFSCSVMHEALHNHYT QKSLSLSPGK |
| 19. | Ab-A1 Xmab²⁺¹ XVHMx | MGWSCIILFLVATATGVHSQVQLVQSGAEVKKPGASVKVSCKASGYTFSTYWIEWVRQAPGQRLEWMGEILPGSG NTDFNEKFQGRVTFTADTSSDTAYMELSSLRSEDTAVYYCTRWGYYGTRGYFNVWGQGTLVTVSSASTKGPSVFPL APSSKSTSGGTAALGCLVKDYFPEPVTVSWNSGALTSGVHTFPAVLQSSGLYSLSSVVTVPSSSLGTQTYICNVNHKPS NTKVDKKVEPKSCGGGGSGGGGSGGGGSEVQLVESGGGLVQPGGSLRLSCAASGFTFSTYAMNWVRQAPGKGLEWVGRI RSKYNNYATYADSVKGRFTISRDDSKNTLYLQMNSLRAEDTAVYYCVRHGNFGDSYVSWFAYWGQGTLVTVSSG KPGSGKPGSGKPGSGKPGSQAVVTQEPSLTVSPGGTVTLTCGSSTGAVTTSNYANWVQQKPGKSPRGLIGGTNKR APGVPARFSGSLLGGKAALTISGAQPEDEADYYCALWYSNHWVFGGGTKLTVLGGGSGGGGSKTHTCPPCPAPP VAGPSVFLFPPKPKDTLMISRTPEVTCVVVDVKHEDPEVKFNWYVDGVEVHNAKTKPREEQYNSTYRVVSVLTVLH QDWLNGKEYKCKVSNKALPAPIEKTISKAKGQPREPQVYTLPPSREQMTKNQVKLTCLVKGFYPSDIAVEWESNGQ PENNYKTTPPVLDSDGSFFLYSKLTVDKSRWQQGNVFSCSVMHEALHNHYTQKSLSLPGK |

FIGURE 19 Cont.

| | | |
|---|---|---|
| 20. | Ab-A2 (N67Q) Xmab²⁺¹ XVHMx | MDMRVPAQLLGLLLLWLRGARCQVQLVQSGAEVKKPGASVKVSCKASGYTFSTYWIEWVRQAPGQRLEWMGEIL PGSGQTDFNEKFQGRVTFTADTSSDTAYMELSSLRSEDTAVYYCTRWGYYGTRGYFNVWGQGTLVTVSSASTKGPS VFPLAPSSKSTSGGTAALGCLVKDYFPEPVTVSWNSGALTSGVHTFPAVLQSSGLYSLSSVVTVPSSSLGTQTYICNVN HKPSNTKVDKKVEPKSCGGGGSGGGGSEVQLVESGGGLVQPGGSLRLSCAASGFTFSTYAMNWVRQAPGKGLEW VGRIRSKYNNYATYYADSVKGRFTISRDDSKNTLYLQMNSLRAEDTAVYYCVRHGNFGDSYVSWFAYWGQGTLVTV SSGKPGSGKPGSGKPGSGKPGSGKPGSQAVVTQEPSLTVSPGGTVTLTCGSSTGAVTTSNYANWVQQKPGKSPRGLIGGTN KRAPGVPARFSGSLLGGKAALTISGAQPEDEADYYCALWYSNHWVFGGGTKLTVLGGGGSGGGGSKTHTCPPCPA PPVAGPSVFLFPPKPKDTLMISRTPEVTCVVVDVKHEDPEVKFNWYVDGVEVHNAKTKPCEEQYGSTYRCVSVLTVL HQDWLNGKEYKCKVSNKALPAPIEKTISKAKGQPREPQVYTLPPSREQMTKNQVKLTCLVKGFYPSDIAVEWESNG QPENNYKTTPPVLDSDGSFFLYSKLTVDKSRWQQGNVFSCSVMHEALHNHYTQKSLSLSPGK |
| 21. | Ab-A2 (N67Q) Xmab²⁺¹ HCDR2 (all other CDRs the same as Ab-A1 Xmab²⁺¹) | EILPGSGQTDFNEKFQG |
| 22. | Ab-B1 heavy variable | QIQLVQSGPELKKPGETVKISCKASGYTFTNYGMNWVKQAPGKGLQWMGWMNTYTGEPTYADDFKGRFAFSLET SARTVSLDINDLKNEDTATYFCTRAGGQLRPGAMDYWGQGTSVTVSS |
| 23. | Ab-B1 HCDR1 | NYGMN |
| 24. | Ab-B1 HCDR2 | WMNTYTGEPTYADDFKG |
| 25. | Ab-B1 HCDR3 | AGGQLRPGAMDY |
| 26. | Ab-B1 light variable | DIVLTQSPASLAVSLGQRATISCKASQSVDYDGDSFMNWYQQKPGQPPKLLIYVASNLESGIPDRFSGSGSGTDFTLN IHPVEEEDAATYCQQSNEEPPTFGGGTKLEIK |
| 27. | Ab-B1 LCDR1 | KASQSVDYDGDSFMN |
| 28. | Ab-B1 LCDR2 | VASNLES |
| 29. | Ab-B1 LCDR3 | QQSNEEPPT |
| 30. | Ab-B1 Xmab²⁺¹ | KASQSVDYDGDSFMN |

FIGURE 19 Cont.

| | | |
|---|---|---|
| 31. | Ab-B1 Xmab²⁺¹ LCDR1 LCDR2 | VASNLES |
| 32. | Ab-B1 Xmab²⁺¹ LCDR3 | QQSNEEPPT |
| 33. | Ab-B1 Xmab²⁺¹ HCDR1 | NYGMN |
| 34. | Ab-B1 Xmab²⁺¹ HCDR2 | WMNTYTGEPTYADKFQG |
| 35. | Ab-B1 Xmab²⁺¹ HCDR3 | AGGQLRPGAMDY |
| 36. | Ab-B1 Xmab²⁺¹ Light chain | MGWSCIILFLVATATGVHSDIVLTQTPLSLSVTPGQPASISCKASQSVDYDGDSFMNWYLQKPGQPPQLLIYVASNL ESGVPDRFSGSGSGTDFTLKISRVEAEDVGVYCQQSNEEPPTFGQGTKLEIKRTVAAPSVFIFPPSDEQLKSGTASVV CLLNNFYPREAKVQWKVDNALQSGNSQESVTEQDSKDSTYSLSSTLTLSKADYEKHKVYACEVTHQGLSSPVTKSFN RGEC |
| 37. | Ab-B1 Xmab²⁺¹ Heavy chain | MGWSCIILFLVATATGVHSEIQLVQSGAEVKKPGATVKISCKASGYTFTNYGMNWVQQAPGQGLEWMGWMNTY TGEPTYADKFQGRVTFTLDTSARTVYMELSSLRSEDTAVYFCARAGGQLRPGAMDYWGQGTMVTVSS ASTKGPSVFPLAPSSKSTSGGTAALGCLVKDYFPEPVTVSWNSGALTSGVHTFPAVLQSSGLYSLSSVVTVPSSSLGTQ TYICNVNHKPSDTKVDKKVEPKSCDKTHTCPPCPAPPVAGPSVFLFPPKPKDTLMISRTPEVTCVVVDVKHEDPEVKF NWYVDGVEVHNAKTKPREEEYNSTYRVVSVLTVLHQDWLNGKEYKCKVSNKALPAPIEKTISKAKGQPREPQVYTLP PSREEMTKNQVSLTCDVSGFYPSDIAVEWESDGQPENNYKTTPPVLDSDGSFFLYSKLTVDKSRWEQGDVFSCSVM HEALHNHYTQKSLSLSPGK |
| 38. | Ab-B1 Xmab²⁺¹ XMVHx | MGWSCIILFLVATATGVHSEIQLVQSGAEVKKPGATVKISCKASGYTFTNYGMNWVQQAPGQGLEWMGWMNTY TGEPTYADKFQGRVTFTLDTSARTVYMELSSLRSEDTAVYFCARAGGQLRPGAMDYWGQGTMVTVSSASTKGPSV FPLAPSSKSTSGGTAALGCLVKDYFPEPVTVSWNSGALTSGVHTFPAVLQSSGLYSLSSVVTVPSSSLGTQTYICNVNH KPSNTKVDKKVEPKSCGGGSGGGGSGGGGSEVQLVESGGGLVQPGGSLRLSCAASGFTFSTYAMNWVRQAPGKGLEWV GRIRSKYNNYATYYADSVKGRFTISRDDSKNTLYLQMNSLRAEDTAVYCVRHGNFGDSYVSWFAYWGQGTLVTVS SGKGPGSGKPGSGKPGSGKPGSQAVVTQEPSLTVSPGGTVTLTCGSSTGAVTTSNYANWVQQKPGKSPRGLIGGTN KRAPGVPARFSGSLLGGKAALTISGAQPEDEADYCALWYSNHWVFGGGTKLTVLGGGSGGGGSKTHTCPPCPA PPVAGPSVFLFPPKPKDTLMISRTPEVTCVVVDVKHEDPEVKFNWYVDGVEVHNAKTKPREEQYNSTYRVVSVLTVL HQDWLNGKEYKCKVSNKALPAPIEKTISKAKGQPREPQVYTLPPSREQMTKNQVKLTCLVKGFYPSDIAVEWESNG QPENNYKTTPPVLDSDGSFFLYSKLTVDKSRWQQGNVFSCSVMHEALHNHYTQKSLSLSPGK |
| 39. | Anti-CD3 H1_L1.4 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYCVRHGNFGDSYVSWFAYWGQGTLVTVSSGKPGSGKPGSGKPGSGKPGSQAVV |

FIGURE 19 Cont.

| # | Name | Sequence |
|---|---|---|
| 40. | Anti-CD3 H1_L1.4 | TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 41. | Anti-CD3 H1_L1.4 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDSYVSWFAYWGQGTLVTVSS |
| 42. | Anti-CD3 H1_L1.4 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 43. | Anti-CD3 H1.30_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 44. | Anti-CD3 H1.30_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDSYVSWFAYWGQGTLVTVSS |
| 45. | Anti-CD3 H1.30_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 46. | Anti-CD3 H1.30_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDSYVSWFEDYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 47. | Anti-CD3 H1.33_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDSYVSWFEDYWGQGTLVTVSS |
| 48. | Anti-CD3 H1.33_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 49. | Anti-CD3 H1.33_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDSYVSWFEDYWGQGTLVTVSS |
| 50. | Anti-CD3 H1.33_L1.47 | QAVVTQEPSLTVSPGGTVTLTCGSSTGAVTTSNYANWVQQKPGKSPRGLIGGTNKRAPGVPARFSGSLLGGKAALTI |

FIGURE 19 Cont.

| | | |
|---|---|---|
| 51. | Anti-CD3 H1.31_L147 | EVQLVESGGGLVQPGGSLRLSCAASGFTFSTYAMSWVRQAPGKGLEWVGRIRSKYNNYATYYADSVKGRFTISRDD SKNTLYLQMNSLRAEDTAVYYCVRHGNFGDSYVSWFAYWGQGTLVTVSSGKPGSGKPGSGKPGSQAVVT QEPSLTVSPGGTVTLTCGSSTGAVTTSNYANWVQQKPGKSPRGLIGGTNKRAPGVPARFSGSLLGGKAALTISGAQP EDEADYYCALWYSNHWVFGGGTKLTVLGSHHHHHH |
| 52. | Anti-CD3 H1.31_L147 | EVQLVESGGGLVQPGGSLRLSCAASGFTFSTYAMSWVRQAPGKGLEWVGRIRSKYNNYATYYADSVKGRFTISRDD SKNTLYLQMNSLRAEDTAVYYCVRHGNFGDSYVSWFAYWGQGTLVTVSSGKPGSGKPGSGKPGSQAVVT QEPSLTVSPGGTVTLTCGSSTGAVTTSNYANWVQQKPGKSPRGLIGGTNKRAPGVPARFSGSLLGGKAALTISGAQP EDEADYYCALWYSNHWVFGGGTKLTVL |
| 53. | Anti-CD3 H1.31_L147 | EVQLVESGGGLVQPGGSLRLSCAASGFTFSTYAMSWVRQAPGKGLEWVGRIRSKYNNYATYYADSVKGRFTISRDD SKNTLYLQMNSLRAEDTAVYYCVRHGNFGDSYVSWFAYWGQGTLVTVSS |
| 54. | Anti-CD3 H1.31_L147 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 55. | Anti-CD3 H1.32_L147 | EVQLVESGGGLVQPGGSLRLSCAASGFTFSTYAMNWVRQAPGKGLEWVGRIRSKANNYATYYADSVKGRFTISRD DSKNTLYLQMNSLRAEDTAVYYCVRHGNFGDSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 56. | Anti-CD3 H1.32_L147 | EVQLVESGGGLVQPGGSLRLSCAASGFTFSTYAMNWVRQAPGKGLEWVGRIRSKANNYATYYADSVKGRFTISRD DSKNTLYLQMNSLRAEDTAVYYCVRHGNFGDSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |
| 57. | Anti-CD3 H1.32_L147 | EVQLVESGGGLVQPGGSLRLSCAASGFTFSTYAMNWVRQAPGKGLEWVGRIRSKANNYATYYADSVKGRFTISRD DSKNTLYLQMNSLRAEDTAVYYCVRHGNFGDSYVSWFAYWGQGTLVTVSS |
| 58. | Anti-CD3 H1.32_L147 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 59. | Anti-CD3 H1.88_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGPSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |
| 60. | Anti-CD3 H1.88_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGPSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 61. | Anti-CD3 H1.88_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGPSYVSWFAYWGQGTLVTVSS |

FIGURE 19 Cont.

| 62. | Anti-CD3 H1.88_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
|---|---|---|
| 63. | Anti-CD3 H1.88_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDEYVSWFAYWGQGTLVTVSSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 64. | Anti-CD3 H1.89_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDEYVSWFAYWGQGTLVTVSSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |
| 65. | Anti-CD3 H1.89_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDEYVSWFAYWGQGTLVTVSS |
| 66. | Anti-CD3 H1.89_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 67. | Anti-CD3 H1.89_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDPYVSWFAYWGQGTLVTVSSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 68. | Anti-CD3 H1.90_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDPYVSWFAYWGQGTLVTVSSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |
| 69. | Anti-CD3 H1.90_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDPYVSWFAYWGQGTLVTVSS |
| 70. | Anti-CD3 H1.90_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 71. | Anti-CD3 H1.91_L1.47 | EVQLVESGGGLVQPGGSLRLSCAASGFTFSTYAMNWVRQAPGKGLEWVGRIRSKANNYATYYADSVKGRFTISRD DSKNTLYLQMNSLRAEDTAVYYCVRHGNFGDSYVSWFAYWGQGTLVTVSSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 72. | Anti-CD3 H1.91_L1.47 | EVQLVESGGGLVQPGGSLRLSCAASGFTFSTYAMNWVRQAPGKGLEWVGRIRSKANNYATYYADSVKGRFTISRD DSKNTLYLQMNSLRAEDTAVYYCVRHGNFGDSYVSWFAYWGQGTLVTVSSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |

FIGURE 19 Cont.

| | | |
|---|---|---|
| 73. | Anti-CD3 H1.91_L1.47 | EVQLVESGGGLVQPGGSLRLSCAASGFTFSTYAMNWVRQAPGKGLEWVGRIRSKANNYATYYADSVKGRFTISRD DSKNTLYLQMNSLRAEDTAVYYCVRHGNFGDSYVSWFAYWGQGTLVTVSS |
| 74. | Anti-CD3 H1.91_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 75. | Anti-CD3 H1.92_L1.47 | EVQLVESGGGLVQPGGSLRLSCAASGFTFSTYAMNWVRQAPGKGLEWVGRIRSKYNNYATAYADSVKGRFTISRD DSKNTLYLQMNSLRAEDTAVYYCVRHGNFGDSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 76. | Anti-CD3 H1.92_L1.47 | EVQLVESGGGLVQPGGSLRLSCAASGFTFSTYAMNWVRQAPGKGLEWVGRIRSKYNNYATAYADSVKGRFTISRD DSKNTLYLQMNSLRAEDTAVYYCVRHGNFGDSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |
| 77. | Anti-CD3 H1.92_L1.47 | EVQLVESGGGLVQPGGSLRLSCAASGFTFSTYAMNWVRQAPGKGLEWVGRIRSKYNNYATAYADSVKGRFTISRD DSKNTLYLQMNSLRAEDTAVYYCVRHGNFGDSYVSWFAYWGQGTLVTVSS |
| 78. | Anti-CD3 H1.92_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 79. | Anti-CD3 H1.93_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGESYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 80. | Anti-CD3 H1.93_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGESYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |
| 81. | Anti-CD3 H1.93_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGESYVSWFAYWGQGTLVTVSS |
| 82. | Anti-CD3 H1.93_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 83. | Anti-CD3 H1.94_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGQSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 84. | Anti-CD3 H1.94_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGQSYVSWFAYWGQGTLVTVSSGKPGSGKPGSGKPGSQAVV |

FIGURE 19 Cont.

| | | |
|---|---|---|
| 85. | Anti-CD3 H1.94_L1.47 | TQEPSLTVSPGGTVTLTCGSSTGAVTTSNYANWVQQKPGKSPRGLIIGGTNKRAPGVPARFSGSLLGGKAALTISGAQ PEDEADYYCALWYSNHWVFGGGTKLTVL |
| 86. | Anti-CD3 H1.94_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGQSYVSWFAYWGQGTLVTVSS |
| 87. | Anti-CD3 H1.94_L1.47 | QAVVTQEPSLTVSPGGTVTLTCGSSTGAVTSNYANWVQQKPGKSPRGLIGGTNKRAPGVPARFSGSLLGGKAALTI SGAQPEDEADYYCALWYSNHWVFGGGTKLTVLSHHHHHH |
| 88. | Anti-CD3 H1.96_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDNYVSWFAYWGQGTLVTVSSGKPGSGKPGSGKPGSQAVV TQEPSLTVSPGGTVTLTCGSSTGAVTTSNYANWVQQKPGKSPRGLIIGGTNKRAPGVPARFSGSLLGGKAALTISGAQ PEDEADYYCALWYSNHWVFGGGTKLTVL |
| 89. | Anti-CD3 H1.96_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDNYVSWFAYWGQGTLVTVSS |
| 90. | Anti-CD3 H1.96_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 91. | Anti-CD3 H1.97_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDQYVSWFAYWGQGTLVTVSSGKPGSGKPGSGKPGSQAVV TQEPSLTVSPGGTVTLTCGSSTGAVTTSNYANWVQQKPGKSPRGLIIGGTNKRAPGVPARFSGSLLGGKAALTISGAQ PEDEADYYCALWYSNHWVFGGGTKLTVLGSHHHHHH |
| 92. | Anti-CD3 H1.97_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDQYVSWFAYWGQGTLVTVSSGKPGSGKPGSGKPGSQAVV TQEPSLTVSPGGTVTLTCGSSTGAVTTSNYANWVQQKPGKSPRGLIIGGTNKRAPGVPARFSGSLLGGKAALTISGAQ PEDEADYYCALWYSNHWVFGGGTKLTVL |
| 93. | Anti-CD3 H1.97_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDQYVSWFAYWGQGTLVTVSS |
| 94. | Anti-CD3 H1.97_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 95. | Anti-CD3 H1.98_L1.47 | EVQLVESGGGLVQPGGSLRLSCAASGFTFSTYAMNWVRQAPGKGLEWVGRIRSKANNYATYYADSVKGRFTISRD DSKNTLYLQMNSLRAEDTAVYYCVRHGNFGDSYVSWFDYWGQGTLVTVSSGKPGSGKPGSGKPGSQAVV TQEPSLTVSPGGTVTLTCGSSTGAVTTSNYANWVQQKPGKSPRGLIIGGTNKRAPGVPARFSGSLLGGKAALTISGAQ PEDEADYYCALWYSNHWVFGGGTKLTVLGSHHHHHH |

FIGURE 19 Cont.

| # | Name | Sequence |
|---|---|---|
| 96. | Anti-CD3 H1.98_L1.47 | EVQLVESGGGLVQPGGSLRLSCAASGFTFSTYAMNWVRQAPGKGLEWVGRIRSKANNYATYYADSVKGRFTISRD DSKNTLYLQMNSLRAEDTAVYYCVRHGNFGDSYVSWFDYWGQGTLVTVSSGKPGSGKPGSGKPGSQAVV TQEPSLTVSPGGTVTLTCGSSTGAVTTSNYANWVQQKPGKSPRGLIIGGTNKRAPGVPARFSGSLLGGKAALTISGAQ PEDEADYYCALWYSNHWVFGGGTKLTVL |
| 97. | Anti-CD3 H1.98_L1.47 | EVQLVESGGGLVQPGGSLRLSCAASGFTFSTYAMNWVRQAPGKGLEWVGRIRSKANNYATYYADSVKGRFTISRD DSKNTLYLQMNSLRAEDTAVYYCVRHGNFGDSYVSWFDYWGQGTLVTVSS |
| 98. | Anti-CD3 H1.98_L1.47 | QAVVTQEPSLTVSPGGTVTLTCGSSTGAVTTSNYANWVQQKPGKSPRGLIIGGTNKRAPGVPARFSGSLLGGKAALTI SGAQPEDEADYYCALWYSNHWVFGGGTKLTVL |
| 99. | Anti-CD3 H1.99_L1.47 | EVQLVESGGGLVQPGGSLRLSCAASGFTFSTYAMNWVRQAPGKGLEWVGRIRSKYNNYATAYADSVKGRFTISRD DSKNTLYLQMNSLRAEDTAVYYCVRHGNFGDSYVSWFDYWGQGTLVTVSSGKPGSGKPGSGKPGSQAVV TQEPSLTVSPGGTVTLTCGSSTGAVTTSNYANWVQQKPGKSPRGLIIGGTNKRAPGVPARFSGSLLGGKAALTISGAQ PEDEADYYCALWYSNHWVFGGGTKLTVLGSHHHHHH |
| 100. | Anti-CD3 H1.99_L1.47 | EVQLVESGGGLVQPGGSLRLSCAASGFTFSTYAMNWVRQAPGKGLEWVGRIRSKYNNYATAYADSVKGRFTISRD DSKNTLYLQMNSLRAEDTAVYYCVRHGNFGDSYVSWFDYWGQGTLVTVSSGKPGSGKPGSGKPGSQAVV TQEPSLTVSPGGTVTLTCGSSTGAVTTSNYANWVQQKPGKSPRGLIIGGTNKRAPGVPARFSGSLLGGKAALTISGAQ PEDEADYYCALWYSNHWVFGGGTKLTVL |
| 101. | Anti-CD3 H1.99_L1.47 | EVQLVESGGGLVQPGGSLRLSCAASGFTFSTYAMNWVRQAPGKGLEWVGRIRSKYNNYATAYADSVKGRFTISRD DSKNTLYLQMNSLRAEDTAVYYCVRHGNFGDSYVSWFDYWGQGTLVTVSS |
| 102. | Anti-CD3 H1.99_L1.47 | QAVVTQEPSLTVSPGGTVTLTCGSSTGAVTTSNYANWVQQKPGKSPRGLIIGGTNKRAPGVPARFSGSLLGGKAALTI SGAQPEDEADYYCALWYSNHWVFGGGTKLTVL |
| 103. | Anti-CD3 H1.100_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGASYVSWFDYWGQGTLVTVSSGKPGSGKPGSGKPGSQAVV TQEPSLTVSPGGTVTLTCGSSTGAVTTSNYANWVQQKPGKSPRGLIIGGTNKRAPGVPARFSGSLLGGKAALTISGAQ PEDEADYYCALWYSNHWVFGGGTKLTVLGSHHHHHH |
| 104. | Anti-CD3 H1.100_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGASYVSWFDYWGQGTLVTVSSGKPGSGKPGSGKPGSQAVV TQEPSLTVSPGGTVTLTCGSSTGAVTTSNYANWVQQKPGKSPRGLIIGGTNKRAPGVPARFSGSLLGGKAALTISGAQ PEDEADYYCALWYSNHWVFGGGTKLTVL |
| 105. | Anti-CD3 H1.100_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGASYVSWFDYWGQGTLVTVSS |
| 106. | Anti-CD3 H1.100_L1.47 | QAVVTQEPSLTVSPGGTVTLTCGSSTGAVTTSNYANWVQQKPGKSPRGLIIGGTNKRAPGVPARFSGSLLGGKAALTI SGAQPEDEADYYCALWYSNHWVFGGGTKLTVL |
| 107. | Anti-CD3 H1.101_L1.47 | EVQLVESGGGLVQPGGSLRLSCAASGFTFSTYAVYYCVRHGNFGQSYVSWFDYWGQGTLVTVSSGKPGSGKPGSGKPGSQAVV |

FIGURE 19 Cont.

| | | |
|---|---|---|
| 108. | Anti-CD3 H1.101_L1.47 | TQEPSLTVSPGGTVTLTCGSSTGAVTSNYANWVQQKPGKSPRGLIGGTNKRAPGVPARFSGSLLGGKAALTISGAQ PEDEADYYCALWYSNHWVFGGGTKLTVLGSHHHHHH |
| 109. | Anti-CD3 H1.101_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGQSYVSWFDYWGQGTLVTVSS |
| 110. | Anti-CD3 H1.101_L1.47 | QAVVTQEPSLTVSPGGTVTLTCGSSTGAVTSNYANWVQQKPGKSPRGLIGGTNKRAPGVPARFSGSLLGGKAALTI SGAQPEDEADYYCALWYSNHWVFGGGTKLTVL |
| 111. | Anti-CD3 H1.102_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDEYVSWFDYWGQGTLVTVSSGKPGSGKPGSGKPGSQAVV TQEPSLTVSPGGTVTLTCGSSTGAVTSNYANWVQQKPGKSPRGLIGGTNKRAPGVPARFSGSLLGGKAALTISGAQ PEDEADYYCALWYSNHWVFGGGTKLTVLGSHHHHHH |
| 112. | Anti-CD3 H1.102_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDEYVSWFDYWGQGTLVTVSS |
| 113. | Anti-CD3 H1.102_L1.47 | QAVVTQEPSLTVSPGGTVTLTCGSSTGAVTSNYANWVQQKPGKSPRGLIGGTNKRAPGVPARFSGSLLGGKAALTI SGAQPEDEADYYCALWYSNHWVFGGGTKLTVL |
| 114. | Anti-CD3 H1.103_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDNYVSWFDYWGQGTLVTVSSGKPGSGKPGSGKPGSQAVV TQEPSLTVSPGGTVTLTCGSSTGAVTSNYANWVQQKPGKSPRGLIGGTNKRAPGVPARFSGSLLGGKAALTISGAQ PEDEADYYCALWYSNHWVFGGGTKLTVLGSHHHHHH |
| 115. | Anti-CD3 H1.103_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDNYVSWFDYWGQGTLVTVSS |
| 116. | Anti-CD3 H1.103_L1.47 | QAVVTQEPSLTVSPGGTVTLTCGSSTGAVTSNYANWVQQKPGKSPRGLIGGTNKRAPGVPARFSGSLLGGKAALTI SGAQPEDEADYYCALWYSNHWVFGGGTKLTVL |

FIGURE 19 Cont.

| | | |
|---|---|---|
| 119. | Anti-CD3 H1.104_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDPYVSWFDYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 120. | Anti-CD3 H1.104_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDPYVSWFDYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |
| 121. | Anti-CD3 H1.104_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDPYVSWFDYWGQGTLVTVSS |
| 122. | Anti-CD3 H1.104_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 123. | Anti-CD3 H1.105_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDQYVSWFDYWGQGTLVTVSSGKPGSGKPGSGKPGSQAV VTQEPSLTVSPGGTVTLTCGSSTGAVTTSNYANWVQQKPGKSPRGLIGGTNKRAPGVPARFSGSLLGGKAALTISGA QPEDEADYYCALWYSNHWVFGGGTKLTVLGSHHHHHH |
| 124. | Anti-CD3 H1.105_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDQYVSWFDYWGQGTLVTVSSGKPGSGKPGSGKPGSQAV VTQEPSLTVSPGGTVTLTCGSSTGAVTTSNYANWVQQKPGKSPRGLIGGTNKRAPGVPARFSGSLLGGKAALTISGA QPEDEADYYCALWYSNHWVFGGGTKLTVL |
| 125. | Anti-CD3 H1.105_L1.47 | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDQYVSWFDYWGQGTLVTVSS |
| 126. | Anti-CD3 H1.105_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 127. | Anti-CD3 H1.106_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGDSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 128. | Anti-CD3 H1.106_L1.47 (ScFv) | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGDSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |
| 129. | Anti-CD3 H1.106_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGDSYVSWFAYWGQGTLVTVSS |

FIGURE 19 Cont.

| | | |
|---|---|---|
| 130. | Anti-CD3 H1.106_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 131. | Anti-CD3 H1.107_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGASYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 132. | Anti-CD3 H1.107_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGASYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |
| 133. | Anti-CD3 H1.107_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGASYVSWFAYWGQGTLVTVSS |
| 134. | Anti-CD3 H1.107_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 135. | Anti-CD3 H1.108_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGQSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 136. | Anti-CD3 H1.108_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGQSYVSWFAYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |
| 137. | Anti-CD3 H1.108_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGQSYVSWFAYWGQGTLVTVSS |
| 138. | Anti-CD3 H1.108_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 139. | Anti-CD3 H1.109_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGDSYVSWFDYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVLGSHHHHHH |
| 140. | Anti-CD3 H1.109_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGDSYVSWFDYWGQGTLVTVSSGKPGSGKPGSGKPGSQAVV TQEPSLTVSPGGTVTLTCGSSTGAVTTSNYANWVQQKPGKSPRGLIGGTNKRAPGVPARFSGSLLGGKAALTISGAQ PEDEADYYCALWYSNHWVFGGGTKLTVL |

FIGURE 19 Cont.

| # | Name | Sequence |
|---|---|---|
| 141. | Anti-CD3 H1.109_L1.47 | EVQLVESGGGLVQPGGSLRLSCAASGFTFSTYAMNWVRQAPGKGLEWVGRIRSKANNYATAYADSVKGRFTISRD DSKNTLYLQMNSLRAEDTAVYYCVRHGNFGDSYVSWFDYWGQGTLVTVSS |
| 142. | Anti-CD3 H1.109_L1.47 | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 143. | Linker | GGGGSGGGGSGGGGS |
| 144. | Whitlow linker | GSTSGSGKPGSGEGSTKG |
| 145. | Linker | IRPRAIGGSKPRVA |
| 146. | Linker | GKGGSGKGGSGKGGS |
| 147. | Linker | GGKGSGKGSGGKGS |
| 148. | Linker | GGGKSGGGKSGGGKS |
| 149. | Linker | GKGKSGKGKSGKGKS |
| 150. | Linker | GGGKSGGKGSGKGGS |
| 151. | Linker | GKPGSGKPGSGKPGS |
| 152. | Linker | GKPGSGKPGSGKPGSGKPGS |
| 153. | Linker | GKGKSGKGKSGKGKSGKGKS |
| 154. | Linker | GGGGSGGGGSGGGGSGGGGS |
| 155. | Linker | STAGDTHLGGEDFD |
| 156. | Linker | GEGGSGEGGSGEGGS |
| 157. | Linker | GGEGSGGEGSGGEGS |
| 158. | Linker | GGGESGGGESGGGES |
| 159. | Linker | GEGESGEGESGEGES |
| 160. | Linker | GGGESGGEGSGEGGS |
| 161. | Linker | GEGESGEGESGEGESGEGES |
| 162. | Linker | GGGGSGGGGSGGGGS |
| 163. | Linker | GGGGSGGGGSGGGGSGGGGS |
| 164. | Linker | GSTSGSGKPGSGEGSTKG |
| 165. | Linker | PRGASKSGSASQTGSAPGS |
| 166. | Linker | GTAAAGAGAAGGAAAGAAG |
| 167. | Linker | GTSGSSGSGSGSGGGG |
| 168. | Linker | GKPGSGKPGSGKPGSGKPGS |
| 169. | Ab-A1 XmAb²⁺¹, Ab-A2 (N67Q) XmAb²⁺¹, Ab-B1 XmAb²⁺¹ | EVQLVESGGGLVQPGGSLRLSCAASGFTFSTYAMNWVRQAPGKGLEWVGRIRSKYNNYATYYADSVKGRFTISRD DSKNTLYLQMNSLRAEDTAVYYCVRHGNFGDSYVSWFAYWGQGTLVTVSS |

FIGURE 19 Cont.

| | Anti-CD3, heavy variable | |
|---|---|---|
| 170. | Ab-A1 XmAb²⁺¹, Ab-A2 (N67Q) XmAb²⁺¹, Ab-B1 XmAb²⁺¹ Anti-CD3, HCDR1 | TYAMN |
| 171. | Ab-A1 XmAb²⁺¹, Ab-A2 (N67Q) XmAb²⁺¹, Ab-B1 XmAb²⁺¹ Anti-CD3, HCDR2 | RIRSKYNNYATYYADSVKG |
| 172. | Ab-A1 XmAb²⁺¹, Ab-A2 (N67Q) XmAb²⁺¹, Ab-B1 XmAb²⁺¹ Anti-CD3, HCDR3 | HGNFGDSYVSWFAY |
| 173. | Ab-A1 XmAb²⁺, Ab-A2 (N67Q) XmAb²⁺¹, Ab-B1 XmAb²⁺¹ Anti-CD3, light variable | QAVVTQEPSLTVSPGGTVTLTCGSSTGAVTTSNYANWVQQKPGKSPRGLIGGTNKRAPGVPARFSGSLLGGKAALTI SGAQPEDEADYYCALWYSNHWVFGGGTKLTVL |
| 174. | Ab-A1 XmAb²⁺¹, Ab-A2 (N67Q) XmAb²⁺¹, Ab-B1 XmAb²⁺¹ Anti-CD3, LCDR1 | GSSTGAVTTSNYAN |
| 175. | Ab-A1 XmAb²⁺¹, Ab-A2 (N67Q) XmAb²⁺¹, Ab-B1 XmAb²⁺¹ Anti-CD3, LCDR2 | GTNKRAP |
| 176. | Ab-A1 XmAb²⁺¹, Ab-A2 (N67Q) XmAb²⁺¹, Ab-B1 XmAb²⁺¹ Anti-CD3, LCDR3 | ALWYSNHWV |
| 177. | STEAP2 - human | MESISMMGSPKSLSETFLPNGINGIKDARKVTVGVIGSGDFAKSLTIRLIRCGYHVVIGS RNPKFASEFFPHVVDVTHHEDALTKTNIIFVAIHREHYTSLWDLRHLLVGKILIDVSNNM RINQYPESNAEYLASLFPDSLIVKGFNVVSAWALQLGPKDASRQVYICSNNIQARQQVIE |

FIGURE 19 Cont.

| | | |
|---|---|---|
| | | LARQLNFIPIDLGSLSSAREIENLPLRLFTLWRGPVVAISLATFFFLYSFVRDVIHPYA RNQQSDFYKIPIEIVNKTLPIVAITLLSLVYLAGLLAAAYQLYYGTKYRRFPPWLETWLQ CRKQLGLLSFFFAMVHVAYSLCLPMRRSERYLFLNMAYQQVHANIENSWNEEEVWRIEMY ISFGIMSLGLLSLLAVTSIPSVSNALNWREFSFIQSTLGYVALLISTFHVLIYGWKRAFE EEYYRFYTPPNFVLALVLPSIVILGKIILFLPCISRKLKRIKKGWEKSQFLEEGMGGTIP HVSPERVTVM |
| 178. | Linker | GSGGS |
| 179. | Linker | GGGGS |
| 180. | Linker | GGGS |
| 181. | Linker | GFLG |
| 182. | Ab-A1 Xmab²⁺¹ heavy variable | QVQLVQSGAEVKKPGASVKVSCKASGYTFSTYWIEWVRQAPGQRLEWMGEILPGSGNTDFNEKFQGRVTFTADTS SDTAYMELSSLRSEDTAVVYCTRWGYYGTRGYFNVWGQGTLVTVSS |
| 183. | Ab-A1/A2(N67Q) Xmab²⁺¹ light variable | EIVLTQSPATLSLSPGERATLSCRASSSVSYMHWFQQKPGQAPRLLIYSTSNLASGIPARFSGSGSGTDYTLTISSLEPE DFAVYYCQQRRSFPYTFGQGTKLEIK |
| 184. | Ab-A2 (N67Q) Xmab²⁺¹ heavy variable | QVQLVQSGAEVKKPGASVKVSCKASGYTFSTYWIEWVRQAPGQRLEWMGEILPGSGQTDFNEKFQGRVTFTADTS SDTAYMELSSLRSEDTAVVYCTRWGYYGTRGYFNVWGQGTLVTVSS |
| 185. | Ab-B1 Xmab²⁺¹ heavy variable | EIQLVQSGAEVKKPGATVKISCKASGYTFTNYGMNWVQQAPGQGLEWMGWMNTYTGEPTYADKFQGRVTFTLD TSARTVYMELSSLRSEDTAVVFCARAGGQLRPGAMDYWGQGTMVTVSS |
| 186. | Ab-B1 Xmab²⁺¹ light variable | DIVLTQTPLSLSVTPGQPASISCKASQSVDYDGDSFMNWYLQKPGQPPQLLIYVASNLESGVPDRFSGSGSGTDFTLK ISRVEAEDVGVYYCQQSNEEPPTFGQGTKLEIK |
| 187. | human PD-1 | PGWFLDSPDRPWNPPTFSPALLVVTEGDNATFTCSFSNTSESFVLNWYRMSPSNQTDKLAAFPEDRSQPGQDCRF RVTQLPNGRDFHMSVVRARRNDSGTYLCGAISLAPKAQIKESLRAELRVTERRAEVPTAHPSPSPRPAGQFQTLVVG VVGGLLGSLVLLVWLLAVICSRAARGTIGARRTGQPLKEDPSAVPVFSVDYGELDFQWREKTPEPPVPCVPEQTEYA TIVFPSGMGTSSPARRGSADGPRSAQPLRPEDGHCSWPL |
| 188. | cynomologous PD-1 | MQIPQAPWPVVWAVLQLGWRPGWFLESPDRPWNAPTFSPALLLVTEGDNATFTCSFSNASESFVLNWYRMSPS NQTDKLAAFPEDRSQPGQDCRFRVTRLPNGRDFHMSVVRARRNDSGTYLCGAISLAPKAQIKESLRAELRVTERRAE VPTAHPSPSPRPAGQFOALVVGVVGGLLGSLVLLVWVLAVICSRAAQGTIEARRTGOPLKEDPSAVPVFSVDYGELD FQWREKTPEPPAPCVPEQTEYATIVFPSGLGTSSPARRGSADGPRSPRPLRPEDGHCSWPL |
| 189. | Anti-PD-1 antibody HC | SYDMS |

FIGURE 19 Cont.

| | | CDR1 | |
|---|---|---|---|
| 190. | Anti-PD-1 antibody HC CDR2 | LISGGGSQTYYAESVK | |
| 191. | Anti-PD-1 antibody HC CDR3 | PSGHYFYAMDV | |
| 192. | Anti-PD-1 antibody LC CDR1 | RASQGISNWLA | |
| 193. | Anti-PD-1 antibody LC CDR2 | AASSLQS | |
| 194. | Anti-PD-1 antibody LC CDR3 | QQAESFPHT | |
| 195. | Anti-PD-1 antibody HC VARIABLE | EVQLLESGGGLVQPGGSLRLSCAASGFTFSSYDMSWVRQAPGKGLEWVSLISGGGSQTYYAESVKGRFTISRDNSK NTLYLQMNSLRAEDTAVYFCASPSGHYFYAMDVWGQGTTVTVSS | |
| 196. | Anti-PD-1 antibody LC VARIABLE | DIQMTQSPSSVSASVGDRVTITCRASQGISNWLAWYQQKPGKAPKLLIFAASSLQSGVPSRFSGSGSGTDFTLTISSL QPEDFATYYCQQAESFPHTFGGGTKVEIK | |
| 197. | Anti-PD-1 antibody HC FULL LENGTH | MDMRVPAQLLGLLLLWLRGARCEVQLLESGGGLVQPGGSLRLSCAASGFTFSSYDMSWVRQAPGKGLEWVSLISG GGSQTYYAESVKGRFTISRDNSKNTLYLQMNSLRAEDTAVYFCASPSGHYFYAMDVWGQGTTVTVSSASTKGPSVF PLAPSSKSTSGGTAALGCLVKDYFPEPVTVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRTPEVTCVVVDVSHEDPEVKFNWYVDGV EVHNAKTKPCEEQYGSTYRCVSVLTVLHQDWLNGKEYKCKVSNKALPAPIEKTISKAKGQPREPQVYTLPPSREEMT KNQVSLTCLVKGFYPSDIAVEWESNGQPENNYKTTPPVLDSDGSFFLYSKLTVDKSRWQQGNVFSCSVMHEALHN HYTQKSLSLSPGK | |
| 198. | Anti-PD-1 antibody LC | MDMRVPAQLLGLLLLWLRGARCDIQMTQSPSSVSASVGDRVTITCRASQGISNWLAWYQQKPGKAPKLLIFAASSL QSGVPSRFSGSGSGTDFTLTISSLQPEDFATYYCQQAESFPHTFGGGTKVEIKRTVAAPSVFIFPPSDEQLKSGTASVV | |

FIGURE 19 Cont.

| | | FULL LENGTH | |
|---|---|---|---|
| 199. | Ab-A2 (N67Q) Xmab 2+1 heavy chain | CLLNNFYPREAKVQWKVDNALQSGNSQESVTEQDSKDSTYSLSSTLTLSKADYEKHKVYACEVTHQGLSSPVTKSFNRGEC | |
| | | MDMRVPAQLLGLLLLWLRGARCQVQLVQSGAEVKKPGASVKVSCKASGYTFSTYWIEWVRQAPGQRLEWMGEILPGSGQTDFNEKFQGRVTFTADTSSDIAYMELSSLRSEDTAVYYCTRWGYYGTRGYFNVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTPEVTCVVVDVKHEDPEVKFNWYVDGVEVHNAKTKPCEEEYGSTYRCVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK | |
| 200. | Ab-A1/A2 (N67Q) Xmab[2+1] light chain minus signal sequence | EIVLTQSPATLSLSPGERATLSCRASSSVSYMHWFQQKPGQAPRLLIYSTNLASGIPARFSGSGSGTDYTLTISSLEPEDFAVYYCQQRRSFPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | |
| 201. | Ab-A1 Xmab[2+1] heavy chain minus the signal sequence | QVQLVQSGAEVKKPGASVKVSCKASGYTFSTYWIEWVRQAPGQRLEWMGEILPGSGNTDFNEKFQGRVTFTADTSSDTAYMELSSLRSEDTAVYYCTRWGYYGTRGYFNVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSDTKVDKKVEPKSCDKTHTCPPCPAPPVAGPSVFLFPPKPKDTLMISRTPEVTCVVVDVKHEDPEVKFNWYVDGVEVHNAKTKPREEEYNSTYRVVSVLTVLHQDWLNGKEYKCKVSNKALPAPIEKTISKAKGQPREPQVYTLPPSREEMTKNQVSLTCDVSGFYPSDIAVEWESDGQPENNYKTTPPVLDSDGSFFLYSKLTVDKSRWEQGDVFSCSVMHEALHNHYTQKSLSLSPGK | |
| 202. | Ab-A1 Xmab[2+1] XVHMx minus the signal sequence | QVQLVQSGAEVKKPGASVKVSCKASGYTFSTYWIEWVRQAPGQRLEWMGEILPGSGNTDFNEKFQGRVTFTADTSSDTAYMELSSLRSEDTAVYYCTRWGYYGTRGYFNVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGGSGGGGSEVQLVESGGGLVQPGGSLRLSCAASGFTFSTYAMNWVRQAPGKGLEWVGRIRSKYNNYATYYADSVKGRFTISRDDSKNTLYLQMNSLRAEDTAVYYCVRHGNFGDSYVSWFAYWGQGTLVTVSSGKPGSGKPGSGKPGSGKPGSQAVVTQEPSLTVSPGGTVTLTCGSSTGAVTTSNYANWVQQKPGKSPRGLIGGTNKRAPGVPARFSGSLLGGKAALTISGAQPEDEADYYCALWYSNHWVFGGGTKLTVLGGGGSGGGGSKTHTCPPCPAPPVAGPSVFLFPPKPKDTLMIS | |

FIGURE 19 Cont.

| | | |
|---|---|---|
| | | RTPEVTCVVVDKHEDPEVKFNWYVDGVEVHNAKTKPREEQYNSTYRVVSVLTVLHQDWLNGKEYKCKVSNKALP APIEKTISKAKGQPREPQVYTLPPSREQMTKNQVKLTCLVKGFYPSDIAVEWESNGQPENNYKTTPPVLDSDGSFFLY SKLTVDKSRWQQGNVFSCSVMHEALHNHYTQKSLSLSPGK |
| 203. | Ab-A2 (N67Q) Xmab 2+1<br><br>heavy chain minus signal sequence | QVQLVQSGAEVKKPGASVKVSCKASGYTFSTYWIEWVRQAPGQRLEWMGEILPGSGQTDFNEKFQGRVTFTADTS SDTAYMELSSLRSEDTAVYYCTRWGYYGTRGYFNVWGQGTLVTVSSASTKGPSVFPLAPSSKSTSGGTAALGCLVKD YFPEPVTVSWNSGALTSGVHTFPAVLQSSGLYSLSSVVTVPSSSLGTQTYICNVNHKPSDTKVDKKVEPKSCDKTHTC PPCPAPPVAGPSVFLFPPKPKDTLMISRTPEVTCVVVDVKHEDPEVKFNWYVDGVEVHNAKTKPCEEEYGSTYRCVS VLTVLHQDWLNGKEYKCKVSNKALPAPIEKTISKAKGQPREPQVYTLPPSREEMTKNQVSLTCDVSGFYPSDIAVEW ESDGQPENNYKTTPPVLDSDGSFFLYSKLTVDKSRWEQGDVFSCSVMHEALHNHYTQKSLSLSPGK |
| 204. | Ab-B1 Xmab2+1<br><br>light chain minus signal sequence | DIVLTQTPLSLSVTPGQPASISCKASQSVDYDGDSFMNWYLQKPGQPPQLLIYVASNLESGVPDRFSGSGSGTDFTLK ISRVEAEDVGVYYCQQSNEEPPTFGQGTKLEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSPVTKSFNRGEC |
| 205. | Ab-B1 Xmab2+1<br><br>heavy chain minus signal sequence | QLVQSGAEVKKPGATVKISCKASGYTFTNYGMNWVQQAPGQGLEWMGWMNTYTGEPTYADKFQGRVTFTLDT SARTVYMELSSLRSEDTAVVFCARAGGQLRPGAMDYWGQGTMVTVSSASTKGPSVFPLAPSSKSTSGGTAALGCLV KDYFPEPVTVSWNSGALTSGVHTFPAVLQSSGLYSLSSVVTVPSSSLGTQTYICNVNHKPSDTKVDKKVEPKSCDKTH TCPPCPAPPVAGPSVFLFPPKPKDTLMISRTPEVTCVVVDVKHEDPEVKFNWYVDGVEVHNAKTKPREEEYNSTYRV VSVLTVLHQDWLNGKEYKCKVSNKALPAPIEKTISKAKGQPREPQVYTLPPSREEMTKNQVSLTCDVSGFYPSDIAVE WESDGQPENNYKTTPPVLDSDGSFFLYSKLTVDKSRWEQGDVFSCSVMHEALHNHYTQKSLSLSPGK |
| 206. | Ab-B1 Xmab2+1 XMVHx<br><br>minus signal sequence | QLVQSGAEVKKPGATVKISCKASGYTFTNYGMNWVQQAPGQGLEWMGWMNTYTGEPTYADKFQGRVTFTLDT SARTVYMELSSLRSEDTAVVFCARAGGQLRPGAMDYWGQGTMVTVSSASTKGPSVFPLAPSSKSTSGGTAALGCLV KDYFPEPVTVSWNSGALTSGVHTFPAVLQSSGLYSLSSVVTVPSSSLGTQTYICNVNHKPSNTKVDKKVEPKSCGGG GSGGGGSEVQLVESGGGLVQPGGSLRLSCAASGFTFSTYAMNWVRQAPGKGLEWVGRIRSKYNNYATYYADSVK GRFTISRDDSKNTLYLQMNSLRAEDTAVYYCVRHGNFGDSYVSWFAYWGQGTLVTVSSGKPGSGKPGSGKPGSGK PGSQAVVTQEPSLTVSPGGTVTLTCGSSTGAVTTSNYANWVQQKPGKSPRGLIGGTNKRAPGVPARFSGSLLGGKA ALTISGAQPEDEADYYCALWYSNHWVFGGGTKLTVLGGGSGGGGSKTHTCPPCPAPPVAGPSVFLFPPKPKDTL MISRTPEVTCVVVDVKHEDPEVKFNWYVDGVEVHNAKTKPREEQYNSTYRVVSVLTVLHQDWLNGKEYKCKVSNK ALPAPIEKTISKAKGQPREPQVYTLPPSREQMTKNQVKLTCLVKGFYPSDIAVEWESNGQPENNYKTTPPVLDSDGSF FLYSKLTVDKSRWQQGNVFSCSVMHEALHNHYTQKSLSLSPGK |
| 207. | Ab-A2 (N67Q) Xmab2+1 XVHMx | QVQLVQSGAEVKKPGASVKVSCKASGYTFSTYWIEWVRQAPGQRLEWMGEILPGSGQTDFNEKFQGRVTFTADTS SDTAYMELSSLRSEDTAVYYCTRWGYYGTRGYFNVWGQGTLVTVSSASTKGPSVFPLAPSSKSTSGGTAALGCLVKD |

FIGURE 19 Cont.

| | | |
|---|---|---|
| | minus signal sequence | YFPEPVTVSWNSGALTSGVHTFPAVLQSSGLYSLSSVVTVPSSSLGTQTYICNVNHKPSNTKVDKKVEPKSCGGGGS GGGGSEVQLVESGGGLVQPGGSLRLSCAASGFTFSTYAMNWVRQAPGKGLEWVGRIRSKYNNYATYYADSVKGR FTISRDDSKNTLYLQMNSLRAEDTAVYYCVRHGNFGDSYVSWFAYWGQGTLVTVSSGKPGSGKPGSGKPGSGKPG SQAVVTQEPSLTVSPGGTVTLTCGSSTGAVTTSNYANWVQQKPGKSPRGLIGGTNKRAPGVPARFSGSLLGKAAL TISGAQPEDEADYYCALWYSNHWVFGGGTKLTVLGGGSGGGGSKTHTCPPCPAPPVAGPSVFLFPPKPKDTLMIS RTPEVTCVVVDVKHEDPEVKFNWYVDGVEVHNAKTKPCEEQYGSTYRCVSVLTVLHQDWLNGKEYKCKVSNKALP APIEKTISKAKGQPREPQVYTLPPSREQMTKNQVKLTCLVLKGFYPSDIAVEWESNGQPENNYKTTPPVLDSDGSFFLY SKLTVDKSRWQQGNVFSCSVMHEALHNHYTQKSLSLSPGK |
| 208. | Anti-PD-1 antibody HC FULL LENGTH minus signal sequence | EVQLLESGGGLVQPGGSLRLSCAASGFTFSSYDMSWVRQAPGKGLEWVSLISGGGSQTYYAESVKGRFTISRDNSK NTLYLQMNSLRAEDTAVYFCASPSGHYFYAMDVWGQGTTVTVSSASTKGPSVFPLAPSSKSTSGGTAALGCLVKDY FPEPVTVSWNSGALTSGVHTFPAVLQSSGLYSLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKFNWYVDGVEVHNAKTKPCEEQYGSTYRCVS VLTVLHQDWLNGKEYKCKVSNKALPAPIEKTISKAKGQPREPQVYTLPPSREEMTKNQVSLTCLVKGFYPSDIAVEW ESNGQPENNYKTTPPVLDSDGSFFLYSKLTVDKSRWQQGNVFSCSVMHEALHNHYTQKSLSLSPGK |
| 209. | Anti-PD-1 antibody LC FULL LENGTH minus signal sequence | DIQMTQSPSSVSASVGDRVTITCRASQGISNWLAWYQQKPGKAPKLLIFAASSLQSGVPSRFSGSGSGTDFTLTISSL QPEDFATYYCCQQAESFPHTFGGGTKVEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFNRGEC |

FIGURE 23. Mean and Median SK-N-MC Human Neuroblastoma Tumor Volumes in Female NOD/SCID Mice

| Dose Group | Parameter | Tumor Volume [mm$^3$] | | | | | | | | | |
|---|---|---|---|---|---|---|---|---|---|---|---|
| | | Day 5 | Day 8 | Day 11 | Day 13 | Day 15 | Day 18 | Day 20 | Day 22 | Day 25 | Day 28 |
| 1 Vehicle w/o T cells | Mean | 81.42 | 115.24 | 198.79 | 212.62 | 282.70 | 373.05 | 578.73 | 698.38 | 827.31 | 985.94 |
| | Median | 90.28 | 122.85 | 203.63 | 229.86 | 286.81 | 323.09 | 563.09 | 598.48 | 673.42 | 885.10 |
| | SEM | 9.84 | 10.43 | 15.69 | 18.48 | 12.75 | 48.70 | 117.46 | 104.52 | 106.45 | 108.87 |
| | Animals [N] | 5 | 5 | 5 | 5 | 5 | 5 | 5 | 5 | 5 | 5 |
| | Significance | n.p. | n.p. | n.s. | n.s. | n.s. | n.s. | n.s. | n.s. | n.s. | n.s. |
| 2 Vehicle | Mean | 81.70 | 115.59 | 192.91 | 227.63 | 260.98 | 360.22 | 456.04 | 557.15 | 746.68 | 1013.67 |
| | Median | 80.44 | 118.24 | 196.61 | 225.01 | 253.27 | 348.93 | 468.93 | 590.08 | 837.07 | 955.14 |
| | SEM | 3.26 | 5.84 | 5.65 | 8.43 | 8.27 | 22.88 | 31.99 | 49.93 | 73.79 | 82.53 |
| | Animals [N] | 10 | 10 | 10 | 10 | 10 | 10 | 10 | 10 | 10 | 10 |
| 3 Ab-A2 XmAb2+1 (1.0 mg/kg) | Mean | 90.20 | 116.48 | 194.16 | 210.85 | 174.59 | 98.67 | 89.06 | 69.26 | 76.53 | 114.65 |
| | Median | 87.90 | 115.14 | 197.87 | 206.94 | 166.09 | 78.41 | 59.90 | 33.53 | 27.07 | 29.77 |
| | SEM | 6.06 | 6.83 | 5.86 | 10.05 | 12.61 | 24.54 | 30.99 | 34.20 | 49.48 | 85.58 |
| | Animals [N] | 10 | 10 | 10 | 10 | 10 | 10 | 10 | 10 | 10 | 10 |
| | Significance | n.p. | n.p. | n.s. | n.s. | *** | *** | *** | *** | *** | *** |
| 4 Ab-A2 XmAb2+1 (0.1 mg/kg) | Mean | 92.85 | 120.80 | 192.45 | 196.10 | 152.32 | 94.10 | 80.21 | 52.33 | 96.21 | 214.04 |
| | Median | 92.42 | 117.60 | 197.59 | 198.67 | 144.59 | 88.07 | 76.73 | 41.56 | 55.86 | 106.87 |
| | SEM | 4.26 | 7.36 | 5.14 | 12.56 | 14.21 | 9.02 | 10.31 | 12.89 | 40.62 | 73.43 |
| | Animals [N] | 10 | 10 | 10 | 10 | 10 | 10 | 10 | 10 | 10 | 10 |
| | Significance | n.p. | n.p. | n.s. | n.s. | *** | *** | *** | *** | *** | *** |
| 5 Ab-A2 XmAb2+1 (0.01 mg/kg) | Mean | 88.12 | 120.82 | 196.68 | 230.31 | 168.00 | 145.00 | 122.92 | 183.51 | 484.07 | 832.45 |
| | Median | 90.29 | 119.04 | 200.97 | 217.31 | 150.74 | 121.75 | 115.60 | 202.07 | 431.89 | 867.08 |
| | SEM | 5.07 | 7.38 | 5.23 | 15.01 | 13.55 | 14.25 | 14.81 | 29.98 | 69.24 | 109.11 |
| | Animals [N] | 10 | 10 | 10 | 10 | 10 | 10 | 10 | 10 | 10 | 10 |
| | Significance | n.p. | n.p. | n.s. | n.s. | *** | *** | *** | *** | * | n.s. |

One-way ANOVA and assessment of experimental results for tumor growth by Dunnett's post-test in comparison to group 2; significant: * = $p < 0.05$;  = $p < 0.01$; * = $p < 0.001$. Statistical analysis from day 11 (one day before treatment start) until day 28.
N = number of animals; n.p. = not performed; n.s. = not significant; SEM = standard error of the mean; w/o = without.

ANTI-STEAP1 ANTIGEN-BINDING PROTEIN

CROSS-REFERENCE TO RELATED APPLICATIONS

This application is a U.S. national stage of International Patent Application No. PCT/US2019/040296 filed Jul. 2, 2019, which claims priority to U.S. Provisional Patent Application No. 62/693,216, filed Jul. 2, 2018, and U.S. Provisional Patent Application No. 62/800,259, filed Feb. 1, 2019, the disclosures of which are hereby incorporated by reference in their entireties.

SEQUENCE LISTING

This application contains, as a separate part of the disclosure, a sequence listing in computer-readable form (Filename: 52601_Seqlisting.txt; Size: 298,964 Bytes; Created: Jan. 27, 2020), which is incorporated by reference in its entirety.

TECHNICAL FIELD

The disclosure provides a novel antigen-binding protein that binds Six Transmembrane Epithelial Antigen of the Prostate 1 (STEAP1) and uses thereof.

BACKGROUND

Prostate cancer remains one of the most common cancers among men in the United States. U.S. Cancer Statistics Working Group. United States Cancer Statistics: 1999-2014 Incidence and Mortality Web-based Report. Atlanta (Ga.): Department of Health and Human Services, Centers for Disease Control and Prevention, and National Cancer Institute; 2017. While the survival rate for prostate cancer is relatively high compared to other cancer types, current treatment options are accompanied by risk and unwanted side effects. For example, surgery is accompanied by risk of nerve damage and impotence, and radiation therapy can increase the risk of development bladder or gastrointestinal cancers. Traditional chemotherapy is associated with a host of side effects that limit the patient's quality of life during treatment.

Antibody-based therapeutics have been successful in treating a variety of diseases, including cancer and autoimmune/inflammatory disorders. Prostate cancer is believed to be particularly amenable to antibody-based therapy due, at least in part, to the existence of prostate cancer-specific antigens. Despite recent progress in elucidating the underlying biological mechanism of carcinogenesis and potential biomarkers, there exists a need for alternative antibody-based therapeutic options for cancer, including prostate cancer.

SUMMARY

The disclosure provides an antigen-binding protein that binds STEAP1 of SEQ ID NO: 2 and comprises: (a) heavy chain CDRs comprising amino acid sequences that differ by no more than 3, 2, or 1 amino acid from i) vhCDR1 SEQ ID NO: 14, vhCDR2 SEQ ID NO:15 or vhCDR2 SEQ ID NO: 21, and vhCDR3 SEQ ID NO: 16, or ii) vhCDR1 SEQ ID NO: 33, vhCDR2 SEQ ID NO: 34, and vhCDR3 SEQ ID NO: 35; or (b) light chain CDRs comprising amino acid sequences that differ by no more than 3, 2, or 1 amino acid from i) vlCDR1 SEQ ID NO: 11, vlCDR2 SEQ ID NO: 12, and vlCDR3 SEQ ID NO: 13; or ii) vlCDR1 SEQ ID NO: 30, vlCDR2 SEQ ID NO: 31, and vlCDR3 SEQ ID NO: 32; or (c) a light chain variable domain comprising an amino acid sequence at least 90% identical to SEQ ID NO: 183 or SEQ ID NO: 186; or (d) a heavy chain variable domain comprising an amino acid sequence at least 90% identical to SEQ ID NO: 182, SEQ ID NO: 184, or SEQ ID NO: 185. In various aspects, the antigen-binding protein comprises a vhCDR1 comprising SEQ ID NO: 14, a vhCDR2 comprising SEQ ID NO: 15 or SEQ ID NO: 21, a vhCDR3 comprising SEQ ID NO: 16, a vlCDR1 comprising SEQ ID NO: 11, a vlCDR2 comprising SEQ ID NO: 12, and a vlCDR3 comprising SEQ ID NO: 13. Alternatively, the antigen-binding protein comprises a vhCDR1 comprising SEQ ID NO: 33, a vhCDR2 comprising SEQ ID NO: 34, a vhCDR3 comprising SEQ ID NO: 35, a vlCDR1 comprising SEQ ID NO: 30, a vlCDR2 comprising SEQ ID NO: 31, and a vlCDR3 comprising SEQ ID NO: 32. In various aspects, the antigen-binding protein comprises a variable heavy domain comprising SEQ ID NO: 182 or SEQ ID NO: 184 and a variable light domain comprising SEQ ID NO: 183; for example, the antigen-binding protein comprises a variable heavy domain comprising SEQ ID NO: 182 and a variable light domain comprising SEQ ID NO: 183, or variable heavy domain comprising SEQ ID NO: 184 and a variable light domain comprising SEQ ID NO: 183. Alternatively, the antigen-binding protein comprises a variable heavy domain comprising SEQ ID NO: 185 and a variable light domain comprising SEQ ID NO: 186. The disclosure further provides an antigen-binding protein comprising a heavy chain comprising SEQ ID NO: 201 and a light chain comprising SEQ ID NO: 200; or a heavy chain comprising SEQ ID NO: 203 and a light chain comprising SEQ ID NO: 200.

The disclosure further provides a heterodimeric antibody comprising a first monomer comprising a first heavy chain comprising: 1) a first variable heavy domain; 2) a first constant heavy chain comprising a first CH1 domain and a first Fc domain; and 3) a scFv that binds human CD3 and comprises a scFv variable light domain, an scFv linker, and a scFv variable heavy domain; wherein said scFv is covalently attached between the C-terminus of said CH1 domain and the N-terminus of said first Fc domain using domain linker(s). The heterodimeric antibody further comprises a second monomer comprising a second heavy chain comprising a second variable heavy domain and a second constant heavy chain comprising a second Fc domain; and a common light chain comprising a variable light domain and a constant light domain. The first variable heavy domain and the variable light domain bind human STEAP1, the second variable heavy domain and the variable light domain bind human STEAP1, and wherein (i) the first variable heavy domain and the second variable heavy domain comprise heavy chain CDRs comprising amino acid sequences that differ by no more than 3, 2, or 1 amino acid from vhCDR1 SEQ ID NO: 14, vhCDR2 SEQ ID NO: 15 or vhCDR2 SEQ ID NO: 21, and vhCDR3 SEQ ID NO: 16, and the variable light domain comprises light chain CDRs comprising amino acid sequences that differ by no more than 3, 2, or 1 amino acid from vlCDR1 SEQ ID NO: 11, vlCDR2 SEQ ID NO: 12, and vlCDR3 SEQ ID NO: 13; or (ii) the first variable heavy domain and the second variable heavy domain comprise heavy chain CDRs comprising amino acid sequences that differ by no more than 3, 2, or 1 amino acid from vhCDR1 SEQ ID NO: 33, vhCDR2 SEQ ID NO: 34, and vhCDR3 SEQ ID NO: 35, and the variable light domain comprises light chain CDRs comprising amino acid sequences that differ by no more than 3, 2, or 1 amino acid from vlCDR1 SEQ ID NO: 30, vlCDR2 SEQ ID NO: 31, and vlCDR3 SEQ ID NO: 32; or (iii) the first variable heavy domain and the second variable heavy domain comprise an amino acid sequence at least 90% identical to SEQ ID NO: 182 or SEQ ID NO: 184 and the variable light domain comprises an amino acid sequence at least 90% identical to SEQ ID NO: 183; or (iv) the first variable heavy domain and the second variable heavy domain comprise an amino acid sequence at least 90% identical to SEQ ID NO: 185 and the variable light domain comprises an amino acid sequence at least 90% identical to SEQ ID NO:186. In various aspects, the first variable heavy domain and the second variable heavy domain comprise CDR sequences: vhCDR1 comprising SEQ ID NO: 14, vhCDR2 comprising SEQ ID NO: 15 or SEQ ID NO: 21, and vhCDR3 comprising SEQ ID NO: 16; and the variable light domain comprises CDR sequences: vlCDR1 comprising SEQ ID NO: 11, vlCDR2 comprising SEQ ID NO: 12, and vlCDR3 comprising SEQ ID NO: 13. In various aspects, the first variable heavy domain and the second variable heavy domain comprise CDR sequences: vhCDR1 comprising SEQ ID NO: 33, vhCDR2 comprising SEQ ID NO: 34, and vhCDR3 comprising SEQ ID NO: 35; and the variable light domain comprises CDR sequences: vlCDR1 comprising SEQ ID NO: 30, vlCDR2 comprising SEQ ID NO: 31, and vlCDR3 comprising SEQ ID NO: 32. In various aspects, the first variable heavy domain and the second variable heavy domain comprise SEQ ID NO: 182 or SEQ ID NO: 184 and the variable light domain comprises SEQ ID NO: 183 (e.g., SEQ ID NOs: 182 and 183 or SEQ ID NOs: 184 and 183), or the first variable heavy domain and the second variable heavy domain comprise SEQ ID NO: 185 and the variable light domain comprises SEQ ID NO: 186. The scFv comprises CDRs comprising: vhCDR1 comprising SEQ ID NO: 170, vhCDR2 comprising SEQ ID NO: 171, vhCDR3 comprising SEQ ID NO: 172, vlCDR1 comprising SEQ ID NO:174, vlCDR2 comprising SEQ ID NO: 175, and vlCDR3 comprising SEQ ID NO: 176; or a variable heavy region and a variable light region of SEQ ID NO:169 and SEQ ID NO:173.

Methods of treating cancer, such as prostate cancer, comprising administering to a subject in need thereof the antigen-binding protein described herein also are provided.

The use of section headings herein is merely for the convenience of reading, and not intended to be limiting per se. The entire document is intended to be viewed as a unified disclosure, and it should be understood that all combinations of features described herein are contemplated.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. The terms "comprising," "having," "including," and "containing" are to be construed as open-ended terms unless otherwise noted. If aspects of the invention are described as "comprising" a feature, embodiments also are contemplated "consisting of" or "consisting essentially of" the feature. The use of any and all examples, or exemplary language (e.g., "such as") provided herein, is intended merely to better illustrate the disclosure and does not pose a limitation on the scope of the disclosure unless otherwise claimed. No language in the specification should be construed as indicating any non-claimed element as essential to the practice of the disclosure. Other than in the operating examples, or where otherwise indicated, all numbers expressing quantities of ingredients or reaction conditions used herein should be understood as modified in all instances by the term "about" as that term would be interpreted by the person skilled in the relevant art.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

Generally, the terminology and techniques of cell and tissue culture, molecular biology, immunology, microbiology, genetics, protein and nucleic acid chemistry, manufacturing, formulation, pharmacology, and medicine described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art, or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients. Percent identity is calculated using methodology routinely used in the art, including the methodology described in, e.g., U.S. Patent Publication No. 2017/0342155, incorporated herein by reference in its entirety and particularly with respect to paragraphs [0075]-[0083].

BRIEF DESCRIPTION OF THE DRAWINGS

FIG. 1 depicts a bispecific antibody of the disclosure.

FIG. 2 depicts the sequence of human CD3 epsilon chain (SEQ ID NO: 1).

FIG. 3 depicts the sequence of human STEAP1 (SEQ ID NO: 2). Sequences of extracellular loops are underlined.

FIGS. 4A-4E depict useful pairs of heterodimerization variant sets (including skew and pI variants).

FIG. 5 depicts a list of isosteric variant antibody constant regions and their respective substitutions. pI_(−) indicates lower pI variants, while pI_(+) indicates higher pI variants. These can be optionally and independently combined with other heterodimerization variants of the disclosure (and other variant types as well, as outlined herein).

FIG. 6 depicts useful ablation variants that ablate FcγR binding (sometimes referred to as "knock outs" or "KO" variants).

FIG. 7 describes two embodiments of the disclosure.

FIGS. 8A and 8B depict useful linkers, including charged scFv linkers and domain linkers that can be used in the antigen binding proteins and heterodimeric antibody formats provided herein. Charged linkers, in various aspects of the disclosure, are useful for, e.g., increasing or decreasing the pI of heterodimeric antibodies that utilize one or more scFv as a component. A single prior art scFv linker with a single charge is referenced as "Whitlow," from Whitlow et al., Protein Engineering 6(8):989-995 (1993). This linker was used for reducing aggregation and enhancing proteolytic stability in scFvs.

FIG. 9 depicts a list of engineered heterodimer-skewing Fc variants with heterodimer yields (determined by HPLC-CIEX) and thermal stabilities (determined by DSC). Not determined thermal stability is denoted by "n.d." Additional information is provided in U.S. Pat. No. 9,822,186, incorporated by reference herein in its entirety.

FIGS. 10A and 10B depict stability-optimized, humanized anti-CD3 variant scFvs. Substitutions are given relative to the H1_L1.4 scFv sequence. Amino acid numbering is Kabat numbering. Specific variable light and variable heavy regions are noted; the substitutions listed may be employed for variable light and variable heavy regions other than those specifically listed. Additional information is provided in International Patent Publication No. 2017/091656, incorporated by reference herein in its entirety.

(FIG. 12B) and antibody Ab-A1 XmAb$^{2+1}$ (FIG. 12C).

FIGS. 18A-18I depict several formats of antigen-binding proteins: the "bottle opener" format, mAb-Fv, mAb-scFv, central-scFv, central-Fv, one armed central-scFv, one scFv-mAb, scFv-mAb and dual scFv. For all of the scFv domains depicted, they can be either N-to C-terminus variable heavy-(optional linker)-variable light, or the opposite. In addition, for the one armed scFv-mAb, the scFv can be attached either to the N-terminus of a heavy chain monomer or to the N-terminus of the light chain.

FIG. 19 provides the sequences of CDRs, variable heavy domains, variable light domains, scFvs, linker sequences, and monomer sequences of the disclosure. Underlining in variable region sequences denotes CDR sequences.

FIG. 20A is a graph illustrating specific cytotoxicity (%) mediated by Ab-A2 (N67Q) XmAb$^{2+1}$ alone (open circles) and Ab-A2 (N67Q) XmAb$^{2+1}$ in combination with an anti-PD-1 antibody (closed circles) in one representative T-cell donor (y-axis=Log (pM)). FIG. 20B illustrates the EC50 (pM) of Ab-A2 (N67Q) XmAb$^{2+1}$ alone (left) and Ab-A2 (N67Q) XmAb$^{2+1}$ in combination with an anti-PD-1 antibody (right) from four different T-cell donors.

FIG. 23. Mean and Median SK-N-MC Human Neuroblastoma Tumor Volumes in Female NOD/SCID Mice.

DETAILED DESCRIPTION

Figure 11:
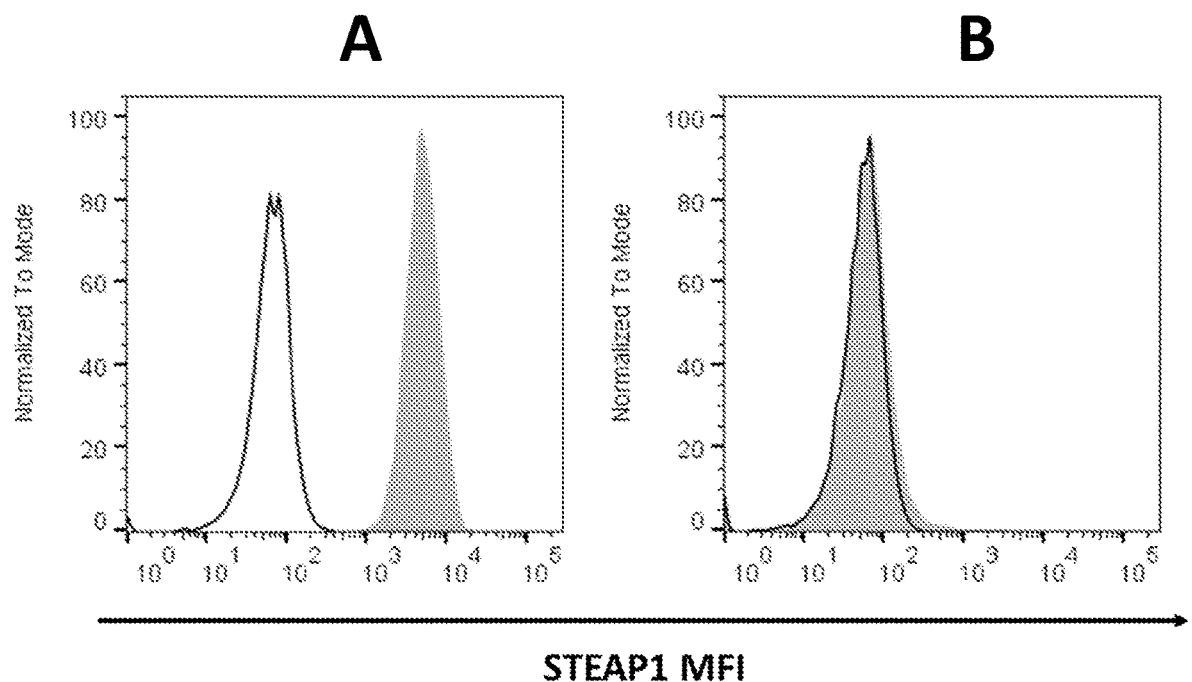
FIGS. 11A and 11B show specific detection of STEAP1 at the surface of C4-2B luc cells with murine STEAP1 antibody Ab-Am.
Figure 12A:
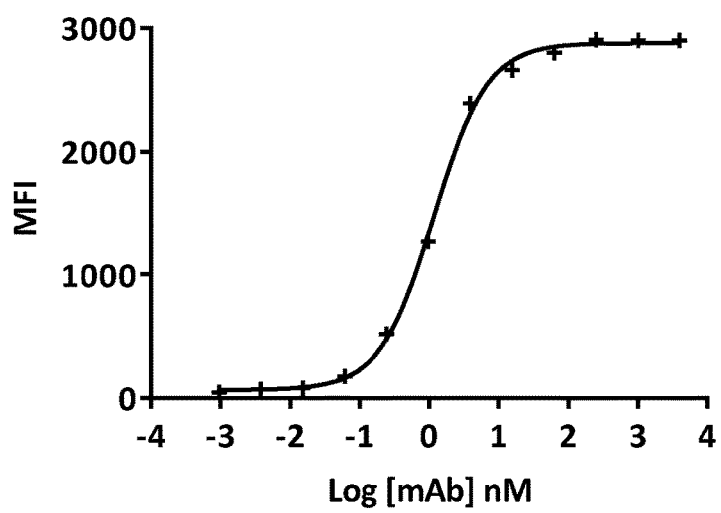
FIGS. 12A-12C shows specific detection of STEAP1 on C4-2B luc prostate cancer cells using murine STEAP1 antibody Ab-Am (FIG. 12A); Ab-A1 XmAb (●) or Ab-A1 XmAb$^{2+1}$ (■) for 1 hr at 4° C.
Figure 12B:
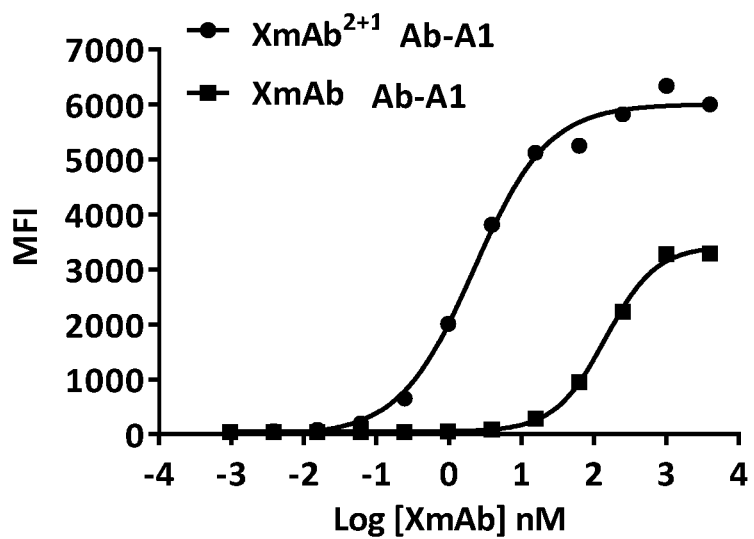
Figure 12C:
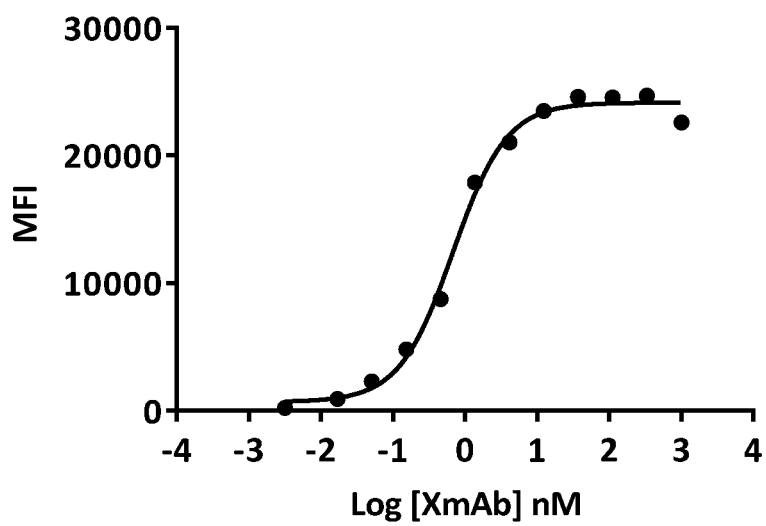
Figure 13:
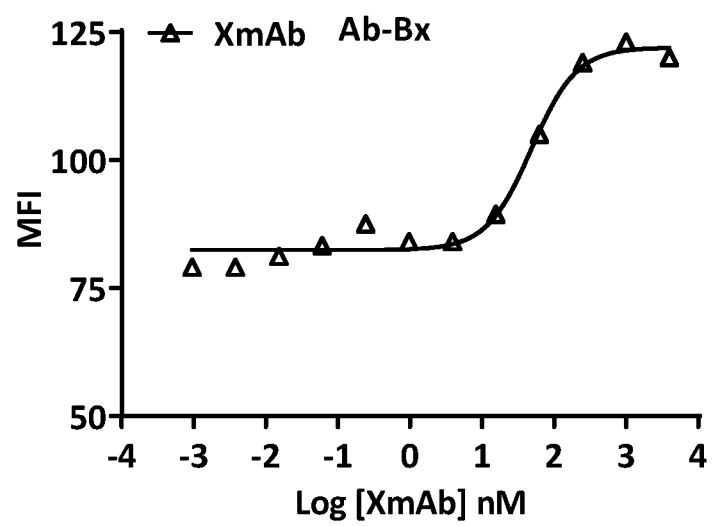
FIG. 13 shows specific detection of STEAP1 on C4-2B luc prostate cancer cells with STEAP1 antibody Ab-Bx (Ab-B1 XmAb).

STEAP1 is a 339 amino acid protein comprising six transmembrane domains, resulting in three extracellular loops and two intracellular loops. The amino acid sequence of human STEAP1 is set forth herein as SEQ ID NO: 2. The estimated positions of the extracellular loops are amino acids 92-118 (extracellular loop 1), amino acids 185-217 (extracellular loop 2), and amino acids 279-290 (extracellular loop 3). STEAP1 is differentially expressed in prostate cancer compared to normal tissues, and increased expression in bone and lymph node prostate cancer metastatic lesions was observed compared to primary prostate cancer samples. STEAP1 represents an ideal target for diagnostics and antibody-based therapeutics, such as a bispecific anti-STEAP1/anti-CD3 T cell recruiting antibody to, e.g., trigger T cell dependent cellular cytotoxicity or redirected lysis of prostate cancer cells. The disclosure provides antigen-binding proteins that bind STEAP1, as described further herein.

Antigen-Binding Protein

An "antigen-binding protein" is a protein comprising a portion that binds a specified target antigen (such as STEAP1). An antigen-binding protein comprises a scaffold or framework portion that allows the antigen-binding portion to adopt a conformation that promotes binding of the antigen-binding protein to the antigen. In exemplary aspects, the antigen-binding protein is an antibody or immunoglobulin (e.g., a heterodimeric and/or bispecific antibody), or an antigen-binding antibody fragment, or an antibody protein product.

The term "antibody" refers to an intact antigen-binding immunoglobulin. An "antibody" is a type of an antigen-binding protein. The antibody can be an IgA, IgD, IgE, IgG, or IgM antibody, including any one of IgG1, IgG2, IgG3 or IgG4. In various embodiments, an intact antibody comprises two full-length heavy chains and two full-length light chains. An antibody has a variable region and a constant region. In IgG formats, a variable region is generally about 100-110 or more amino acids, comprises three complementarity determining regions (CDRs), is primarily responsible for antigen recognition, and substantially varies among other antibodies that bind to different antigens. A variable region typically comprises at least three heavy or light chain CDRs (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987, supra). The constant region allows the antibody to recruit cells and molecules of the immune system.

In various aspects, the antibody is a monoclonal antibody. In certain aspects, the antibody is a human antibody. In certain aspects, the antibody (or other antigen-binding protein) is chimeric or humanized. The term "chimeric" refers to an antibody containing domains from two or more different antibodies. A chimeric antibody can, for example, contain the constant domains from one species and the variable domains from a second, or more generally, can contain stretches of amino acid sequence from at least two species. Both "chimeric" and "humanized" often refer to antigen-binding proteins that combine regions from more than one species. A chimeric antibody also can contain domains of two or more different antibodies within the same species. In one embodiment, the chimeric antibody is a CDR grafted antibody.

The term "humanized" when used in relation to antigen-binding proteins refers to antigen-binding proteins (e.g., antibodies) having at least CDR region from a non-human source and which are engineered to have a structure and immunological function more similar to true human antibodies than the original source antibodies. For example, humanizing can involve grafting a CDR from a non-human antibody, such as a mouse antibody, into a human framework region. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., International Patent Publication No. WO 92/11018; Jones, 1986, Nature 321: 522-525; and Verhoeyen et al., 1988, Science 239:1534-1536, all entirely incorporated by reference. "Back mutation" of selected acceptor framework residues to the corresponding donor residues is often employed to regain affinity that is lost in the initial grafted construct (See, e.g., U.S. Pat. Nos. 5,530,101; 5,585,089; 5,693,761; 5,693,762; 6,180,370; 5,859,205; 5,821,337; 6,054,297; and 6,407,213, all entirely incorporated by reference). The humanized antibody optimally also will comprise at least a portion of an immunoglobulin constant region, typically that of a human immunoglobulin, and thus will typically comprise a human Fc region.

A variety of techniques and methods for generating chimeric antibodies, humanized antibodies, and reshaping non-human antibodies are well known in the art. See Tsurushita & Vasquez, 2004, Humanization of Monoclonal Antibodies, Molecular Biology of B Cells, 533-545, Elsevier Science (USA), and references cited therein; Jones et al., 1986, Nature 321:522-525; Riechmann et al., 1988; Nature 332: 323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8, U.S. Patent Publication No. 20030039649; U.S. Pat. Nos. 5,869,619, 5,225,539, 5,821, 337, 5,859,205; Padlan et al., 1995, FASEB J. 9:133-39; and Tamura et al., 2000, J. Immunol. 164:1432-41, all entirely incorporated by reference. Humanization or other methods of reducing the immunogenicity of nonhuman antibody variable regions may include resurfacing methods, as described for example in Roguska et al., 1994, Proc. Natl. Acad. Sci. USA 91:969-973, entirely incorporated by reference. A parent antibody may be affinity matured, which is well understood in the art. Structure-based methods may be employed for humanization and affinity maturation, for example as described in U.S. Patent Publication No. 20060008883. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759, all entirely incorporated by reference. Humanizing also can involve select amino acid substitutions to make a non-human sequence more similar to a human sequence. Other humanization methods may involve the grafting of only parts of the CDRs, including but not limited to methods described in Tan et al., 2002, J. Immunol. 169:1119-1125; De Pascalis et al., 2002, J. Immunol. 169:3076-3084, all entirely incorporated by reference.

In other embodiments, the antigen-binding protein is an antigen-binding antibody fragment, i.e., a fragment of an antibody that lacks part or all of an antibody's light chains and/or part or all of an antibody's heavy chains. Antibody fragments can be recombinantly produced or can be prepared by cleaving an intact antibody using enzymes, such as, e.g., papain and pepsin. Papain cleaves an antibody to produce two Fab fragments and a single Fc fragment. Pepsin cleaves an antibody to produce a F(ab')$_2$ fragment and a pFc' fragment. In exemplary instances, the antigen-binding antibody fragment is a Fab fragment or a F(ab')$_2$ fragment. A Fab fragment is a monovalent fragment having the VL, VH, CL and CH1 domains. Fab may refer to this region in isolation, or this region in the context of a full length antibody, antibody fragment, etc. A F(ab')$_2$ fragment is a bivalent fragment having two Fab fragments linked by a disulfide bridge at the hinge region.

The architecture of antibodies has been exploited to create a growing range of alternative formats that span a molecular-weight range of at least about 12-150 kDa and has a valency (n) range from monomeric (n=1), to dimeric (n=2), to trimeric (n=3), to tetrameric (n=4), and potentially higher; such alternative formats are referred to herein as "antibody protein products" and are examples of antigen-binding proteins. Antibody protein products include those based on the full antibody structure and those that mimic antibody fragments which retain full antigen-binding capacity, e.g., scFvs and VHH/VH (discussed below). A single-chain antibody (scFv) is an antibody in which a VL and a VH region are joined via a linker (e.g., a synthetic sequence of amino acid residues usually about 15 amino acids in length) to form a continuous protein chain wherein the linker is long enough to allow the protein chain to fold back on itself and form a monovalent antigen-binding site (see, e.g., Bird et al., 1988, Science 242:423-26 and Huston et al., 1988, Proc. Natl. Acad. Sci. USA 85:5879-83).

An antigen-binding fragment that retains its complete antigen-binding site is the Fv fragment, which consists entirely of a variable (V) region (the VL and VH domain of a single antibody). A soluble, flexible amino acid peptide linker is often used to connect the V regions to a scFv (single chain fragment variable) fragment for stabilization of the molecule, or a constant (C) domain is added to the V regions to generate a Fab fragment (fragment, antigen-binding). scFv and Fab fragments can be easily produced in host cells, e.g., prokaryotic or eukaryotic host cells. Other antibody protein products include disulfide-bond stabilized scFv (ds-scFv), single chain Fab (scFab), single chain antibody (SCA), domain antibodies (dAbs) (e.g., peptides comprising VH domain, a VL domain, or an antigen-binding fragment of a VH or VL domain), peptides comprising an Fd fragment (comprising VH and CH1 domains), complementarity determining region (CDR) fragments, as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). A peptibody or peptide-Fc fusion is yet another antibody protein product. The structure of a peptibody consists of a biologically active peptide grafted onto an Fc domain. Peptibodies are further described in the art. See, e.g., Shimamoto et al., mAbs 4(5): 586-591 (2012).

Alternatively, an antibody protein product can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen-binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronectin components as a scaffold.

In various aspects, the antigen-binding protein comprises heavy chain CDRs comprising amino acid sequences that differ by no more than 3, 2, or 1 amino acid from i) vhCDR1 SEQ ID NO: 14, vhCDR2 SEQ ID NO: 15 or vhCDR2 SEQ ID NO: 21, and vhCDR3 SEQ ID NO: 16, or ii) vhCDR1 SEQ ID NO: 33, vhCDR2 SEQ ID NO: 34, and vhCDR3 SEQ ID NO: 35; and/or light chain CDRs comprising amino acid sequences that differ by no more than 3, 2, or 1 amino acid from i) vlCDR1 SEQ ID NO: 11, vlCDR2 SEQ ID NO: 12, and vlCDR3 SEQ ID NO: 13; or ii) vlCDR1 SEQ ID NO: 30, vlCDR2 SEQ ID NO: 31, and vlCDR3 SEQ ID NO: 32. Each such sequence difference is independently either a deletion, insertion, or substitution, although substitutions (e.g., conservative substitutions) are preferred. Examples of conservative substitutions include, but are not limited to, exchanges within the following groups: small aliphatic, nonpolar or slightly polar residues, Ala, Ser, Thr, Pro, Gly; polar, negatively charged residues and their amides and esters, Asp, Asn, Glu, Gln, cysteic acid and homocysteic acid; polar, positively charged residues, His, Arg, Lys, Ornithine (Orn); large, aliphatic, nonpolar residues, Met, Leu, Ile, Val, Cys, Norleucine (Nle), homocysteine; and large, aromatic residues: Phe, Tyr, Trp, acetyl phenylalanine.

In various aspects, the antigen-binding protein comprises the following CDR sequences: a) vhCDR1 comprising SEQ ID NO: 14, vhCDR2 comprising SEQ ID NO:15 or SEQ ID NO: 21, and vhCDR3 comprising SEQ ID NO: 16; or b) vhCDR1 comprising SEQ ID NO: 33, vhCDR2 comprising SEQ ID NO: 34, and vhCDR3 comprising SEQ ID NO: 35. Alternatively or in addition, the antigen-binding protein comprises the following CDR sequences: a) vlCDR1 comprising SEQ ID NO: 11, vlCDR2 comprising SEQ ID NO: 12, and vlCDR3 comprising SEQ ID NO: 13; or b) vlCDR1 comprising SEQ ID NO: 30, vlCDR2 comprising SEQ ID NO: 32, and vlCDR3 comprising SEQ ID NO: 33.

Thus, in various aspects, the antigen-binding protein comprises vhCDR1 comprising SEQ ID NO: 14, vhCDR2 comprising SEQ ID NO: 15 or SEQ ID NO: 21, vhCDR3 comprising SEQ ID NO: 16, vlCDR1 comprising SEQ ID NO: 11, vlCDR2 comprising SEQ ID NO: 12, and vlCDR3 comprising SEQ ID NO: 13. In alternative aspects, the antigen-binding protein comprises vhCDR1 comprising SEQ ID NO: 33, vhCDR2 comprising SEQ ID NO: 34, vhCDR3 comprising SEQ ID NO: 35, vlCDR1 comprising SEQ ID NO: 30, vlCDR2 comprising SEQ ID NO: 31, and vlCDR3 comprising SEQ ID NO: 32.

In various embodiments, the antigen-binding protein comprises a light chain variable domain comprising an amino acid sequence at least 90% identical (e.g., at least 95% identical or 100% identical) to SEQ ID NO: 183 or SEQ ID NO:186; and/or a heavy chain variable domain comprising an amino acid sequence at least 90% identical (e.g., at least 95% identical or 100% identical) to SEQ ID NO: 182, SEQ ID NO: 184, or SEQ ID NO:185. For example, the antigen-binding protein can comprise (i) SEQ ID NO: 183 and SEQ ID NO: 182, (ii) SEQ ID NO: 184 and SEQ ID NO: 183, or (iii) SEQ ID NO: 185 and SEQ ID NO: 186. In various aspects, the antigen-binding protein comprises a light chain variable region and/or a heavy chain variable region comprising a sequence of amino acids that differs from the aforementioned amino acid sequences only at 15, 14, 13, 12, 11, 10, 9, 8, 7, 6, 5, 4, 3, 2, or 1 residue(s), wherein each such sequence difference is independently either a deletion, insertion, or substitution (e.g., conservative substitution). In various aspects, the sequence difference(s) is located outside the CDR (e.g., within the framework region).

In various embodiments, the antigen-binding protein comprises a light chain comprising an amino acid sequence at least 90% identical (e.g., at least 95% identical or 100% identical) to SEQ ID NO: 17 or SEQ ID NO: 36; and/or a heavy chain comprising an amino acid sequence at least 90% identical (e.g., at least 95% identical or 100% identical) to SEQ ID NO: 18, SEQ ID NO: 199 or SEQ ID NO: 37. For example, the antigen-binding protein can comprise (i) SEQ ID NO: 17 and SEQ ID NO: 18; (ii) SEQ ID NO: 17 and SEQ ID NO: 199; or (iii) SEQ ID NO: 36 and SEQ ID NO: 37.

In various embodiments, the antigen-binding protein comprises a light chain comprising an amino acid sequence at least 90% identical (e.g., at least 95% identical or 100% identical) to SEQ ID NO: 200 or SEQ ID NO: 204; and/or a heavy chain comprising an amino acid sequence at least 90% identical (e.g., at least 95% identical or 100% identical) to SEQ ID NO: 201, SEQ ID NO: 203 or SEQ ID NO: 205. For example, the antigen-binding protein can comprise (i) SEQ ID NO: 200 and SEQ ID NO: 201; (ii) SEQ ID NO: 200 or SEQ ID NO: 203; (iii) SEQ ID NO: 204 and SEQ ID NO: 205.

Competition, Epitope, Binding Affinity

The antigen-binding protein binds STEAP1 of SEQ ID NO: 2. Specific binding (i.e., binding to STEAP1 that is measurably different from a non-specific interaction) can be determined, for example, by determining binding of a molecule compared to binding of a control molecule, which generally is a molecule of similar structure that does not have binding activity. For example, specific binding can be determined by competition with a control molecule that is similar to the target.

The binding affinity of the antigen-binding protein to STEAP1 may be described in terms of dissociation constant (Kd). In exemplary aspects, the Kd of the antigen-binding protein provided herein is micromolar, nanomolar, picomolar, or femtomolar. Typically, an antigen-binding protein that specifically binds an antigen will have a Kd that is 20-, 50-, 100-, 500-, 1000-, 5,000-, 10,000- or more times greater for a control molecule relative to the target antigen or epitope. Also, specific binding for a particular antigen can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction. In exemplary aspects, the KD of the antigen-binding protein provided herein for STEAP1 is less than or equal to $10^{-7}$ M, less than or equal to $10^{-8}$ M, less than or equal to $10^{-9}$ M, less than or equal to $10^{-10}$ M, less than or equal to $10^{-11}$ M, or less than or equal to $10^{-12}$ M. For example, the KD of the antigen-binding protein is optionally within a range of about $10^{-4}$ to $10^{-6}$ M, or about $10^{-7}$ to $10^{-9}$ M, or about $10^{-10}$ to $10^{-12}$ M, or about $10^{-7}$ to $10^{-12}$, or about $10^{-9}$ to $10^{-12}$, or about $10^{-13}$ to $10^{-15}$ M. Alternatively (or in addition), the antigen-binding protein has a low dissociation rate from STEAP1. In some embodiments, the antigen-binding protein has a $K_{off}$ of $1 \times 10^{-4}$ s$^{-1}$ or lower. In another embodiment, the $K_{off}$ is $5 \times 10^{-5}$ s$^{-1}$ or lower. In various aspects, the antigen-binding protein differentiates between target cells expressing a high level of STEAP1 and those off-target cells that display less STEAP1. For example, in various aspects, the antigen-binding protein preferentially binds cells comprising more than about 100,000 STEAP1 receptors per cell (e.g., about 200,000 STEAP1 receptors per cell) down to about 10,000 STEAP1 receptors per cell. It will be appreciated the disclosure regarding competition, binding affinity, and binding specificity relating to STEAP1 also applies to a multispecific antigen-binding protein's binding to a second or third antigen (e.g., CD3) or a different antibody which is used in conjunction with the anti-STEAP1 antigen-binding protein. For example, in exemplary aspects, the Kd of the antigen-binding protein provided herein for CD3 (or PD-1, as described below) is less than or equal to $10^{-7}$ M, less than or equal to $10^{-8}$ M, less than or equal to $10^{-9}$ M, less than or equal to $10^{-10}$ M, less than or equal to $10^{-11}$ M, or less than or equal to $10^{-12}$ M. For example, the Kd of the antigen-binding protein is optionally within a range of about $10^{-4}$ to $10^{-6}$ M, or about $10^{-7}$ to $10^{-9}$ M, or about $10^{-10}$ to $10^{-12}$ M, or about $10^{-7}$ to $10^{-12}$, or about $10^{-9}$ to $10^{-12}$, or about $10^{-13}$ to $10^{-15}$ M. Alternatively (or in addition), the antigen-binding protein has a low dissociation rate from CD3. In some embodiments, the antigen-binding protein has a $K_{off}$ of $1 \times 10^{-4}$ s$^{-1}$ or lower. In another embodiment, the $K_{off}$ is $5 \times 10^{-5}$ s$^{-1}$ or lower with respect to CD3.

The disclosure further provides an antigen-binding protein (e.g., an antibody) that competes for binding to STEAP1 with any of the antigen-binding proteins described herein (e.g., Ab-A, Ab-A1, Ab-A2, Ab-B, or Ab-B1, including in the $^{XmAb2+1}$ format as described herein). Put another way, the disclosure provides an antigen-binding protein that cross-blocks the binding of a reference antigen-binding protein described herein to STEAP1 or is cross-blocked from binding to STEAP1 by the reference antigen-binding protein. By "compete" is meant that one antigen-binding protein prevents, reduces or inhibits binding of a reference antigen-binding protein to STEAP1. Numerous types of competitive binding assays can be used, for example, surface plasmon resonance, solid phase direct or indirect radioimmunoassay (RIA), solid phase direct or indirect enzyme immunoassay (EIA), sandwich competition assay (see, e.g., Stahli et al., 1983, Methods in Enzymology 9:242-253), solid phase direct biotin-avidin EIA (see, e.g., Kirkland et al., 1986, J. Immunol. 137:3614-3619), solid phase direct labeled assay, solid phase direct labeled sandwich assay (see, e.g., Harlow and Lane, 1988, Antibodies, A Laboratory Manual, Cold Spring Harbor Press), solid phase direct label RIA using 1-125 label (see, e.g., Morel et al., 1988, Molec. Immunol. 25:7-15), solid phase direct biotin-avidin EIA (see, e.g., Cheung, et al., 1990, Virology 176:546-552), and direct labeled RIA (Moldenhauer et al., 1990, Scand. J. Immunol. 32:77-82). Typically, such an assay involves the use of purified antigen bound to a solid surface or exposed on cells, an unlabeled test antigen-binding protein, and a labeled reference antigen-binding protein. Competitive inhibition is measured by determining the amount of label bound to the solid surface or cells in the presence of the test antigen-binding protein. Usually the test antigen-binding protein is present in excess. Antigen-binding proteins identified by competition assay (competing antigen-binding proteins) include antigen-binding proteins binding to the same epitope as the reference antigen-binding proteins, an epitope that overlaps the epitope recognized by the reference antigen-binding protein, and epitopes that do not overlap but that allow for steric hindrance to occur between the test and reference antigen-binding proteins. Usually, when a competing antigen-binding protein is present in excess, it will inhibit binding of a reference antigen-binding protein to a common antigen by at least 20%, 25%, 30%, 35%, 40%, 45%, 50%, 55%, 60%, 65%, 70%, or 75%. In some instances, binding is inhibited by at least 80%, 85%, 90%, 95%, or 97% or more. In at least one aspect, the antigen-binding protein (e.g., antibody) competes with a reference antigen-binding protein (e.g., Ab-A, Ab-A1, Ab-A2, Ab-B, or Ab-B1 described herein, optionally in a bispecific antibody format, such as the bispecific antibody format described in the Examples (e.g., XmAb$^{2+1}$)) such that binding of the reference antigen-binding protein to STEAP1 is reduced by at least 80% or at least 90%.

The antigen-binding protein binds STEAP1 of SEQ ID NO: 2. A competing (or cross-blocking) antigen-binding protein may bind an epitope that overlaps the epitope recognized by the reference antigen-binding protein, or an epitope that does not overlap but that allows for steric hindrance to occur between the test and reference antigen-binding proteins. In various aspects, the antigen-binding protein binds to the same epitope as the reference antigen-binding protein, such as Ab-A, Ab-A1, Ab-A2 (N67Q), Ab-B, or Ab-B1 or bispecific or heterodimeric versions thereof (e.g., Ab-A1 XmAb$^{2+1}$, Ab-A2 (N67Q) XmAb$^{2+1}$, or Ab-B1 XmAb$^{2+1}$) described herein. For example, the antigen-binding protein of the disclosure optionally binds STEAP1 in a region outside of the second extracellular loop. The antigen-binding protein, in at least one embodiment, binds a region of STEAP1 within amino acids 92-118 (extracellular loop 1) and/or amino acids 279-290 (extracellular loop 3). In various aspects, the disclosure provides an antigen-binding protein binds a region of STEAP1 within amino acids 92-118 and amino acids 279-290. Also optionally, the antigen-binding protein does not bind STEAP2 (UniProtKB No. Q8NFT2; SEQ ID NO: 177). If desired, the epitope of the reference antigen-binding protein and/or the tested antigen-binding protein can be determined by solving the X-ray crystal structure of the antigen-binding protein bound to STEAP1 or a portion thereof. In one such embodiment, the epitope is defined as those residues on extracellular portion of STEAP1 that show at least a 10% reduction in solvent accessibility when the antigen-binding protein (reference or tested) is bound to it as compared to when it is not.

Methods of Making Antigen-Binding Proteins

Suitable methods of making antigen-binding proteins (e.g., antibodies, antigen-binding antibody fragments, and antibody protein products) are known in the art. For instance, standard hybridoma methods for producing antibodies are described in, e.g., Harlow and Lane (eds.), Antibodies: A Laboratory Manual, CSH Press (1988), and CA. Janeway et al. (eds.), Immunobiology, 5th Ed., Garland Publishing, New York, N.Y. (2001)). EBV-hybridoma methods and Bacteriophage vector expression systems are described in, e.g., Haskard and Archer, J. Immunol. Methods, 74(2), 361-67 (1984), Roder et al., Methods Enzymol., 121, 140-67 (1986), and Huse et al., Science, 246, 1275-81 (1989)). Methods of producing antibodies in non-human animals are described in, e.g., U.S. Pat. Nos. 5,545,806, 5,569,825, 5,714,352, and 5,814,318; and U.S. Patent Application Publication No. 2002/0197266 (all incorporated herein by reference). In certain aspects, a recombinant antigen-binding protein that binds STEAP1 is provided. In this context, a "recombinant protein" is a protein made using recombinant techniques, e.g., through the expression of a recombinant nucleic acid. Methods and techniques for the production of recombinant proteins are well known in the art.

Molecular evolution of the CDRs in the binding site also has been used to generate antigen-binding proteins (e.g., antibodies) with increased affinity, for example, antibodies having increased affinity for c-erbB-2, as described by Schier et al., 1996, J. Mol. Biol. 263:551. Such techniques are useful in preparing anti-STEAP1 antigen-binding proteins (or other antigen-binding proteins described herein).

Methods of testing antigen-binding proteins for the ability to bind to an antigen, such as STEAP1, are known in the art and include, e.g., radioimmunoassay (RIA), ELISA, Western blot, immunoprecipitation, surface plasmon resonance (e.g., BIAcore), and competitive inhibition assays (see, e.g., Janeway et al., infra; U.S. Patent Publication No. 2002/0197266; and U.S. Pat. No. 7,872,106, all of which are hereby incorporated by reference in their entirety and particularly with respect to disclosure of competition assays). Indeed, assays which test the ability of an antigen-binding protein to compete with a second antigen-binding proteins for binding to an antigen, or to an epitope thereof, are known in the art and can be used to test the ability of an antibody to bind to, e.g., STEAP1. See, e.g., U.S. Patent Application Publication No. 2014/0178905, Chand et al., Biologicals 46: 168-171 (2017); Liu et al., Anal Biochem 525: 89-91 (2017); and Goolia et al., J Vet Diagn Invest 29(2): 250-253 (2017). Surface plasmon resonance can be used to determine the binding constants of the antigen-binding protein and a second antigen-binding protein and the two binding constants can be compared.

Multi-Specific Antigen-Binding Proteins

An ongoing problem in antibody technologies is the desire for bispecific (and/or multispecific) antibodies that bind to two (or more) different antigens simultaneously, in general allowing the different antigens to be brought into proximity and resulting in new functionalities and new therapies. The disclosure provides a novel multispecific antigen-binding protein that binds STEAP1 and one or more additional target antigens. In a preferred embodiment, the disclosure provides a novel bispecific antigen-binding protein (e.g., bispecific antibody) comprising an anti-STEAP1 binding domain as described above and a binding region that binds a second target antigen (which may be a different STEAP1 epitope, but which generally is a different antigen). In various aspects, the second antigen is cell surface molecule present on an effector cell, i.e., a leukocyte which expresses one or more FcRs (e.g., FcγRIII) and performs one or more effector functions attributable to the Fc region of an antibody.

Examples of effector functions include, but are not limited to, C1q binding and complement dependent cytotoxicity (CDC), Fc receptor binding, antibody-dependent cell-mediated cytotoxicity (ADCC), phagocytosis, down regulation of cell surface receptors, and B cell activation. Examples of effector cells involved in ADCC include, but are not limited to, cytotoxic T cells, peripheral blood mononuclear cells (PBMC), natural killer (NK) cells, monocytes, and neutrophils. In various aspects, the disclosure provides a bispecific antigen-binding protein (e.g., bispecific antibody) that binds to both CD3 (e.g., SEQ ID NO: 1) and STEAP1 (SEQ ID NO: 2). In various aspects, the disclosure provides a bispecific antigen-binding protein (e.g., bispecific antibody) that binds to both CD3 and extracellular loops 1 and 3 of STEAP1.

In various aspects, the multispecific antigen-binding protein differentiates between target cells expressing a high level of STEAP1 and those off-target cells that display less STEAP1. In this regard, in some embodiments, a bispecific antigen-binding protein (e.g., heterodimeric antibody) of the disclosure is able to preferentially mediate T cell dependent killing of tumor cells, demonstrating reduced "off target" effects. For example, in some aspects, a bispecific antibody comprising the STEAP1 antigen-binding protein described herein alongside a CD3 antigen-binding region preferentially mediates T cell dependent killing of cells with a surface density of STEAP1 of greater than 10,000 (e.g., the EC90 is at least 10-fold less for cells with a surface density of STEAP1 of greater than 10,000 compared to cells having a surface density of STEAP1 less than 10,000).

The disclosure provides a bispecific antigen-binding protein comprising novel anti-CD3 sequences, including sets of CDRs and full variable light and heavy chains. In some aspects, the CD3 binding domain (optionally an scFv as discussed below) of the bispecific construct comprises a variable heavy domain comprising heavy chain CDRs comprising amino acid sequences that differ by no more than 3, 2, or 1 amino acid from vhCDR1 SEQ ID NO: 170, vhCDR2 SEQ ID NO: 171, and vhCDR3 SEQ ID NO: 172, and a variable light domain comprising light chain CDRs comprising amino acid sequences that differ by no more than 3, 2, or 1 amino acid from vlCDR1 SEQ ID NO: 174, vlCDR2 SEQ ID NO:175, and vlCDR3 SEQ ID NO: 176. For example, the disclosure provides a multispecific (e.g., bispecific) construct comprising a variable heavy domain comprising an amino acid sequence at least 90% identical (e.g., at least 95% identical or 100% identical) to SEQ ID NO:169 and a variable light domain comprising an amino acid sequence at least 90% identical (e.g., at least 95% identical or 100% identical) to SEQ ID NO:173.

For example, the anti-CD3 portion optionally comprises the CDR sequences vhCDR1 comprising SEQ ID NO:170, vhCDR2 comprising SEQ ID NO: 171, vhCDR3 comprising SEQ ID NO: 172, vlCDR1 comprising SEQ ID NO: 174, vlCDR2 comprising SEQ ID NO: 175, and vlCDR3 comprising SEQ ID NO: 176. In this regard, the CD3 binding region optionally comprises a variable heavy region of SEQ ID NO:169 and a variable light region of SEQ ID NO:173.

Bispecific antigen-binding proteins may comprise two antigen-binding domains (e.g., each antigen is bound monovalently) or three (or more) antigen-binding domains (e.g., one antigen is bound bivalently and the other is bound monovalently), such as the STEAP1 and CD3 binding domains described herein. Bispecific antibodies include, but are not limited to, traditional bispecific immunoglobulins (e.g., BsIgG), IgG comprising an appended antigen-binding domain (e.g., the amino or carboxy termini of light or heavy chains are connected to additional antigen-binding domains, such as single domain antibodies or paired antibody variable domains (e.g., Fv or scFv)), BsAb fragments (e.g., bispecific single chain antibodies), bispecific fusion proteins (e.g., antigen-binding domains fused to an effector moiety), and BsAb conjugates. See, e.g., Spiess et al., Molecular Immunology 67(2) Part A: 97-106 (2015), which describes various bispecific formats and is hereby incorporated by reference. Examples of bispecific constructs include, but are not limited to, diabodies, single chain diabodies, tandem scFvs, and Fab$_2$ bispecifics, as well as engineered constructs comprising full length antibodies. See, e.g., Chames & Baty, 2009, mAbs 1[6]:1-9; and Holliger & Hudson, 2005, Nature Biotechnology 23[9]:1126-1136; Wu et al., 2007, Nature Biotechnology 25[11]:1290-1297; Michaelson et al., 2009, mAbs 1[2]:128-141; International Patent Publication No. 2009032782 and 2006020258; Zuo et al., 2000, Protein Engineering 13[5]: 361-367; U.S. Patent Application Publication No. 20020103345; Shen et al., 2006, J Biol Chem 281[16]: 10706-10714; Lu et al., 2005, J Biol Chem 280[20]:19665-19672; and Kontermann, 2012 MAbs 4(2):182, all of which are expressly incorporated herein.

In various aspects, the bispecific antigen-binding protein is a bispecific single chain antibody (BiScFv). A light chain variable region and a heavy chain variable region are connected to one another as a single chain as a first antigen-binding domain, which is connected to a second antigen-binding domain of similar structure, optionally via a linker. In the event that a linker is used, the linker is preferably of a length and sequence sufficient to ensure that each of the first and second antigen-binding domains can, independently from one another, retain their differential binding specificities. Bispecific single chain molecules are known in the art and are further described in U.S. Pat. No. 7,635,472, International Patent Publication No. WO 99/54440; Mack, J. Immunol. (1997), 158, 3965-3970; Mack, PNAS, (1995), 92, 7021-7025; Kufer, Cancer Immunol. Immunother., (1997), 45, 193-197; Loffler, Blood, (2000), 95, 6, 2098-2103; Bruhl, Immunol., (2001), 166, 2420-2426; and Kipriyanov, J. Mol. Biol., (1999), 293,41-56, which are all incorporated by reference in their entireties.

Alternative bispecific antigen-binding formats are described in, e.g., U.S. Patent Application Publication No. 2011/0054151, incorporated by reference herein. For example, the bispecific antigen-binding protein may comprise a mAb-Fv format, wherein an IgG antibody is fused at the C-terminus with an Fv fragment. Alternatively, a mAb-Fab format may be used wherein an IgG antibody is fused at the C-terminus with a Fab. The mAb-Fab construct contains CH and CL constant domains C-terminal to the C-terminal Fv fusion, whereas mAb-Fv does not. See FIG. 8 of U.S. Patent Application Publication No. 2011/0054151. Optionally, the N-terminal binding region of the mAb-Fv and mAb-Fab constructs lack a light chain and a CH1 domain (i.e., comprise a single domain VHH region). mAb-Fv and mAb-Fab constructs contain three variable regions, such that they bind a first antigen bivalently and a second antigen monovalently. Suitable bispecific antigen-binding formats also include Fab-Fv and Fab-Fab constructs described in U.S. Patent Application Publication No. 2011/0054151. The Fab-Fv and Fab-Fab immunoglobulins comprise an N-terminal Fab fragment that binds a first antigen and a C-terminal Fv or Fab fragment binds a second antigen.

In one aspect, the present disclosure is directed to the creation of heterodimeric antibodies that co-engage antigens and rely on amino acid variants in the constant regions that are different on each chain to promote heterodimeric formation and/or allow for ease of purification of heterodimers over the homodimers. In general, bispecific antibodies are made by including genes for each heavy and light chain into the host cells. This generally results in the formation of the desired heterodimer (A-B), as well as the two homodimers (A-A and B-B). However, a major obstacle in the formation of multispecific antibodies is the difficulty in purifying the heterodimeric antibodies away from the homodimeric antibodies and/or biasing the formation of the heterodimer over the formation of the homodimers.

The present disclosure provides heterodimeric antibody formats that overcome hurdles associated with previous technologies. Additionally, in the context of STEAP1/CD3 bispecific antigen-binding proteins, the heterodimeric antibody of the disclosure allows for monovalent binding of CD3. CD3 activation of T-cells occurs only when its associated T-cell receptor (TCR) engages antigen-loaded MHC on antigen presenting cells in a highly avid cell-to-cell synapse (Kuhns et al., 2006, Immunity 24:133-139). Non-specific bivalent crosslinking of CD3 using an anti-CD3 antibody elicits a cytokine storm and toxicity (Perruche et al., 2009, J Immunol 183[2]:953-61; Chatenoud & Bluestone, 2007, Nature Reviews Immunology 7:622-632; expressly incorporated by reference). Thus for practical clinical use, a preferred mode of CD3 co-engagement for redirected killing of targets cells is monovalent binding that results in activation only upon engagement with the co-engaged target. Thus, in one embodiment, the heterodimeric antibody of the disclosure provides the advantage of monovalent binding to CD3 and bivalent binding to STEAP1 in a format that provides efficient antibody production.

An exemplary heterodimeric antibody format comprising one heavy chain having a single chain Fv (scFv) and a second heavy chain in a "regular" Fab format, i.e., comprising a variable heavy chain and a light chain. Put another way, the heterodimeric antibody comprises a) a first heavy chain comprising a first variable Fc domain and a single chain Fv region (scFv) that binds a first antigen (optionally CD3); b) a second heavy chain comprising a second variable Fc domain and a first variable heavy domain; and c) a first light chain comprising a first variable light domain and a first constant light domain, wherein the first variable heavy domain and the first variable light domain bind to a second antigen (optionally STEAP1). To illustrate, the construct comprises one monomer having scFv region-domain linker-Fc domain and a second monomer having a VH-CH1-hinge-CH2-CH3 plus associated light chain, optionally with heterodimerization variants, including steric and pI variants, Fc and FcRn variants, and additional antigen-binding domains (with optional linkers) included in these regions. In some embodiments, the linker is a hinge region or a fragment thereof. This structure is sometimes referred to herein as the XmAb format, the "triple F" format (scFv-FAb-Fc) or the "bottle-opener" format. The two chains are preferably brought together by the use of amino acid variants in the constant regions (e.g., the Fc domain and/or the hinge region) that promote the formation of heterodimeric antibodies as is described more fully below. Preferably, the scFv binds CD3, and optionally includes a positively charged scFv linker. Alternatively, the scFv binds STEAP1. The "triple F" format is further described in U.S. Pat. No. 9,822,186, incorporated by reference herein in its entirety and particularly with respect to the disclosure of heterodimeric antibody structure.

In another aspect, the bispecific antigen-binding protein is a heterodimeric antibody comprising a first monomer comprising a first heavy chain comprising a first variable heavy domain, first constant heavy chain comprising a first CH1 domain and a first Fc domain, with a scFv comprising a scFv variable light domain, an scFv linker, and a scFv variable heavy domain. The scFv is covalently attached between the C-terminus of the CH1 domain of the heavy constant domain and the N-terminus of the first Fc domain using domain linker(s), and the scFv binds CD3. The heterodimeric antibody further comprises a second monomer comprising a second heavy chain comprising a second variable heavy domain and a second constant heavy chain comprising a second Fc domain. The heterodimeric antibody further utilizes a common light chain comprising a variable light domain and a constant light domain, that associates with the heavy chains to form two identical Fabs that bind STEAP1. This format is sometimes referred to herein as the "XmAb$^{2+1}$" format due to the bivalent binding to one target antigen. Thus, in one embodiment, the heterodimeric antibody of the disclosure provides the advantage of monovalent binding to CD3 and bivalent binding to STEAP1 in a format that provides efficient antibody production.

As described further below, the heterodimeric antibody may also include mutations to produce skew variants, pI variants, ablation variants, additional Fc variants, etc. For example, in various aspects, the first and said second Fc domains have a set of amino acid substitutions selected from the group consisting of S364K/E357Q:L368D/K370S; L368D/K370S:S364K; L368E/K370S:S364K; T411T/E360E/Q362E:D401K; L368D/K370S:S364K/E357L and K370S:S364K/E357Q.

An illustration of the XmAb$^{2+1}$ heterodimeric antibody format of the instant disclosure is provided in FIG. 1. The scFv domain and provision of two Fab portions form three antigen-binding domains, wherein the Fab portions of the two monomers bind STEAP1 and the scFv domain binds CD3. The scFv domain is inserted between the Fc domain and the CH1-Fv region of one of the monomers.

The heterodimeric antibody is preferably of the IgG class, which has several subclasses, including, but not limited to IgG1, IgG2, IgG3, and IgG4, although IgM, IgD, IgG, IgA, and IgE also are contemplated. It should be understood that antibodies can also comprise hybrids of isotypes and/or subclasses. For example, pI engineering of IgG1/G2 hybrids, as shown in U.S. Patent Publication No. 2009/0163699, incorporated by reference, is contemplated as part of the disclosure.

There are a number of mechanisms that can be used to generate the heterodimers of the present disclosure. In addition, as will be appreciated by those in the art and described more fully below, these mechanisms can be combined to ensure high heterodimerization.

One mechanism is generally referred to in the art as "knobs and holes" ("KIH"), referring to amino acid engineering that creates steric influences to favor heterodimeric formation and disfavor homodimeric formation can also optionally be used; this is sometimes referred to as "knobs and holes," as described in U.S. Patent Publication No. 20130205756, Ridgway et al., Protein Engineering 9(7):617 (1996); Atwell et al., J. Mol. Biol. 1997 270:26; and U.S. Pat. No. 8,216,805, all of which are hereby incorporated by reference in their entirety, particularly with respect to the disclosure of heterodimeric antibody production. In addition, as described in Merchant et al., Nature Biotech. 16:677 (1998), these "knobs and hole" mutations can be combined with disulfide bonds to skew formation to heterodimerization. An example of mutations includes T366S/L368A/Y407V paired with T366W, as well as this variant with a bridging disulfide, T366S/L368A/Y407V/Y349C paired with T366W/S354C, particularly in combination with other heterodimerization variants including pi variants as outlined below.

An additional mechanism that finds use in the generation of heterodimers is sometimes referred to as "electrostatic steering" as described in Gunasekaran et al., J. Biol. Chem. 285(25):19637 (2010), hereby incorporated by reference in its entirety. This is sometimes referred to herein as "charge pairs." In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants." These include, but are not limited to, D221E/P228E/L368E paired with D221R/P228R/K409R (i.e., these are monomer corresponding sets) and C220E/P228E/368E paired with C220R/E224R/P228R/K409R. In some embodiments of framework regions, a position 220 mutation removes a cysteine no longer needed for heavy and light chain disulfide formation. "Steric variants" are an optional embodiment of the disclosure.

There are several mechanisms that can lead to ease of purifying heterodimeric proteins; one relies on the use of pI variants, such that each monomer has a different pI, thus allowing the isoelectric purification of A-A, A-B and B-B dimeric proteins. Alternatively, separation may be performed on the basis of size. It is also possible to "skew" the formation of heterodimers over homodimers, as is generally outlined below. Thus, a combination of steric heterodimerization variants and pI or charge pair variants may be used in the context of the disclosure. Additionally, the scFv can include a charged scFv linker (either positive or negative), that give a further pI boost for purification purposes. As will be appreciated by those in the art, some Triple F formats are useful with just charged scFv linkers and no additional pi adjustments, although the invention does provide the use of skew variants with charged scFv linkers as well (and combinations of Fc, FcRn and KO variants discussed herein).

In embodiments that utilize pI as a separation mechanism, amino acid variants can be introduced into one or both of the monomer polypeptides; that is, the pI of one of the monomers (referred to herein for simplicity as "monomer A") can be engineered away from monomer B, or both monomer A and B change be changed, with the pI of monomer A increasing and the pI of monomer B decreasing. The pI changes of either or both monomers can be done by removing or adding a charged residue (for example, a neutral amino acid is replaced by a positively or negatively charged amino acid residue, e.g., glycine to glutamic acid), changing a charged residue from positive or negative to the opposite charge (e.g., aspartic acid to lysine), or changing a charged residue to a neutral residue (e.g., loss of a charge; lysine to serine). In addition, suitable pI variants for use in the creation of heterodimeric antibodies herein are those that are isotypic, e.g., importing pI variants from different IgG isotypes such that pI is changed without introducing significant immunogenicity; see FIG. 29 from U.S. Patent Publication No. 20140288275, hereby incorporated by reference in its entirety.

Accordingly, an embodiment provides for creating a sufficient change in pI in at least one of the monomers such that heterodimers can be separated from homodimers. This can be accomplished using a "wild type" heavy chain constant region and a variant region that has been engineered to either increase or decrease its pI (wt A−+B or wt A−−B), or by increasing one region and decreasing the other region (A+−B− or A−B+). It should be noted that in this discussion it does not matter which monomer comprises the scFv and which the Fab. A schematic associated with the use of pI variants is set forth in FIG. 34 of U.S. Pat. No. 9,822,186 (incorporated herein by reference in its entirety, and particularly with respect to the discussion of heterodimeric antibody variants and anti-CD3 sequences). pI variants may be combined with skew variants in a "plug and play" format, in that the effects of the variants transfer into different antibodies with different Fv regions easily and are very stable.

Thus, in general, an aspect of the disclosure includes amino acid variants in the constant regions of antibodies that are directed to altering the isoelectric point (pI) of at least one, if not both, of the monomers of the antibody to form "pI heterodimers" (i.e., "pI antibodies") by incorporating amino acid substitutions ("pI variants" or "pI substitutions") into one or both of the monomers. The separation of the heterodimers from the two homodimers can be accomplished if the pIs of the two monomers differ by as little as 0.1 pH unit, e.g., a difference of 0.2, 0.3, 0.4 and 0.5 pH or greater.

The number of pI variants to be included on each or both monomer(s) to achieve desired separation will depend, in part, on the starting pI of the scFv and Fab(s). That is, to determine which monomer to engineer or in which "direction" (e.g., more positive or more negative), the Fv sequences of the two target antigens are calculated and a decision is made from there. As is known in the art, different Fvs will have different starting pIs which are exploited. In general, the pIs are engineered to result in a total pI difference of each monomer of at least about 0.1 logs, with 0.2 to 0.5 being preferred.

Furthermore, in some cases (depending on the format) heterodimers can be separated from homodimers on the basis of size (e.g., molecular weight). For example, as shown in some embodiments of FIG. 18A-I, some formats result in homodimers and heterodimers with different sizes (e.g., for bottle openers, one homodimer is a "dual scFv" format, one homodimer is a standard antibody, and the heterodimer has one Fab and one scFv). In addition, as depicted in FIG. 18A-I, it is possible that some antigens are bound bivalently (e.g., two antigen-binding sites to a single antigen). As will be appreciated, any combination of Fab and scFvs can be utilized to achieve the desired result and combinations.

In the case where pI variants are used to achieve heterodimerization, by using the constant region(s) of the heavy chain(s), a more modular approach to designing and purifying multispecific proteins, including antibodies, is provided. Thus, in some embodiments, heterodimerization variants (including skew and purification heterodimerization variants) are not included in the variable regions, such that each individual antibody must be engineered. In addition, in some embodiments, the possibility of immunogenicity resulting from the pI variants is significantly reduced by importing pI variants from different IgG isotypes such that pI is changed without introducing significant immunogenicity. Thus, an additional problem to be solved is the elucidation of low pI constant domains with high human sequence content, e.g., the minimization or avoidance of non-human residues at any particular position.

A side benefit that can occur with pI engineering is also the extension of serum half-life and increased FcRn binding. That is, as described in U.S. Patent Publication No. 20120028304 (incorporated by reference in its entirety), lowering the pI of antibody constant domains (including those found in antibodies and Fc fusions) can lead to longer serum retention in vivo. These pI variants for increased serum half life also facilitate pI changes for purification.

The heterodimeric fusion proteins of the disclosure can take on a variety of configurations, as are generally depicted in FIGS. 18A-I. Some figures depict "single ended" configurations, where there is one type of specificity on one "arm" of the molecule and a different specificity on the other "arm." Other figures depict "dual ended" configurations, where there is at least one type of specificity at the "top" of the molecule and one or more different specificities at the "bottom" of the molecule. One heterodimeric scaffold that finds use in the present disclosure is the "triple F" or "bottle opener" scaffold format as depicted in FIG. 18A and described above. There are several distinct advantages to the "triple F" format. Antibody analogs relying on two scFv constructs often have stability and aggregation problems, which can be alleviated by the construct described herein by the addition of a "regular" heavy and light chain pairing. In addition, as opposed to formats that rely on two heavy chains and two light chains, there is no issue with the incorrect pairing of heavy and light chains (e.g., heavy 1 pairing with light 2, etc.). Additional useful antigen-binding protein formats are described below.

In various aspects, the scFv of the heterodimeric antibody comprises the anti-CD3 CDR sequences described herein. For example, in various aspects, the scFv comprises vhCDR1 comprising SEQ ID NO: 170, vhCDR2 comprising SEQ ID NO: 171, vhCDR3 comprising SEQ ID NO: 172, vlCDR1 comprising SEQ ID NO: 174, vlCDR2 comprising SEQ ID NO: 175, and vlCDR3 comprising SEQ ID NO: 176. For example, the scFv optionally comprises a variable heavy region of SEQ ID NO: 169 and a variable light region of SEQ ID NO: 173. In various aspects, the scFv comprises the sequence of SEQ ID NO: 44.

In some embodiments, the scFv comprises an amino acid sequence set forth in FIG. 19, e.g., the amino acid sequence set forth in SEQ ID NO: 44. The sequences set forth in FIG.

19 provide antigen-binding domains of differing affinities. In some indications, stronger affinities may be preferred, while in others, lesser affinities can find use. Accordingly, in some embodiments the disclosure provides heterodimeric antibodies comprising anti-CD3 antigen-binding domains that are "strong" or "high affinity" binders to CD3 (e.g., one example are heavy and light variable domains depicted as H1.30_L1.47 (optionally including a charged linker as appropriate)). In other embodiments, the disclosure provides heterodimeric antibodies comprising anti-CD3 antigen-binding domains that are "lite" or "lower affinity" binders to CD3.

Typical scFv linkers are well known in the art and are generally 10 to 25 amino acids in length and include glycines and serines. By "charged scFv linker" is meant a scFv linker that utilizes charged amino acids for use in the creation and purification of heterodimeric antibodies that include at least one scFv. Suitable charged scFv linkers are shown in FIGS. 8A, 8B and 19, although others can be used. In general, the charged scFv linkers contemplated for use in the context of the disclosure have a charge change from 3 to 8 (3, 4, 5, 6, 7 or 8 all being possible) as compared to the standard uncharged scFv linkers such as (GGGGS)$_{3-5}$ (SEQ ID NO:179) sequences traditionally used (either negative or positive). The charged scFv optionally comprises an amino acid sequence selected from IRPRAIGGSKPRVA (SEQ ID NO: 145), GKGGSGKGGSGKGGS (SEQ ID NO: 146), GGKGSGGKGSGGKGS (SEQ ID NO: 147), GGGKSGGGKSGGGKS (SEQ ID NO: 148), GKGKSGKGKSGKGKS (SEQ ID NO: 149), GGGKSGGKGSGKGGS (SEQ ID NO: 150), GKPGSGKPGSGKPGS (SEQ ID NO: 151), GKPGSGKPGSGKPGSGKPGS (SEQ ID NO: 152), or GKGKSGKGKSGKGKSGKGKS (SEQ ID NO: 153). In various aspects, the scFv comprises the amino acid sequence GKPGSGKPGSGKPGSGKPGS (SEQ ID NO: 152).

In exemplary aspects, the scFv comprises CDR sequences, variable region sequences, a scFv linker sequence, or a scFv sequence having at least about 70%, at least about 80%, at least about 85%, at least about 90%, or has greater than about 90% (e.g., about 91%, about 92%, about 93%, about 94%, about 95%, about 96%, about 97%, about 98%, or about 99%) sequence identity to any of the sequences provided herein (e.g., CDR sequences of any one or more of SEQ ID NOs: 4-6, 8-10, 11-17, 21, 23-25, 27-29, 30-35, 170-173, and 174-176, variable region sequences of any one or more of SEQ ID NOs: 3, 7, 22, 26, 41, 42, 45, 46, 49, 50, 53, 54, 57, 58, 61, 62, 65, 66, 69, 70, 73, 74, 77, 78, 81, 82, 85, 86, 89, 90, 93, 94, 97, 98, 101, 102, 105, 106, 109, 110, 113, 114, 117, 118, 121, 122, 125, 126, 129, 130, 133, 134, 137, 138, 141, 142, 169, 173, and 182-186; scFv linker sequence of any one of SEQ ID NOs: 143-168, and/or scFv sequence of any one of SEQ ID NO: 19, 20, 38, 40, 43, 44, 47, 48, 51, 52, 55, 56, 59, 60, 63, 64, 67, 68, 71, 72, 75, 76, 79, 80, 83, 84, 87, 88, 91, 92, 95, 96, 99, 100, 104, 104, 107, 108, 111, 112, 115, 116, 119, 120, 123, 124, 127, 128, 131, 132, 135, 136, 139, and 140). For example, the scFv may comprise CDR sequences as set forth in any one or more of SEQ ID NO: 4-6, 8-10, 11-17, 21, 23-25, 27-29, 30-35, 170-173, and 174-176 but comprising one or two amino acid substitutions. Alternatively, in various aspects, the scFv may comprise variable region sequences which are modified with respect to SEQ ID NO: 3, 7, 22, 26, 41, 42, 45, 46, 49, 50, 53, 54, 57, 58, 61, 62, 65, 66, 69, 70, 73, 74, 77, 78, 81, 82, 85, 86, 89, 90, 93, 94, 97, 98, 101, 102, 105, 106, 109, 110, 113, 114, 117, 118, 121, 122, 125, 126, 129, 130, 133, 134, 137, 138, 141, 142, 169, 173, or 182-186, wherein the modifications are outside the CDR sequences.

The first variable heavy domain and the second variable heavy domain of the heterodimeric antibody, in various aspects, comprises the anti-STEAP1 CDR or variable region sequences described herein. For example, in some embodiments, the first variable heavy domain and the second variable heavy domain of the heterodimeric antibody comprise vhCDR1 comprising SEQ ID NO: 14, vhCDR2 comprising SEQ ID NO: 15 or SEQ ID NO: 21, and vhCDR3 comprising SEQ ID NO: 16; and the variable light domain comprises vlCDR1 comprising SEQ ID NO: 11, vlCDR2 comprising SEQ ID NO: 12, and vlCDR3 comprising SEQ ID NO: 13. Alternatively, the first variable heavy domain and the second variable heavy domain comprise vhCDR1 comprising SEQ ID NO: 33, vhCDR2 comprising SEQ ID NO: 34, and vhCDR3 comprising SEQ ID NO: 35; and the variable light domain comprises vlCDR1 comprising SEQ ID NO: 30, vlCDR2 comprising SEQ ID NO: 31, and vlCDR3 comprising SEQ ID NO: 32. In preferred embodiments, the first variable heavy domain and the second variable heavy domain comprise SEQ ID NO: 182 or SEQ ID NO: 184 and the variable light domain comprises SEQ ID NO: 183. Alternatively, the first variable heavy domain and the second variable heavy domain comprise SEQ ID NO: 185 and the variable light domain comprises SEQ ID NO: 186.

In various aspects of the disclosure, the heterodimeric antibody comprises a) a first monomer comprising the sequence of SEQ ID NO: 19 or 20, a second monomer comprising the sequence of SEQ ID NO: 18, and a common light chain comprising the sequence of SEQ ID NO: 17; or b) a first monomer comprising the sequence of SEQ ID NO: 38, a second monomer comprising the sequence of SEQ ID NO: 37, and a common light chain comprising the sequence of SEQ ID NO: 36.

In various aspects of the disclosure, the heterodimeric antibody comprises a first monomer comprising the sequence of SEQ ID NO: 202 or 207, a second monomer comprising the sequence of SEQ ID NO: 201 or 203, and a common light chain comprising the sequence of SEQ ID NO: 200 (e.g., a first monomer comprising the sequence SEQ ID NO: 202, a second monomer comprising the sequence of SEQ ID NO: 201, and a light chain comprising the sequence of SEQ ID NO: 200; or a first monomer comprising the sequence SEQ ID NO: 207, a second monomer comprising the sequence of SEQ ID NO: 203, and a light chain comprising the sequence of SEQ ID NO: 200). Alternatively; the heterodimeric antibody may comprise a first monomer comprising the sequence of SEQ ID NO: 206, a second monomer comprising the sequence of SEQ ID NO: 205, and a common light chain comprising the sequence of SEQ ID NO: 204.

In exemplary aspects, the first and/or second variable heavy domain may comprise CDR sequences or variable region sequences having at least about 70%, at least about 80%, at least about 85%, at least about 90%, or has greater than about 90% (e.g., about 91%, about 92%, about 93%, about 94%, about 95%, about 96%, about 97%, about 98%, or about 99%) sequence identity to any of the sequences provided herein (e.g., CDR sequences of any one or more of SEQ ID NO: 4-6, 14-17, 21, 23-25, 33-35, and 170-172 or variable region sequences of any one of SEQ ID NO: 3, 22, 41, 45, 49, 53, 57, 61, 65, 69, 73, 77, 81, 85, 89, 93, 97, 101, 105, 109, 113, 117, 121, 125, 129, 133, 137, 141, 169, 182, 184, and 185). For example, the first and/or second variable heavy domain may comprise CDR sequences as set forth in any one or more of SEQ ID NO: 4-6, 14-17, 21, 23-25, 33-35, and 170-172 but comprising one or two amino acid substitutions. Alternatively, in various aspects, the first and/or second variable heavy domain may comprise variable region sequences which are modified with respect to SEQ ID NO: 3, 22, 41, 45, 49, 53, 57, 61, 65, 69, 73, 77, 81, 85, 89, 93, 97, 101, 105, 109, 113, 117, 121, 125, 129, 133, 137, 141, 169 182, 184, or 185, wherein the modifications are outside the CDR sequences. Similarly, the variable light domain may comprise CDR sequences or variable region sequences having at least about 70%, at least about 80%, at least about 85%, at least about 90%, or has greater than about 90% (e.g., about 91%, about 92%, about 93%, about 94%, about 95%, about 96%, about 97%, about 98%, or about 99%) sequence identity to any of the sequences provided herein (e.g., CDR sequences of any one or more of SEQ ID NO: 8-10, 11-13, 27-29, 30-32, and 174-176 or variable region sequences of any one of SEQ ID NO: 7, 26, 42, 46, 50, 54, 58, 62, 66, 70, 74, 78, 82, 86, 90, 94, 98, 102, 106, 110, 114, 118, 122, 126, 130, 134, 138, 142, 173, 183, and 186), in various aspects. For example, the variable light domain may comprise CDR sequences as set forth in any one or more of SEQ ID NO: 8-10, 11-13, 27-29, 30-32, and 174-176, but comprising one or two amino acid substitutions. Alternatively, in various aspects, the variable light domain may comprise variable region sequences which are modified with respect to SEQ ID NO: 7, 26,42,46,50,54,58, 62,66,70,74,78,82,86,90,94,98,102,106,110,114,118,122, 126, 130, 134, 138, 142, 173, 183, or 186, wherein the modifications are outside the CDR sequences. If desired, the first monomer may comprise an amino acid sequence having at least about 70%, at least about 80%, at least about 85%, at least about 90%, or has greater than about 90% (e.g., about 91%, about 92%, about 93%, about 94%, about 95%, about 96%, about 97%, about 98%, or about 99%) sequence identity to any of the sequences provided herein (SEQ ID NO: 19, 20, 38, 202, 206 or 207); the second monomer may comprise an amino acid sequence having at least about 70%, at least about 80%, at least about 85%, at least about 90%, or has greater than about 90% (e.g., about 91%, about 92%, about 93%, about 94%, about 95%, about 96%, about 97%, about 98%, or about 99%) sequence identity to any of the sequences provided herein (SEQ ID NO: 18, 199 or 37; or SEQ ID NO: 202, 207 or 206); and/or the common light chain may comprise an amino acid sequence having at least about 70%, at least about 80%, at least about 85%, at least about 90%, or has greater than about 90% (e.g., about 91%, about 92%, about 93%, about 94%, about 95%, about 96%, about 97%, about 98%, or about 99%) sequence identity to any of the sequences provided herein (SEQ ID NO: 17, 36, 200 or 204).

In some embodiments, a full length heterodimeric antibody is employed. By "full length" is meant the structure that constitutes the natural biological form of an antibody, including variable and constant regions, including one or more modifications as outlined herein. The heterodimeric antibody of the disclosure can be monoclonal, synthetic, chimeric, and/or humanized. Antigen-binding antibody fragments in the context of the heterodimeric antibody contain at least one constant domain which can be engineered to produce heterodimers, such as pI engineering. Other antibody fragments include those that contain one or more of the CH1, CH2, CH3, hinge and CL domains of the invention that have been pI engineered. For example, Fc fusions are fusions of the Fc region (CH2 and CH3, optionally with the hinge region) fused to another protein. A number of Fc fusions are known the art and can be improved by the addition of the heterodimerization variants of the invention. Antibody fusions can be made comprising CH1; CH1, CH2 and CH3; CH2; CH3; CH2 and CH3; CH1 and CH3, any or all of which can be made optionally with the hinge region, utilizing any combination of heterodimerization variants described herein.

The antigen-binding proteins, including heterodimeric antibodies, of the disclosure are generally isolated or recombinant. Nucleic acids encoding all or part of the heterodimeric antibody described herein, vectors, and host cells are described herein and contemplated as part of the disclosure.

Antibody Structure/Fc Region Modifications

The disclosure includes antibodies with modified Fc variants having amino acid modifications relative to the wild-type antibody sequence. The variants are defined according to the amino acid modifications that compose them. Thus, for example, N434S or 434S is an Fc variant with the substitution serine at position 434 relative to the parent Fc polypeptide, wherein the numbering is according to the EU index. Likewise, M428L/N434S defines an Fc variant with the substitutions M428L and N434S relative to the parent Fc polypeptide. The identity of the wildtype amino acid may be unspecified, in which case the aforementioned variant is referred to as 428L/434S. The order in which substitutions are provided is arbitrary, i.e., for example, 428L/434S is the same Fc variant as M428L/N434S, and so on. The modification can be an addition, deletion, or substitution. Substitutions can include naturally occurring amino acids and, in some cases, synthetic amino acids. Examples include U.S. Pat. No. 6,586,207; U.S. Publication No. 20040214988; International Patent Publication Nos. WO 98/48032, WO 03/073238, WO 05/35727A2, and WO 05/74524A2; J. W. Chin et al., (2002), Journal of the American Chemical Society 124:9026-9027; J. W. Chin, & P. G. Schultz, (2002), ChemBioChem 11:1135-1137; J. W. Chin, et al., (2002), PICAS United States of America 99:11020-11024; and, L. Wang, & P. G. Schultz, (2002), Chem. 1-10, all entirely incorporated by reference.

For all positions discussed in the disclosure that relate to antibodies and other antigen-binding proteins, unless otherwise noted, amino acid position numbering is according to the EU index. The EU index or EU index as in Kabat or EU numbering scheme refers to the numbering of the EU antibody (Edelman et al., 1969, Proc Natl Acad Sci USA 63:78-85, hereby entirely incorporated by reference.) For example, it is understood that each variable heavy region (VH) and variable light region (VL) is composed of three hypervariable regions ("complementary determining regions," "CDRs") and four FRs, arranged from amino-terminus to carboxy-terminus in the following order: FR1-CDR1-FR2-CDR2-FR3-CDR3-FR4. The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g., residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917).

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3). A useful comparison of CDR numbering is as below, see Lafranc et al, Dev. Comp. Immunol. 27(1):55-77 (2003):

|  | Kabat + Chothia | IMGT | Kabat | AM | Chothia | Contact |
|---|---|---|---|---|---|---|
| vhCDR1 | 26-35 | 27-38 | 31-35 | 26-35 | 26-32 | 30-35 |
| vhCDR2 | 50-65 | 56-65 | 50-65 | 50-58 | 52-56 | 47-58 |
| vhCDR3 | 95-102 | 105-117 | 95-102 | 95-102 | 95-102 | 93-101 |
| vlCDR1 | 24-34 | 27-38 | 24-34 | 24-34 | 24-34 | 30-36 |
| vlCDR2 | 50-56 | 56-65 | 50-56 | 50-56 | 50-56 | 46-55 |
| vlCDR3 | 89-97 | 105-117 | 89-97 | 89-97 | 89-97 | 89-96 |

Throughout the specification, the Kabat numbering system is generally used when referring to a residue in the variable domain (approximately, residues 1-107 of the light chain variable region and residues 1-113 of the heavy chain variable region) (e.g, Kabat et al., supra (1991)).

The carboxy-terminal portion of each chain defines a constant region primarily responsible for effector function. Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, NIH publication, No. 91-3242, E. A. Kabat et al., entirely incorporated by reference).

In the IgG subclass of immunoglobulins, there are several immunoglobulin domains in the heavy chain. By "immunoglobulin (Ig) domain" herein is meant a region of an immunoglobulin having a distinct tertiary structure. Of interest are the heavy chain domains, including, the constant heavy (CH) domains and the hinge domains. In the context of IgG antibodies, the IgG isotypes each have three CH regions. Accordingly, "CH" domains in the context of IgG are as follows: "CH1" refers to positions 118-220 according to the EU index as in Kabat. "CH2" refers to positions 237-340 according to the EU index as in Kabat, and "CH3" refers to positions 341-447 according to the EU index as in Kabat. As shown herein and described below, the pI variants can be in one or more of the CH regions, as well as the hinge region, discussed below. In various aspects, the sequences depicted herein start at the CH1 region, position 118; the variable regions are not included except as noted.

Another type of Ig domain of the heavy chain is the hinge region. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230. As noted herein, pI variants can be made in the hinge region as well.

By "Fc" or "Fc region" or "Fc domain" as used herein is meant the polypeptide comprising the constant region of an antibody excluding the first constant region immunoglobulin domain and in some cases, part of the hinge. Thus Fc refers to the last two constant region immunoglobulin domains of IgA, IgD, and IgG, the last three constant region immunoglobulin domains of IgE and IgM, and the flexible hinge N-terminal to these domains. For IgA and IgM, Fc may include the J chain. For IgG, the Fc domain comprises immunoglobulin domains Cγ2 and Cγ3 (Cγ2 and Cγ3) and the lower hinge region between Cγ1 (Cγ1) and Cγ2 (Cγ2). Although the boundaries of the Fc region may vary, the human IgG heavy chain Fc region is usually defined to include residues C226 or P230 to its carboxyl-terminus, wherein the numbering is according to the EU index as in Kabat.

Amino acid variants may be introduced into the antigen-binding protein (e.g., bispecific antibody) of the disclosure to add additional functionalities. For example, amino acid changes within the Fc region can be added (either to one monomer or both) to facilitate increased ADCC or CDC (e.g., altered binding to Fcγ receptors), to allow or increase yield of the addition of toxins and drugs (e.g., for ADC), as well as to increase binding to FcRn and/or increase serum half-life of the resulting molecules. Effector functions that may be adjusted by varying the amino acid sequence include, but are not limited to, ADCC, ADCP, and CDC. Any and all of the variants outlined herein can be optionally and independently combined with other variants.

By "FcRn" or "neonatal Fc Receptor" is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. A variety of FcRn variants used to increase binding to the FcRn receptor, and in some cases, to increase serum half-life. Fc variants conferring increased binding to the FcRn receptor and corresponding increases in serum half life include, but are not limited to, 434A, 434S, 428L, 308F, 259I, 428L/434S, 259I/308F, 436I/428L, 436I or V/434S, 436V/428L, 252Y, 252Y/254T/256E and 259I/308F/428L. For clarity, as each heavy chain is different, FcRn variants (as well as the Fc variants) can reside on one or both monomers.

Another category of functional variants are "Fcγ ablation variants" or "Fc knock out (FcKO or KO) variants." In these embodiments, for some therapeutic applications, it is desirable to reduce or remove the normal binding of the Fc domain to one or more or all of the Fcγ receptors (e.g. FcγR1, FcγRIIa, FcγRIIb, FcγRIIIa, etc.) to avoid additional mechanisms of action. By "Fc gamma receptor," "FcγR" or "FcgammaR" is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference). An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2). In many embodiments, it is generally desirable to ablate FcγRIIIa binding to eliminate or significantly reduce ADCC activity. FIG. 36 of U.S. Pat. No. 9,822,186 depicts the use of an Fc knock-out (or ablation variant) that retains wild type stability but removes all FcγR binding.

Representative ablation variants include those selected from the group consisting of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G, and E233P/L234V/L235A/G236del. It should be noted that the ablation variants referenced herein ablate FcγR binding but generally not FcRn binding.

As is known in the art, the Fc domain of human IgG1 has the highest binding to the Fγ receptors, and thus ablation variants can be used when the constant domain (or Fc domain) in the backbone of the heterodimeric antibody is IgG1. Alternatively, or in addition to ablation variants in an IgG1 background, mutations at the glycosylation position 297 (generally to A or S) can significantly ablate binding to FcγRIIIa, for example. Human IgG2 and IgG4 have naturally reduced binding to the Fcγ receptors, and thus those backbones can be used with or without the ablation variants.

Deamidation can severely impact antibody activity and stability. In various aspects, the heterodimeric antibody comprises one or more substitutions to remove deamidation sites. In this regard, the heterodimeric antibody optionally comprises a substitution at position N67, such as the substitution N67Q.

Heterodimeric Heavy Chain Constant Regions

The disclosure provides heterodimeric antibodies based on the use of monomers containing variant heavy chain constant regions as a first domain. By "monomer" herein is meant one half of the heterodimeric protein. It should be noted that traditional antibodies are actually tetrameric (two heavy chains and two light chains). For ease of reference, in the context of the present disclosure, a pair comprising a heavy chain and a light chain is considered a "monomer." A heavy chain region comprising the scFv (and, in some instances a Fab) is considered a monomer. Essentially, each monomer comprises sufficient heavy chain constant region to allow heterodimerization engineering, whether that be the entire constant region, e.g., CH1-hinge-CH2-CH3, the Fc region (CH2-CH3), or just the CH3 domain.

The variant heavy chain constant regions can comprise all or part of the heavy chain constant region, including the full length construct, CH1-hinge-CH2-CH3, or portions thereof, including for example CH2-CH3 or CH3 alone. In addition, the heavy chain region of each monomer can be the same backbone (CH1-hinge-CH2-CH3 or CH2-CH3) or different. N- and C-terminal truncations and additions are also included within the definition; for example, some pI variants include the addition of charged amino acids to the C-terminus of the heavy chain domain.

In addition to the heterodimerization variants (e.g., steric and pI variants) outlined herein, the heavy chain regions may also contain additional amino acid substitutions, including changes for altering FcγR and FcRn binding.

The heterodimerization variants include a number of different types of variants, including, but not limited to, steric variants (including charge variants) and pI variants, that can be optionally and independently combined with any other variants. In these embodiments, it is important to match "monomer A" with "monomer B," that is, if a heterodimeric protein relies on both steric variants and pI variants, these need to be correctly matched to each monomer, e.g., the set of steric variants that work (1 set on monomer A, 1 set on monomer B) is combined with pI variant sets (1 set on monomer A, 1 set on monomer B), such that the variants on each monomer are designed to achieve the desired function. In the case for example where steric variants may also change the charge, the correct sets have to be matched to the correct monomer.

The heterodimerization variants outlined herein (for example, including but not limited to those variants shown in the Figures), can be optionally and independently combined with any other variants, and on any other monomer. What is important for the heterodimerization is that there are "sets" of variants, one set for one monomer and one set for the other. Whether these are combined 1 to 1 (e.g., monomer 1 listings can go together) or switched (monomer 1 pI variants with monomer 2 steric variants) is irrelevant. However, "strandedness" should be preserved when combinations are made as outlined above such that heterodimerization is favored; e.g., charge variants that increase pI should be used with increased pI variants and/or an scFv linker with increase pI, etc. By "strandedness" in the context of the monomers of the heterodimeric proteins is meant that, similar to the two strands of DNA that "match," heterodimerization variants are incorporated into each monomer so as to preserve the ability to "match" to form heterodimers. For example, if some pI variants are engineered into monomer A (e.g., making the pI higher) then steric variants that are "charge pairs" that can be utilized as well do not interfere with the pI variants, e.g., the charge variants that make a pI higher are put on the same "strand" or "monomer" to preserve both functionalities. Furthermore, for the additional Fc variants (such as for FcγR binding, FcRn binding, ablation variants etc.), either monomer, or both monomers, can include any of the listed variants, independently and optionally. In some cases, both monomers have the additional variants, and in some only one monomer has the additional variants, or they can be combined.

Steric Variants

In some embodiments, the formation of heterodimers is facilitated by the addition of steric variants. That is, by changing amino acids in each heavy chain, different heavy chains are more likely to associate to form the heterodimeric structure than to form homodimers with the same Fc amino acid sequences. Representative suitable steric variants are shown in the Figures.

One mechanism for producing steric variants is the "knobs and holes" mechanism described above. An additional mechanism that finds use in the generation of heterodimers is sometimes referred to as "electrostatic steering" as described in Gunasekaran et al., J. Biol. Chem. 285(25): 19637 (2010), hereby incorporated by reference in its entirety. This is sometimes referred to herein as "charge pairs." In this embodiment, electrostatics are used to skew the formation towards heterodimerization. These may also have an effect on pI, and thus on purification, and thus could, in some cases, also be considered pI variants. However, as these were generated to force heterodimerization and were not used as purification tools, they are classified as "steric variants." These include, but are not limited to, variants resulting in greater than 75% heterodimerization such as D221E/P228E/L368E paired with D221R/P228R/K409R (e.g., these are "monomer corresponding sets") and C220E/P228E/368E paired with C220R/E224R/P228R/K409R.

In some embodiments, the skew variants advantageously and simultaneously favor heterodimerization based on both the "knobs and holes" mechanism as well as the "electrostatic steering" mechanism. These variants come in "pairs" of "sets." That is, one set of the pair is incorporated into the first monomer and the other set of the pair is incorporated into the second monomer. It should be noted that these sets do not necessarily behave as "knobs in holes" variants, with a one-to-one correspondence between a residue on one monomer and a residue on the other. That is, these pairs of sets may instead form an interface between the two monomers that encourages heterodimer formation and discourages homodimer formation, allowing the percentage of heterodimers that spontaneously form under biological conditions to be over 90%, rather than the expected 50% (25% homodimer A/A:50% heterodimer A/B:25% homodimer B/B). Exemplary heterodimerization "skew" variants are depicted in FIG. 4. Examples of such skew variants include pairs of sets of mutations including, but not limited to, S364K/E357Q:L368D/K370S; L368D/K370S S364K; L368E/K370S:S364K; T411T/E360E/Q362E:D401K; L368D/K370S: S364K/E357L, K370S:S364K/E357Q; and T366S/L368A/Y407V:T366W (optionally including abridging disulfide, T366S/L368A/Y407V/Y349C:T366W/S354C).

Additional monomer A and monomer B variants that can be combined with other variants, optionally and independently in any amount, such as pI variants outlined herein or other steric variants that are shown in FIG. 37 of U.S. Publication No. 2012/0149876, the figure and legend of which are incorporated expressly by reference herein.

In some embodiments, the steric variants outlined herein can be optionally and independently incorporated with any heterodimerization variants including pI variants (or other variants such as Fc variants, FcRn variants, ablation variants, etc.) into one or both monomers.

pI (Isoelectric Point) Variants for Heterodimers

In general, there are two categories of pI variants: those that increase the pI of the protein (basic changes) and those that decrease the pI of the protein (acidic changes). As described herein, all combinations of these variants can be performed: one monomer may be wild type, or a variant that does not display a significantly different pI from wild-type, and the other can be either more basic or more acidic. Alternatively, each monomer is changed, one to more basic and one to more acidic. Exemplary combinations of pI variants are shown in the Figures.

In various embodiments, for example in the FIGS. 18A, E, F, G, H and I formats, a preferred combination of pI variants has one monomer (the negative Fab side) comprising 208D/295E/384D/418E/421D variants (N208D/Q295E/N384D/Q418E/N421D when relative to human IgG1) and a second monomer (the positive scFv side) comprising a positively charged scFv linker, including (GKPGS)$_4$. However, as will be appreciated by those in the art, the first monomer includes a CH1 domain, including position 208. Accordingly, in constructs that do not include a CH1 domain (for example for antibodies that do not utilize a CH1 domain on one of the domains, for example in a dual scFv format or a "one armed" format such as those depicted in FIG. 18B, C or D), a preferred negative pI variant Fc set includes 295E/384D/418E/421D variants (Q295E/N384D/Q418E/N421D when relative to human IgG1).

Acidic pI Changes

When one monomer comprising a variant heavy chain constant domain is to be made more positive (e.g., lower the pI), one or more of the following modifications (e.g., substitutions) are suitable in the context of the disclosure: S119E, K133E, K133Q, T164E, K205E, K205Q, N208D, K210E, K210Q, K274E, K320E, K322E, K326E, K334E, R355E, K392E, a deletion of K447, adding peptide DEDE at the C-terminus, G137E, N203D, K274Q, R355Q, K392N, and Q419E. These changes are described relative to IgG1, but all isotypes can be altered this way, as well as isotype hybrids. In the case where the heavy chain constant domain is from IgG2-4, R133E and R133Q can also be used.

Basic pI Changes

When one monomer comprising a variant heavy chain constant domain is to be made more negative (e.g., increase the pI), one or more of the following exemplary substitutions are suitable in the context of the disclosure: Q196K, P217R, P228R, N276K, and H435R. These changes are described relative to IgG1, but all isotypes can be altered this way, as well as isotype hybrids.

Heterodimeric Antibody Light Chain Variants pI variants can also be made in an antibody light chain. Amino acid modifications for lowering the pI of the light chain include, but are not limited to, K126E, K126Q, K145E, K145Q, N152D, S156E, K169E, S202E, K207E, and adding peptide DEDE at the C-terminus of the light chain. Changes in this category based on the constant lambda light chain include but are not limited to one or more substitutions at R108Q, Q124E, K126Q, N138D, K145T, and Q199E. In addition, increasing the pI of the light chain also is possible and contemplated in various aspects of the disclosure.

Isotypic Variants

Figures 21A, 21B, 21C:
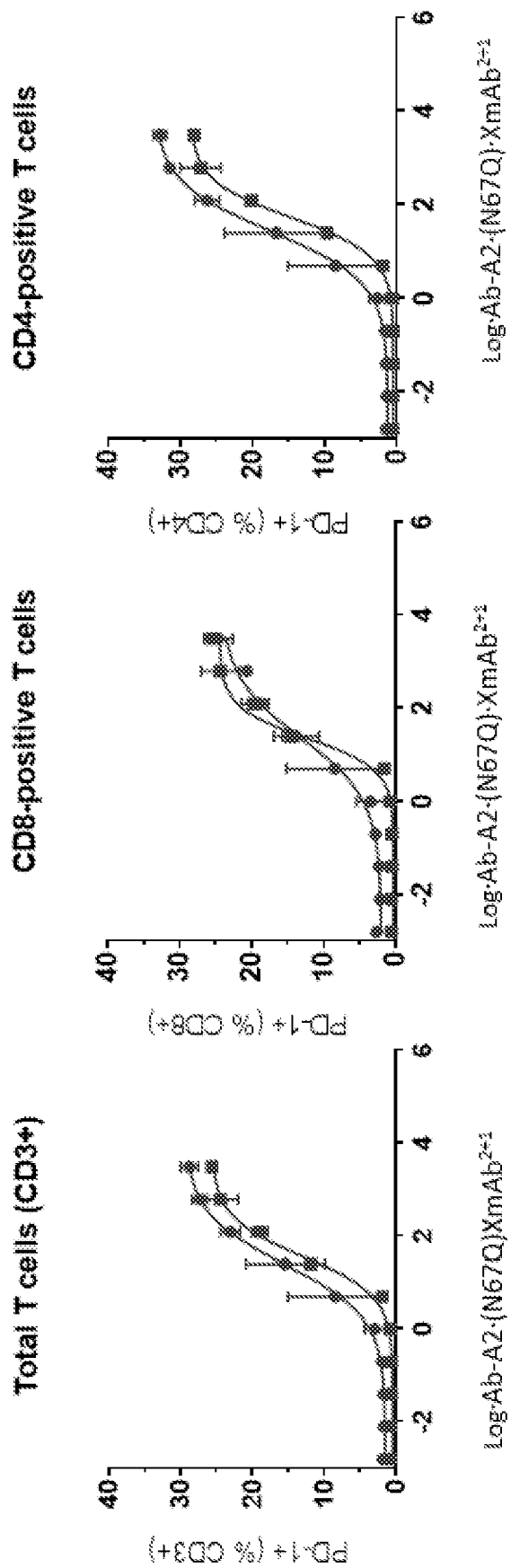
FIGS. 21A-21C are line graphs illustrating PD-1 expression (% CD3+) in total T cells (FIG. 21A), CD8$^+$ T cells (FIG. 21B), and CD4$^+$ T cells (FIG. 21C) exposed to varying amounts of Ab-A2 (N67Q) XmAb$^{2+1}$. Circles and squares in the graph denote different donors of the T cells. PD-1 expression increases in T cells exposed to a heterodimeric antibody of the disclosure.

In addition, various embodiments of the disclosure entail the "importation" of pI amino acids at particular positions from one IgG isotype into another, thus reducing or eliminating the possibility of unwanted immunogenicity being introduced into the variants. A number of these are shown in FIG. 21 of U.S. Patent Publication No. 2014/0370013, hereby incorporated by reference. That is, IgG1 is a common isotype for therapeutic antibodies for a variety of reasons, including high effector function. However, the heavy constant region of IgG1 has a higher pI than that of IgG2 (8.10 versus 7.31). By introducing IgG2 residues at particular positions into the IgG1 backbone, the pI of the resulting monomer is lowered (or increased) and additionally exhibits longer serum half-life. For example, IgG1 has a glycine (pI 5.97) at position 137, and IgG2 has a glutamic acid (pI 3.22); importing the glutamic acid will affect the pI of the resulting protein. A number of amino acid substitutions are generally required to significant affect the pI of the variant antibody. However, it should be noted as discussed below that even changes in IgG2 molecules allow for increased serum half-life.

In other embodiments, non-isotypic amino acid changes are made, either to reduce the overall charge state of the resulting protein (e.g., by changing a higher pI amino acid to a lower pI amino acid) or to allow accommodations in structure for stability, etc.

In addition, by pI engineering both the heavy and light constant domains, significant changes in each monomer of the heterodimer can be observed. As discussed herein, having the pIs of the two monomers differ by at least 0.5 can allow separation by ion exchange chromatography or isoelectric focusing, or other methods sensitive to isoelectric point.

In addition, pI variants that are isosteric, e.g., charge variants that are roughly the same size as the parent amino acid, can be generated and are contemplated herein.

Calculating pI

The pI of each monomer can depend on the pI of the variant heavy chain constant domain and the pI of the total monomer, including the variant heavy chain constant domain and the fusion partner. Thus, in some embodiments, the change in pI is calculated on the basis of the variant heavy chain constant domain. Alternatively, the pI of each monomer can be compared. Similarly, the pIs of the "starting" variable regions (e.g., either scFv or Fab) are calculated to inform which monomer will be engineered in which direction.

pI Variants Conferring Better FcRn Binding In Vivo pI variants decreasing the pI of the monomer may display the added benefit of improving serum retention in vivo.

Fc regions are believed to have longer half-lives in vivo because binding to FcRn at pH 6 in an endosome sequesters the Fc (Ghetie and Ward, 1997 Immunol Today. 18(12): 592-598, hereby incorporated by reference). The endosomal compartment then recycles the Fc to the cell surface. Once the compartment opens to the extracellular space, the higher pH, ~7.4, induces the release of Fc back into the blood. The increased affinity of Fc for FcRn at pH 7.4 is thought to forbid the release of the Fc back into the blood. Therefore, the Fc mutations that will increase Fc's half-life in vivo will ideally increase FcRn binding at the lower pH while still allowing release of Fc at higher pH. The amino acid histidine changes its charge state in the pH range of 6.0 to 7.4. Therefore, it is not surprising to find His residues at important positions in the Fc/FcRn complex.

Recently it has been suggested that antibodies with variable regions that have lower isoelectric points may also have longer serum half-lives (Igawa et al., 2010 PEDS. 23(5): 385-392, entirely incorporated by reference). Constant region variants with reduced pI and extended half-life provide a more modular approach to improving the pharmacokinetic properties of antibodies.

pI variants that find use in this embodiment, as well as their use for purification optimization, are disclosed in the Figures.

Combination of Variants

As will be appreciated by those in the art, all of the recited heterodimerization variants can be optionally and independently combined in any way, as long as they retain their "strandedness" or "monomer partition." In addition, all of these variants can be combined into any of the heterodimerization formats. In the case of pI variants, while exemplary embodiments are shown in the Figures, other combinations can be generated, following the basic rule of altering the pI difference between two monomers to facilitate purification.

Antigen-Binding Protein (e.g., Antibody) Formats

One heterodimeric scaffold that finds use in the context of the present disclosure is the "triple F" or "bottle opener" scaffold format described above and set forth in FIG. 18. In this embodiment, one heavy chain of the antibody contains a single chain Fv ("scFv", as defined below) and the other heavy chain is a "regular" Fab format, comprising a variable heavy chain and a light chain. Many of the embodiments outlined herein rely in general on the bottle opener format that comprises a first monomer comprising an scFv, comprising a variable heavy and a variable light domain, covalently attached using an scFv linker (charged in many, but not all, instances), where the scFv is covalently attached to the N-terminus of a first Fc domain usually through a domain linker (which, as outlined herein can either be uncharged or charged and can be exogenous or endogeneous (e.g. all or part of the native hinge domain)). The second monomer of the bottle opener format is a heavy chain, and the composition further comprises a light chain.

In addition, the Fc domains of the bottle opener format generally comprise skew variants (e.g., selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W; and T366S/L368A/Y407V/Y349C:T366W/S354C), optionally ablation variants, optionally charged scFv linkers, and the heavy chain comprises pI variants. In some embodiments, the bottle opener format includes skew variants, pI variants, and ablation variants. Accordingly, some embodiments include bottle opener formats that comprise: a) a first monomer (the "scFv monomer") that comprises a charged scFv linker, the skew variants S364K/E357Q, the ablation variants E233P/L234V/L235A/G236del/S267K, and an Fv; b) a second monomer (the "Fab monomer") that comprises the skew variants L368D/K370S, the pI variants N208D/Q295E/N384D/Q418E/N421D, the ablation variants E233P/L234V/L235A/G236del/S267K, and a variable heavy domain that, with the variable light domain, makes up an Fv that binds to a second antigen; and c) a light chain.

In some embodiments, the bottle opener format includes skew variants, pI variants, ablation variants and FcRn variants. Accordingly, some embodiments include bottle opener formats that comprise: a) a first monomer (the "scFv monomer") that comprises a charged scFv linker, the skew variants S364K/E357Q, the ablation variants E233P/L234V/L235A/G236del/S267K, the FcRn variants M428L/N434S and an Fv that binds to a first antigen; b) a second monomer (the "Fab monomer") that comprises the skew variants L368D/K370S, the pI variants N208D/Q295E/N384D/Q418E/N421D, the ablation variants E233P/L234V/L235A/G236del/S267K, the FcRn variants M428L/N434S and a variable heavy domain that, with the variable light domain, makes up an Fv that binds to a second antigen; and c) a light chain.

Another heterodimeric scaffold that finds use in the present disclosure is the mAb-Fv format shown in FIG. 18H. In this embodiment, the format relies on the use of a C-terminal attachment of an "extra" variable heavy domain to one monomer and the C-terminal attachment of an "extra" variable light domain to the other monomer, thus forming a third antigen-binding domain, wherein the Fab portions of the two monomers bind one antigen and the "extra" scFv domain binds a different antigen.

In this embodiment, the first monomer comprises a first heavy chain, comprising a first variable heavy domain and a first constant heavy domain comprising a first Fc domain, with a first variable light domain covalently attached to the C-terminus of the first Fc domain using a domain linker (vh1-CH1-[domain linker (e.g., hinge)]-CH2-CH3-[optional domain linker]-v2). The second monomer comprises a second variable heavy domain of the second constant heavy domain comprising a second Fc domain, and a third variable heavy domain covalently attached to the C-terminus of the second Fc domain using a domain linker (vh1-CH1-domain linker (e.g., hinge)-CH2-CH3-[optional domain linker]-vh2). The two C-terminally attached variable domains make up a scFv. This embodiment further utilizes a common light chain comprising a variable light domain and a constant light domain, which associates with the heavy chains to form two identical Fabs. As for many of the embodiments herein, these constructs include skew variants, pI variants, ablation variants, additional Fc variants, etc. as desired and described herein.

Optionally, the Fc domains of the mAb-Fv format comprise skew variants (e.g., selected from the group consisting of S364K/E357Q:L368D/K370S; L368D/K370S S364K; L368E/K370S:S364K; T411T/E360E/Q362E:D401K; L368D/K370S: S364K/E357L, K370S:S364K/E357Q, T366S/L368A/Y407V:T366W; and T366S/L368A/Y407V/Y349C:T366W/S354C), optionally ablation variants, optionally charged scFv linkers, and the heavy chain comprises pI variants. In some embodiments, the mAb-Fv format includes skew variants, pI variants, and ablation variants. Accordingly, some embodiments include bottle opener formats that comprise: a) a first monomer that comprises the skew variants S364K/E357Q, the ablation variants 233P/L234V/L235A/G236del/S267K, and a first variable heavy domain that, with the first variable light domain of the light chain, makes up an Fv that binds to an antigen, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first antigen, and a second variable light chain, that together with the second variable heavy chain forms an Fv that binds a second antigen; and c) a light chain comprising a first variable light domain and a constant light domain.

Yet another heterodimeric scaffold that finds use in the present disclosure is the mAb-scFv format shown in FIG. 18. In this embodiment, the format relies on the use of a C-terminal attachment of an scFv to one of the monomers, thus forming a third antigen-binding domain, wherein the Fab portions of the two monomers bind one antigen and the "extra" scFv domain binds a different antigen. In this embodiment, the first monomer comprises a first heavy chain (comprising a variable heavy domain and a constant domain), with a C-terminally covalently attached scFv comprising a scFv variable light domain, an scFv linker and a scFv variable heavy domain in either orientation (vh1-CH1-domain linker-CH2-CH3-[optional domain linker]-vh2-scFv linker-vl2 or vh1-CH1-domain linker-CH2-CH3-[optional domain linker]-vl2-scFv linker-vh2). This embodiment further utilizes a common light chain comprising a variable light domain and a constant light domain, which associates with the heavy chains to form two identical Fabs that bind one of the target antigens. As for many of the embodiments herein, these constructs include skew variants, pI variants, ablation variants, additional Fc variants, etc., as desired and described herein.

In addition, the Fc domains of the mAb-scFv format optionally comprise skew variants (e.g., selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W; and T366S/L368A/Y407V/Y349C:T366W/S354C), optionally ablation variants, optionally charged scFv linkers, and the heavy chain comprises pI variants. In some embodiments, the mAb-scFv format includes skew variants, pI variants, and ablation variants. Accordingly, some embodiments include formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first antigen, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first antigen, and a second variable light chain, that together with the second variable heavy chain forms an Fv that binds a second antigen; and c) a light chain comprising a first variable light domain and a constant light domain.

Yet another heterodimeric scaffold that finds use in the present disclosure is the central-scFv or "XmAb$^{2+1}$" format shown in FIG. 18F. The format relies on the use of an inserted scFv domain thus forming a third antigen-binding domain, wherein the Fab portions of the two monomers bind one target and the "extra" scFv domain binds another. The scFv domain is inserted between the Fc domain and the CH1-Fv region of one of the monomers, thus providing a third antigen-binding domain. In this embodiment, one monomer comprises a first heavy chain comprising a first variable heavy domain, a CH1 domain (and optional linker/hinge) and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using optional domain linkers (VH-CH1-[optional domain linker]-VH2-scFv linker-VL2-[optional domain linker including the hinge]-CH2-CH3, or the opposite orientation for the scFv, VH1-CH1-[optional domain linker]-VL2-scFv linker-VH2-[optional domain linker including the hinge]-CH2-CH3). In some embodiments, the first monomer is VH1-CH1-domain linker-VH2-scFv linker-VL2-domain linker-CH2-CH3. The other monomer is a standard Fab side (i.e., VH1-CH1-domain linker (e.g., hinge)-CH2-CH3). This embodiment further utilizes a common light chain comprising a variable light domain and a constant light domain, which associates with the heavy chains to form two identical Fabs that bind a target. As for many of the embodiments herein, these constructs include skew variants, pI variants, ablation variants, additional Fc variants, etc. as desired and described herein.

In various aspects, the antigen-binding protein comprises a first heavy chain comprising VH1-CH1-[domain linker]-VH2-scFv linker-VL2-[domain linker (optionally including the hinge)]-CH2-CH3; a second heavy chain comprising a VH1-CH1-domain linker-CH2-CH3; and a common light chain comprising a VL1; wherein VH1 and VL1 bind STEAP1 and VH2 and VL2 bind CD3. In this format, VH2 optionally comprises CDR sequences of SEQ ID NO: 170 (CDR1), SEQ ID NO: 171 (CDR2), and SEQ ID NO: 172 (CDR3), while VL2 comprises CDR sequences of SEQ ID NO: 174 (CDR1), SEQ ID NO: 175 (CDR2), and SEQ ID NO:176 (CDR3). VH1 comprises CDR sequences of SEQ ID NO: 14 (CDR1), SEQ ID NO: 15 or 21 (CDR2), and SEQ ID NO: 16 (CDR3); and VL1 comprises CDR sequences of SEQ ID NO: 11 (CDR1), SEQ ID NO: 12 (CDR2), and SEQ ID NO: 13 (CDR3). Alternatively, VH1 comprises CDR sequences of SEQ ID NO: 33 (CDR1), SEQ ID NO: 34 (CDR2), and SEQ ID NO: 35 (CDR3); and VL1 comprises CDR sequences of SEQ ID NO: 30 (CDR1), SEQ ID NO: 31 (CDR2), and SEQ ID NO: 32 (CDR3). Optionally, the antigen-binding protein comprises modifications in the first heavy chain including, but not limited to, E233P, deL234, L235V, G236A, S267K, r292c, n297g, v302c, E357Q, and S364K (EU numbering, lower case letters referencing SEFL2 substitutions described further herein), and the second heavy chain comprises modifications including, but not limited to, N208D, E233P, deL234, L235V, G236A, S267K, r292c Q295E, n297g, v302c, L368D, K370S, N384D, Q418E, and N421D (EU numbering, lower case letters referencing SEFL2 substitutions described further herein). A linker for use in the context of this embodiment is optionally GKPGSGKPGSGKPGSGKPGS (SEQ ID NO: 152).

The Fc domains of the central scFv format optionally comprise skew variants (e.g., selected from the group consisting of S364K/E357Q:L368D/K370S; L368D/K370S: S364K; L368E/K370S:S364K; T411T/E360E/Q362E: D401K; L368D/K370S: S364K/E357L, K370S:S364K/ E357Q, T366S/L368A/Y407V:T366W and T366S/L368A/ Y407V/Y349C:T366W/S354C), optionally ablation variants, optionally charged scFv linkers, and the heavy chain comprises pI variants. In some embodiments, the central scFv format includes skew variants, pI variants, and ablation variants. Accordingly, some embodiments include formats that comprise: a) a first monomer that comprises the skew variants S364K/E357Q, the ablation variants E233P/ L234V/L235A/G236del/S267K, and a first variable heavy domain that, with the first variable light domain of the light chain, makes up an Fv that binds to a first target, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first target, and a second variable light chain, that together with the second variable heavy chain forms an Fv that binds a second target; and c) a light chain comprising a first variable light domain and a constant light domain.

Another heterodimeric scaffold that finds particular use in the disclosure is the central-Fv format shown in FIG. 18G. The format relies on the use of an inserted scFv domain thus forming a third antigen-binding domain, wherein the Fab portions of the two monomers bind one target and the "extra" scFv domain binds another. The scFv domain is inserted between the Fc domain and the CH1-Fv region of the monomers, thus providing a third antigen-binding domain, wherein each monomer contains a component of the scFv (e.g., one monomer comprises a variable heavy domain and the other a variable light domain). In this embodiment, one monomer comprises a first heavy chain comprising a first variable heavy domain, a CH1 domain, and Fc domain and an additional variable light domain. The light domain is covalently attached between the C-terminus of the CH1 domain of the heavy constant domain and the N-terminus of the first Fc domain using domain linkers (vhl-CH1-[optional domain linker]-v12-hinge-CH2-CH3). The other monomer comprises a first heavy chain comprising a first variable heavy domain, a CH1 domain and Fc domain and an additional variable heavy domain (vhl-CH1- [optional domain linker]-vh2-hinge-CH2-CH3). The light domain is covalently attached between the C-terminus of the CH1 domain of the heavy constant domain and the N-terminus of the first Fc domain using domain linkers. This embodiment further utilizes a common light chain comprising a variable light domain and a constant light domain, that associates with the heavy chains to form two identical Fabs that bind a target. As for many of the embodiments herein, these constructs include skew variants, pI variants, ablation variants, additional Fc variants, etc. as desired and described herein.

A further heterodimeric scaffold that finds use in the context of the disclosure is the one armed central-scFv format shown in FIG. 18C. In this embodiment, one monomer comprises just an Fc domain, while the other monomer uses an inserted scFv domain thus forming the second antigen-binding domain. In this format, the Fab portion binds one target and the scFv binds another. The scFv domain is inserted between the Fc domain and the CH1-Fv region of one of the monomers. In this embodiment, one monomer comprises a first heavy chain comprising a first variable heavy domain, a CH1 domain and Fc domain, with a scFv comprising a scFv variable light domain, an scFv linker and a scFv variable heavy domain. The scFv is covalently attached between the C-terminus of the CH1 domain of the heavy constant domain and the N-terminus of the first Fc domain using domain linkers. The second monomer comprises an Fc domain. This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein.

In addition, the Fe domains of the one armed central-scFv format optionally comprise skew variants (e.g., selected from the group consisting of S364K/E357Q: L368D/K370S; L368D/K370S:S364K; L368E/K370S:S364K; T411T/ E360E/Q362E: D401K; L368D/K370S:S364K/E357L, K370S:S364K/E357Q, T366S/L368A/Y407V: T366W and T366S/L368A/Y407V Y349C:T366W/S354C), optionally ablation variants, optionally charged scFv linkers, and the heavy chain comprises pI variants. In some embodiments, the one armed central-scFv format includes skew variants, pI variants, and ablation variants. Accordingly, some embodiments include bottle opener formats that comprise: a) a first monomer that comprises the skew variants S364K/E357Q, the ablation variants E233P/L234V/L235A/G236del/ S267K, and a first variable heavy domain that, with the first variable light domain of the light chain, makes up an Fv that binds to a first target, and a second variable heavy domain; b) a second monomer that comprises the skew variants L368D/K370S, the pI variants N208D/Q295E/N384D/ Q418E/N421D, the ablation variants E233P/L234V/L235A/ G236del/S267K, and a first variable heavy domain that, with the first variable light domain, makes up the Fv that binds to the first target, and a second variable light chain, that together with the second variable heavy chain forms an Fv that binds a second target; and c) a light chain comprising a first variable light domain and a constant light domain. In some embodiments, the one armed central-scFv format includes skew variants, pi variants, ablation variants and FcRn variants. Accordingly, some embodiments include formats that comprise: a) a first monomer that comprises the skew variants S364K/E357Q, the ablation variants E233P/ L234V/L235A/G236del/S267K, the FcRn variants M428L/ N434S and a first variable heavy domain that, with the first variable light domain of the light chain, makes up an Fv that binds to a first target, and a second variable heavy domain; b) a second monomer that comprises the skew variants L368D/K370S, the pi variants N208D/Q295E/N384D/ Q418E/N421D, the ablation variants E233P/L234V/L235A/ G236del/S267K, the FcRn variants M428L/N434S and a first variable heavy domain that, with the first variable light domain, makes up the Fv that binds to the first target as outlined herein, and a second variable light chain, that together with the second variable heavy chain forms an Fv that binds a second target; and c) a light chain comprising a first variable light domain and a constant light domain.

A further heterodimeric scaffold that finds use in the disclosure is the one armed scFv-mAb format shown in FIG. 18D. In this embodiment, one monomer comprises just an Fc domain, while the other monomer uses a scFv domain attached at the N-terminus of the heavy chain, generally through the use of a linker: vh-scFv linker-vl-[optional domain linker]-CH1-hinge-CH2-CH3 or (in the opposite orientation) vl-scFv linker-vh-[optional domain linker]-CH1-hinge-CH2-CH3. In this format, the Fab portion binds one target and the scFv binds another. This embodiment further utilizes a light chain comprising a variable light domain and a constant light domain, that associates with the heavy chain to form a Fab. As for many of the embodiments herein, these constructs include skew variants, pI variants, ablation variants, additional Fc variants, etc. as desired and described herein.

The Fc domains of the one armed scFv-mAb comprise skew variants (e.g., selected from the group consisting of S364K/E357Q:L368D/K370S; L368D/K370S:S364K; L368E/K370S:S364K; T411T/E360E/Q362E:D401K; L368D/K370S:S364K/E357L, K370S:S364K/E357Q, T366S/L368A/Y407V:T366W; and T366S/L368A/Y407V:Y349C:T366W/S354C), optionally ablation variants, optionally charged scFv linkers, and the heavy chain comprises pI variants. In some embodiments, the one armed scFv-mAb format includes skew variants, pi variants, and ablation variants. Accordingly, some embodiments include bottle opener formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first target, and a second variable heavy domain; b) a second monomer that comprises the skew variants L368D/K370S, the pI variants N208D/Q295E/N384D/Q418E/N421D, the ablation variants E233P/L234V/L235A/G236del/S267K, and a first variable heavy domain that, with the first variable light domain, makes up the Fv that binds to the first target as outlined herein, and a second variable light chain, that together with the second variable heavy chain forms an Fv that binds a second target; and c) a light chain comprising a first variable light domain and a constant light domain. In some embodiments, the one armed scFv-mAb format includes skew variants, pI variants, ablation variants and FcRn variants. Accordingly, some embodiments include bottle opener formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first target, and a second variable heavy domain; b) a second monomer that comprises the skew variants L368D/K370S, the pi variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first target as outlined herein, and a second variable light chain, that together with the second variable heavy chain forms an Fv that binds a second target; and c) a light chain comprising a first variable light domain and a constant light domain.

Another heterodimeric scaffold that finds use in the disclosure is the mAb-scFv format shown in FIG. 18E. In this embodiment, the format relies on the use of an N-terminal attachment of a scFv to one of the monomers, thus forming a third antigen-binding domain, wherein the Fab portions of the two monomers bind one target and the "extra" scFv domain binds a different target. In this embodiment, the first monomer comprises a first heavy chain (comprising a variable heavy domain and a constant domain), with a N-terminally covalently attached scFv comprising a scFv variable light domain, an scFv linker and a scFv variable heavy domain in either orientation ((vhl-scFv linker-vll-[optional domain linker]-vh2-CH1-hinge-CH2-CH3) or (with the scFv in the opposite orientation) (vll-scFv linker-vhl-[optional domain linker]-vh2-CH1-hinge-CH2-CH3)). This embodiment further utilizes a common light chain comprising a variable light domain and a constant light domain, that associates with the heavy chains to form two identical Fabs that bind one of the target antigens. As for many of the embodiments herein, these constructs include skew variants, pi variants, ablation variants, additional Fc variants, etc. as desired and described herein.

The Fc domains of the scFv-mAb format optionally comprise skew variants (e.g., being selected from the group consisting of S364K/E357Q:L368D/K370S; L368D/K370S S364K; L368E/K370S:S364K; T411T/E360E/Q362E: D401K; L368D/K370S: S364K/E357L, K370S:S364K/E357Q, T366S/L368A/Y407V:T366W; and T366S/L368A/Y407V/Y349C:T366W/S354C), optionally ablation variants, optionally charged scFv linkers, and the heavy chain comprises pI variants. In some embodiments, the mAb-scFv format includes skew variants, pI variants, and ablation variants. Accordingly, some embodiments include bottle opener formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first target, and a second variable heavy domain; b) a second monomer that comprises the skew variants L368D/K370S, the pi variants N208D/Q295E/N384D/Q418E/N421D, the ablation variants E233P/L234V/L235A/G236del/S267K, and a first variable heavy domain that, with the first variable light domain, makes up the Fv that binds to the first target as outlined herein, and a second variable light chain, that together with the second variable heavy chain forms an Fv that binds a second target; and c) a light chain comprising a first variable light domain and a constant light domain. In some embodiments, the mAb-scFv format includes skew variants, pI variants, ablation variants and FcRn variants. Accordingly, some embodiments include bottle opener formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first target, and a second variable heavy domain; b) a second monomer that comprises the skew variants L368D/K370S, the pI variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first target, and a second variable light chain, that together with the second variable heavy chain forms an Fv that binds a second target; and c) a light chain comprising a first variable light domain and a constant light domain.

The disclosure also provides dual scFv formats, such as that depicted in FIG. 18B. In this embodiment, the heterodimeric antigen-binding protein is made up of two scFv-Fc monomers (both in either (vh-scFv linker-vl-[optional domain linker]-CH2-CH3) format or (vl-scFv linker-vh-[optional domain linker]-CH2-CH3) format, or with one monomer in one orientation and the other in the other orientation). The Fc domains of the dual scFv format optionally comprise skew variants (e.g., selected from the group consisting of S364K/E357Q:L368D/K370S; L368D/K370S:

S364K; L368E/K370S:S364K; T411T/E360E/Q362E: D401K; L368D/K370S:S364K/E357L, K370S:S364K/E357Q, T366S/L368A/Y407V:T366W; and T366S/L368A/Y407V/Y349C:T366W/S354C), optionally ablation variants, optionally charged scFv linkers, and the heavy chain comprises pI variants.

In some embodiments, the dual scFv format includes skew variants, pI variants, and ablation variants. Accordingly, some embodiments include formats that comprise: a) a first monomer that comprises the skew variants S364K/E357Q, the ablation variants E233P/L234V/L235A/G236del/S267K, and a first variable heavy domain that, with the first variable light domain of the light chain, makes up an Fv that binds to a first target, and a second variable heavy domain; b) a second monomer that comprises the skew variants L368D/K370S, the pi variants N208D/Q295E/N384D/Q418E/N421D, the ablation variants E233P/L234V/L235A/G236del/S267K, and a first variable heavy domain that, with the first variable light domain, makes up the Fv that binds to the first target as outlined herein, and a second variable light chain, that together with the second variable heavy chain forms an Fv that binds a second target; and c) a light chain comprising a first variable light domain and a constant light domain. In some embodiments, the dual scFv format includes skew variants, pI variants, ablation variants and FcRn variants. Accordingly, some embodiments include bottle opener formats that comprise: a) a first monomer that comprises the skew variants S364K/E357Q, the ablation variants E233P/L234V/L235A/G236del/S267K, the FcRn variants M428L/N434S and a first variable heavy domain that, with the first variable light domain of the light chain, makes up an Fv that binds to a first target, and a second variable heavy domain; b) a second monomer that comprises the skew variants L368D/K370S, the pi variants N208D/Q295E/N384D/Q418E/N421D, the ablation variants E233P/L234V/L235A/G236del/S267K, the FcRn variants M428L/N434S and a first variable heavy domain that, with the first variable light domain, makes up the Fv that binds to the first target, and a second variable light chain, that together with the second variable heavy chain forms an Fv that binds a second target; and c) a light chain comprising a first variable light domain and a constant light domain.

Additional description of antibody formats is provided in International Patent Publication No. WO 2017/218707, hereby incorporated by reference.

Antibody Binding

The bispecific antigen-binding protein (e.g., heterodimeric antibody) of the disclosure, in various aspects, binds CD3 and STEAP1. The different binding regions independently display a KD for their respective antigen of less than or equal to 104 M, less than or equal to $10^{-5}$ M, less than or equal to $10^{-6}$ M, less than or equal to $10^{-7}$ M, less than or equal to $10^{-8}$ M, less than or equal to $10^{-9}$ M, less than or equal to $10^{-10}$ M, less than or equal to $10^{-11}$ M, or less than or equal to $10^{-12}$ M, where KD refers to a dissociation rate of a particular antibody-antigen interaction. Binding affinity is further described above. The STEAP1 binding region need not bind STEAP1 with the same affinity as, e.g., the CD3 binding region binds CD3. Binding affinity disclosed in the context of bispecific antigen-binding protein also applies to any of the monospecific constructs described herein, including constructs that bind PD-1.

Additional Antibody Modifications

In addition to the modifications outlined above, other modifications can be made. For example, the molecules may be stabilized by the incorporation of disulphide bridges linking the VH and VL domains (Reiter et al., 1996, Nature Biotech. 14:1239-1245, entirely incorporated by reference). In addition, there are a variety of covalent modifications of antibodies that can be made as outlined below.

Covalent modifications of antibodies are included within the scope of this disclosure, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues may also be derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole and the like.

In addition, modifications at cysteines are particularly useful in antibody-drug conjugate (ADC) applications, further described below. In some embodiments, the constant region of the antibodies can be engineered to contain one or more cysteines that are particularly "thiol reactive," so as to allow more specific and controlled placement of the drug moiety. See for example U.S. Pat. No. 7,521,541, incorporated by reference in its entirety herein.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents reverses the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using 125I or 131I to prepare labeled proteins for use in radioimmunoassay, the chloramine T method described above being suitable.

Carboxyl side groups (aspartyl or glutamyl) are selectively modified by reaction with carbodiimides (R'—N═C═N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking antibodies to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440, all entirely incorporated by reference, are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this disclosure.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983], entirely incorporated by reference), acetylation of the N-terminal amine, and amidation of any C-terminal carboxyl group.

In addition, as will be appreciated by those in the art, labels (including fluorescent, enzymatic, magnetic, radioactive, etc.) can be added to any of the antigen-binding proteins described herein (as well as the other compositions of the disclosure).

Glycosylation

Another type of covalent modification is alteration in glycosylation. In another embodiment, the antibodies (or other types of antigen-binding protein) disclosed herein can be modified to include one or more engineered glycoforms. By "engineered glycoform" as used herein is meant a carbohydrate composition that is covalently attached to the antibody, wherein said carbohydrate composition differs chemically from that of a parent antibody. Engineered glycoforms may be useful for a variety of purposes, including but not limited to enhancing or reducing effector function. A preferred form of engineered glycoform is afucosylation, which has been shown to be correlated to an increase in ADCC function, presumably through tighter binding to the FcγRIIIa receptor. In this context, "afucosylation" means that the majority of the antibody produced in the host cells is substantially devoid of fucose, e.g., 90%, 95%, or 98% of the generated antibodies do not have appreciable fucose as a component of the carbohydrate moiety of the antibody (generally attached at N297 in the Fc region). Defined functionally, afucosylated antibodies generally exhibit at least a 50% or higher affinity to the FcγRIIIa receptor.

Optionally, the heterodimeric antibody comprises a sequence modification that removes one more glycosylation sites, e.g., at one or more of positions 292, 297, or 302. One non-limiting example comprises introduction of one or more stable effector functionless (SEFL2) mutations (e.g., in an IgG1 backbone), which are further described in, e.g., U.S. Pat. No. 9,546,203, incorporated by reference herein in its entirety and particularly with respect to the description of SEFL2 mutations. This modification may be used in additional to any other modification disclosed herein, e.g., the N67Q modification to decrease deamidation.

Engineered glycoforms may be generated by a variety of methods known in the art. See, e.g., Umana et al., 1999, Nat Biotechnol 17:176-180; Davies et al., 2001, Biotechnol Bioeng 74:288-294; Shields et al., 2002, J Biol Chem 277:26733-26740; Shinkawa et al., 2003, J Biol Chem 278:3466-3473; U.S. Pat. No. 6,602,684; U.S. Publication Nos. 2003/0157108 and 2003; 0003097; and International Patent Publication Nos. WO 00/61739A1, WO 01/29246A1, WO 02/31140A1, and WO 02/30954A1, all entirely incorporated by reference, as well as Potelligent® technology [Biowa, Inc., Princeton, N.J.] and GlycoMAb® glycosylation engineering technology [Glycart Biotechnology AG, Zurich, Switzerland]. Many of these techniques are based on controlling the level of fucosylated and/or bisecting oligosaccharides that are covalently attached to the Fc region, for example by expressing an IgG in various organisms or cell lines, engineered or otherwise (for example, Lec-13 CHO cells or rat hybridoma YB2/0 cells), by regulating enzymes involved in the glycosylation pathway (for example FUT8 [α1,6-fucosyltranserase] and/or β1-4-N-acetylglucosaminyltransferase III [GnTIII])), or by modifying carbohydrate(s) after the IgG has been expressed. For example, the "sugar engineered antibody technology" functions by adding modified saccharides that inhibit fucosylation during production; see for example U.S. Publication No. 20090317869, hereby incorporated by reference in its entirety. Engineered glycoform typically refers to the different carbohydrate or oligosaccharide; thus an antibody can include an engineered glycoform.

Alternatively, engineered glycoform may refer to the IgG variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antigen-binding protein (e.g., antibody) is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in International Patent Publication No. WO 87/05330 and in Aplin and Wriston, 1981, CRC Crit. Rev. Biochem., pp. 259-306, both entirely incorporated by reference.

Removal of carbohydrate moieties present on the starting antibody (e.g., post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website), or U.S. Pat. Nos. 4,640,835; 4,496,689; 4,301,144; 4,670,417; 4,791,192; or 4,179,337, all entirely incorporated by reference. In addition, as is known in the art, amino acid substitutions may be made in various positions within the antibody to facilitate the addition of polymers such as PEG. See for example, U.S. Publication No. 2005/0114037A1, entirely incorporated by reference.

Additional Fc Variants for Additional Functionality

In addition to pI amino acid variants and other variants described above, there are a number of useful Fc amino acid modifications that can be made for a variety of reasons, including, but not limited to, altering binding to one or more FcγR receptors, altered binding to FcRn receptors, etc. The following modifications may be employed in addition or in the alternative to any of the modifications described above.

FcγR Variants

There are a number of useful Fc substitutions that can be made to alter binding to one or more of the FcγR receptors. Substitutions that result in increased binding as well as decreased binding can be useful. For example, it is known that increased binding to FcγRIIIa generally results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell). Similarly, decreased binding to FcγRIIb (an inhibitory receptor) can be beneficial as well in some circumstances. Amino acid substitutions that find use in the present disclosure include those listed in U.S. Patent Publication Nos. 2006/0024298 (particularly FIG. 41), 2006/0121032, 2006/0235208, 2007/0148170, all of which are expressly incorporated herein by reference in their entirety and specifically for the variants disclosed therein. Particular variants that find use include, but are not limited to, 236A, 239D, 239E, 332E, 332D, 239D/332E, 267D, 267E, 328F, 267E/328F, 236A/332E, 239D/332E, 239D/332E/330Y, 239D, 332E/330L, and 299T.

In addition, there are additional Fc substitutions that find use in increased binding to the FcRn receptor and increased serum half life, as specifically disclosed in U.S. Patent Publication No. 2009/0163699, hereby incorporated by reference in its entirety, including, but not limited to, 434S, 428L, 308F, 259, 428L/434S, 259I/308F, 436I/428L, 436I or V/434S, 436V/428L and 259/308F/428L.

Fc Ablation Variants

Additional variants which find use in the context of the present disclosure are those that ablate (e.g., reduce or eliminate) binding to Fcγ receptors. This can be desirable to reduce the potential mechanisms of action (e.g., reduce ADCC activity) of the heterodimeric antibody. A number of suitable Fc ablation variants are depicted in FIG. 6, and can be optionally and independently included or excluded in combination with any other heterodimerization variants, including pI and steric variants.

Of particular use in some embodiments are a first monomer (the "negative side") that contains the pI variants N208D/Q295E/N384D/Q418E/N421D, skew variants 368D/370S, and ablation variants E233P/L234V/L235A/G236del/S267K, paired with a positive side comprising no pI variants, skew variants S364K/E357Q and ablation variants E233P/L234V/L235A/G236del/S267K (optionally both monomers containing FcRn variants 428L/434S), where the positive side is the monomer comprising the scFv and contains a charged scFv linker. A second embodiment utilizes a first negative side monomer comprising I199T/N203D/K274Q/R355Q/Q419E/K447del, skew variants S364K/E357Q and ablation variants E233P/L234V/L235A/G236del/S267K (optionally both monomers containing FcRn variants 428L/434S), paired with a positive side comprising pI variants Q196K/I199T/P271R/P228R/N276K, skew variants S364K/E357Q and ablation variants E233P/L234V/L235A/G236del/S267K (optionally both monomers containing FcRn variants 428L/434S), where the positive side is the monomer comprising the scFv and contains a charged scFv linker. A third embodiment utilizes a first negative side monomer comprising I199T/N203D/K274Q/R355Q/N384S/K392N/V397M/Q419E/K447del, skew variants S364K/E357Q and ablation variants E233P/L234V/L235A/G236del/S267K (optionally both monomers containing FcRn variants 428L/434S), paired with a positive side monomer with no pI variants, skew variants S364K/E357Q and ablation variants E233P/L234V/L235A/G236del/S267K (optionally both monomers containing FcRn variants 428L/434S), where the positive side is the monomer comprising the scFv and contains a charged scFv linker. A fourth embodiment utilizes a first monomer (the "negative side") that contains the pI variants N208D/Q295E/N384D/Q418E/N421D, skew variants 368D/370S, and ablation variants E233P/L234V/L235A/G236del/S239K, paired with a positive side comprising no pI variants, skew variants S364K/E357Q and ablation variants E233P/L234V/L235A/G236del/S239K (optionally both monomers containing FcRn variants 428L/434S). A fifth embodiment utilizes a first negative side monomer comprising I199T/N203D/K274Q/R355Q/Q419E/K447del, skew variants S364K/E357Q and ablation variants E233P/L234V/L235A/G236del/S239K (optionally both monomers containing FcRn variants 428L/434S), paired with a positive side comprising pI variants Q196K/I199T/P271R/P228R/N276K, skew variants S364K/E357Q and ablation variants E233P/L234V/L235A/G236del/S239K (optionally both monomers containing FcRn variants 428L/434). A sixth embodiment utilizes a first negative side monomer comprising I199T/N203D/K274Q/R355Q/N384S/K392N/V397M/Q419E/K447del, skew variants S364K/E357Q and ablation variants E233P/L234V/L235A/G236del/S267K (optionally both monomers containing FcRn variants 428L/434S), paired with a positive side monomer skew variants S364K/E357Q and ablation variants E233P/L234V/L235A/G236del/S239K (optionally both monomers containing FcRn variants 428L/434S), where the positive side is the scFv monomer and contains a charged scFv linker (particularly when the scFv is anti-CD3). A seventh embodiment utilizes a first monomer (the "negative side") that contains the pI variants N208D/Q295E/N384D/Q418E/N421D, skew variants 368D/370S, and ablation variants S239K/S267K, paired with a positive side comprising no pI variants, skew variants S364K/E357Q and ablation variants S239K/S267K (optionally both monomers containing FcRn variants 428L/434S), where the positive side is the scFv monomer and contains a charged scFv linker. An eighth embodiment utilizes a first negative side monomer comprising I199T/N203D/K274Q/R355Q/Q419E/K447del, skew variants S364K/E357Q and ablation variants S239K/S267K, (optionally both monomers containing FcRn variants 428L/434S), paired with a positive side comprising pI variants Q196K/I199T/P271R/P228R/N276K, skew variants S364K/E357Q and ablation variants S239K/S267K (optionally both monomers containing FcRn variants 428L/434S), where the positive side is the scFv monomer and contains a charged scFv linker. A ninth embodiment utilizes a first negative side monomer comprising I199T/N203D/K274Q/R355Q/N384S/K392N/V397M/Q419E/K447del, skew variants S364K/E357Q and ablation variants S239K/S267K (optionally both monomers containing FcRn variants 428L/434S), paired with a positive side monomer with no pI variants, skew variants S364K/E357Q and ablation variants S239K/S267K (optionally both monomers containing FcRn variants 428L/434S), where the positive side is the scFv monomer and contains a charged scFv linker. A tenth embodiment utilizes a first monomer (the "negative side") that contains the pI variants N208D/Q295E/N384D/Q418E/N421D, skew variants 368D/370S, and ablation variants S267K/P329K, paired with a positive side comprising no pI variants, skew variants S364K/E357Q and ablation variants S267K/P329K (optionally both monomers containing FcRn variants 428L/434S), where the positive side is the scFv monomer and contains a charged scFv linker. An eleventh embodiment utilizes a first negative side monomer comprising I199T/N203D/K274Q/R355Q/Q419E/K447del, skew variants S364K/E357Q and ablation variants S267K/P329K (optionally both monomers containing FcRn variants 428L/434S), paired with a positive side comprising pI variants Q196K/I199T/P271R/P228R/N276K, skew variants S364K/E357Q and ablation variants S267K/P329K (optionally both monomers containing FcRn variants 428L/434S), where the positive side is the scFv monomer and contains a charged scFv linker. A 12th embodiment utilizes a first negative side monomer comprising I199T/N203D/K274Q/R355Q/N384S/K392N/V397M/Q419E/K447del, skew variants S364K/E357Q and ablation variants S267K/P329K (optionally both monomers containing FcRn variants 428L/434S), paired with a positive side monomer with no pI variants, skew variants S364K/E357Q and ablation variants S267K/P329K (optionally both monomers containing FcRn variants 428L/434S), where the positive side is the scFv monomer and contains a charged scFv linker.

In various aspects, the first monomer comprising a first heavy chain comprising a first variable heavy domain, a first constant heavy chain comprising a first CH1 domain and a first Fc domain, a scFv that binds human CD3 and comprises a scFv variable light domain, an scFv linker and a scFv variable heavy domain (i.e., the "Fab-scFv-Fc" heavy chain) comprises a deletion in the upper hinge and CH2 and CH3 substitutions are introduced. The substitutions include, for example, one or more (e.g., all) of E233P, deL234, L235V, G236A, S267K, r292c, n297g, v302c, E357Q, and S364K (EU numbering, lower case letters referencing SEFL2 substitutions). The second monomer comprising a second heavy chain comprising a second variable heavy domain and a second constant heavy chain comprising a second Fc domain optionally comprises one or more (e.g., all) of the following mutations: N208D, E233P, delL234, L235V, G236A, S267K, r292c, Q295E, n297g, v302c, L368D, K370S, N384D, Q418E, and N421D (EU numbering, lower case letters referencing SEFL2 substitutions).

Linkers

"Linker" herein is also referred to as "linker sequence" or "spacer" or grammatical equivalent. Homo- or hetero-bifunctional linkers as are well known (see, 1994 Pierce Chemical Company catalog, technical section on cross-linkers, pages 155-200, incorporated entirely by reference). (Note the distinction between generic "linkers" and "scFv linkers and "charged scFv linkers.") A number of strategies may be used to covalently link molecules together. These include, but are not limited to polypeptide linkages between N- and C-termini of proteins or protein domains, linkage via disulfide bonds, and linkage via chemical crosslinking reagents. In one aspect of this embodiment, the linker is a peptide bond, generated by recombinant techniques or peptide synthesis. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used. Useful linkers include glycine-serine polymers, including for example (GS)n, (GSGGS)n (SEQ ID NO: 178), (GGGGS)n (SEQ ID NO: 179), and (GGGS)n (SEQ ID NO: 180), where n is an integer of at least one; glycine-alanine polymers; alanine-serine polymers; and other flexible linkers. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers, that is may find use as linkers.

Other linker sequences may include any sequence of any length of CL/CH1 domain but not all residues of CL/CH1 domain; for example the first 5-12 amino acid residues of the CL/CH1 domains. Linkers can be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g., TCR, FcR, KIR), hinge region-derived sequences, and other natural sequences from other proteins.

In some embodiments, the linker is a "domain linker," used to link any two domains as outlined herein together. For example, in FIG. 18F, there may be a domain linker that attaches the C-terminus of the CH1 domain of the Fab to the N-terminus of the scFv, with another optional domain linker attaching the C-terminus of the scFv to the CH2 domain (although in many embodiments the hinge is used as this domain linker). In some embodiments, the linker is a hinge region or a fragment thereof.

Antibody-Drug Conjugates

The antigen-binding protein (e.g., antibody or heterodimeric antibody) of the disclosure is optionally conjugated with drugs to form antibody-drug conjugates (ADCs). In general, ADCs are used in a variety of contexts, including oncology applications, where the use of antibody-drug conjugates for the local delivery of cytotoxic or cytostatic agents allows for the targeted delivery of the drug moiety to tumors, which can allow higher efficacy, lower toxicity, etc. An overview of this technology is provided in Ducry et al., Bioconjugate Chem., 21:5-13 (2010); Carter et al., Cancer J. 14(3):154 (2008); and Senter, Current Opin. Chem. Biol. 13:235-244 (2009), all of which are hereby incorporated by reference in their entirety.

Generally, conjugation is performed by covalent attachment to an antibody, as further described below, and generally relies on a linker, often a peptide linkage (which, as described herein, may be designed to be sensitive to cleavage by proteases at the target site or not). In addition, linkage of the linker-drug unit (LU-D) can be achieved by attachment to cysteines within the antibody. The number of drug moieties per antibody can change, depending on the conditions of the reaction, and can vary from 1:1 to 10:1 drug: antibody. As will be appreciated by those in the art, the actual number is an average.

The drug of the ADC can be selected from any of a number of agents, including but not limited to cytotoxic agents such as chemotherapeutic agents, growth inhibitory agents, toxins (for example, an enzymatically active toxin of bacterial, fungal, plant, or animal origin, or fragments thereof), or a radioactive isotope (that is, a radioconjugate). The disclosure further provides methods of using the ADCs.

Drugs for use in the context of the disclosure include cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, vinca drugs, mitomycins, bleomycins, cytotoxic nucleosides, the pteridine family of drugs, diynenes, podophyllotoxins, dolastatins, maytansinoids, differentiation inducers, and taxols.

Members of these classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, maytansinoids (including DM1), monomethylauristatin E (MMAE), monomethylauristatin F (MMAF), and maytansinoids (DM4) and their analogues.

Toxins may be used as antibody-toxin conjugates and include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). Toxins may exert their cytotoxic and cytostatic effects by mechanisms including tubulin binding, DNA binding, or topoisomerase inhibition.

Conjugates of an antibody (or other antigen-binding protein) and one or more small molecule toxins, such as a maytansinoids, dolastatins, auristatins, a trichothecene, calicheamicin, and CC1065, and the derivatives of these toxins that have toxin activity, are contemplated.

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. As described below, drugs may be modified by the incorporation of a functionally active group such as a thiol or amine group for conjugation to the antibody.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions Exemplary maytansinoid drug moieties also include those having modifications such as: C-9-SH (U.S. Pat. No. 4,424,219) (prepared by the reaction of maytansinol with H2S or P2S5); C-14-alkoxymethyl(demethoxy/CH2OR) (U.S. Pat. No. 4,331,598); C-14-hydroxymethyl or acyloxymethyl (CH2OH or CH2OAc) (U.S. Pat. No. 4,450,254) (prepared from *Nocardia*); C-15-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from *Trewia nudlflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

Of particular use are DM1 (disclosed in U.S. Pat. No. 5,208,020, incorporated by reference) and DM4 (disclosed in U.S. Pat. No. 7,276,497, incorporated by reference). See also a number of additional maytansinoid derivatives and methods in U.S. Pat. Nos. 5,416,064; 6,441,163; 7,303,749; 7,368,565; and 7,601,354; International Publication Nos. WO/01/24763, WO02/098883, WO02/16368 and WO04/1033272; and U.S. Ser. No. 12/631,508, all of which are expressly incorporated by reference in their entirety.

ADCs containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference. Liu et al., Proc. Natl. Acad. Sci. USA 93:8618-8623 (1996) described ADCs comprising a maytansinoid designated DM1 linked to the monoclonal antibody C242 directed against human colorectal cancer.

Chari et al., Cancer Research 52:127-131 (1992) describe ADCs in which a maytansinoid was conjugated via a disulfide linker to the murine antibody A7 binding to an antigen on human colon cancer cell lines, or to another murine monoclonal antibody TA.1 that binds the HER-2/neu oncogene. The drug conjugate achieved a degree of cytotoxicity similar to the free maytansinoid drug, which could be increased by increasing the number of maytansinoid molecules per antibody molecule.

In some embodiments, the ADC comprises a dolastatin or dolostatin peptidic analog or derivative, or an auristatin (U.S. Pat. Nos. 5,635,483 and 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (International Patent Publication No. WO 02/088172). In various aspects, the heterodimeric antibody is part of a treatment plan that also includes administration of eribulin.

Exemplary auristatin embodiments include the N-terminus linked monomethylauristatin drug moieties DE and DF, disclosed in "Senter et al, Proceedings of the American Association for Cancer Research, Volume 45, Abstract Number 623, presented Mar. 28, 2004 and described in United States Patent Publication No. 2005/0238648, the disclosure of which is expressly incorporated by reference in its entirety. An exemplary auristatin embodiment is MMAE (see U.S. Pat. No. 6,884,869 expressly incorporated by reference in its entirety). Another exemplary auristatin embodiment is MMAF (see U.S. Publication No 2005/0238649 and U.S. Pat. Nos. 5,767,237 and 6,124,431, expressly incorporated by reference in their entirety).

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat Biotechnol 21(7):778-784.

In other embodiments, the ADC comprises one or more calicheamicin molecules. For example, Mylotarg is the first commercial ADC drug and utilizes calicheamicin 71 as the payload (see U.S. Pat. No. 4,970,198, incorporated by reference in its entirety). Additional calicheamicin derivatives are described in U.S. Pat. Nos. 5,264,586, 5,384,412, 5,550,246, 5,739,116, 5,773,001, 5,767,285 and 5,877,296, all expressly incorporated by reference. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma 1I$, $\alpha 2I$, $\alpha 2I$, N-acetyl-$\gamma 1I$, PSAG and $\theta I1$ (Hinman et al., Cancer Research 53:3336-3342 (1993), Lode et al., Cancer Research 58:2925-2928 (1998), and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

CC-1065 (see U.S. Pat. No. 4,169,888, incorporated by reference) and duocarmycins are members of a family of antitumor antibiotics utilized in ADCs. These antibiotics appear to work through sequence-selectively alkylating DNA at the N3 of adenine in the minor groove, which initiates a cascade of events that result in apoptosis. Important members of the duocarmycins include duocarmycin A (U.S. Pat. No. 4,923,990, incorporated by reference) and duocarmycin SA (U.S. Pat. No. 5,101,038, incorporated by reference), and a large number of analogues as described in U.S. Pat. Nos. 7,517,903, 7,691,962, 5,101,038; 5,641,780; 5,187,186; 5,070,092; 5,070,092; 5,641,780; 5,101,038; 5,084,468; 5,475,092; 5,585,499; 5,703,080; 6,989,452; 7,087,600; 7,129,261; 7,498,302; 7,507,420; and 5,846,545; and International Patent Publication Nos. WO2007/089149 and WO2009/017394A1, all of which are expressly incorporated by reference.

Other Cytotoxic Agents

Other antitumor agents that can be conjugated to an antigen-binding protein include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, International Patent Publication No. WO 93/21232.

The disclosure further contemplates an ADC formed between an antigen-binding protein and a compound with nucleolytic activity (e.g., a ribonuclease or a DNA endonuclease such as a deoxyribonuclease; DNase).

For selective destruction of the tumor, the antigen-binding protein (e.g., antibody or heterodimeric antibody) may comprise a highly radioactive atom. A variety of radioactive isotopes are available for the production of radioconjugates. Examples include At211, I131, I125, Y90, Re186, Re188, Sm153, Bi212, P32, Pb212 and radioactive isotopes of Lu.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc99m or I123, Re186, Re188, and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate Iodine-123. "Monoclonal Antibodies in Immunoscintigraphy" (Chatal, CRC Press 1989) describes other methods in detail.

In some instances, separation, purification, and characterization of homogeneous ADCs where p is a certain value from ADCs with other drug loadings may be achieved by means such as reverse phase HPLC or electrophoresis. In exemplary embodiments, p is 2, 3, 4, 5, 6, 7, or 8 or a fraction thereof.

It will be understood that chemical modifications may also be made to the desired compound in order to make reactions of that compound more convenient for purposes of preparing conjugates of the invention. For example a functional group e.g., amine, hydroxyl, or sulfhydryl, may be appended to the drug at a position which has minimal or an acceptable effect on the activity or other properties of the drug Linker Units Typically, the antigen-binding protein-drug conjugate comprises a linker unit between the drug unit and the antigen-binding protein unit. In some embodiments, the linker is cleavable under intracellular or extracellular conditions, such that cleavage of the linker releases the drug unit from the antigen-binding protein in the appropriate environment. For example, solid tumors that secrete certain proteases may serve as the target of the cleavable linker; in other embodiments, it is the intracellular proteases that are utilized. In yet other embodiments, the linker unit is not cleavable and the drug is released, for example, by antibody degradation in lysosomes.

In some embodiments, the linker is cleavable by a cleaving agent that is present in the intracellular environment (for example, within a lysosome or endosome or caveolea). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long or more.

Cleaving agents can include, without limitation, cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Peptidyl linkers that are cleavable by enzymes that are present in CD38-expressing cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker (SEQ ID NO: 181)). Other examples of such linkers are described, e.g., in U.S. Pat. No. 6,214,345, incorporated herein by reference in its entirety.

In some embodiments, the peptidyl linker cleavable by an intracellular protease is a Val-Cit linker or a Phe-Lys linker (see, e.g., U.S. Pat. No. 6,214,345, which describes the synthesis of doxorubicin with the val-cit linker).

In other embodiments, the cleavable linker is pH-sensitive, that is, sensitive to hydrolysis at certain pH values. Typically, the pH-sensitive linker hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) may be used. (See, e.g., U.S. Pat. Nos. 5,122,368; 5,824,805; and 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

In yet other embodiments, the linker is cleavable under reducing conditions (for example, a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, and SPDB and SMPT. See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987). See also U.S. Pat. No. 4,880,935.

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation. See, e.g., U.S. Patent Publication No. 2005/0238649 incorporated by reference herein in its entirety.

In many embodiments, the linker is self-immolative. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved. See, for example, International Patent Publication Nos. WO 2007059404A2, WO06110476A2, WO05112919A2, WO2010/062171, WO09/017394, WO07/089149, WO 07/018431, WO04/043493, and WO02/083180, which are directed to drug-cleavable substrate conjugates where the drug and cleavable substrate are optionally linked through a self-immolative linker and which are all expressly incorporated by reference.

Often the linker is not substantially sensitive to the extracellular environment, i.e., no more than about 20%, 15%, 10%, 5%, 3%, or no more than about 1% of the linkers, in a sample of antigen-binding protein-drug conjugate, are cleaved when the antigen-binding protein-drug conjugate presents in an extracellular environment (for example, in plasma). Whether a linker is not substantially sensitive to the extracellular environment can be determined, for example, by incubating with plasma the antigen-binding protein-drug conjugate compound for a predetermined time period (for example, 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (that is, in the milieu of the linker-therapeutic agent moiety of the ADC as described herein). In yet other embodiments, the linker promotes cellular internalization when conjugated to both the auristatin compound and the antigen-binding protein of the disclosure.

A variety of exemplary linkers that can be used with the present compositions and methods are described in International Patent Publication No. WO 2004-010957 and U.S. Publication Nos. 2006/0074008, 20050238649, and 2006/0024317 (each of which is incorporated by reference herein in its entirety).

It will be appreciated that the therapeutics described above may be administered separately, i.e., not conjugated to the antigen-binding protein, in various embodiments.

Drug Loading

Drug loading is represented by p and is the average number of drug moieties per antigen-binding protein in a molecule. Drug loading ("p") may be 1, 2, 3, 4, 5, 6, 7, 8, 9, 10, 11, 12, 13, 14, 15, 16, 17, 18, 19, 20 or more moieties (D) per antigen-binding protein, although frequently the average number is a fraction or a decimal. Generally, drug loading of from 1 to 4 is frequently useful, and from 1 to 2 is also useful. ADCs of the disclosure include collections of antigen-binding protein conjugated with a range of drug moieties, from 1 to 20. The average number of drug moieties per antigen-binding protein in preparations of ADC from conjugation reactions may be characterized by conventional means such as mass spectroscopy and, ELISA assay.

The quantitative distribution of ADC in terms of p may also be determined. In some instances, separation, purification, and characterization of homogeneous ADC where p is a certain value from ADC with other drug loadings may be achieved by means such as electrophoresis.

For some ADCs, p may be limited by the number of attachment sites on the antigen-binding protein. For example, where the attachment is a cysteine thiol, as in the exemplary embodiments above, an antigen-binding protein may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the drug loading for an ADC of the disclosure ranges from 1 to about 8; from about 2 to about 6; from about 3 to about 5; from about 3 to about 4; from about 3.1 to about 3.9; from about 3.2 to about 3.8; from about 3.2 to about 3.7; from about 3.2 to about 3.6; from about 3.3 to about 3.8; or from about 3.3 to about 3.7. Indeed, it has been shown that for certain ADCs, the optimal ratio of drug moieties per antigen-binding protein may be less than 8, and may be about 2 to about 5. See U.S. Publication No. 2005/0238649 A1 (herein incorporated by reference in its entirety).

In certain embodiments, fewer than the theoretical maximum of drug moieties are conjugated to an antigen-binding protein during a conjugation reaction. An antigen-binding protein may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antigen-binding protein ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antigen-binding protein such that the number and position of cysteine residues is modified for control of the number and/or position of linker-drug attachments (such as thioMab or thioFab prepared as disclosed in, e.g., International Patent Publication No. WO2006/034488 (herein incorporated by reference in its entirety)).

It is to be understood that where more than one nucleophilic group reacts with a drug-linker intermediate or linker reagent followed by drug moiety reagent, then the resulting product is a mixture of ADC compounds with a distribution of one or more drug moieties attached to an antigen-binding protein. The average number of drugs per antigen-binding protein may be calculated from the mixture by a dual ELISA antibody assay, which is specific for antigen-binding protein and specific for the drug. Individual ADC molecules may be identified in the mixture by mass spectroscopy and separated by HPLC, e.g., hydrophobic interaction chromatography.

In some embodiments, a homogeneous ADC with a single loading value may be isolated from the conjugation mixture by electrophoresis or chromatography.

Compositions

Formulations for use in accordance with the present disclosure are prepared for storage by mixing an antigen-binding protein having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. The compositions of the disclosure are preferably sterile. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation may also contain more than one active compound as necessary for the particular indication being treated, preferably those with complementary activities that do not adversely affect each other. For example, it may be desirable to provide antigen-binding proteins with other specificities. Alternatively, or in addition, the composition may comprise a cytotoxic agent, cytokine, growth inhibitory agent and/or small molecule antagonist, such as any of the drugs mentioned herein. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antigen-binding protein, which matrices are in the form of shaped articles, e.g., film or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

When encapsulated antibodies remain in the body for a long time, they may denature or aggregate as a result of exposure to moisture at 37C, resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Administrative Modalities

The antigen-binding protein and, optionally, a co-therapy, such as chemotherapeutic agent(s) or another antibody therapeutic (e.g., anti-PD-1 antibody) are administered to a subject in accordance with clinically-acceptable methods, such as intravenous, intramuscular, intraperitoneal, subcutaneous, intra-articular, intralesional, intrasynovial, intrathecal, oral, topical, intratumoral, via an afferent lymph vessel, or inhalation routes. Intravenous or subcutaneous administration of the antigen-binding protein is preferred. Bolus injection and continuous infusion are contemplated, as is localized administration, e.g., at a site of disease or injury. Use of the antigen-binding protein (optionally with another therapeutic agent) in ex vivo procedures also is contemplated. For example, a patient's blood or other bodily fluid may be contacted with the antigen-binding protein ex vivo, and optionally administered. The antigen-binding protein may be bound to a suitable insoluble matrix or solid support material.

Methods of Use

The disclosure provides a method of treating a subject in need thereof, the method comprising administering to the subject the antigen-binding protein (e.g., antibody or heterodimeric antibody) described herein. In various embodiments, the disclosure provides a method of treating cancer (such as prostate cancer or Ewing sarcoma) in a subject in need thereof, the method comprising administering to the subject the antigen-binding protein (e.g., antibody or heterodimeric antibody) described herein. The disclosure further provides use of the antigen-binding protein (e.g., antibody or heterodimeric antibody) of the disclosure for treating a subject in need thereof, such as use for the treatment of cancer (e.g., prostate cancer or Ewing sarcoma) in a subject. The cancer is preferably a cancer associated with increased expression of STEAP1 (e.g., greater than 10,000 STEAP1/cell). Examples of cancer include, but are not limited to, cancers of the prostate, breast, pancreas, bladder, gastrointestinal tract, testis, ovary, cervix, as well as sarcoma (Ewing sarcoma) and melanoma.

The methods of treating a subject described herein are intended to provide an improvement in a disease or condition, and/or an improvement in the symptoms associated with the disease or condition. For example, a therapeutic response would refer to one or more of the following improvements in the disease: (1) a reduction in the number of neoplastic cells; (2) an increase in neoplastic cell death; (3) inhibition of neoplastic cell survival; (5) inhibition (i.e., slowing to some extent, preferably halting) of tumor growth or appearance of new lesions; (6) an increased patient survival rate; and/or (7) some relief from one or more symptoms associated with the disease or condition (e.g., in the context of prostate cancer, frequent urination, nocturia, hematuria, dysuria, or bone pain; in the context of Ewing sarcoma, pain, swelling, or tenderness in affected area).

Therapeutic responses in any given disease or condition can be determined by standardized response criteria specific to that disease or condition. Tumor response can be assessed using screening techniques such as magnetic resonance imaging (MRI) scan, x-radiographic imaging, computed tomographic (CT) scan, positron emission tomography (PET) scan, bone scan, ultrasound, tumor biopsy sampling, counting of tumor cells in circulation, and/or measurement of tumor antigen (e.g., prostate specific antigen (PSA) and/or alphafeltoprotein (AFP)). In addition to these therapeutic responses, the subject undergoing therapy may experience the beneficial effect of an improvement in the symptoms associated with the disease.

The subject is a mammal, preferably a human, optionally a human male. In the context of cancer, the subject may be diagnosed with any stage of the disease (i.e., stage I, stage II, stage III, or stage IV prostate cancer), or may be at risk of developing cancer which has not yet been clinically confirmed.

For prostate cancer, the subject may experience a decrease in prostate cancer-related symptoms (such as those described herein), decrease in tumor size, decrease in levels of prostate cancer markers, decrease in the rate of appearance of new lesions, and the like. In various aspects, the methods of the disclosure further comprise monitoring treatment in the subject. Any improvement in the subject's well being is contemplated (e.g., absence of clinically detectable disease, any decrease (such as at least about a 50% decrease) in measurable tumor burden (i.e., the number of malignant cells present in the subject or the measured bulk of tumor masses) in the absence of new lesions, reduction in pain, improvement in urination).

Treatment according to the present disclosure includes a "therapeutically effective amount" of the medicaments used. A "therapeutically effective amount" refers to an amount effective, at dosages and for periods of time necessary, to achieve a desired therapeutic result. A therapeutically effective amount may vary according to factors such as the disease state, age, sex, and weight of the individual, and the ability of the medicaments to elicit a desired response in the individual. A therapeutically effective amount is also one in which any toxic or detrimental effects are outweighed by the therapeutically beneficial effects. A "therapeutically effective amount" for tumor therapy may also be measured by its ability to stabilize the progression of disease. An exemplary, non-limiting range for a therapeutically effective amount of an antigen-binding protein of the present disclosure is about 0.1-100 mg/kg. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of therapeutic calculated to produce the desired biological effect in association with the required pharmaceutical carrier.

In some embodiments the antigen-binding protein (e.g., a monospecific antibody or heterodimeric antibody) is used in combination with one or more additional therapeutic agents, e.g., a chemotherapeutic agent or immunotherapy agent. The additional therapeutic agent(s) may be administered serially (within minutes, hours, days, or weeks of each other) or in parallel; they also may be administered to the patient in a pre-mixed single composition.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, epirubicin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include, but are not limited to, paclitaxel, docetaxel, and related analogs; cabzitaxel; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

In some embodiments, the antigen-binding protein (e.g., a monospecific antibody or heterodimeric antibody) of the disclosure can be used prior to, concurrent with, or after treatment with docetaxol. In various aspects, the antigen-binding protein (e.g., monospecific antibody or heterodimeric antibody) is administered as part of a treatment plan that includes surgery and/or radiation (e.g., external beam or brachytherapy).

In various aspects, the antigen-binding protein (e.g., a monospecific antibody or heterodimeric antibody) is provided as part of a treatment plan that also includes administration of hormone therapy (e.g., androgen-deprivation therapy, such as agents that block the release or production of luteinizing-hormone releasing hormone (e.g., leuprolide, goserelin, triptorelin, or degarelix), anti-androgens (e.g., bicalutamide, flutamide, or nilutamide), ketoconazole, abiraterone acetate, enzalutamide)), In various aspects, the antigen-binding protein (e.g., a monospecific antibody or heterodimeric antibody) is provided as part of a treatment plan that also includes administration of another immunotherapy (e.g., sipuleucel-T, bevacizumab, atezolizumab, avelumab, ipilimumab, tremelimumab, AM-224, MDX-1105, eftilagimod alpha (IMP321), or enoblituzumab (MGA271)). In this regard, the method optionally comprises administration of another antigen-binding protein that targets a different antigen, such as a cancer-related antigen or an antigen associated with an immune response. For example, in various embodiments, the anti-STEAP1 antigen-binding protein is administered to a subject alongside a PD-1 targeting antigen-binding protein (e.g., antibody) that decreases, blocks, inhibits, abrogates, or interferes with signal transduction resulting from the interaction of PD-1 with one or more of its binding partners, such as PD-L1 or PD-L2. In a specific aspect, the PD-1 antigen-binding protein inhibits the binding of PD-1 to PD-L1 and/or PD-L2. In one embodiment, a PD-1 antigen-binding protein reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). Examples of anti-PD-1 antibodies include nivolumab (BMS-936558), pembrolizumab (MK-3475), BMS 936558, BMS-936559, TSR-042 (Tesaro), ePDR001 (Novartis), and pidilizumab (CT-011). While the disclosure references PD-1 antigen-binding proteins, the disclosure also contemplates use of other PD-1 binding antagonists that decrease, block, inhibit, abrogate, or interfere with signal transduction resulting from the interaction of PD-1 with one or more of its binding partners, such as PD-L1 or PD-L2.

The disclosure provided herein with respect to anti-STEAP1 antigen-binding proteins also applies to anti-PD-1 antigen-binding proteins. For example, in various instances, the anti-PD-1 antigen-binding protein is an antibody, such as a monoclonal IgG. The anti-PD-1 antibody, antigen-binding antibody fragment thereof, or anti-PD-1 antibody protein product is a monovalent or bivalent. In exemplary aspects, the anti-PD-1 antibody, antigen-binding antibody fragment thereof, or anti-PD-1 antibody protein product binds to human PD-1, which has the amino acid sequence of SEQ ID NO: 187. In exemplary aspects, the anti-PD-1 antibody, antigen-binding antibody fragment thereof, or anti-PD-1 antibody protein product binds to cynomolgus PD-1, which has the amino acid sequence of SEQ ID NO: 188. In exemplary instances, the anti-PD-1 antibody, antigen-binding antibody fragment thereof, or anti-PD-1 antibody protein product binds to both human PD-1 and cynomolgus PD-1.

In exemplary embodiments, the binding strength of the anti-PD-1 antibody, antigen-binding antibody fragment thereof, or anti-PD-1 antibody protein product to PD-1 may be described in terms of KD. In exemplary aspects, the KD of the anti-PD-1 antibody, antigen-binding antibody fragment thereof, or anti-PD-1 antibody protein product provided herein is about $10^{-1}$ M, about $10^{-2}$ M, about $10^{-3}$ M, about $10^{-4}$ M, about $10^{-5}$ M, about $10^{-6}$ M, about $10^{-7}$ M, about $10^{-8}$ M, about $10^{-9}$ M, or less. In exemplary aspects, the KD of the anti-PD-1 antibody, antigen-binding antibody fragment thereof, or anti-PD-1 antibody protein product provided herein is micromolar, nanomolar, picomolar, or femtomolar. In exemplary aspects, the KD of the anti-PD-1 antibody, antigen-binding antibody fragment thereof, or anti-PD-1 antibody protein product provided herein is within a range of about 104 to $10^{-6}$ M, or $10^{-7}$ to $10^{-9}$ M, or $10^{-10}$ to $10^{-12}$ M, or $10^{-13}$ to $10^{-1}$ M. In exemplary aspects, the anti-PD-1 antibody, antigen-binding antibody fragment thereof, or anti-PD-1 antibody protein product has high affinity for human PD-1, cynomolgus PD-1, or both. In exemplary aspects, the anti-PD-1 antibody, antigen-binding antibody fragment thereof, or anti-PD-1 antibody protein product has a KD for human PD-1 of less than 100 pM, optionally, about 1 pM to about 50 pM. In exemplary aspects, the anti-PD-1 antibody, antigen-binding antibody fragment thereof, or anti-PD-1 antibody protein product has a KD for human PD-1 within about 1 pM to about 20 pM or less than about 10 pM. In exemplary aspects, the anti-PD-1 antibody, an antigen-binding antibody fragment thereof, or anti-PD-1 antibody protein product has a KD for cynomolgus PD-1 of less than 100 pM, optionally, about 1 pM to about 75 pM. In exemplary aspects, the anti-PD-1 antibody, antigen-binding antibody fragment thereof, or anti-PD-1 antibody protein product has a KD for cynomolgus PD-1 within about 1 pM to about 20 pM or less than 10 pM.

In exemplary aspects, the anti-PD-1 antibody, antigen-binding antibody fragment thereof, or anti-PD-1 antibody protein product inhibits at least 50% of the binding interactions between PD-1 and PD-L1 or PD-L2. In exemplary aspects, the anti-PD-1 antibody, antigen-binding antibody fragment thereof, or anti-PD-1 antibody protein product exhibits at least about 50%, at least about 60%, or at least about 70% inhibition of the binding interaction between PD-1 and PD-L1 or PD-L2.

In exemplary instances, the anti-PD-1 antibody, antigen-binding antibody fragment thereof, or anti-PD-1 antibody protein product inhibits PD-1-mediated production of IL-2 by T cells in a mixed lymphocyte reaction (MLR). In exemplary aspects, the IC50 of the anti-PD-1 antibody, antigen-binding antibody fragment thereof, or anti-PD-1 antibody protein product in the MLR is within about 0.1 nM to about 5 nM. In exemplary aspects, the IC50 of the anti-PD-1 antibody, antigen-binding antibody fragment thereof, or anti-PD-1 antibody protein product in the MLR is less than 2 nM or less than 1 nM. In exemplary aspects, the IC50 of the anti-PD-1 antibody, antigen-binding antibody fragment thereof, or anti-PD-1 antibody protein product in the MLR is about 0.5 nM to about 2 nM.

Methods of testing antibodies for the ability to bind to PD-1 are known in the art and include any suitable antibody-antigen binding assay, such as, for example, radioimmunoassay (RIA), ELISA, Western blot, immunoprecipitation, SPR, and competitive inhibition assays (see, e.g., Janeway et al., infra, and U.S. Patent Application Publication No. 2002/0197266, and the above section relating to competition assays). Other binding assays, e.g., competitive binding assays or competition assays, which test the ability of an antibody to compete with a second antibody for binding to an antigen or to an epitope thereof can be used to test the ability of an antibody to bind to PD-1. See, e.g., U.S. Patent Application Publication No. 2014/0178905; Chand et al., Biologicals 46: 168-171 (2017); Liu et al., Anal Biochem 525: 89-91 (2017); and Goolia et al., J Vet Diagn Invest 29(2): 250-253 (2017). Also, other methods of comparing two antibodies are known in the art, and include, for example, surface plasmon resonance (SPR). SPR can be used to determine the binding constants of the antibody and second antibody and the two binding constants can be compared. The disclosure contemplates use of an anti-PD1 antigen-binding protein that competes with, or cross-blocks, the binding of any of the anti-PD-1 antibodies described herein to the PD-1 protein in the context of the disclosed method.

A representative method for characterizing human and cynomolgus monkey PD-1 binding affinity is as follows. Antibodies are incubated in wells containing a 3-fold serial dilution of soluble, recombinant receptors human PD-1(1-170)-FLAG-His or cynomolgus monkey PD-1(1-167)-FLAG-His. In both cases, a top PD-1 concentration of 30 nM may be selected. Association for 300 seconds and dissociation for 500 seconds may be used, as these parameters typically produce enough curvature for accurate kinetic fits. Human/cynomolgus monkey PD-1 binding affinities may be quantitated with ForteBio Octet HTX and RED384 instruments. Standard Octet sample buffer may be used for sample dilution and binding baseline, association, and dissociation steps (e.g., 10 mM Tris, pH 7.5, 150 mM NaCl, 1 mM $CaCl_2$), 0.10 mg·ml BSA, 0.13% (v/v) Triton X-100). ForteBio raw data may be processed in the following manner using the standard instrument data analysis software (v9 and v0): (a) two reference curves which have immobilized target but no interaction (i.e., buffer only) are averaged and subtracted from the remaining sample curves in the same column; (b) the association and dissociation curves are isolated and aligned to the Y axis; (c) the association and dissociation interstep are aligned; (d) Savitzky-Golay filtering is implemented to reduce the signal noise and (e) the resulting set of association and dissociation curves for each sample-target interaction are globally fit with a single 1:1 binding model to determine the measured values of the association rate constant ka and the dissociation rates constants kd; the equilibrium dissociation constant KD is calculated as a ratio of the dissociation and association rates constants (=kd/ka).

In exemplary instances, the anti-PD-1 antibody (or antigen-binding antibody fragment thereof or antibody protein product) comprises the heavy chain (HC) complementarity-determining region 1 (vhCDR1) amino acid sequence set forth in SEQ ID NO: 189, the HC CDR2 (vhCDR2) amino acid sequence set forth in SEQ ID NO: 190, the HC CDR3 (vhCDR3) amino acid sequence set forth in SEQ ID NO: 191, the light chain (LC) CDR1 (vlCDR1) amino acid sequence set forth in SEQ ID NO: 192, the LC CDR2 (vCDR2) amino acid sequence set forth in SEQ ID NO: 193, and the LC CDR3 (vCDR3) amino acid sequence set forth in SEQ ID NO: 194. In exemplary embodiments, the anti-PD-1 antibody (or antigen-binding antibody fragment thereof or antibody protein product) comprises a heavy chain variable region (vh) comprising an amino acid sequence that is at least 90% identical (e.g., 91%, 92%, 93%, 94%, 95%, 96%, 97%, 98%, 99%, or 100% identical) to the amino acid sequence of SEQ ID NO: 195 and/or a light chain variable region (vl) comprising an amino acid sequence that is at least 90% identical (e.g., 91%, 92%, 93%, 94%, 95%, 96%, 97%, 98%, 99%, or 100% identical) to the amino acid sequence of SEQ ID NO: 196. In exemplary embodiments, the anti-PD-1 antibody (or antigen-binding antibody fragment thereof or antibody protein product) comprises a heavy chain comprising an amino acid sequence that is at least 90% identical (e.g., 91%, 92%, 93%, 94%, 95%, 96%, 97%, 98%, 99%, or 100% identical) to the amino acid sequence of SEQ ID NO: 197 and/or a light chain comprising an amino acid sequence that is at least 90% identical (e.g., 91%, 92%, 93%, 94%, 95%, 96%, 97%, 98%, 99%, or 100% identical) to the amino acid sequence of SEQ ID NO: 198.

In exemplary aspects, the anti-STEAP1 construct described herein is part of a treatment regimen that includes administration of a cytokine, lymphokine, growth factor, or hematopoietic factor effective in inhibiting tumor metastasis and/or having an antiproliferative effect on at least one cell population. Such cytokines, lymphokines, growth factors, or other hematopoietic factors include, but are not limited to: M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin. Additional growth factors include, e.g., angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor α, cytokine-induced neutrophil chemotactic factor 1, cytokine-induced neutrophil, chemotactic factor 2 α, cytokine-induced neutrophil chemotactic factor 2 β, β endothelial cell growth factor, endothelin 1, epithelial-derived neutrophil attractant, glial cell line-derived neutrophic factor receptor α 1, glial cell line-derived neutrophic factor receptor α 2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor, nerve growth factor receptor, neurotrophin-3, neurotrophin-4, pre-B cell growth stimulating factor, stem cell factor, stem cell factor receptor, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, and chimeric proteins and biologically or immunologically active fragments thereof. In exemplary embodiments, the anti-STEAP1 construct is administered as part of a therapeutic regimen involving administration of an antibody specific for any one of the aforementioned cytokines, lymphokines, growth factors, or other hematopoietic factors.

The disclosure contemplates use of the anti-STEAP1 antigen-binding protein or a heterodimeric antibody in the preparation of a medicament for treating cancer in a subject in need thereof. Optionally, the medicament is for administering an effective amount of the anti-STEAP1 antigen-binding protein or heterodimeric antibody in association with an effective amount of anti-PD-1 antigen-binding protein (e.g., any of the anti-PD-1 antigen-binding proteins described herein).

The disclosure further contemplates the anti-STEAP1 antigen-binding protein or heterodimeric antibody described herein for use in treating cancer in a subject in need thereof (i.e., in a method of treating cancer, such as prostate cancer or Ewing sarcoma, in a subject in need thereof). Optionally, the anti-STEAP1 antigen-binding protein or heterodimeric antibody is administered with an anti-PD1 antigen-binding protein. By "administer with" is meant that the anti-STEAP1 antigen-binding protein or heterodimeric antibody is part of a therapeutic regimen that includes administration of an anti-PD1 antigen-binding protein. Indeed, the anti-STEAP1 antigen-binding protein (e.g., heterodimeric antibody) can be used prior to, concurrent with, or after treatment with an anti-PD1 antigen-binding protein. The administration of the anti-STEAP1 antigen-binding protein or heterodimeric antibody and the anti-PD1 antigen-binding protein need not occur simultaneously, although the disclosure contemplates embodiments wherein the components are included in the same pharmaceutical composition and administered together. The disclosure also provides a method of treatment wherein the anti-STEAP1 antigen-binding protein or heterodimeric antibody and the anti-PD1 antigen-binding protein are present in separate pharmaceutical compositions which are administered in parallel or administered near in time. The anti-STEAP1 antigen-binding protein or heterodimeric antibody and the anti-PD1 antigen-binding protein may be administered serially (e.g., within minutes, hours, days, or weeks within each other), in any order. Administration modalities are described above.

The anti-STEAP1 antigen-binding protein described herein also can be used, for example, in assays to detect the presence of STEAP1, either in vitro or in vivo. The antigen-binding protein also may be employed to purify STEAP1 by, e.g., immunoaffinity chromatography.

Nucleic Acids, Vectors, Host Cells

The disclosure further provides nucleic acid compositions encoding the antigen-binding protein (e.g., monospecific antibody or heterodimeric antibody) described herein. The nucleic acids encoding the components of the antigen-binding protein of the disclosure can be incorporated into expression vectors as is known in the art and depending on the host cells used to produce the antigen-binding protein. Examples of expression vectors include, but are not limited to, plasmids, viral vectors, non-episomal mammalian vectors and other expression vectors. Generally, the nucleic acid sequence encoding a desired polypeptide is operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the disclosure are optionally introduced into any number of different types of host cells as is well known in the art, including mammalian, bacterial, yeast, insect and/or fungal cells, with mammalian cells (e.g., CHO cells) finding use in many embodiments. In another aspect, the disclosure provides such host cells into which an expression vector encoding an antigen-binding protein has been introduced. Examples of suitable mammalian host cell lines include the COS-7 line of monkey kidney cells (ATCC CRL 1651) (Gluzman et al., 1981, Cell 23:175), L cells, human embryonic kidney 293 cells or derivatives thereof (e.g., HEK293T, HEK293-EBNA), C127 cells, mouse embryo fibroblast cells (3T3 cells) (ATCC CCL 163), Chinese hamster ovary (CHO) cells and derivatives thereof (e.g., CHO-K1, CHO pro-3), mouse myeloma cells (e.g., NSO, GS-NSO, Sp2/0), human cervical cancer cells (HeLa cells), baby hamster kidney (BHK) cells (ATCC CRL 10) cell lines, human bone osteosarcoma epithelial cells U2-OS, adenocarcinomic human alveolar basal epithelial cells (A549), human fibrosarcoma cells (HT1080), mouse brain tumor cells (CAD), embryonic carcinoma cells (P19), mouse neuroblastoma cells (N2a), human breast cancer cells (MCF-7), retinoblastoma cells (Y79), human retinoblastoma cells (SO-Rb50), human liver cancer cells (Hep G2), mouse B myeloma cells (J558L), and African green monkey kidney cells (e.g., COS cells, VERO cells and derivatives thereof (including the CVI/EBNA cell line derived from the African green monkey kidney cell line CVI (ATCC CCL 70) as described by McMahan et al., 1991, EMBO J. 10: 2821)). The transformed cells can be cultured under conditions that promote expression of the antigen-binding protein, and the protein recovered by conventional protein purification procedures. One such purification procedure includes the use of affinity chromatography, e.g., over a matrix having all or a portion (e.g., one or more extracellular loops) of STEAP1 bound thereto. Antigen-binding proteins contemplated for use herein include substantially homogeneous recombinant antigen-binding proteins substantially free of contaminating endogenous materials.

With respect to heterodimeric antibodies, in various aspects, a composition is provided which comprises a nucleic acid encoding the first monomer, a nucleic acid encoding the second monomer, and a nucleic acid encoding the common light chain. The disclosure also provides nucleic acid constructs encoding portions of the monomers and common light chain, e.g., the anti-STEAP1 Fab or antibody fragments comprising six CDRs disclosed herein which bind STEAP1, the anti-CD3 scFv, the variable light and/or variable heavy domains that bind STEAP1 and/or CD3, and the like.

In some embodiments, nucleic acids encoding each monomer and, optionally, the nucleic acid encoding the common light chain, are each contained within a single expression vector, generally under different or the same promoter controls. In various embodiments, each of these two or three nucleic acids are contained on a different expression vector. As described in U.S. Patent Publication No. 2016/0215063 (hereby incorporated by reference in its entirety and particularly with respect to the discussion of recombinant antibody production), different vector ratios can be used to drive heterodimer formation. Surprisingly, in instances where antibody constructs comprise first monomer:second monomer:light chains in a 1:1:2 ratio, these are not necessarily the ratios that give the best results. See FIG. 65 of U.S. Patent Publication No. 2016/0215063, incorporated herein by reference. In various aspects, the disclosure provides a nucleic acid composition comprising: a) a first expression vector comprising a first nucleic acid encoding the first monomer; b) a second expression vector comprising a second nucleic acid encoding the second monomer; and c) a third expression vector comprising a third nucleic acid encoding the common light chain. In alternative embodiments, the third nucleic acid encoding the common light chain is present on the same expression vector as the first or second nucleic acid.

The heterodimeric antibodies are optionally made by culturing host cells comprising the expression vector(s). Once produced, antibody purification steps are performed, typically including an ion exchange chromatography step. As discussed herein, having the pIs of the two monomers differ by at least 0.5 can allow separation by ion exchange chromatography or isoelectric focusing, or other methods sensitive to isoelectric point. That is, the inclusion of pI substitutions that alter the isoelectric point (pI) of each monomer so that such that each monomer has a different pI and the heterodimer also has a distinct pI, thus facilitating isoelectric purification heterodimer (e.g., anionic exchange columns, cationic exchange columns). These substitutions also aid in the determination and monitoring of any contaminating mAb homodimers post-purification (e.g., IEF gels, cIEF, and analytical IEX columns).

Kits

In some embodiments, the antigen-binding protein of the present disclosure is provided in a kit. In exemplary aspects, the kit comprises the antigen-binding protein as a unit dose (i.e., a discrete amount dispersed in a suitable carrier). In exemplary aspects, the kit comprises several unit doses, e.g., a week or month supply of unit doses, optionally, each of which is individually packaged or otherwise separated from other unit doses. In some embodiments, the components of the kit/unit dose are packaged with instructions for administration to a patient. In some embodiments, the kit comprises one or more devices for administration to a patient, e.g., a needle and delivery device (such as a syringe), and the like. In some aspects, the antigen-binding protein is prepackaged in a ready to use form, e.g., a syringe, an intravenous bag, etc., although it is also contemplated that the antigen-binding protein may be provided in lyophilized form requiring reconstitution. In some aspects, the kit further comprises other therapeutic or diagnostic agents or pharmaceutically acceptable carriers (e.g., solvents, buffers, diluents, etc.), including any of those described herein.

All references, including publications, patent applications, and patents, cited herein are hereby incorporated by reference to the same extent as if each reference were individually and specifically indicated to be incorporated by reference and were set forth in its entirety herein.

The following examples are given merely to illustrate the present disclosure and not in any way to limit its scope.

EXAMPLES

Example 1

This Example describes detection of STEAP1 at the surface of prostate cancer cells using a monospecific antibody as described above.

Prostate cancer cells (C4-2B luc cells (FIG. 11A) or C4-2B luc$^{STEAP1\ KO}$ cells (FIG. 11B)) that were engineered to have lost STEAP1 expression using a CRISPR construct directed against STEAP1 were incubated with an isotype control antibody or the anti-STEAP1 mouse monoclonal antibody (Ab-Am) at a concentration of 10 g/mL for 1 h at 4° C. Cell-bound Ab-Am was detected by flow cytometry after incubation with a FITC-conjugated (FIG. 11A) or an APC-conjugated anti-mouse IgG secondary antibody (FIG. 11B). FITC or APC fluorescence, identifying a STEAP1-dependent signal, were plotted in histograms (solid gray histograms) and compared to the isotype control (white histograms). Results are shown in FIGS. 11A and 11B.

Example 2

This Example describes the characterization of anti-STEAP1 antibodies.

A panel of 22 anti-human STEAP1 mouse monoclonal antibodies was generated. Antibody A demonstrated improved flow cytometry binding properties (parental mAb binding LnCAP(+)/DU145(−) FACS shift (fold)) compared to others tested: Ab-A (60.1), Ab-B (3.6), Ab-C (2.4), and Ab-D (4.3).

To determine the region of STEAP1 recognized by an antibody of the disclosure, chimeric constructs were generated wherein each of three extracellular loops of STEAP1 was replaced with the corresponding region of STEAP2 and expressed in 293 cells. Ab-A binds STEAP1 and does not bind STEAP2. Replacing extracellular loops 1 and 3 of STEAP1 with the corresponding loops from STEAP2 abrogated binding, while Ab-A binding to STEAP1 was not destroyed when extracellular loop 2 was replaced with the STEAP2 counterpart. Ab-A appears to bind to STEAP1 outside of extracellular loop 2.

Heterodimeric antibodies comprising the STEAP-1 binding arm of Ab-A1, Ab-A2 (N67Q), and Ab-B1 and an anti-CD3 binding arm were prepared in the "XmAb" format as described in, e.g., U.S. Patent Publication No. 2016/

0215063. These heterodimeric antibodies displayed TDCC activity (pM): Ab-A1x (273.8), Ab-A2x (387.9), and Ab-B1x (128.7).

Example 3

This Example compares binding (characterized by EC50) of an anti-STEAP1/anti-CD3 bispecific antibody (XmAb) with a different scaffold with the heterodimeric anti-STEAP1/anti-CD3 of the disclosure (Xmab$^{2+1}$) to C4-2B cells.

Three anti-STEAP1 humanized antibodies (Ab-A1, Ab-A2(N67Q) and Ab-B1) in the "XmAb" format were generated as described in, e.g., U.S. Patent Publication No. 2016/0215063 (incorporated by reference herein, particularly with respect to the discussion of "bottle opener" formats). The XmAb format entails a first heavy chain comprising a Fe domain attached to an anti-CD3 scFv; a second heavy chain comprising an Fe domain and a first variable heavy domain; and a light chain comprising a variable light domain and a constant light domain. The variable heavy domain and said variable light domain bind to STEAP1. Two anti-STEAP1 humanized antibodies were generated in the heterodimeric XmAb$^{2+1}$ format (Ab-A1 XmAb$^{2+1}$ and Ab-B1 XmAb$^{2+1}$). The CDR sequences of Ab-A1 XmAb$^{2+1}$ and Ab-B1 XmAb$^{2+1}$ are set forth in SEQ ID NOs: 11-16 (Ab-A1 XmAb$^{2+1}$) and SEQ ID NOs: 30-35 (Ab-B1 XmAb$^{2+1}$). A variant of Ab-A1 XmAb$^{2+1}$ having a N67Q modification, designated herein as Ab-A2(N67Q) XmAb$^{2+1}$ was also generated. The CDR sequences of Ab-A2 (N67Q) XmAb$^{2+1}$ are set forth in SEQ ID NOs: 11-13, 14, 16 and 21. The antibody designations Ab-A2 and Ab-A2 (N67Q) XmAb$^{2+1}$ are used interchangeably herein. The ability of the heterodimeric bispecific antibodies to bind to STEAP1 expressed on the surface of C4-2B prostate cancer cells was assessed, alongside three mouse anti-STEAP1 antibodies in the XmAb format (Ab-Mx1, Ab-Mx2, and Ab-Mx3) that had not been humanized.

C4-2B-Luc cells were incubated with increasing concentrations of Ab-A1 XmAb$^{2+1}$, Ab-A1 Xmab, Ab-B1 Xmab, Ab-Mx1, Ab-Mx2 and Ab-Mx3 up to 5 M, for 1 hour at 4° C. Cell-bound antibodies were detected by flow cytometry after incubation with an APC-conjugated anti-human IgG secondary antibody and mean fluorescence intensity (MFI) of the APC channel at increasing concentrations of respective antibodies tested. As shown in Table 3, Ab-A1 Xmab$^{2+1}$ demonstrated cell binding that was 65-fold lower than the binding EC50 of the same binder in the XmAb format (i.e., Ab-A1 Xmab), demonstrating very strong avidity beyond that of the corresponding XmAb. The XmAb$^{2+1}$ format considerably improved binding of the Ab-A binder to STEAP1 expressed on prostate cancer cells.

TABLE 3

Binding EC50 of anti-STEAP XmAb and anti-STEAP Xmab$^{2+1}$ to C4-2B cells

| Antibody molecule | EC50 (nM) |
| --- | --- |
| Ab-A1 Xmab | 144.0 |
| Ab-B1 Xmab | 798.1 |
| Ab-Mx1 | 1226 |
| Ab-Mx2 | 1252 |
| Ab-Mx3 | 5005 |
| Ab-A1 XmAb$^{2+1}$ | 2.203 |

The experiment was repeated with Ab-A in various formats (Ab-A (traditional, monospecific antibody, not humanized), Ab-A1 XmAb format, Ab-A1 Xmab$^{2+1}$ format, and Ab-A2(N67Q) Xmab$^{2+1}$ format (with N67Q modification)) and Ab-B XmAb format. C4-2B-Luc cells were incubated with increasing concentrations of anti-STEAP1 XmAb or XmAb$^{2+1}$ molecules up to 5 M, for one hour at 4° C. Cell-bound XmAb were detected by flow cytometry after incubation with an APC-conjugated anti-human IgG secondary antibody and mean fluorescence intensity (MFI) of the APC channel at increasing concentrations of respective anti-STEAP1 XmAb molecules were displayed. Results are shown in FIGS. 12A-12C and FIG. 13 and Table 4 below.

TABLE 4

Binding EC50 to C4-2B luc cells

| Format | STEAP1 Binder | Binder Species | EC$_{50}$ (nM) |
| --- | --- | --- | --- |
| mAb | Ab-A | Mouse | 1.2 |
| XmAb | Ab-A1 Xmab | Humanized | 144 |
| XmAb$^{2+1}$ | Ab-A1 XmAb$^{2+1}$ | Humanized | 2.2 |
| XmAb$^{2+1}$ | AbA2-(N67Q) XmAb$^{2+1}$ | Humanized | 1.2 |
| XmAb | Ab-B1 XmAb | Humanized | 48.9 |

The antibodies all bound STEAP1 regardless of heterodimeric format. The XmAb$^{2+1}$ format demonstrated improved binding to STEAP1 compared to other antibody formats.

TDCC activity also was evaluated using methods similar to those described above. All tested antibodies displayed TDCC activity, with antibodies in the XmAb$^{2+1}$ demonstrating better activity than Xmab antibodies: Ab-A XmAb (EC50=274 pM, EC90=438 pM), Ab-A1 Xmab (EC50=388 pM, EC90=722 pM), Ab-B1 Xmab (EC50=129 pM, EC90=265 pM), Ab-A1 Xmab$^{2+1}$ (EC50=6 pM, EC90=11 pM), and Ab-B1 Xmab$^{2+1}$ (EC50=19 pM, EC90=43 pM).

Example 5

This Example characterizes lysis of human tumor cell line C4-2B luc by human T cells mediated by anti-STEAP1 XmAb and XmAb$^{2+1}$.

Figure 14:
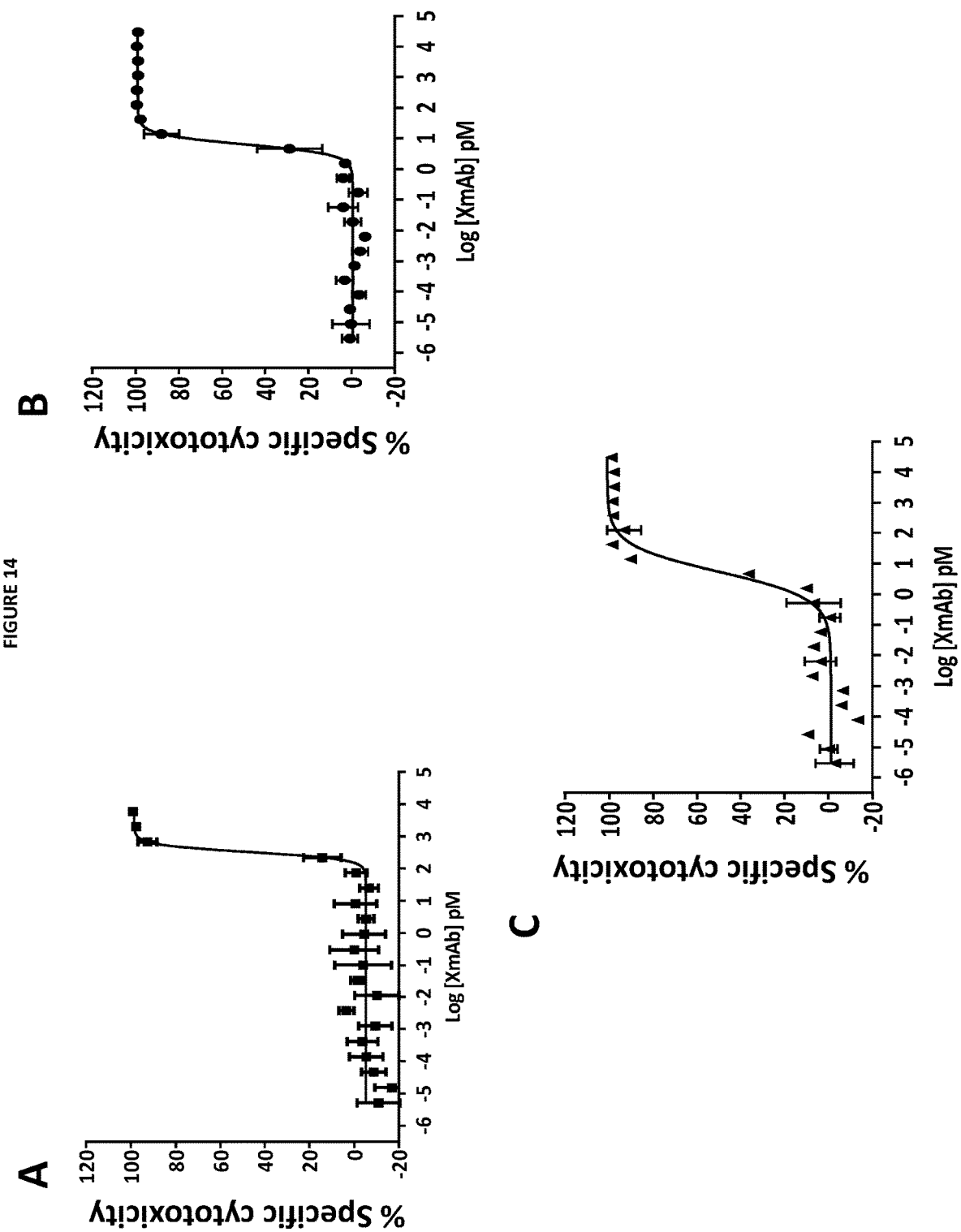
FIGS. 14A-14C show that STEAP1 antibody Ab-Ax (FIG. 14A), STEAP1 antibody Ab-A1 Xmab$^{2+1}$ (FIG. 14B), and STEAP1 antibody Ab-A2(N67Q) Xmab$^{2+1}$ (FIG. 14C) mediated target cell lysis of human tumor cell line C4-2B luc by human T cells.

C4-2B luc prostate cancer cells were co-cultivated with human pan-T cells at an E:T cell ratio of 10 to 1 and increasing concentrations of (FIG. 14A) Ab-A1 XmAb, (FIG. 14B) Ab-A1 XmAb$^{2+1}$, or (FIG. 14C) Ab-A2(N67Q) XmAb$^{2+1}$ format (with N67Q substitution) for 48 hours. Target cell lysis was monitored by luciferase activity measurement and the specific cytotoxicity was plotted at each concentration in comparison with no XmAb control conditions. As shown in FIGS. 14A-14C, Ab-A1 Xmab, Ab-A1 XmAb$^{2+1}$, and Ab-A2(N67Q) XmAb$^{2+1}$ were successful in mediating target cell lysis.

Example 6

This Example demonstrates the ability of a heterodimeric antibody of the disclosure to distinguish between STEAP1-expressing cells and cells which do not express STEAP.

Figure 15:
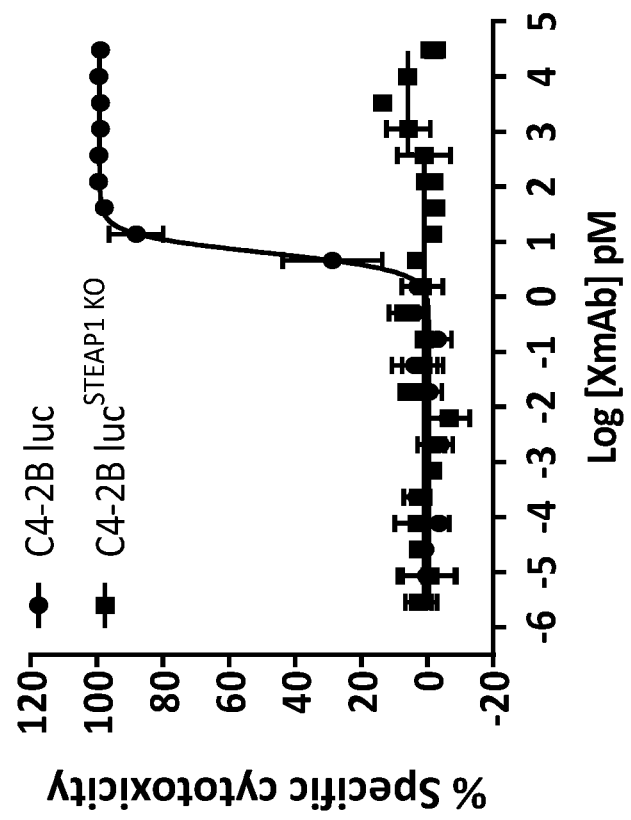
FIG. 15 shows that STEAP1 antibody Ab-A1 Xmab$^{2+1}$ and Ab-A2(N67Q) Xmab$^{2+1}$ mediated dose-dependent target cell lysis of human tumor cell line C4-2B luc but not C4-2B luc STEAP1 KO by human T cells.

STEAP1-positive C4-2B luc prostate cancer cells (●) and STEAP1-negative C4-2B luc$^{STEAP1\ KO}$ ells (■) were co-cultivated with human pan-T cells at an E:T cell ratio of 10 to 1 and increasing concentrations of Ab-A1 XmAb$^{2+1}$ for 48 hours. Target cell lysis was monitored by luciferase activity measurement, and the specific cytotoxicity was plotted at each concentration in comparison with control conditions (lacking XmAb). The results are shown in FIG. 15 and Table 5 below. Ab-A1 XmAb$^{2+1}$ dose-dependently mediated target cell lysis of human tumor cell line C4-2B luc, but not C4-2B luc cells modified to knock out STEAP1 expression.

TABLE 5

T cell dependent cellular cytotoxicity (TDCC) EC50 against C4-2B luc and C4-2B luc$^{STEAP1KO}$ with anti-STEAP1 XmAb (Ab-A1 XmAb) and XmAb$^{2+1}$ (Ab-A1 and Ab-A2(N67Q)) variants

| Format | STEAP1 Binder | Binder Species | Target Cell Line | TDCC EC$_{50}$ (pM) |
|---|---|---|---|---|
| XmAb | Ab-A1 | Humanized | C4-2B luc | 324.9 |
| XmAb$^{2+1}$ | Ab-A1 | Humanized | | 6.3 |
| XmAb$^{2+1}$ | Ab-A2 (N67Q) | Humanized | | 5.4 |
| XmAb$^{2+1}$ | Ab-A1 | Humanized | C4-2B luc$^{STEAP1KO}$ | >10,000 |

Figure 16:
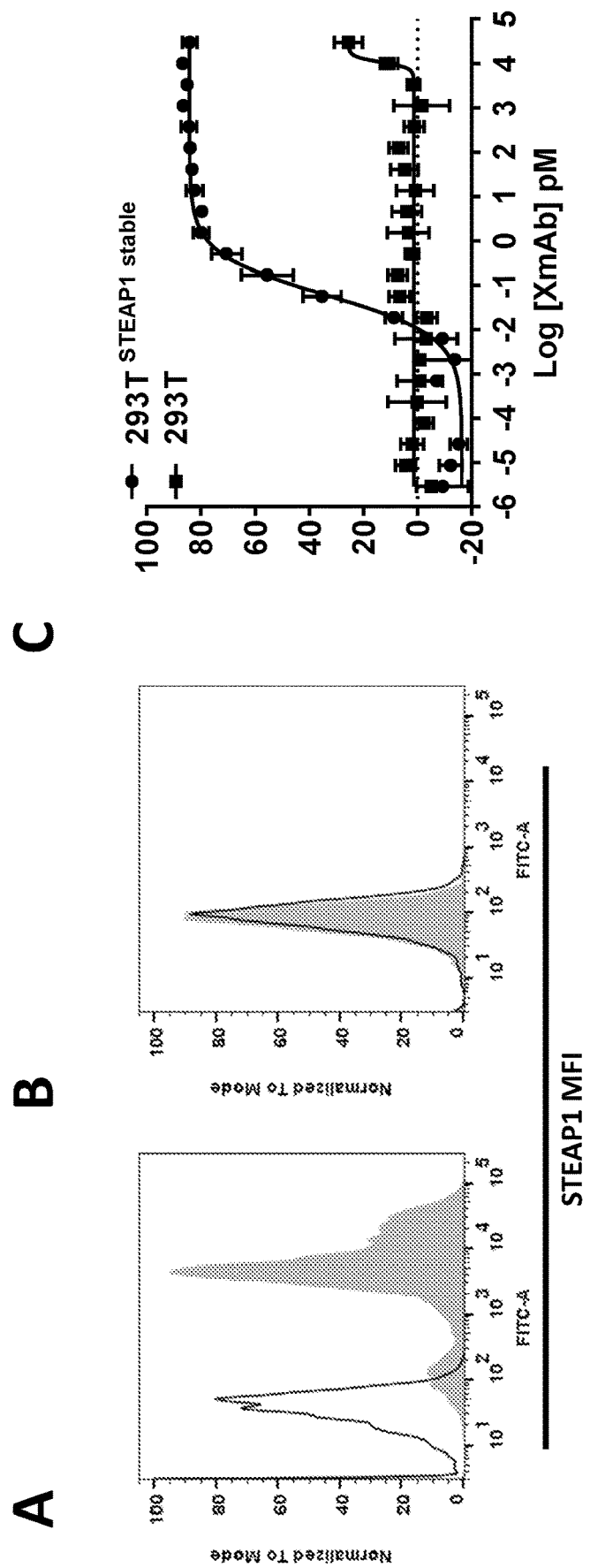
FIGS. 16A-16B show that murine STEAP1 antibody Ab-Am detected STEAP1 expressed by tested 293 T cells.
FIG. 16C shows that STEAP1 binder Ab-A2(N67Q) Xmab$^{2+1}$ mediated dose-dependent target cell lysis of human cell line 293T stably transfected with human STEAP1 and not of parental human 293T cell line.

Additionally, 293T cells stably transfected with human STEAP1 (FIG. 16A) or parental 293T cells (FIG. 16B) were incubated with an isotype control antibody or the anti-STEAP1 Ab-A mouse monoclonal antibody (Ab-Am; no bispecific format) at a concentration of 10 g/mL for 1 h at 4° C. Cell-bound Ab-Am was detected by flow cytometry after incubation with a FITC-conjugated anti-mouse IgG secondary antibody (FIG. 16A). FITC fluorescence, identifying a STEAP1-dependent signal, was plotted in histograms (solid gray histograms) and compared to the isotype control (white histograms). As shown in FIGS. 16A and 16B, Ab-Am detected STEAP-1 expressed in both cell populations tested.

FIG. 16C illustrates the results of co-cultivating STEAP1-stable 293T cells (●) and STEAP1-negative parental 293T cells (■) with human pan-T cells at an E:T cell ratio of 10 to 1 and increasing concentrations of Ab-A2(N67Q) XmAb$^{2+1}$ for 48 hours. Target cell lysis was monitored by luciferase activity measurement, and the specific cytotoxicity was plotted at each concentration in comparison with no XmAb control conditions. Results are shown in FIGS. 16A-16C and Table 6 below. The anti-STEAP1/anti-CD3 heterodimeric antibody selectively mediated cell lysis of STEAP1-expressing cells.

TABLE 6

T cell dependent cellular cytotoxicity (TDCC) EC50 against 293T cells stably transfected with human STEAP1 and parental 293T cells with Ab-A2-N67Q XmAb$^{2+1}$

| Molecule Format | STEAP1 Binder | Binder Species | Target Cell Line | TDCC EC$_{50}$ (PM) |
|---|---|---|---|---|
| XmAb$^{2+1}$ | Ab-A2 (N67Q) | Humanized | 293T / STEAP1 | 0.1 |
| XmAb$^{2+1}$ | Ab-A2 (N67Q) | Humanized | 293T / Parental | >10,000 |

Figure 17:
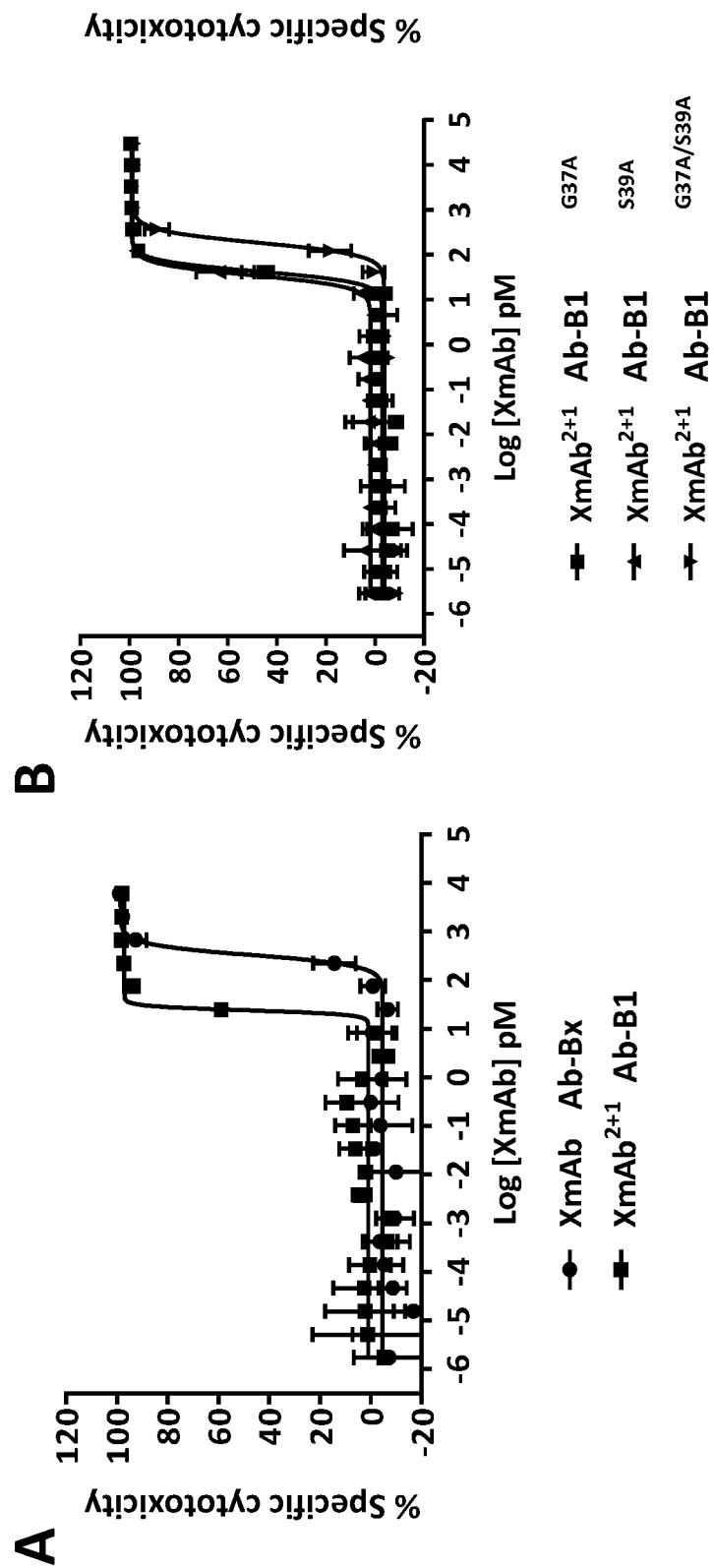
FIG. 17A shows that Ab-Bx (Ab-B1-XmAb) and Ab-B1 Xmab$^{2+1}$ mediated target cell lysis of C4-2B luc prostate cancer cells.
FIG. 17B shows that Xmab$^{2+1}$ Ab-B1 variants (i.e., Ab-B1-G37A, Ab-B1-S39A, and Ab-B1-G37A/S39A) mediated target cell lysis of C4-2B luc prostate cancer cells.
FIG. 17C shows that Xmab$^{2+1}$ Ab-B1 variants (i.e., Ab-B1-G37A, Ab-B1-S39A, and Ab-B1-G37A/S39A) did not mediate target cell lysis of C4-2B luc STEAP1 knockout prostate cancer cells.

STEAP1-positive C4-2B luc prostate cancer cells also were co-cultivated with human pan-T cells at an E:T cell ratio of 10 to 1 and increasing concentrations of Ab-B1 Xmab (●) or Ab-B1 XmAb$^{2+1}$ (■) for 48 hours. As shown in FIG. 17A, Ab-B1 Xmab and Ab-B1 XmAb$^{2+1}$ mediated target cell lysis of C4-2B luc prostate cancer cells.

Figure 17C:
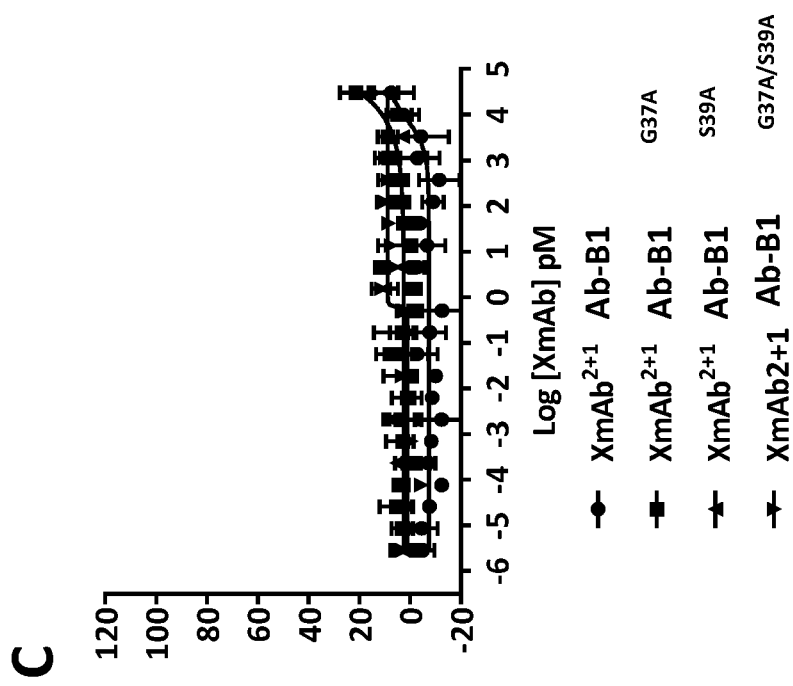

C4-2B luc prostate cancer cells were co-cultivated with human pan-T cells at an E:T cell ratio of 10 to 1 and increasing concentrations of XmAb$^{2+1}$ Ab-B1-G37A (XmAb$^{2+1}$ with G37A substitution) (■), XmAb$^{2+1}$ Ab-B1-S39A (XmAb$^{2+1}$ format with S39A substitution) (▲), or XmAb$^{2+1}$ Ab-B1-G37A/S39A (XmAb$^{2+1}$ format with both G37A and S39A substitutions) (▼) for 48 hours. As shown in FIG. 17B, Ab-B1 variants (i.e., Ab-B1-G37A, Ab-B1-S39A, and Ab-B1-G37A/S39A) mediated target cell lysis of C4-2B luc prostate cancer cells. See also Table 7 below. Similarly, STEAP-negative C4-2B luc$^{STEAP1\ KO}$ caner cells were co-cultivated with human pan-T cells at an E:T cell ratio of 10 to 1 and increasing concentrations of Ab-B1 XmAb$^{2+1}$ (●), Ab-B1-G37A (■), Ab-B1-S39A (▲), or Ab-B1-G37A/S39A (▼) for 48 hours. Target cell lysis was monitored by luciferase activity measurement and the specific cytotoxicity was plotted at each concentration in comparison with no XmAb control conditions. Results are shown in FIG. 17C and Table 7 below. The anti-STEAP/anti-CD3 heterodimeric antibody selectively mediated cell lysis of STEAP1-expressing cells, and the XmAb$^{2+1}$ format of the disclosure outperformed other formats.

TABLE 7

T cell dependent cellular cytotoxicity (TDCC) EC50 against C4-2B luc and C4-2B luc$^{STEAP1KO}$ with Ab-B1 variants

| Molecule Format | STEAP1 Binder | Target Cell line | TDCC EC$_{50}$ (PM) |
|---|---|---|---|
| XmAb | Ab-B1 | C4-2B luc | 326.2 |
| XmAb$^{2+1}$ | Ab-B1 | | 111.9 |
| XmAb$^{2+1}$ | Ab-B1-G37A | | 42.5 |
| XmAb$^{2+1}$ | Ab-B1-S39A | | 34.9 |
| XmAb$^{2+1}$ | Ab-B1-G37A/S39A | | 184.8 |
| XmAb$^{2+1}$ | Ab-B1 | C4-2B luc$^{STEAP1\ KO}$ | >10,000 |
| XmAb$^{2+1}$ | Ab-B1-G37A | | >10,000 |
| XmAb$^{2+1}$ | Ab-B1-S39A | | >10,000 |
| XmAb$^{2+1}$ | Ab-B1-G37A/S39A | | >10,000 |

Example 7

This Example characterizes the equilibrium binding constant (KD) of a heterodimeric antibody of the disclosure, Ab-A2(N67Q) XmAb$^{2+1}$, for human and cynomolgus CD3e.

The affinity Ab-A2(N67Q) XmAb$^{2+1}$ for recombinant human or cynomolgus CD3E was measured using surface plasmon resonance (SPR-Pioneer FE). Recombinant human CD3&-Fc and cynomolgus CD3&-Fc were immobilized on a CM5 chip surface using standard amine coupling procedure at ~60 RU. Ab-A2(N67Q) XmAb$^{2+1}$ was injected concentrations of 100, 33.3, 11.1 and 3.7 nM. The association and dissociation rates of Ab-A2(N67Q) XmAb$^{21}$ interaction to the ligands were recorded for 120 sec and 300 sec, respectively, as set forth below in Table 8. The equilibrium dissociation constant (K$_D$) values were derived as a ratio of the dissociation rate constant and the association rate constant ($k_{off}/k_{on}$).

TABLE 8

Association and dissociation rates of Ab-A2-N67Q
XmAb$^{2+}$ interaction with human and cynomolgus CD3.
"a" denotes data generated using BIAcore ®
and "b" denotes data generated using Octet

| Molecule Format | STEAP1 Binder | Measurement Method | $K_D$ to human CD3ε (nM) | $K_D$ to cynomolgus CD3ε (nM) |
|---|---|---|---|---|
| XmAb$^{2+1}$ | Ab-A2 (N67Q) | SPR | 16.3$^a$ to 27.6$^b$ | 15.1$^a$ to 25.8$^b$ |

Example 8

This Example demonstrates that a heterodimeric antibody of the disclosure (Ab-A2(N67Q) XmAb$^{2+1}$) mediates lysis of target cells displaying a range of STEAP1 surface densities.

STEAP-1 density at the surface of various target cell lines (SNU-5, C4-2B, Sk-N-MC, LOX-IMVI, VCaP, IM-95, TYKNU, 22RV-1, HBSCM, HUCCT1, PC3, HCT116 and NCIH1869) was evaluated. See Table 9 below, which identifies the STEAP1 density (number of STEAP1 I antibody binding sites per cell) in column 3 as measured using the Dako Qifikit method.

TABLE 9

STEAP1 surface density and T cell dependent cellular
cytotoxicity (TDCC) EC50 and EC90

| Cell Line | Tissue of Origin | STEAP1 (Qifikit) | EC50 (pM) | EC90 (pM) |
|---|---|---|---|---|
| SNU5 | Stomach | 220,612 | 6.2 | 13.7 |
| C4-2B | Prostate | 150,072 | 6.8 | 16.1 |
| SK-N-MC | Neuroblastoma | 19,057 | 10.4 | 33.9 |
| LOX-IMVI | Skin | 9,765 | 36.6 | 112 |
| VCaP | Prostate | 8,148 | 722 | 9,904 |
| IM-95 | Stomach | 7,824 | 344.7 | 1,643 |
| TYKNU | Ovary | 6,293 | 1,716 | >10,000 |
| 22RV-1 | Prostate | 5,671 | 257.3 | 1,604 |
| HBSMC | Smooth Muscle | ~5,000 | 1,517.5 | >10,000 |
| HUCCT1 | Biliary Tract | 4,295 | >10,000 | >10,000 |
| PC3 | Prostate | ~4,000 | >10,000 | >10,000 |
| HCT116 | Colon | 3,785 | 336 | 1,796 |
| NCIH1869 | Lung | 1,915 | >10,000 | >10,000 |

In a separate study, STEAP-1 density at the surface of OE33, EBC1, and A673 cell lines was evaluated. See Table 10 below, which identifies the STEAP1 density (number of STEAP1 I antibody binding sites per cell) in column 3 as measured using the Dako Qifikit method.

| Cell Line | Tissue of Origin | STEAP1 (Qifikit) | EC50 (pM) | EC90 (pM) |
|---|---|---|---|---|
| OE33 | Esophagus | 83,303 | 145 | 3,022 |
| EBC1 | Lung | 32,718 | 162 | 2,741 |
| A673 | Bone | 25,241 | 122 | 1,587 |

T cells from a human donor were incubated with the target cell lines, alongside increasing concentrations of the Ab-A2 (N67Q)XmAb$^{2+1}$ molecule for 48 hours at 37° C. After 48 hours, target cell viability was measured using steady glo (B) or cell titer glo to measure cell viability. Ab-A2(N67Q) XmAb$^{2+1}$ killed all the cell lines with varying EC90.

Ab-A2 (N67Q) XmAb$^{2+1}$ is capable of killing cancer cell lines with STEAP1 densities ranging from ~200,000 STEAP1 receptors per cell (SNU5 cell line) down to ~10,000 STEAP1 receptors per cell (LOX-IMV cell line). The potency of Ab-A2 (N67Q) XmAb$^{2+1}$ decreases when the STEAP1 receptor density drops below 10,000 per cell. In this regard, Ab-A2 (N67Q) XmAb$^{2+1}$ preferentially mediates T cell dependent killing of cells with a surface density of STEAP1 of greater than 10,000 (e.g., the EC90 is at least 10-fold less for cells with a surface density of STEAP1 of greater than 10,000 compared to cells having a surface density of STEAP1 less than 10,000).

The differential killing of cancer cells was assessed with other antibodies in the Xmab$^{2+1}$ format (Ab-B-G52A XmAb$^{2+1}$ and mouse antibody Ab-Cm XmAb$^{2+1}$) compared to Ab-A2-N67G XmAb$^{2+1}$. Ab-A2-N67G XmAb$^{2+1}$ demonstrated differential killing between high- and low-STEAP1-expressing cells, whereas Ab-B-G52A XmAb$^{2+1}$ did not discriminate between high- and low-STEAP1-expressing cells, instead killing every STEAP1 expressing cell. See Table 11. Ab-A2-N67G XmAb$^{2+1}$ spares normal cells which express STEAP1 at lower levels (i.e., lower than 10,000/cell), such as HSMBC (primary human smooth muscle bronchial cells).

TABLE 11

Ab-B1 XmAb$^{2+1}$ and Ab-Cm XmAb$^{2+1}$ kill
high- and low-STEAP1-expressing cells.

| Ab (XmAb$^{2+1}$) | C4-2B-Luc ~150,000 R/C | | C4-2B K-O ~0 R/C | | LOX-IMVI ~10,000 R/C | | IM95-Luc ~8,000 R/C | |
|---|---|---|---|---|---|---|---|---|
| | Ec50 (pM) | EC90 (pM) | Ec50 (pM) | EC90 (pM) | Ec50 (pM) | EC90 (pM) | Ec50 (pM) | EC90 (pM) |
| Ab-A2-N67G | 5 | 19.4 | >30,000 | >30,000 | 47.1 | 445.2 | 344.7 | 1,643 |
| Ab-B1-G52A | 48.9 | 205 | >30,000 | >30,000 | 22 | 45.6 | 13.2 | 37.7 |
| Ab-Cm | 23.3 | 64.3 | >30,000 | >30,000 | 27.6 | 464.7 | 6.6 | 21.1 |

TABLE 11-continued

Ab-B1 XmAb$^{2+1}$ and Ab-Cm XmAb$^{2+1}$ kill high- and low-STEAP1-expressing cells.

| Ab (XmAb$^{2+1}$) | HCT116-Luc ~4,000 R/C | | HSMBC ~4,000 R/C | | OVCARB Below FACS Detection | | NB-4-Luc o R/C - No mRNA | |
|---|---|---|---|---|---|---|---|---|
| | Ec50 (pM) | EC90 (pM) | Ec50 (pM) | EC90 (pM) | Ec50 (pM) | EC90 (pM) | Ec50 (pM) | EC90 (pM) |
| Ab-A2-N67G | 336 | 1,796 | 2,008 | >6000 | 3,623 | 12,946 | >30,000 | >30,000 |
| Ab-B1-G52A | 43.6 | 207.4 | 27.5 | 108 | 80.5 | 609 | >30,000 | >30,000 |
| Ab-Cm | 11.6 | 75.8 | 48.5 | 109.2 | 18.7 | 207.9 | >30,000 | >30,000 |

Example 9

This Example demonstrates that T-cell dependent cellular cytotoxicity is enhanced using a combination of an anti-CD3/anti-STEAP1 heterodimeric antibody described herein with an anti-PD-1 antibody.

Generation of PD-L1 overexpression cell lines: GP2-293 cells were cultured in DMEM media supplemented with 10% fetal bovine serum, 1% Pen/Strep, 1% HEPES, and 1% GlutaMAX. Cells were plated at 75% confluency in 10 cm dishes and incubated at 37° C., 5% C02 overnight. The next morning, cells were transfected. To tube A, 45 μL of Lipofectamine 3000 and 500 μL of OptiMEM media were added. To tube B, 15 μg of MSCV_GFP_PD-L1 plasmid, 1.8 μg of VSV-g plasmid, 30 μL P3000 reagent, and 500 μL of OptiMEM media were added. Tubes A and B were mixed and incubated at room temperature for 10 minutes. The mixture was added dropwise to dishes of GP2-293 cells which were incubated at 37° C., 5% C02 overnight. The next morning, the media was removed and replaced with 10 mL of fresh culture media. That afternoon, target cells were plated at 75% confluence in 6 well plates and incubated at 37° C., 5% C02 overnight. The following morning, viral supernatants were collected from GP2-293 cells and centrifuged (5 minutes, 1200 rpm). Supernatants were collected in a new tube, and polybrene was added at 1:1000. Media was removed from plates containing target cells and 2 mL of viral supernatant was added. For suspension cells, 1E6 cells were centrifuged at 1500 rpm for 5 minutes, resuspended in 500 μL RPMI supplemented with 10% fetal bovine serum and 1% pen/strep, and plated in 6 wells plates to which was added 2 mL of viral supernatant. Plates containing target cells and viral supernatants were centrifuged for 1.5 hours at 1200×g at 32° C. then incubated at 37° C., 5% C02. Culture media was added after 5 hours. Four days later, cells were analyzed for GFP and PD-L1 expression by flow cytometry with a FACSymphony. PD-L1 was detected using a PE-conjugated antibody, clone 29E.2A3. Cells <70% positive for PD-L1 expression were sorted on a BD Melody sorter to select for cells expressing high levels of PD-L1.

T cell dependent cellular cytotoxicity (TDCC) assay: Ab-A2 (N67Q) XmAb$^{2+1}$ was diluted in cell culture media (RPMI, 10% heat inactivated fetal bovine serum, 1× GlutaMAX, 1× Pen/Strep), serially diluted (1:3, 22 total) and transferred to black, clear bottom 384-well plates using a Bravo liquid handling robot. Human pan T cells (n=4), pre-activated with CD3/CD28 Dynabeads (1:1, 48 hours) were separated from beads using a magnet and diluted in cell culture media. (An aliquot of activated T cells from each donor was assessed for PD-1 expression by flow cytometry.

Cells were stained as described above and data was collected on a FACSymphony flow cytometer and analyzed using FlowJo v0.1.) Activated T cells (2500 cells/20 μL; 4 rows/donor) followed by target cells overexpressing PD-L1 were plated in 384-well assay plates (2500 cells/20 μL; full plate) such that the final effector to target cell (E:T) ratio was 1:1. An anti-PD-1 antibody of the disclosure comprising CDR sequences of SEQ ID NOs: 189-194 (10 μg/mL final in 5 μL) was added to two rows of each T cell donor. Plates were covered with MicroClime lids and incubated at 37° C., 5% CO$_2$ for 24 hours. For assays with target cells expressing luciferase, 30 μL of Steady-Glo, Bright-Glo, or One-Glo reagent (Promega) was added. Plates with adherent target cells not expressing luciferase were washed with PBS to remove T cells using EL406 plate washer and 25 μL Cell Titer Glo reagent was added. Plates were incubated with reagent for 10 minutes in the dark at room temperature. Luminescence was detected using a BioTek Neo plate reader. Specific cytotoxicity was calculated relative to target cells incubated with T cells without Ab-A2 XmAb$^{2+1}$. Graphpad Prism software was used to plot dose curves and calculate EC50 values with four parameter variable slope curve fitting.

Figure 20A:
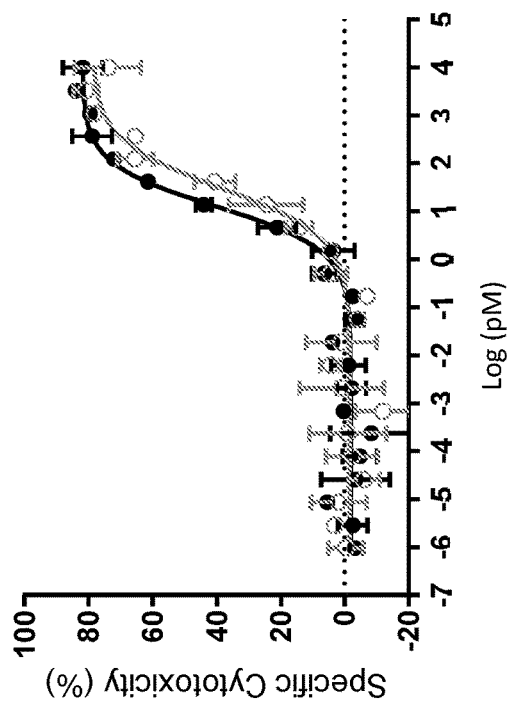
FIGS. 20A and 20B illustrate the results of the T-cell dependent cytotoxicity assay described in Example 9.
Figure 20B:
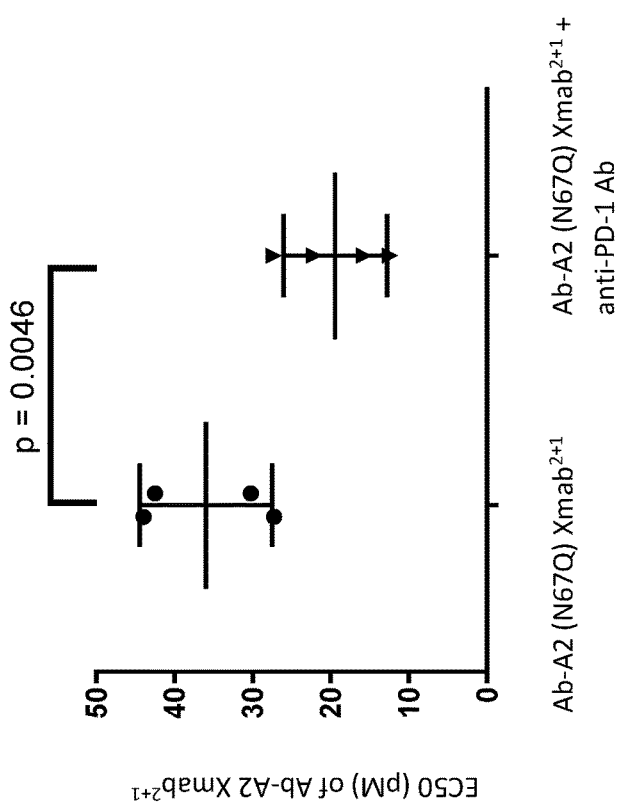

The results of the TDCC assay are illustrated in FIGS. 20A and 20B. The combination of Ab-A2 (N67Q) XmAb$^{2+1}$ and anti-PD-1 antibody demonstrated enhanced cytotoxicity and reduced EC50 compared to Ab-A2 (N67Q) XmAb$^{2+1}$ alone.

Example 10

This Example demonstrates the ability of a heterodimeric antibody of the disclosure (e.g., Ab-A2 (N67Q) XmAb$^{2+1}$) to reduce Ewing sarcoma tumor volumes in vivo.

Figure 22:
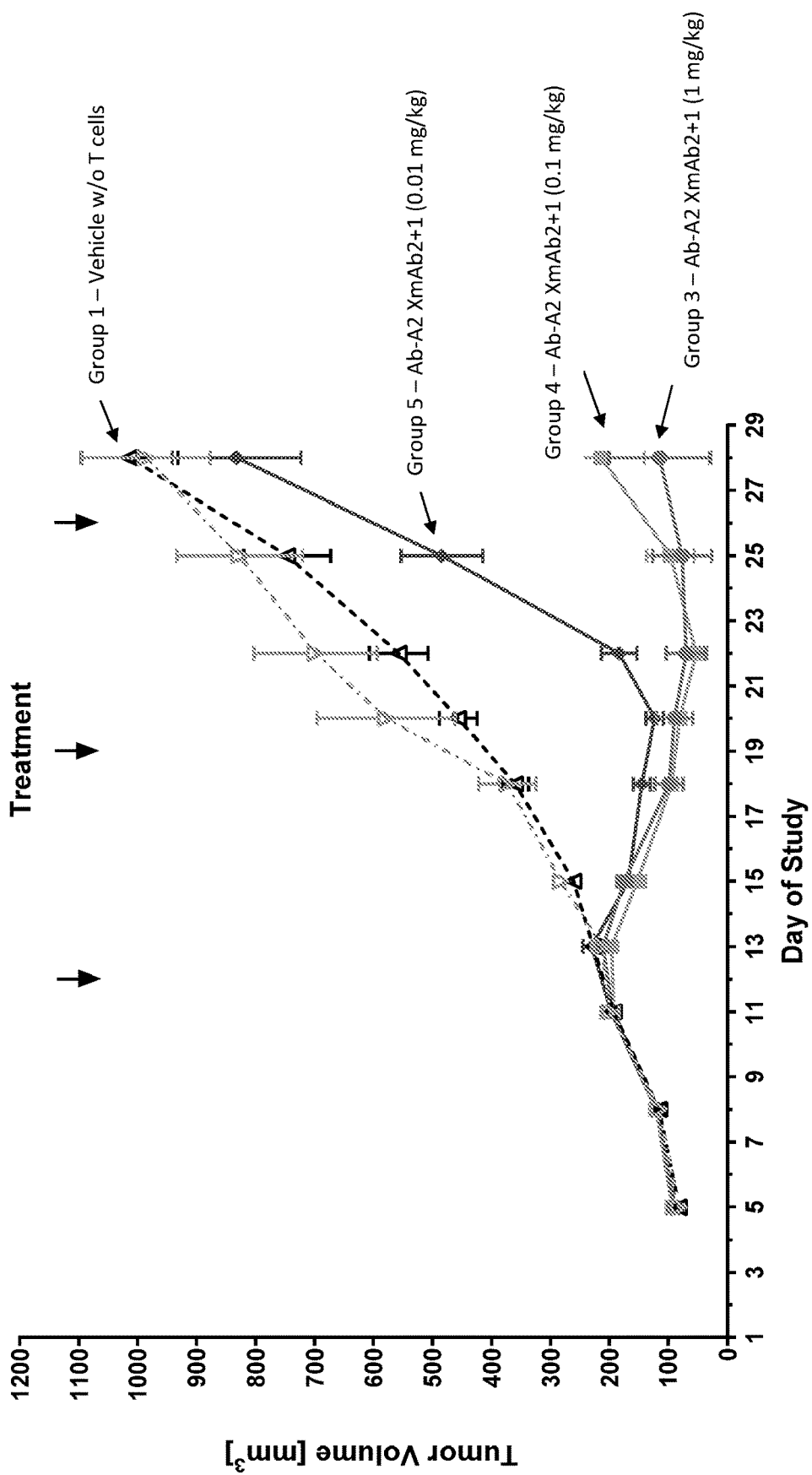
FIG. 22 is a line graph illustrating tumor volume (mm$^3$; y-axis) over time (days of study, x-axis). Human SK-N-MC cells (5×10$^6$ cells/mouse) were injected subcutaneously into the right dorsal flank of female, sub-lethally irradiated NOD/SCID mice on day 1. On day 8, human CD3+ T cells (2×10$^7$ cells/mouse) were injected into the peritoneal cavity of all animals, except of group 1. Vehicle (groups 1 and 2) or Ab-A2 (N67Q) XmAb$^{2+}$ at dose levels of 1.0, 0.1, or 0.01 mg/kg (groups 3, 4, 5, respectively) was administered by intravenous bolus injections on days 12, 19 and 26 (arrows at top of graph). Tumor volumes were determined three times/week using an electronic caliper. Group mean tumor volume [mm$^3$]+/−SEM are shown. Asterisks in the figure denote statistically significant differences (one-way ANOVA; *=p<0.05; ***=p<0.001) between vehicle (group 2) and Ab-A2(N67Q) XmAb$^{2+}$-treated groups.

Sub-lethally irradiated NOD/SCID female immuno-compromised mice were transplanted with 5×10$^6$ cells STEAP1-expressing SK-N-MC tumor cells on day 1. On day 8, 2×10$^7$ CD3+ human T cells were injected intra-peritoneally. Ab-A2 (N67Q) XmAb$^{2+1}$ or vehicle control was administered by intravenous (IV) bolus injection at 0.01, 0.1 or 1 mg/kg on days 12, 19 and 26. Tumor volume data over time are presented graphically (FIG. 22).

Ab-A2 (N67Q) XmAb$^{2+1}$ induced an initial tumor regression with relative tumor volumes (RTV) being <1 in all dose groups between days 15 and 22, while the RTV of vehicle-treated animals increased continuously until study end. Tumors from animals receiving the lowest dose of Ab-A2 (N67Q) XmAb$^{2+1}$ (0.01 mg/kg) started to regrow after day 22, while the mean RTV for mice treated with higher Ab-A2 (N67Q) XmAb$^{2+1}$ doses (0.1 and 1 mg/kg) were <1 until days 28 and 25, respectively (Table 12).

TABLE 12

Relative Tumor Volumes as Compared to Day 11

| Dose Group | Parameter | Day 11 | Day 13 | Day 15 | Day 18 | Day 20 | Day 22 | Day 25 | Day 28 |
|---|---|---|---|---|---|---|---|---|---|
| 2. Vehicle | Mean | 1.00 | 1.19 | 1.36 | 1.88 | 2.40 | 2.93 | 3.89 | 5.29 |
|  | SEM | 0.00 | 0.05 | 0.05 | 0.13 | 0.20 | 0.30 | 0.39 | 0.45 |
| 1. Vehicle w/o T cells | Mean | 1.00 | 1.07 | 1.46 | 1.88 | 2.87 | 3.48 | 4.17 | 5.02 |
|  | SEM | 0.00 | 0.02 | 0.14 | 0.17 | 0.44 | 0.32 | 0.39 | 0.52 |
| 3. Ab-A2 XmAb$^{2+1}$ (1.0 mg/kg) | Mean | 1.00 | 1.09 | 0.91 | 0.51 | 0.47 | 0.37 | 0.41 | 0.61 |
|  | SEM | 0.00 | 0.05 | 0.07 | 0.13 | 0.17 | 0.19 | 0.27 | 0.46 |
| 4. Ab-A2 XmAb$^{2+1}$ (0.1 mg/kg) | Mean | 1.00 | 1.03 | 0.79 | 0.49 | 0.42 | 0.27 | 0.51 | 1.13 |
|  | SEM | 0.00 | 0.07 | 0.06 | 0.05 | 0.06 | 0.07 | 0.22 | 0.39 |
| 5. Ab-A2 XmAb$^{2+1}$ (0.01 mg/kg) | Mean | 1.00 | 1.18 | 0.86 | 0.75 | 0.63 | 0.93 | 2.46 | 4.24 |
|  | SEM | 0.00 | 0.09 | 0.08 | 0.08 | 0.08 | 0.15 | 0.35 | 0.54 |

Between day 15 and day 22, p-values<0.001 were achieved at all Ab-A2 (N67Q) XmAb$^{2+1}$ dose levels, and after day 22, p-values<0.001 were achieved at the 0.1 and 1 mg/kg Ab-A2 (N67Q) XmAb$^{2+1}$ doses, when compared to vehicle-treated control group 2 (FIG. 23). On day 28, tumors of vehicle-treated mice (group 2) had on average 5.29-times larger volumes relative to their starting volumes before treatment initiation, while the group mean RTV in the Ab-A2 (N67Q) XmAb$^{2+1}$-treated groups were 0.61 (group 3), 1.13 (group 4) and 4.24 (group 5) (Table 1). At the end of the in-life phase on day 28, 9/10 animals in the highest Ab-A2 (N67Q) XmAb$^{2+1}$ dose group (group 3) were considered tumor-free with tumor growth inhibition (TGI) of 97% (Table 13).

TABLE 13

Tumor Growth Inhibition (Tumor Volumes)

| Dose Group | Parameter | Day 11 | Day 13 | Day 15 | Day 18 | Day 20 | Day 22 | Day 25 | Day 28 |
|---|---|---|---|---|---|---|---|---|---|
| 2. Vehicle | Median | 196.61 | 225.01 | 253.27 | 348.93 | 468.93 | 590.08 | 837.07 | 955.14 |
|  | T/C (%) | 100 | 100 | 100 | 100 | 100 | 100 | 100 | 100 |
| 1. Vehicle w/o T cells | Median | 203.63 | 229.86 | 286.81 | 323.09 | 563.09 | 598.48 | 673.42 | 885.10 |
|  | T/C (%) | 104 | 102 | 113 | 93 | 120 | 101 | 80 | 93 |
|  | TGI (%) | −4 | −2 | −13 | 7 | −20 | −1 | 20 | 7 |
| 3. Ab-A2 XmAb$^{2+1}$ (1.0 mg/kg) | Median | 197.87 | 206.94 | 166.09 | 78.41 | 59.90 | 33.53 | 27.07 | 29.77 |
|  | T/C (%) | 101 | 92 | 66 | 22 | 13 | 6 | 3 | 3 |
|  | TGI (%) | −1 | 8 | 34 | 78 | 87 | 94 | 97 | 97 |
| 4. Ab-A2 XmAb$^{2+1}$ (0.1 mg/kg) | Median | 197.59 | 198.67 | 144.59 | 88.07 | 76.73 | 41.56 | 55.86 | 106.87 |
|  | T/C (%) | 100 | 88 | 57 | 25 | 16 | 7 | 7 | 11 |
|  | TGI (%) | 0 | 12 | 43 | 75 | 84 | 93 | 93 | 89 |
| 5. Ab-A2 XmAb$^{2+1}$ (0.01 mg/kg) | Median | 200.97 | 217.31 | 150.74 | 121.75 | 115.60 | 202.07 | 431.89 | 867.08 |
|  | T/C (%) | 102 | 97 | 60 | 35 | 25 | 34 | 52 | 91 |
|  | TGI (%) | −2 | 3 | 40 | 65 | 75 | 66 | 48 | 9 |

Thus, in clinically relevant xenograft model, Ab-A2 (N67Q) XmAb$^{2+1}$ exhibited compelling anti-tumor activity.

---

What is claimed is:

1. A bispecific antigen binding protein that binds STEAP1 of SEQ ID NO: 2 and comprises:
   (a) heavy chain CDRs comprising amino acid sequences set forth in vhCDR1 SEQ ID NO: 14, vhCDR2 SEQ ID NO: 15 or vhCDR2 SEQ ID NO: 21, and vhCDR3 SEQ ID NO: 16 and
   (b) light chain CDRs comprising amino acid sequences set forth in vlCDR1 SEQ ID NO: 11, vlCDR2 SEQ ID NO: 12, and vlCDR3 SEQ ID NO: 13.

2. The bispecific antigen-binding protein of claim 1, which binds STEAP1 and CD3.

3. The bispecific antigen-binding protein of claim 2, comprising a CD3 binding domain comprising CDR sequences of SEQ ID NOs: 170-172 and 174-176.

4. The bispecific antigen-binding protein of claim 1, which is a heterodimeric antibody comprising:
   a) a first monomer comprising a first heavy chain comprising:
      1) a first variable heavy domain;
      2) a first constant heavy chain comprising a first CH1 domain and a first Fc domain;
      3) a scFv that binds human CD3 and comprises a scFv variable light domain comprising CDR amino acid sequences set forth in vlCDR1 SEQ ID NO: 174, vlCDR2 SEQ ID NO:175, and vlCDR3 SEQ ID NO: 176, an scFv linker, and a scFv variable heavy domain comprising CDR amino acid sequences set forth in vhCDR1 SEQ ID NO: 170, vhCDR2 SEQ ID NO: 171, and vhCDR3 SEQ ID NO: 172; wherein said scFv is covalently attached between the C-terminus of said CH1 domain and the N-terminus of said first Fc domain using domain linker(s);
   b) a second monomer comprising a second heavy chain comprising a second variable heavy domain and a second constant heavy chain comprising a second Fc domain; and
   c) a common light chain comprising a variable light domain and a constant light domain;
   wherein said first variable heavy domain and said variable light domain bind human STEAP1, said second variable heavy domain and said variable light domain bind human STEAP1, and wherein
      the first variable heavy domain and the second variable heavy domain comprise heavy chain CDRs comprising amino acid sequences (a) vhCDR1 SEQ ID NO: 14, (b) vhCDR2 SEQ ID NO: 15 or SEQ ID NO: 21, and (3) vhCDR3 SEQ ID NO: 16, and the variable light domain comprises light chain CDRs comprising amino acid sequences vlCDR1 SEQ ID NO: 11, vlCDR2 SEQ ID NO: 12, and vlCDR3 SEQ ID NO: 13.

5. The heterodimeric antibody of claim 4, wherein the first monomer comprises amino acid substitutions E233P, L235V, G236A, S267K, R292C, N297G, V302C, E357Q, and S364K; the second monomer comprises the amino acid substitutions N208D, E233P, L235V, G236A, S267K, R292C, Q295E, N297G, V302C, L368D, K370S, N384D, Q418E, and N421D; and both monomers comprise a deletion at position 234.

6. The heterodimeric antibody of claim 4, wherein said scFv comprises
   a variable heavy domain comprising an amino acid sequence at least 90% identical to SEQ ID NO:169 and a variable light domain comprising an amino acid sequence at least 90% identical to SEQ ID NO: 173.

7. The heterodimeric antibody of claim 6, wherein said scFv comprises a variable heavy region and a variable light region of SEQ ID NO:169 and SEQ ID NO:173.

8. The heterodimeric antibody of claim 4, wherein said scFv has a charged scFv linker.

9. The heterodimeric antibody of claim 8, wherein the charged scFv linker has a positive charge from 3 to 8 and is selected from the group consisting of SEQ ID NOs: 143 to 153.

10. The heterodimeric antibody of claim 8, wherein the scFv linker comprises SEQ ID NO: 152.

11. The heterodimeric antibody of claim 4, wherein said scFv comprises the sequence of SEQ ID NO: 44.

12. The heterodimeric antibody of claim 4, wherein the first variable heavy domain and the second variable heavy domain comprise CDR sequences vhCDR1 comprising SEQ ID NO: 14, vhCDR2 comprising SEQ ID NO: 15, vhCDR3 comprising SEQ ID NO: 16.

13. The heterodimeric antibody of claim 12, wherein the first variable heavy domain and the second variable heavy domain comprises an amino acid sequence at least 90% identical to SEQ ID NO: 182, and wherein the variable light domain comprises an amino acid sequence at least 90% identical SEQ ID NO: 183.

14. The heterodimeric antibody of claim 13, wherein the first variable heavy domain and the second variable heavy domain comprise SEQ ID NO:
   182 and the variable light domain comprises SEQ ID NO: 183.

15. The heterodimeric antibody of claim 4, wherein the first variable heavy domain and the second variable heavy domain comprise SEQ ID NO: 184 and the variable light domain comprises SEQ ID NO: 183.

16. A heterodimeric antibody comprising a first monomer comprising the sequence of SEQ ID NO: 202, a second monomer comprising the sequence of SEQ ID NO: 201, and a common light chain comprising the sequence of SEQ ID NO:200.

17. A heterodimeric antibody comprising a first monomer comprising the sequence of SEQ ID NO: 19, a second monomer comprising the sequence of SEQ ID NO:18, and a common light chain comprising the sequence of SEQ ID NO:17.

18. A heterodimeric antibody comprising a first monomer comprises the sequence of SEQ ID NO: 207, a second monomer comprising the sequence of SEQ ID NO: 203, and a common light chain comprising the sequence of SEQ ID NO:200.

19. The heterodimeric antibody
   of claim 4, wherein the first variable heavy domain and the second variable heavy domain comprise CDR sequences vhCDR1 comprising SEQ ID NO: 14, vhCDR2 comprising SEQ ID NO: 21, vhCDR3 comprising SEQ ID NO: 16.

20. A pharmaceutical composition comprising the heterodimeric antibody of claim 4.

21. A method of treating cancer in a subject in need thereof, the method comprising administering to the subject the heterodimeric antibody of claim 4.

22. The method of claim 21, further comprising administering to the subject an anti-PD-1 antigen-binding protein.

23. The method claim 22, wherein the anti-PD1 antigen-binding protein comprises a vhCDR1 comprising the amino acid sequence set forth in SEQ ID NO: 189, a vhCDR2 comprising the amino acid sequence set forth in SEQ ID NO: 190, a vhCDR3 comprising the amino acid sequence set forth in SEQ ID NO: 191, a vlCDR1 comprising the amino acid sequence set forth in SEQ ID NO: 192, a vhCDR2 comprising the amino acid sequence set forth in SEQ ID NO: 193, and a vl CDR3 comprising the amino acid sequence set forth in SEQ ID NO: 194.

24. The method of claim 23, wherein the anti-PD1 antigen-binding protein comprises a heavy chain variable domain comprising an amino acid sequence at least 90% identical to the amino acid sequence of SEQ ID NO: 195 and a light chain variable domain comprising an amino acid sequence at least 90% identical to the amino acid sequence of SEQ ID NO: 196.

25. The method of claim 24, wherein the anti-PD1 antigen-binding protein comprises a heavy chain variable domain comprising the amino acid sequence of SEQ ID NO: 195 and a light chain variable domain comprising the amino acid sequence of SEQ ID NO: 196.

26. The method of claim 23, wherein the anti-PD-1 antigen-binding protein is an antigen-binding antibody fragment.

27. The method of claim 23, wherein the anti-PD-1 antigen-binding protein is an antibody.

28. The method of claim 23, wherein the anti-PD1 antigen-binding protein comprises a heavy chain comprising the amino acid sequence of SEQ ID NO: 197 and a light chain comprising the amino acid sequence of SEQ ID NO: 198.

29. The method of claim 23, wherein the anti-PD1 antigen-binding protein comprises a heavy chain comprising the amino acid sequence of SEQ ID NO: 208 and a light chain comprising the amino acid sequence of SEQ ID NO: 209.

30. The method of claim 21, wherein the cancer is prostate cancer.

31. The method of claim 21, wherein the cancer is Ewing sarcoma.

32. A method of treating cancer in a subject in need thereof, the method comprising administering to the subject the heterodimeric antibody of claim 16.

33. The method of claim 32, further comprising administering to the subject an anti-PD-1 antigen-binding protein.

34. The method of claim 33, wherein the anti-PD1 antigen-binding protein comprises a vhCDR1 comprising the amino acid sequence set forth in SEQ ID NO: 189, a vhCDR2 comprising the amino acid sequence set forth in SEQ ID NO: 190, a vhCDR3 comprising the amino acid sequence set forth in SEQ ID NO: 191, a vlCDR1 comprising the amino acid sequence set forth in SEQ ID NO: 192, a vhCDR2 comprising the amino acid sequence set forth in SEQ ID NO: 193, and a vl CDR3 comprising the amino acid sequence set forth in SEQ ID NO: 194.

35. The method of claim 34, wherein the anti-PD1 antigen-binding protein comprises a heavy chain variable domain comprising an amino acid sequence at least 90% identical to the amino acid sequence of SEQ ID NO: 195 and a light chain variable domain comprising an amino acid sequence at least 90% identical to the amino acid sequence of SEQ ID NO: 196.

36. The method of claim 35, wherein the anti-PD1 antigen-binding protein comprises a heavy chain variable domain comprising the amino acid sequence of SEQ ID NO: 195 and a light chain variable domain comprising the amino acid sequence of SEQ ID NO: 196.

37. The method of claim 34, wherein the anti-PD-1 antigen-binding protein is an antigen-binding antibody fragment.

38. The method of claim 34, wherein the anti-PD-1 antigen-binding protein is an antibody.

39. The method of claim 34, wherein the anti-PD1 antigen-binding protein comprises a heavy chain comprising the amino acid sequence of SEQ ID NO: 197 and a light chain comprising the amino acid sequence of SEQ ID NO: 198.

40. The method of claim 34, wherein the anti-PD1 antigen-binding protein comprises a heavy chain comprising the amino acid sequence of SEQ ID NO: 208 and a light chain comprising the amino acid sequence of SEQ ID NO: 209.

41. The method of claim 32, wherein the cancer is prostate cancer.

42. The method of claim 32, wherein the cancer is Ewing sarcoma.

43. A method of treating cancer in a subject in need thereof, the method comprising administering to the subject the heterodimeric antibody of claim 17.

44. The method of claim 43, further comprising administering to the subject an anti-PD-1 antigen-binding protein.

45. The method of claim 44, wherein the anti-PD1 antigen-binding protein comprises a vhCDR1 comprising the amino acid sequence set forth in SEQ ID NO: 189, a vhCDR2 comprising the amino acid sequence set forth in SEQ ID NO: 190, a vhCDR3 comprising the amino acid sequence set forth in SEQ ID NO: 191, a vlCDR1 comprising the amino acid sequence set forth in SEQ ID NO: 192, a vhCDR2 comprising the amino acid sequence set forth in SEQ ID NO: 193, and a vl CDR3 comprising the amino acid sequence set forth in SEQ ID NO: 194.

46. The method of claim 45, wherein the anti-PD1 antigen-binding protein comprises a heavy chain variable domain comprising an amino acid sequence at least 90% identical to the amino acid sequence of SEQ ID NO: 195 and a light chain variable domain comprising an amino acid sequence at least 90% identical to the amino acid sequence of SEQ ID NO: 196.

47. The method of claim 46, wherein the anti-PD1 antigen-binding protein comprises a heavy chain variable domain comprising the amino acid sequence of SEQ ID NO: 195 and a light chain variable domain comprising the amino acid sequence of SEQ ID NO: 196.

48. The method of claim 45, wherein the anti-PD-1 antigen-binding protein is an antigen-binding antibody fragment.

49. The method of claim 45, wherein the anti-PD-1 antigen-binding protein is an antibody.

50. The method of claim 45, wherein the anti-PD1 antigen-binding protein comprises a heavy chain comprising the amino acid sequence of SEQ ID NO: 197 and a light chain comprising the amino acid sequence of SEQ ID NO: 198.

51. The method of claim 45, wherein the anti-PD1 antigen-binding protein comprises a heavy chain comprising the amino acid sequence of SEQ ID NO: 208 and a light chain comprising the amino acid sequence of SEQ ID NO: 209.

52. The method of claim 43, wherein the cancer is prostate cancer.

53. The method of claim 43, wherein the cancer is Ewing sarcoma.

54. A method of treating cancer in a subject in need thereof, the method comprising administering to the subject the heterodimeric antibody of claim 18.

55. The method of claim 54, further comprising administering to the subject an anti-PD-1 antigen-binding protein.

56. The method of claim 55, wherein the anti-PD1 antigen-binding protein comprises a vhCDR1 comprising the amino acid sequence set forth in SEQ ID NO: 189, a vhCDR2 comprising the amino acid sequence set forth in SEQ ID NO: 190, a vhCDR3 comprising the amino acid sequence set forth in SEQ ID NO: 191, a vlCDR1 comprising the amino acid sequence set forth in SEQ ID NO: 192, a vhCDR2 comprising the amino acid sequence set forth in SEQ ID NO: 193, and a vl CDR3 comprising the amino acid sequence set forth in SEQ ID NO: 194.

57. The method of claim 56, wherein the anti-PD1 antigen-binding protein comprises a heavy chain variable domain comprising an amino acid sequence at least 90% identical to the amino acid sequence of SEQ ID NO: 195 and a light chain variable domain comprising an amino acid sequence at least 90% identical to the amino acid sequence of SEQ ID NO: 196.

58. The method of claim 57, wherein the anti-PD1 antigen-binding protein comprises a heavy chain variable domain comprising the amino acid sequence of SEQ ID NO: 195 and a light chain variable domain comprising the amino acid sequence of SEQ ID NO: 196.

59. The method of claim 56, wherein the anti-PD-1 antigen-binding protein is an antigen-binding antibody fragment.

60. The method of claim 56, wherein the anti-PD-1 antigen-binding protein is an antibody.

61. The method of claim 56, wherein the anti-PD1 antigen-binding protein comprises a heavy chain comprising the amino acid sequence of SEQ ID NO: 197 and a light chain comprising the amino acid sequence of SEQ ID NO: 198.

62. The method of claim 56, wherein the anti-PD1 antigen-binding protein comprises a heavy chain comprising the amino acid sequence of SEQ ID NO: 208 and a light chain comprising the amino acid sequence of SEQ ID NO: 209.

63. The method of claim 54, wherein the cancer is prostate cancer.

64. The method of claim 54, wherein the cancer is Ewing sarcoma.

65. The method of claim 21, further comprising administering to the subject an effective amount of abiraterone acetate or enzalutamide.

66. The method of claim 22, wherein the anti-PD1 antigen-binding protein is pembrolizumab.

67. The method of claim 32, further comprising administering to the subject an effective amount of abiraterone acetate or enzalutamide.

68. The method of claim 33, wherein the anti-PD1 antigen-binding protein is pembrolizumab.

69. The method of claim 43, further comprising administering to the subject an effective amount of abiraterone acetate or enzalutamide.

70. The method of claim 44, wherein the anti-PD1 antigen-binding protein is pembrolizumab.

71. The method of claim 54, further comprising administering to the subject an effective amount of abiraterone acetate or enzalutamide.

72. The method of claim 55, wherein the anti-PD1 antigen-binding protein is pembrolizumab.

* * * * *

SEQUENCE LISTING

<160> NUMBER OF SEQ ID NOS: 214

<210> SEQ ID NO 1
<211> LENGTH: 207
<212> TYPE: PRT
<213> ORGANISM: Homo sapiens

<400> SEQUENCE: 1

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

-continued

```
His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 2
<211> LENGTH: 339
<212> TYPE: PRT
<213> ORGANISM: Homo sapiens

<400> SEQUENCE: 2

Met Glu Ser Arg Lys Asp Ile Thr Asn Gln Glu Glu Leu Trp Lys Met
1               5                   10                  15

Lys Pro Arg Arg Asn Leu Glu Glu Asp Asp Tyr Leu His Lys Asp Thr
            20                  25                  30

Gly Glu Thr Ser Met Leu Lys Arg Pro Val Leu Leu His Leu His Gln
        35                  40                  45

Thr Ala His Ala Asp Glu Phe Asp Cys Pro Ser Glu Leu Gln His Thr
    50                  55                  60

Gln Glu Leu Phe Pro Gln Trp His Leu Pro Ile Lys Ile Ala Ala Ile
65                  70                  75                  80

Ile Ala Ser Leu Thr Phe Leu Tyr Thr Leu Leu Arg Glu Val Ile His
                85                  90                  95

Pro Leu Ala Thr Ser His Gln Gln Tyr Phe Tyr Lys Ile Pro Ile Leu
            100                 105                 110

Val Ile Asn Lys Val Leu Pro Met Val Ser Ile Thr Leu Leu Ala Leu
        115                 120                 125

Val Tyr Leu Pro Gly Val Ile Ala Ala Ile Val Gln Leu His Asn Gly
    130                 135                 140

Thr Lys Tyr Lys Lys Phe Pro His Trp Leu Asp Lys Trp Met Leu Thr
145                 150                 155                 160

Arg Lys Gln Phe Gly Leu Leu Ser Phe Phe Ala Val Leu His Ala
                165                 170                 175

Ile Tyr Ser Leu Ser Tyr Pro Met Arg Arg Ser Tyr Arg Tyr Lys Leu
            180                 185                 190

Leu Asn Trp Ala Tyr Gln Gln Val Gln Gln Asn Lys Glu Asp Ala Trp
        195                 200                 205

Ile Glu His Asp Val Trp Arg Met Glu Ile Tyr Val Ser Leu Gly Ile
    210                 215                 220

Val Gly Leu Ala Ile Leu Ala Leu Leu Ala Val Thr Ser Ile Pro Ser
225                 230                 235                 240

Val Ser Asp Ser Leu Thr Trp Arg Glu Phe His Tyr Ile Gln Ser Lys
```

-continued

```
                245                 250                 255
Leu Gly Ile Val Ser Leu Leu Leu Gly Thr Ile His Ala Leu Ile Phe
            260                 265                 270
Ala Trp Asn Lys Trp Ile Asp Ile Lys Gln Phe Val Trp Tyr Thr Pro
        275                 280                 285
Pro Thr Phe Met Ile Ala Val Phe Leu Pro Ile Val Val Leu Ile Phe
    290                 295                 300
Lys Ser Ile Leu Phe Leu Pro Cys Leu Arg Lys Ile Leu Lys Ile
305                 310                 315                 320
Arg His Gly Trp Glu Asp Val Thr Lys Ile Asn Lys Thr Glu Ile Cys
                325                 330                 335
Ser Gln Leu

<210> SEQ ID NO 3
<211> LENGTH: 121
<212> TYPE: PRT
<213> ORGANISM: Mus musculus

<400> SEQUENCE: 3

Gln Val Gln Leu Gln Gln Ser Gly Ala Glu Met Met Lys Pro Gly Ala
1               5                   10                  15
Ser Val Lys Ile Ser Cys Lys Ala Thr Gly Tyr Thr Phe Ser Thr Tyr
            20                  25                  30
Trp Ile Glu Trp Val Lys Gln Arg Pro Gly His Gly Leu Glu Trp Ile
        35                  40                  45
Gly Glu Ile Leu Pro Gly Ser Gly Asn Thr Asp Phe Asn Glu Lys Phe
    50                  55                  60
Lys Gly Lys Ala Thr Phe Thr Ala Asp Thr Ser Ser Asp Thr Ala Tyr
65                  70                  75                  80
Met His Leu Ser Ser Leu Thr Ser Glu Asp Ser Ala Val Tyr Tyr Cys
                85                  90                  95
Thr Arg Trp Gly Tyr Tyr Gly Thr Arg Gly Tyr Phe Asn Val Trp Gly
            100                 105                 110
Ala Gly Ser Thr Val Thr Val Ser Ser
        115                 120

<210> SEQ ID NO 4
<211> LENGTH: 5
<212> TYPE: PRT
<213> ORGANISM: Mus musculus

<400> SEQUENCE: 4

Thr Tyr Trp Ile Glu
1               5

<210> SEQ ID NO 5
<211> LENGTH: 17
<212> TYPE: PRT
<213> ORGANISM: Mus musculus

<400> SEQUENCE: 5

Glu Ile Leu Pro Gly Ser Gly Asn Thr Asp Phe Asn Glu Lys Phe Lys
1               5                   10                  15
Gly

<210> SEQ ID NO 6
<211> LENGTH: 12
<212> TYPE: PRT
```

<213> ORGANISM: Mus musculus

<400> SEQUENCE: 6

Trp Gly Tyr Tyr Gly Thr Arg Gly Tyr Phe Asn Val
1               5                   10

<210> SEQ ID NO 7
<211> LENGTH: 106
<212> TYPE: PRT
<213> ORGANISM: Mus musculus

<400> SEQUENCE: 7

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Arg Ser Phe Pro Tyr Thr
                85                  90                  95

Phe Gly Gly Gly Thr Lys Leu Glu Ile Lys
            100                 105

<210> SEQ ID NO 8
<211> LENGTH: 10
<212> TYPE: PRT
<213> ORGANISM: Mus musculus

<400> SEQUENCE: 8

Ser Ala Ser Ser Ser Val Ser Tyr Met His
1               5                   10

<210> SEQ ID NO 9
<211> LENGTH: 7
<212> TYPE: PRT
<213> ORGANISM: Mus musculus

<400> SEQUENCE: 9

Ser Thr Ser Asn Leu Ala Ser
1               5

<210> SEQ ID NO 10
<211> LENGTH: 9
<212> TYPE: PRT
<213> ORGANISM: Mus musculus

<400> SEQUENCE: 10

Gln Gln Arg Arg Ser Phe Pro Tyr Thr
1               5

<210> SEQ ID NO 11
<211> LENGTH: 10
<212> TYPE: PRT
<213> ORGANISM: Homo sapiens

<400> SEQUENCE: 11

Arg Ala Ser Ser Ser Val Ser Tyr Met His
1               5                   10

<210> SEQ ID NO 12
<211> LENGTH: 7
<212> TYPE: PRT
<213> ORGANISM: Homo sapiens

<400> SEQUENCE: 12

Ser Thr Ser Asn Leu Ala Ser
1               5

<210> SEQ ID NO 13
<211> LENGTH: 9
<212> TYPE: PRT
<213> ORGANISM: Homo sapiens

<400> SEQUENCE: 13

Gln Gln Arg Arg Ser Phe Pro Tyr Thr
1               5

<210> SEQ ID NO 14
<211> LENGTH: 5
<212> TYPE: PRT
<213> ORGANISM: Homo sapiens

<400> SEQUENCE: 14

Thr Tyr Trp Ile Glu
1               5

<210> SEQ ID NO 15
<211> LENGTH: 17
<212> TYPE: PRT
<213> ORGANISM: Homo sapiens

<400> SEQUENCE: 15

Glu Ile Leu Pro Gly Ser Gly Asn Thr Asp Phe Asn Glu Lys Phe Gln
1               5                   10                  15

Gly

<210> SEQ ID NO 16
<211> LENGTH: 12
<212> TYPE: PRT
<213> ORGANISM: Homo sapiens

<400> SEQUENCE: 16

Trp Gly Tyr Tyr Gly Thr Arg Gly Tyr Phe Asn Val
1               5                   10

<210> SEQ ID NO 17
<211> LENGTH: 232
<212> TYPE: PRT
<213> ORGANISM: Homo sapiens

<400> SEQUENCE: 17

Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
                20                  25                  30

Ser Pro Gly Glu Arg Ala Thr Leu Ser Cys Arg Ala Ser Ser Ser Val
            35                  40                  45

Ser Tyr Met His Trp Phe Gln Gln Lys Pro Gly Gln Ala Pro Arg Leu
        50                  55                  60

Leu Ile Tyr Ser Thr Ser Asn Leu Ala Ser Gly Ile Pro Ala Arg Phe

```
                65                  70                  75                  80
        Ser Gly Ser Gly Ser Gly Thr Asp Tyr Thr Leu Thr Ile Ser Ser Leu
                        85                  90                  95

Glu Pro Glu Asp Phe Ala Val Tyr Tyr Cys Gln Gln Arg Arg Ser Phe
                        100                 105                 110

Pro Tyr Thr Phe Gly Gln Gly Thr Lys Leu Glu Ile Lys Arg Thr Val
                        115                 120                 125

Ala Ala Pro Ser Val Phe Ile Phe Pro Pro Ser Asp Glu Gln Leu Lys
                130                 135                 140

Ser Gly Thr Ala Ser Val Val Cys Leu Leu Asn Asn Phe Tyr Pro Arg
        145                 150                 155                 160

Glu Ala Lys Val Gln Trp Lys Val Asp Asn Ala Leu Gln Ser Gly Asn
                        165                 170                 175

Ser Gln Glu Ser Val Thr Glu Gln Asp Ser Lys Asp Ser Thr Tyr Ser
                        180                 185                 190

Leu Ser Ser Thr Leu Thr Leu Ser Lys Ala Asp Tyr Glu Lys His Lys
                        195                 200                 205

Val Tyr Ala Cys Glu Val Thr His Gln Gly Leu Ser Ser Pro Val Thr
                210                 215                 220

Lys Ser Phe Asn Arg Gly Glu Cys
        225                 230

<210> SEQ ID NO 18
<211> LENGTH: 469
<212> TYPE: PRT
<213> ORGANISM: Homo sapiens

<400> SEQUENCE: 18

Met Gly Trp Ser Cys Ile Ile Leu Phe Leu Val Ala Thr Ala Thr Gly
        1               5                   10                  15

Val His Ser Gln Val Gln Leu Val Gln Ser Gly Ala Glu Val Lys Lys
                        20                  25                  30

Pro Gly Ala Ser Val Lys Val Ser Cys Lys Ala Ser Gly Tyr Thr Phe
                        35                  40                  45

Ser Thr Tyr Trp Ile Glu Trp Val Arg Gln Ala Pro Gly Gln Arg Leu
                50                  55                  60

Glu Trp Met Gly Glu Ile Leu Pro Gly Ser Gly Asn Thr Asp Phe Asn
        65                  70                  75                  80

Glu Lys Phe Gln Gly Arg Val Thr Phe Thr Ala Asp Thr Ser Ser Asp
                        85                  90                  95

Thr Ala Tyr Met Glu Leu Ser Ser Leu Arg Ser Glu Asp Thr Ala Val
                        100                 105                 110

Tyr Tyr Cys Thr Arg Trp Gly Tyr Tyr Gly Thr Arg Gly Tyr Phe Asn
                        115                 120                 125

Val Trp Gly Gln Gly Thr Leu Val Thr Val Ser Ser Ala Ser Thr Lys
                130                 135                 140

Gly Pro Ser Val Phe Pro Leu Ala Pro Ser Ser Lys Ser Thr Ser Gly
        145                 150                 155                 160

Gly Thr Ala Ala Leu Gly Cys Leu Val Lys Asp Tyr Phe Pro Glu Pro
                        165                 170                 175

Val Thr Val Ser Trp Asn Ser Gly Ala Leu Thr Ser Gly Val His Thr
                        180                 185                 190

Phe Pro Ala Val Leu Gln Ser Ser Gly Leu Tyr Ser Leu Ser Ser Val
                        195                 200                 205
```

Val Thr Val Pro Ser Ser Leu Gly Thr Gln Thr Tyr Ile Cys Asn
210                 215                 220

Val Asn His Lys Pro Ser Asp Thr Lys Val Asp Lys Lys Val Glu Pro
225                 230                 235                 240

Lys Ser Cys Asp Lys Thr His Thr Cys Pro Pro Cys Pro Ala Pro Pro
                245                 250                 255

Val Ala Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Lys His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Asp Val Ser Gly Phe Tyr Pro Ser Asp Ile Ala
385                 390                 395                 400

Val Glu Trp Glu Ser Asp Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Glu Gln Gly Asp Val Phe Ser Cys Ser
        435                 440                 445

Val Met His Glu Ala Leu His Asn His Tyr Thr Gln Lys Ser Leu Ser
450                 455                 460

Leu Ser Pro Gly Lys
465

<210> SEQ ID NO 19
<211> LENGTH: 742
<212> TYPE: PRT
<213> ORGANISM: Homo sapiens

<400> SEQUENCE: 19

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Ser Thr Tyr Trp Ile Glu Trp Val Arg Gln Ala Pro Gly Gln Arg Leu
    50                  55                  60

Glu Trp Met Gly Glu Ile Leu Pro Gly Ser Gly Asn Thr Asp Phe Asn
65                  70                  75                  80

Glu Lys Phe Gln Gly Arg Val Thr Phe Thr Ala Asp Thr Ser Asp Asp
                85                  90                  95

Thr Ala Tyr Met Glu Leu Ser Ser Leu Arg Ser Glu Asp Thr Ala Val
            100                 105                 110

```
Tyr Tyr Cys Thr Arg Trp Gly Tyr Tyr Gly Thr Arg Gly Tyr Phe Asn
        115                 120                 125

Val Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Gly Gly Gly Gly Ser Gly Gly Gly Ser Glu Val Gln
                245                 250                 255

Leu Val Glu Ser Gly Gly Gly Leu Val Gln Pro Gly Gly Ser Leu Arg
                260                 265                 270

Leu Ser Cys Ala Ala Ser Gly Phe Thr Phe Ser Thr Tyr Ala Met Asn
    275                 280                 285

Trp Val Arg Gln Ala Pro Gly Lys Gly Leu Glu Trp Val Gly Arg Ile
    290                 295                 300

Arg Ser Lys Tyr Asn Asn Tyr Ala Thr Tyr Tyr Ala Asp Ser Val Lys
305                 310                 315                 320

Gly Arg Phe Thr Ile Ser Arg Asp Asp Ser Lys Asn Thr Leu Tyr Leu
                325                 330                 335

Gln Met Asn Ser Leu Arg Ala Glu Asp Thr Ala Val Tyr Tyr Cys Val
                340                 345                 350

Arg His Gly Asn Phe Gly Asp Ser Tyr Val Ser Trp Phe Ala Tyr Trp
    355                 360                 365

Gly Gln Gly Thr Leu Val Thr Val Ser Ser Gly Lys Pro Gly Ser Gly
    370                 375                 380

Lys Pro Gly Ser Gly Lys Pro Gly Ser Gly Lys Pro Gly Ser Gln Ala
385                 390                 395                 400

Val Val Thr Gln Glu Pro Ser Leu Thr Val Ser Pro Gly Gly Thr Val
                405                 410                 415

Thr Leu Thr Cys Gly Ser Ser Thr Gly Ala Val Thr Thr Ser Asn Tyr
                420                 425                 430

Ala Asn Trp Val Gln Gln Lys Pro Gly Lys Ser Pro Arg Gly Leu Ile
    435                 440                 445

Gly Gly Thr Asn Lys Arg Ala Pro Gly Val Pro Ala Arg Phe Ser Gly
    450                 455                 460

Ser Leu Leu Gly Gly Lys Ala Ala Leu Thr Ile Ser Gly Ala Gln Pro
465                 470                 475                 480

Glu Asp Glu Ala Asp Tyr Tyr Cys Ala Leu Trp Tyr Ser Asn His Trp
                485                 490                 495

Val Phe Gly Gly Gly Thr Lys Leu Thr Val Leu Gly Gly Gly Gly Ser
                500                 505                 510

Gly Gly Gly Gly Ser Lys Thr His Thr Cys Pro Pro Cys Pro Ala Pro
    515                 520                 525
```

```
Pro Val Ala Gly Pro Ser Val Phe Leu Phe Pro Pro Lys Pro Lys Asp
            530                 535                 540

Thr Leu Met Ile Ser Arg Thr Pro Glu Val Thr Cys Val Val Val Asp
545                 550                 555                 560

Val Lys His Glu Asp Pro Glu Val Lys Phe Asn Trp Tyr Val Asp Gly
            565                 570                 575

Val Glu Val His Asn Ala Lys Thr Lys Pro Arg Glu Glu Gln Tyr Asn
            580                 585                 590

Ser Thr Tyr Arg Val Val Ser Val Leu Thr Val Leu His Gln Asp Trp
            595                 600                 605

Leu Asn Gly Lys Glu Tyr Lys Cys Lys Val Ser Asn Lys Ala Leu Pro
            610                 615                 620

Ala Pro Ile Glu Lys Thr Ile Ser Lys Ala Lys Gly Gln Pro Arg Glu
625                 630                 635                 640

Pro Gln Val Tyr Thr Leu Pro Pro Ser Arg Glu Gln Met Thr Lys Asn
            645                 650                 655

Gln Val Lys Leu Thr Cys Leu Val Lys Gly Phe Tyr Pro Ser Asp Ile
            660                 665                 670

Ala Val Glu Trp Glu Ser Asn Gly Gln Pro Glu Asn Asn Tyr Lys Thr
            675                 680                 685

Thr Pro Pro Val Leu Asp Ser Asp Gly Ser Phe Phe Leu Tyr Ser Lys
            690                 695                 700

Leu Thr Val Asp Lys Ser Arg Trp Gln Gln Gly Asn Val Phe Ser Cys
705                 710                 715                 720

Ser Val Met His Glu Ala Leu His Asn His Tyr Thr Gln Lys Ser Leu
            725                 730                 735

Ser Leu Ser Pro Gly Lys
            740

<210> SEQ ID NO 20
<211> LENGTH: 745
<212> TYPE: PRT
<213> ORGANISM: Homo sapiens

<400> SEQUENCE: 20

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
            35                  40                  45

Tyr Thr Phe Ser Thr Tyr Trp Ile Glu Trp Val Arg Gln Ala Pro Gly
            50                  55                  60

Gln Arg Leu Glu Trp Met Gly Glu Ile Leu Pro Gly Ser Gly Gln Thr
65                  70                  75                  80

Asp Phe Asn Glu Lys Phe Gln Gly Arg Val Thr Phe Thr Ala Asp Thr
            85                  90                  95

Ser Ser Asp Thr Ala Tyr Met Glu Leu Ser Ser Leu Arg Ser Glu Asp
            100                 105                 110

Thr Ala Val Tyr Tyr Cys Thr Arg Trp Gly Tyr Gly Thr Arg Gly
            115                 120                 125

Tyr Phe Asn Val Trp Gly Gln Gly Thr Leu Val Thr Val Ser Ser Ala
            130                 135                 140

Ser Thr Lys Gly Pro Ser Val Phe Pro Leu Ala Pro Ser Ser Lys Ser
145                 150                 155                 160
```

```
Thr Ser Gly Gly Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Gly Gly Gly Ser Gly Gly Gly Gly Ser
            245                 250                 255

Glu Val Gln Leu Val Glu Ser Gly Gly Gly Leu Val Gln Pro Gly Gly
            260                 265                 270

Ser Leu Arg Leu Ser Cys Ala Ala Ser Gly Phe Thr Phe Ser Thr Tyr
            275                 280                 285

Ala Met Asn Trp Val Arg Gln Ala Pro Gly Lys Gly Leu Glu Trp Val
            290                 295                 300

Gly Arg Ile Arg Ser Lys Tyr Asn Asn Tyr Ala Thr Tyr Tyr Ala Asp
305                 310                 315                 320

Ser Val Lys Gly Arg Phe Thr Ile Ser Arg Asp Asp Ser Lys Asn Thr
            325                 330                 335

Leu Tyr Leu Gln Met Asn Ser Leu Arg Ala Glu Asp Thr Ala Val Tyr
            340                 345                 350

Tyr Cys Val Arg His Gly Asn Phe Gly Asp Ser Tyr Val Ser Trp Phe
            355                 360                 365

Ala Tyr Trp Gly Gln Gly Thr Leu Val Thr Val Ser Ser Gly Lys Pro
            370                 375                 380

Gly Ser Gly Lys Pro Gly Ser Gly Lys Pro Gly Ser Gly Lys Pro Gly
385                 390                 395                 400

Ser Gln Ala Val Val Thr Gln Glu Pro Ser Leu Thr Val Ser Pro Gly
            405                 410                 415

Gly Thr Val Thr Leu Thr Cys Gly Ser Ser Thr Gly Ala Val Thr Thr
            420                 425                 430

Ser Asn Tyr Ala Asn Trp Val Gln Gln Lys Pro Gly Lys Ser Pro Arg
            435                 440                 445

Gly Leu Ile Gly Gly Thr Asn Lys Arg Ala Pro Gly Val Pro Ala Arg
450                 455                 460

Phe Ser Gly Ser Leu Leu Gly Gly Lys Ala Ala Leu Thr Ile Ser Gly
465                 470                 475                 480

Ala Gln Pro Glu Asp Glu Ala Asp Tyr Tyr Cys Ala Leu Trp Tyr Ser
            485                 490                 495

Asn His Trp Val Phe Gly Gly Gly Thr Lys Leu Thr Val Leu Gly Gly
            500                 505                 510

Gly Gly Ser Gly Gly Gly Gly Ser Lys Thr His Thr Cys Pro Pro Cys
            515                 520                 525

Pro Ala Pro Pro Val Ala Gly Pro Ser Val Phe Leu Phe Pro Pro Lys
            530                 535                 540

Pro Lys Asp Thr Leu Met Ile Ser Arg Thr Pro Glu Val Thr Cys Val
545                 550                 555                 560

Val Val Asp Val Lys His Glu Asp Pro Glu Val Lys Phe Asn Trp Tyr
            565                 570                 575
```

```
Val Asp Gly Val Glu Val His Asn Ala Lys Thr Lys Pro Cys Glu Glu
            580                 585                 590

Gln Tyr Gly Ser Thr Tyr Arg Cys Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Thr Leu Pro Pro Ser Arg Glu Gln Met
                645                 650                 655

Thr Lys Asn Gln Val Lys Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Phe Leu
    690                 695                 700

Tyr Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 21
<211> LENGTH: 17
<212> TYPE: PRT
<213> ORGANISM: Homo sapiens

<400> SEQUENCE: 21

Glu Ile Leu Pro Gly Ser Gly Gln Thr Asp Phe Asn Glu Lys Phe Gln
1               5                   10                  15

Gly

<210> SEQ ID NO 22
<211> LENGTH: 121
<212> TYPE: PRT
<213> ORGANISM: Mus musculus

<400> SEQUENCE: 22

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Gln Trp Met
        35                  40                  45

Gly Trp Met Asn Thr Tyr Thr Gly Glu Pro Thr Tyr Ala Asp Asp Phe
    50                  55                  60

Lys Gly Arg Phe Ala Phe Ser Leu Glu Thr Ser Ala Arg Thr Val Ser
65                  70                  75                  80

Leu Asp Ile Asn Asp Leu Lys Asn Glu Asp Thr Ala Thr Tyr Phe Cys
                85                  90                  95

Thr Arg Ala Gly Gly Gln Leu Arg Pro Gly Ala Met Asp Tyr Trp Gly
            100                 105                 110

Gln Gly Thr Ser Val Thr Val Ser Ser
        115                 120
```

-continued

```
<210> SEQ ID NO 23
<211> LENGTH: 5
<212> TYPE: PRT
<213> ORGANISM: Mus musculus

<400> SEQUENCE: 23

Asn Tyr Gly Met Asn
1               5

<210> SEQ ID NO 24
<211> LENGTH: 17
<212> TYPE: PRT
<213> ORGANISM: Mus musculus

<400> SEQUENCE: 24

Trp Met Asn Thr Tyr Thr Gly Glu Pro Thr Tyr Ala Asp Asp Phe Lys
1               5                   10                  15

Gly

<210> SEQ ID NO 25
<211> LENGTH: 12
<212> TYPE: PRT
<213> ORGANISM: Mus musculus

<400> SEQUENCE: 25

Ala Gly Gly Gln Leu Arg Pro Gly Ala Met Asp Tyr
1               5                   10

<210> SEQ ID NO 26
<211> LENGTH: 111
<212> TYPE: PRT
<213> ORGANISM: Mus musculus

<400> SEQUENCE: 26

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Gly Asp Ser Phe Met Asn Trp Tyr Gln Gln Lys Pro Gly Gln Pro Pro
            35                  40                  45

Lys Leu Leu Ile Tyr Val Ala Ser Asn Leu Glu Ser Gly Ile Pro Asp
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Glu Pro Pro Thr Phe Gly Gly Gly Thr Lys Leu Glu Ile Lys
            100                 105                 110

<210> SEQ ID NO 27
<211> LENGTH: 15
<212> TYPE: PRT
<213> ORGANISM: Mus musculus

<400> SEQUENCE: 27

Lys Ala Ser Gln Ser Val Asp Tyr Asp Gly Asp Ser Phe Met Asn
1               5                   10                  15

<210> SEQ ID NO 28
<211> LENGTH: 7
<212> TYPE: PRT
<213> ORGANISM: Mus musculus
```

<400> SEQUENCE: 28

Val Ala Ser Asn Leu Glu Ser
1               5

<210> SEQ ID NO 29
<211> LENGTH: 9
<212> TYPE: PRT
<213> ORGANISM: Mus musculus

<400> SEQUENCE: 29

Gln Gln Ser Asn Glu Glu Pro Pro Thr
1               5

<210> SEQ ID NO 30
<211> LENGTH: 15
<212> TYPE: PRT
<213> ORGANISM: Homo sapiens

<400> SEQUENCE: 30

Lys Ala Ser Gln Ser Val Asp Tyr Asp Gly Asp Ser Phe Met Asn
1               5                   10                  15

<210> SEQ ID NO 31
<211> LENGTH: 7
<212> TYPE: PRT
<213> ORGANISM: Homo sapiens

<400> SEQUENCE: 31

Val Ala Ser Asn Leu Glu Ser
1               5

<210> SEQ ID NO 32
<211> LENGTH: 9
<212> TYPE: PRT
<213> ORGANISM: Homo sapiens

<400> SEQUENCE: 32

Gln Gln Ser Asn Glu Glu Pro Pro Thr
1               5

<210> SEQ ID NO 33
<211> LENGTH: 5
<212> TYPE: PRT
<213> ORGANISM: Homo sapiens

<400> SEQUENCE: 33

Asn Tyr Gly Met Asn
1               5

<210> SEQ ID NO 34
<211> LENGTH: 17
<212> TYPE: PRT
<213> ORGANISM: Homo sapiens

<400> SEQUENCE: 34

Trp Met Asn Thr Tyr Thr Gly Glu Pro Thr Tyr Ala Asp Lys Phe Gln
1               5                   10                  15

Gly

<210> SEQ ID NO 35
<211> LENGTH: 12
<212> TYPE: PRT
<213> ORGANISM: Homo sapiens

<400> SEQUENCE: 35

Ala Gly Gly Gln Leu Arg Pro Gly Ala Met Asp Tyr
1               5                   10

<210> SEQ ID NO 36
<211> LENGTH: 237
<212> TYPE: PRT
<213> ORGANISM: Homo sapiens

<400> SEQUENCE: 36

Met Gly Trp Ser Cys Ile Ile Leu Phe Leu Val Ala Thr Ala Thr Gly
1               5                   10                  15

Val His Ser Asp Ile Val Leu Thr Gln Thr Pro Leu Ser Leu Ser Val
                20                  25                  30

Thr Pro Gly Gln Pro Ala Ser Ile Ser Cys Lys Ala Ser Gln Ser Val
            35                  40                  45

Asp Tyr Asp Gly Asp Ser Phe Met Asn Trp Tyr Leu Gln Lys Pro Gly
    50                  55                  60

Gln Pro Pro Gln Leu Leu Ile Tyr Val Ala Ser Asn Leu Glu Ser Gly
65                  70                  75                  80

Val Pro Asp Arg Phe Ser Gly Ser Gly Ser Gly Thr Asp Phe Thr Leu
                85                  90                  95

Lys Ile Ser Arg Val Glu Ala Glu Asp Val Gly Val Tyr Tyr Cys Gln
            100                 105                 110

Gln Ser Asn Glu Glu Pro Pro Thr Phe Gly Gln Gly Thr Lys Leu Glu
        115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 37
<211> LENGTH: 469
<212> TYPE: PRT
<213> ORGANISM: Homo sapiens

<400> SEQUENCE: 37

Met Gly Trp Ser Cys Ile Ile Leu Phe Leu Val Ala Thr Ala Thr Gly
1               5                   10                  15

Val His Ser Glu Ile Gln Leu Val Gln Ser Gly Ala Glu Val Lys Lys
                20                  25                  30

Pro Gly Ala Thr Val Lys Ile Ser Cys Lys Ala Ser Gly Tyr Thr Phe
            35                  40                  45

Thr Asn Tyr Gly Met Asn Trp Val Gln Gln Ala Pro Gly Gln Gly Leu
    50                  55                  60

```
Glu Trp Met Gly Trp Met Asn Thr Tyr Thr Gly Pro Thr Tyr Ala
65              70                  75                  80

Asp Lys Phe Gln Gly Arg Val Thr Phe Thr Leu Asp Thr Ser Ala Arg
                85                  90                  95

Thr Val Tyr Met Glu Leu Ser Ser Leu Arg Ser Glu Asp Thr Ala Val
            100             105                 110

Tyr Phe Cys Ala Arg Ala Gly Gly Gln Leu Arg Pro Gly Ala Met Asp
        115             120                 125

Tyr Trp Gly Gln Gly Thr Met Val Thr Val Ser Ser Ala Ser Thr Lys
        130             135                 140

Gly Pro Ser Val Phe Pro Leu Ala Pro Ser Ser Lys Ser Thr Ser Gly
145             150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
        210                 215                 220

Val Asn His Lys Pro Ser Asp Thr Lys Val Asp Lys Lys Val Glu Pro
225             230                 235                 240

Lys Ser Cys Asp Lys Thr His Thr Cys Pro Pro Cys Pro Ala Pro Pro
                245                 250                 255

Val Ala Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Lys His Glu Asp Pro Glu Val Lys Phe Asn Trp Tyr Val Asp Gly Val
        290                 295                 300

Glu Val His Asn Ala Lys Thr Lys Pro Arg Glu Glu Tyr Asn Ser
305             310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Asp Val Ser Gly Phe Tyr Pro Ser Asp Ile Ala
385             390                 395                 400

Val Glu Trp Glu Ser Asp Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Glu Gln Gly Asp Val Phe Ser Cys Ser
        435                 440                 445

Val Met His Glu Ala Leu His Asn His Tyr Thr Gln Lys Ser Leu Ser
        450                 455                 460

Leu Ser Pro Gly Lys
465
```

```
<210> SEQ ID NO 38
<211> LENGTH: 742
<212> TYPE: PRT
<213> ORGANISM: Homo sapiens

<400> SEQUENCE: 38

Met Gly Trp Ser Cys Ile Ile Leu Phe Leu Val Ala Thr Ala Thr Gly
1               5                   10                  15

Val His Ser Glu Ile Gln Leu Val Gln Ser Gly Ala Glu Val Lys Lys
            20                  25                  30

Pro Gly Ala Thr Val Lys Ile Ser Cys Lys Ala Ser Gly Tyr Thr Phe
        35                  40                  45

Thr Asn Tyr Gly Met Asn Trp Val Gln Gln Ala Pro Gly Gln Gly Leu
    50                  55                  60

Glu Trp Met Gly Trp Met Asn Thr Tyr Thr Gly Glu Pro Thr Tyr Ala
65                  70                  75                  80

Asp Lys Phe Gln Gly Arg Val Thr Phe Thr Leu Asp Thr Ser Ala Arg
                85                  90                  95

Thr Val Tyr Met Glu Leu Ser Ser Leu Arg Ser Glu Asp Thr Ala Val
            100                 105                 110

Tyr Phe Cys Ala Arg Ala Gly Gly Gln Leu Arg Pro Gly Ala Met Asp
        115                 120                 125

Tyr Trp Gly Gln Gly Thr Met Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Gly Gly Gly Ser Gly Gly Gly Ser Glu Val Gln
                245                 250                 255

Leu Val Glu Ser Gly Gly Gly Leu Val Gln Pro Gly Gly Ser Leu Arg
            260                 265                 270

Leu Ser Cys Ala Ala Ser Gly Phe Thr Phe Ser Thr Tyr Ala Met Asn
        275                 280                 285

Trp Val Arg Gln Ala Pro Gly Lys Gly Leu Glu Trp Val Gly Arg Ile
    290                 295                 300

Arg Ser Lys Tyr Asn Asn Tyr Ala Thr Tyr Tyr Ala Asp Ser Val Lys
305                 310                 315                 320

Gly Arg Phe Thr Ile Ser Arg Asp Asp Ser Lys Asn Thr Leu Tyr Leu
                325                 330                 335

Gln Met Asn Ser Leu Arg Ala Glu Asp Thr Ala Val Tyr Tyr Cys Val
            340                 345                 350

Arg His Gly Asn Phe Gly Asp Ser Tyr Val Ser Trp Phe Ala Tyr Trp
        355                 360                 365

Gly Gln Gly Thr Leu Val Thr Val Ser Ser Gly Lys Pro Gly Ser Gly
    370                 375                 380
```

-continued

```
Lys Pro Gly Ser Gly Lys Pro Gly Ser Gly Lys Pro Gly Ser Gln Ala
385                 390                 395                 400

Val Val Thr Gln Glu Pro Ser Leu Thr Val Ser Pro Gly Gly Thr Val
            405                 410                 415

Thr Leu Thr Cys Gly Ser Ser Thr Gly Ala Val Thr Thr Ser Asn Tyr
        420                 425                 430

Ala Asn Trp Val Gln Gln Lys Pro Gly Lys Ser Pro Arg Gly Leu Ile
    435                 440                 445

Gly Gly Thr Asn Lys Arg Ala Pro Gly Val Pro Ala Arg Phe Ser Gly
450                 455                 460

Ser Leu Leu Gly Gly Lys Ala Ala Leu Thr Ile Ser Gly Ala Gln Pro
465                 470                 475                 480

Glu Asp Glu Ala Asp Tyr Tyr Cys Ala Leu Trp Tyr Ser Asn His Trp
            485                 490                 495

Val Phe Gly Gly Gly Thr Lys Leu Thr Val Leu Gly Gly Gly Gly Ser
        500                 505                 510

Gly Gly Gly Gly Ser Lys Thr His Thr Cys Pro Pro Cys Pro Ala Pro
    515                 520                 525

Pro Val Ala Gly Pro Ser Val Phe Leu Phe Pro Pro Lys Pro Lys Asp
530                 535                 540

Thr Leu Met Ile Ser Arg Thr Pro Glu Val Thr Cys Val Val Val Asp
545                 550                 555                 560

Val Lys His Glu Asp Pro Glu Val Lys Phe Asn Trp Tyr Val Asp Gly
            565                 570                 575

Val Glu Val His Asn Ala Lys Thr Lys Pro Arg Glu Glu Gln Tyr Asn
        580                 585                 590

Ser Thr Tyr Arg Val Val Ser Val Leu Thr Val Leu His Gln Asp Trp
    595                 600                 605

Leu Asn Gly Lys Glu Tyr Lys Cys Lys Val Ser Asn Lys Ala Leu Pro
610                 615                 620

Ala Pro Ile Glu Lys Thr Ile Ser Lys Ala Lys Gly Gln Pro Arg Glu
625                 630                 635                 640

Pro Gln Val Tyr Thr Leu Pro Pro Ser Arg Glu Gln Met Thr Lys Asn
            645                 650                 655

Gln Val Lys Leu Thr Cys Leu Val Lys Gly Phe Tyr Pro Ser Asp Ile
        660                 665                 670

Ala Val Glu Trp Glu Ser Asn Gly Gln Pro Glu Asn Asn Tyr Lys Thr
    675                 680                 685

Thr Pro Pro Val Leu Asp Ser Asp Gly Ser Phe Phe Leu Tyr Ser Lys
690                 695                 700

Leu Thr Val Asp Lys Ser Arg Trp Gln Gln Gly Asn Val Phe Ser Cys
705                 710                 715                 720

Ser Val Met His Glu Ala Leu His Asn His Tyr Thr Gln Lys Ser Leu
            725                 730                 735

Ser Leu Ser Pro Gly Lys
            740

<210> SEQ ID NO 39
<211> LENGTH: 262
<212> TYPE: PRT
<213> ORGANISM: Homo sapiens

<400> SEQUENCE: 39

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 40
<211> LENGTH: 254
<212> TYPE: PRT
<213> ORGANISM: Homo sapiens

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro

```
            115                 120                 125
Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 41
<211> LENGTH: 125
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 42
<211> LENGTH: 109
<212> TYPE: PRT
<213> ORGANISM: Homo sapiens

<400> SEQUENCE: 42

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
```

```
65                  70                  75                  80
Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 43
<211> LENGTH: 262
<212> TYPE: PRT
<213> ORGANISM: Homo sapiens

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 44
<211> LENGTH: 254
<212> TYPE: PRT
<213> ORGANISM: Homo sapiens

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
```

```
            20                  25                  30
Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 45
<211> LENGTH: 125
<212> TYPE: PRT
<213> ORGANISM: Homo sapiens

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 46
<211> LENGTH: 109
```

-continued

```
<212> TYPE: PRT
<213> ORGANISM: Homo sapiens

<400> SEQUENCE: 46

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 47
<211> LENGTH: 262
<212> TYPE: PRT
<213> ORGANISM: Homo sapiens

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240
```

Asn His Trp Val Phe Gly Gly Gly Thr Lys Leu Thr Val Leu Gly Ser
                    245                 250                 255

His His His His His His
            260

<210> SEQ ID NO 48
<211> LENGTH: 254
<212> TYPE: PRT
<213> ORGANISM: Homo sapiens

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 49
<211> LENGTH: 125
<212> TYPE: PRT
<213> ORGANISM: Homo sapiens

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
            50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser
            115                 120                 125

<210> SEQ ID NO 50
<211> LENGTH: 109
<212> TYPE: PRT
<213> ORGANISM: Homo sapiens

<400> SEQUENCE: 50

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 51
<211> LENGTH: 262
<212> TYPE: PRT
<213> ORGANISM: Homo sapiens

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
    130                 135                 140

```
Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Thr Lys Leu Thr Val Leu Gly Ser
                245                 250                 255

His His His His His His
                260

<210> SEQ ID NO 52
<211> LENGTH: 254
<212> TYPE: PRT
<213> ORGANISM: Homo sapiens

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Thr Lys Leu Thr Val Leu
                245                 250
```

```
<210> SEQ ID NO 53
<211> LENGTH: 125
<212> TYPE: PRT
<213> ORGANISM: Homo sapiens

<400> SEQUENCE: 53
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Thr | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Arg | Ile | Arg | Ser | Lys | Tyr | Asn | Asn | Tyr | Ala | Thr | Tyr | Tyr | Ala | Asp |
|---|---|---|---|---|---|---|---|---|---|---|---|---|---|---|---|
| | 50 | | | | | 55 | | | | | 60 | | | | |

| Ser | Val | Lys | Gly | Arg | Phe | Thr | Ile | Ser | Arg | Asp | Asp | Ser | Lys | Asn | Thr |
|---|---|---|---|---|---|---|---|---|---|---|---|---|---|---|---|
| 65 | | | | | 70 | | | | | 75 | | | | | 80 |

| Leu | Tyr | Leu | Gln | Met | Asn | Ser | Leu | Arg | Ala | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Val | Arg | His | Gly | Asn | Phe | Gly | Asp | Ser | Tyr | Val | Ser | Trp | Phe |
|---|---|---|---|---|---|---|---|---|---|---|---|---|---|---|---|
| | | | 100 | | | | | 105 | | | | | 110 | | |

| Ala | Tyr | Trp | Gly | Gln | Gly | Thr | Leu | Val | Thr | Val | Ser | Ser |
|---|---|---|---|---|---|---|---|---|---|---|---|---|
| | | 115 | | | | | 120 | | | | | 125 |

```
<210> SEQ ID NO 54
<211> LENGTH: 109
<212> TYPE: PRT
<213> ORGANISM: Homo sapiens

<400> SEQUENCE: 54
```

| Gln | Ala | Val | Val | Thr | Gln | Glu | Pro | Ser | Leu | Thr | Val | Ser | Pro | Gly | Gly |
|---|---|---|---|---|---|---|---|---|---|---|---|---|---|---|---|
| 1 | | | | 5 | | | | | 10 | | | | | 15 | |

| Thr | Val | Thr | Leu | Thr | Cys | Gly | Ser | Ser | Thr | Gly | Ala | Val | Thr | Thr | Ser |
|---|---|---|---|---|---|---|---|---|---|---|---|---|---|---|---|
| | | | 20 | | | | | 25 | | | | | 30 | | |

| Asn | Tyr | Ala | Asn | Trp | Val | Gln | Gln | Lys | Pro | Gly | Lys | Ser | Pro | Arg | Gly |
|---|---|---|---|---|---|---|---|---|---|---|---|---|---|---|---|
| | | 35 | | | | | 40 | | | | | 45 | | | |

| Leu | Ile | Gly | Gly | Thr | Asn | Lys | Arg | Ala | Pro | Gly | Val | Pro | Ala | Arg | Phe |
|---|---|---|---|---|---|---|---|---|---|---|---|---|---|---|---|
| | 50 | | | | | 55 | | | | | 60 | | | | |

| Ser | Gly | Ser | Leu | Leu | Gly | Gly | Lys | Ala | Ala | Leu | Thr | Ile | Ser | Gly | Ala |
|---|---|---|---|---|---|---|---|---|---|---|---|---|---|---|---|
| 65 | | | | | 70 | | | | | 75 | | | | | 80 |

| Gln | Pro | Glu | Asp | Glu | Ala | Asp | Tyr | Tyr | Cys | Ala | Leu | Trp | Tyr | Ser | Asn |
|---|---|---|---|---|---|---|---|---|---|---|---|---|---|---|---|
| | | | 85 | | | | | 90 | | | | | 95 | | |

| His | Trp | Val | Phe | Gly | Gly | Gly | Thr | Lys | Leu | Thr | Val | Leu |
|---|---|---|---|---|---|---|---|---|---|---|---|---|
| | | | 100 | | | | | 105 | | | | |

```
<210> SEQ ID NO 55
<211> LENGTH: 262
<212> TYPE: PRT
<213> ORGANISM: Homo sapiens

<400> SEQUENCE: 55
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Thr | Tyr |
|---|---|---|---|---|---|---|---|---|---|---|---|---|---|---|---|
| | | | 20 | | | | | 25 | | | | | 30 | | |

| Ala | Met | Asn | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

```
Gly Arg Ile Arg Ser Lys Ala Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                    85                  90                  95

Tyr Cys Val Arg His Gly Asn Phe Gly Asp Ser Tyr Val Ser Trp Phe
                100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
        130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                    165                 170                 175

Ser Asn Tyr Ala Asn Trp Val Gln Gln Lys Pro Gly Ser Pro Arg
                180                 185                 190

Gly Leu Ile Gly Gly Thr Asn Lys Arg Ala Pro Gly Val Pro Ala Arg
            195                 200                 205

Phe Ser Gly Ser Leu Leu Gly Gly Lys Ala Ala Leu Thr Ile Ser Gly
210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                    245                 250                 255

His His His His His His
            260

<210> SEQ ID NO 56
<211> LENGTH: 254
<212> TYPE: PRT
<213> ORGANISM: Homo sapiens

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Gly Arg Ile Arg Ser Lys Ala Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                    85                  90                  95

Tyr Cys Val Arg His Gly Asn Phe Gly Asp Ser Tyr Val Ser Trp Phe
                100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
        130                 135                 140

Ser Gln Ala Val Val Thr Gln Glu Pro Ser Leu Thr Val Ser Pro Gly
145                 150                 155                 160
```

```
Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 57
<211> LENGTH: 125
<212> TYPE: PRT
<213> ORGANISM: Homo sapiens

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 58
<211> LENGTH: 109
<212> TYPE: PRT
<213> ORGANISM: Homo sapiens

<400> SEQUENCE: 58

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105
```

<210> SEQ ID NO 59
<211> LENGTH: 262
<212> TYPE: PRT
<213> ORGANISM: Homo sapiens

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Pro Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 60
<211> LENGTH: 254
<212> TYPE: PRT
<213> ORGANISM: Homo sapiens

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

```
Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Pro Ser Tyr Val Ser Trp Phe
            100                 105                 110

Ala Tyr Trp Gly Gln Gly Thr Leu Val Thr Val Ser Ser Lys Pro
            115                 120                 125

Gly Ser Gly Lys Pro Gly Ser Gly Lys Pro Gly Ser Gly Lys Pro Gly
        130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
            195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 61
<211> LENGTH: 125
<212> TYPE: PRT
<213> ORGANISM: Homo sapiens

<400> SEQUENCE: 61

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Pro Ser Tyr Val Ser Trp Phe
            100                 105                 110

Ala Tyr Trp Gly Gln Gly Thr Leu Val Thr Val Ser Ser
            115                 120                 125

<210> SEQ ID NO 62
<211> LENGTH: 109
<212> TYPE: PRT
<213> ORGANISM: Homo sapiens

<400> SEQUENCE: 62

Gln Ala Val Val Thr Gln Glu Pro Ser Leu Thr Val Ser Pro Gly Gly
 1               5                  10                  15
```

```
Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
            35                  40                  45

Leu Ile Gly Gly Thr Asn Lys Arg Ala Pro Gly Val Pro Ala Arg Phe
 50                  55                  60

Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                 85                  90                  95

His Trp Val Phe Gly Gly Gly Thr Lys Leu Thr Val Leu
                100                 105

<210> SEQ ID NO 63
<211> LENGTH: 262
<212> TYPE: PRT
<213> ORGANISM: Homo sapiens

<400> SEQUENCE: 63

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asp Glu Tyr Val Ser Trp Phe
                100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
            130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
                180                 185                 190

Gly Leu Ile Gly Gly Thr Asn Lys Arg Ala Pro Gly Val Pro Ala Arg
            195                 200                 205

Phe Ser Gly Ser Leu Leu Gly Gly Lys Ala Ala Leu Thr Ile Ser Gly
210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260
```

```
<210> SEQ ID NO 64
<211> LENGTH: 254
<212> TYPE: PRT
<213> ORGANISM: Homo sapiens

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Glu Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 65
<211> LENGTH: 125
<212> TYPE: PRT
<213> ORGANISM: Homo sapiens

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
```

```
                    85                  90                  95

Tyr Cys Val Arg His Gly Asn Phe Gly Asp Glu Tyr Val Ser Trp Phe
            100                 105                 110

Ala Tyr Trp Gly Gln Gly Thr Leu Val Thr Val Ser Ser
            115                 120                 125

<210> SEQ ID NO 66
<211> LENGTH: 109
<212> TYPE: PRT
<213> ORGANISM: Homo sapiens

<400> SEQUENCE: 66

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
            35                  40                  45

Leu Ile Gly Gly Thr Asn Lys Arg Ala Pro Gly Val Pro Ala Arg Phe
        50                  55                  60

Ser Gly Ser Leu Leu Gly Gly Lys Ala Ala Leu Thr Ile Ser Gly Ala
65              70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 67
<211> LENGTH: 262
<212> TYPE: PRT
<213> ORGANISM: Homo sapiens

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65              70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Pro Tyr Val Ser Trp Phe
            100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
            130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
```

```
                    180                 185                 190
Gly Leu Ile Gly Gly Thr Asn Lys Arg Ala Pro Gly Val Pro Ala Arg
                195                 200                 205

Phe Ser Gly Ser Leu Leu Gly Lys Ala Ala Leu Thr Ile Ser Gly
            210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 68
<211> LENGTH: 254
<212> TYPE: PRT
<213> ORGANISM: Homo sapiens

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Pro Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 69
<211> LENGTH: 125
<212> TYPE: PRT
<213> ORGANISM: Homo sapiens
```

```
<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Pro Tyr Val Ser Trp Phe
            100                 105                 110

Ala Tyr Trp Gly Gln Gly Thr Leu Val Thr Val Ser Ser
        115                 120                 125

<210> SEQ ID NO 70
<211> LENGTH: 109
<212> TYPE: PRT
<213> ORGANISM: Homo sapiens

<400> SEQUENCE: 70

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 71
<211> LENGTH: 262
<212> TYPE: PRT
<213> ORGANISM: Homo sapiens

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
```

```
            85                  90                  95
Tyr Cys Val Arg His Gly Asn Phe Gly Asp Ser Tyr Val Ser Trp Phe
                100                 105                 110
Ala Tyr Trp Gly Gln Gly Thr Leu Val Thr Val Ser Ser Gly Lys Pro
            115                 120                 125
Gly Ser Gly Lys Pro Gly Ser Gly Lys Pro Gly Ser Gly Lys Pro Gly
        130                 135                 140
Ser Gln Ala Val Val Thr Gln Glu Pro Ser Leu Thr Val Ser Pro Gly
145                 150                 155                 160
Gly Thr Val Thr Leu Thr Cys Gly Ser Ser Thr Gly Ala Val Thr Thr
                165                 170                 175
Ser Asn Tyr Ala Asn Trp Val Gln Gln Lys Pro Gly Lys Ser Pro Arg
            180                 185                 190
Gly Leu Ile Gly Gly Thr Asn Lys Arg Ala Pro Gly Val Pro Ala Arg
        195                 200                 205
Phe Ser Gly Ser Leu Leu Gly Gly Lys Ala Ala Leu Thr Ile Ser Gly
    210                 215                 220
Ala Gln Pro Glu Asp Glu Ala Asp Tyr Tyr Cys Ala Leu Trp Tyr Ser
225                 230                 235                 240
Asn His Trp Val Phe Gly Gly Thr Lys Leu Thr Val Leu Gly Ser
                245                 250                 255
His His His His His His
            260

<210> SEQ ID NO 72
<211> LENGTH: 254
<212> TYPE: PRT
<213> ORGANISM: Homo sapiens

<400> SEQUENCE: 72

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
            20                  25                  30
Ala Met Asn Trp Val Arg Gln Ala Pro Gly Lys Gly Leu Glu Trp Val
        35                  40                  45
Gly Arg Ile Arg Ser Lys Ala Asn Asn Tyr Ala Thr Tyr Tyr Ala Asp
    50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                85                  90                  95
Tyr Cys Val Arg His Gly Asn Phe Gly Asp Ser Tyr Val Ser Trp Phe
                100                 105                 110
Ala Tyr Trp Gly Gln Gly Thr Leu Val Thr Val Ser Ser Gly Lys Pro
            115                 120                 125
Gly Ser Gly Lys Pro Gly Ser Gly Lys Pro Gly Ser Gly Lys Pro Gly
        130                 135                 140
Ser Gln Ala Val Val Thr Gln Glu Pro Ser Leu Thr Val Ser Pro Gly
145                 150                 155                 160
Gly Thr Val Thr Leu Thr Cys Gly Ser Ser Thr Gly Ala Val Thr Thr
                165                 170                 175
Ser Asn Tyr Ala Asn Trp Val Gln Gln Lys Pro Gly Lys Ser Pro Arg
            180                 185                 190
```

Gly Leu Ile Gly Gly Thr Asn Lys Arg Ala Pro Gly Val Pro Ala Arg
            195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Thr Lys Leu Thr Val Leu
                245                 250

<210> SEQ ID NO 73
<211> LENGTH: 125
<212> TYPE: PRT
<213> ORGANISM: Homo sapiens

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 74
<211> LENGTH: 109
<212> TYPE: PRT
<213> ORGANISM: Homo sapiens

<400> SEQUENCE: 74

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Thr Lys Leu Thr Val Leu
            100                 105

<210> SEQ ID NO 75
<211> LENGTH: 262
<212> TYPE: PRT
<213> ORGANISM: Homo sapiens -continued

```
<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 76
<211> LENGTH: 254
<212> TYPE: PRT
<213> ORGANISM: Homo sapiens

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Val Arg His Gly Asn Phe Gly Asp Ser Tyr Val Ser Trp Phe
                100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
        130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 77
<211> LENGTH: 125
<212> TYPE: PRT
<213> ORGANISM: Homo sapiens

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
                100                 105                 110

Ala Tyr Trp Gly Gln Gly Thr Leu Val Thr Val Ser Ser
            115                 120                 125

<210> SEQ ID NO 78
<211> LENGTH: 109
<212> TYPE: PRT
<213> ORGANISM: Homo sapiens

<400> SEQUENCE: 78

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45
```

```
Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
                100                 105
```

<210> SEQ ID NO 79
<211> LENGTH: 262
<212> TYPE: PRT
<213> ORGANISM: Homo sapiens

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
                35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Glu Ser Tyr Val Ser Trp Phe
                100                 105                 110

Ala Tyr Trp Gly Gln Gly Thr Leu Val Thr Val Ser Ser Gly Lys Pro
                115                 120                 125

Gly Ser Gly Lys Pro Gly Ser Gly Lys Pro Gly Ser Gly Lys Pro Gly
            130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Ser Pro Arg
                180                 185                 190

Gly Leu Ile Gly Gly Thr Asn Lys Arg Ala Pro Gly Val Pro Ala Arg
            195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260
```

<210> SEQ ID NO 80
<211> LENGTH: 254
<212> TYPE: PRT
<213> ORGANISM: Homo sapiens

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Glu Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 81
<211> LENGTH: 125
<212> TYPE: PRT
<213> ORGANISM: Homo sapiens

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Glu Ser Tyr Val Ser Trp Phe
            100                 105                 110

Ala Tyr Trp Gly Gln Gly Thr Leu Val Thr Val Ser Ser
        115                 120                 125

```
<210> SEQ ID NO 82
<211> LENGTH: 109
<212> TYPE: PRT
<213> ORGANISM: Homo sapiens

<400> SEQUENCE: 82

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 83
<211> LENGTH: 262
<212> TYPE: PRT
<213> ORGANISM: Homo sapiens

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Gln Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Gly Lys Pro Gly Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220
```

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
            245                 250                 255

His His His His His His
            260

<210> SEQ ID NO 84
<211> LENGTH: 254
<212> TYPE: PRT
<213> ORGANISM: Homo sapiens

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Gln Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
            245                 250

<210> SEQ ID NO 85
<211> LENGTH: 125
<212> TYPE: PRT
<213> ORGANISM: Homo sapiens

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

```
Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Gln Ser Tyr Val Ser Trp Phe
                100                 105                 110

Ala Tyr Trp Gly Gln Gly Thr Leu Val Thr Val Ser Ser
            115                 120                 125

<210> SEQ ID NO 86
<211> LENGTH: 109
<212> TYPE: PRT
<213> ORGANISM: Homo sapiens

<400> SEQUENCE: 86

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
            35                  40                  45

Leu Ile Gly Gly Thr Asn Lys Arg Ala Pro Gly Val Pro Ala Arg Phe
50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 87
<211> LENGTH: 262
<212> TYPE: PRT
<213> ORGANISM: Homo sapiens

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Asn Tyr Val Ser Trp Phe
                100                 105                 110

Ala Tyr Trp Gly Gln Gly Thr Leu Val Thr Val Ser Ser Gly Lys Pro
            115                 120                 125
```

```
Gly Ser Gly Lys Pro Gly Ser Gly Lys Pro Gly Ser Gly Lys Pro Gly
        130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
                180                 185                 190

Gly Leu Ile Gly Gly Thr Asn Lys Arg Ala Pro Gly Val Pro Ala Arg
                195                 200                 205

Phe Ser Gly Ser Leu Leu Gly Gly Lys Ala Ala Leu Thr Ile Ser Gly
        210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
        260

<210> SEQ ID NO 88
<211> LENGTH: 254
<212> TYPE: PRT
<213> ORGANISM: Homo sapiens

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Asn Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
        130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
                180                 185                 190

Gly Leu Ile Gly Gly Thr Asn Lys Arg Ala Pro Gly Val Pro Ala Arg
                195                 200                 205

Phe Ser Gly Ser Leu Leu Gly Gly Lys Ala Ala Leu Thr Ile Ser Gly
        210                 215                 220

Ala Gln Pro Glu Asp Glu Ala Asp Tyr Tyr Cys Ala Leu Trp Tyr Ser
```

```
                225                 230                 235                 240

Asn His Trp Val Phe Gly Gly Gly Thr Lys Leu Thr Val Leu
                245                 250

<210> SEQ ID NO 89
<211> LENGTH: 125
<212> TYPE: PRT
<213> ORGANISM: Homo sapiens

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Asn Tyr Val Ser Trp Phe
            100                 105                 110

Ala Tyr Trp Gly Gln Gly Thr Leu Val Thr Val Ser Ser
        115                 120                 125

<210> SEQ ID NO 90
<211> LENGTH: 109
<212> TYPE: PRT
<213> ORGANISM: Homo sapiens

<400> SEQUENCE: 90

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 91
<211> LENGTH: 262
<212> TYPE: PRT
<213> ORGANISM: Homo sapiens

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Gln Tyr Val Ser Trp Phe
                100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
        130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
        260

<210> SEQ ID NO 92
<211> LENGTH: 254
<212> TYPE: PRT
<213> ORGANISM: Homo sapiens

<400> SEQUENCE: 92

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Gln Tyr Val Ser Trp Phe
                100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly

```
            130                 135                 140
Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 93
<211> LENGTH: 125
<212> TYPE: PRT
<213> ORGANISM: Homo sapiens

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Gln Tyr Val Ser Trp Phe
            100                 105                 110

Ala Tyr Trp Gly Gln Gly Thr Leu Val Thr Val Ser Ser
        115                 120                 125

<210> SEQ ID NO 94
<211> LENGTH: 109
<212> TYPE: PRT
<213> ORGANISM: Homo sapiens

<400> SEQUENCE: 94

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
```

```
                         85                  90                  95

His Trp Val Phe Gly Gly Gly Thr Lys Leu Thr Val Leu
                100                 105

<210> SEQ ID NO 95
<211> LENGTH: 262
<212> TYPE: PRT
<213> ORGANISM: Homo sapiens

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 96
<211> LENGTH: 254
<212> TYPE: PRT
<213> ORGANISM: Homo sapiens

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
```

-continued

```
                35                  40                  45
Gly Arg Ile Arg Ser Lys Ala Asn Asn Tyr Ala Thr Tyr Tyr Ala Asp
     50                  55                  60
Ser Val Lys Gly Arg Phe Thr Ile Ser Arg Asp Asp Ser Lys Asn Thr
 65                  70                  75                  80
Leu Tyr Leu Gln Met Asn Ser Leu Arg Ala Glu Asp Thr Ala Val Tyr
                 85                  90                  95
Tyr Cys Val Arg His Gly Asn Phe Gly Asp Ser Tyr Val Ser Trp Phe
            100                 105                 110
Asp Tyr Trp Gly Gln Gly Thr Leu Val Thr Val Ser Ser Gly Lys Pro
        115                 120                 125
Gly Ser Gly Lys Pro Gly Ser Gly Lys Pro Gly Ser Gly Lys Pro Gly
    130                 135                 140
Ser Gln Ala Val Val Thr Gln Glu Pro Ser Leu Thr Val Ser Pro Gly
145                 150                 155                 160
Gly Thr Val Thr Leu Thr Cys Gly Ser Ser Thr Gly Ala Val Thr Thr
                165                 170                 175
Ser Asn Tyr Ala Asn Trp Val Gln Gln Lys Pro Gly Lys Ser Pro Arg
            180                 185                 190
Gly Leu Ile Gly Gly Thr Asn Lys Arg Ala Pro Gly Val Pro Ala Arg
        195                 200                 205
Phe Ser Gly Ser Leu Leu Gly Gly Lys Ala Ala Leu Thr Ile Ser Gly
    210                 215                 220
Ala Gln Pro Glu Asp Glu Ala Asp Tyr Tyr Cys Ala Leu Trp Tyr Ser
225                 230                 235                 240
Asn His Trp Val Phe Gly Gly Gly Thr Lys Leu Thr Val Leu
                245                 250
```

<210> SEQ ID NO 97
<211> LENGTH: 125
<212> TYPE: PRT
<213> ORGANISM: Homo sapiens

<400> SEQUENCE: 97

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Thr Tyr
             20                  25                  30
Ala Met Asn Trp Val Arg Gln Ala Pro Gly Lys Gly Leu Glu Trp Val
         35                  40                  45
Gly Arg Ile Arg Ser Lys Ala Asn Asn Tyr Ala Thr Tyr Tyr Ala Asp
     50                  55                  60
Ser Val Lys Gly Arg Phe Thr Ile Ser Arg Asp Asp Ser Lys Asn Thr
 65                  70                  75                  80
Leu Tyr Leu Gln Met Asn Ser Leu Arg Ala Glu Asp Thr Ala Val Tyr
                 85                  90                  95
Tyr Cys Val Arg His Gly Asn Phe Gly Asp Ser Tyr Val Ser Trp Phe
            100                 105                 110
Asp Tyr Trp Gly Gln Gly Thr Leu Val Thr Val Ser Ser
        115                 120                 125
```

<210> SEQ ID NO 98
<211> LENGTH: 109
<212> TYPE: PRT
<213> ORGANISM: Homo sapiens

<400> SEQUENCE: 98

```
Gln Ala Val Val Thr Gln Glu Pro Ser Leu Thr Val Ser Pro Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105
```

<210> SEQ ID NO 99
<211> LENGTH: 262
<212> TYPE: PRT
<213> ORGANISM: Homo sapiens

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255
```

-continued

```
His His His His His His
            260

<210> SEQ ID NO 100
<211> LENGTH: 254
<212> TYPE: PRT
<213> ORGANISM: Homo sapiens

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 101
<211> LENGTH: 125
<212> TYPE: PRT
<213> ORGANISM: Homo sapiens

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Ala Tyr Ala Asp
    50                  55                  60
```

```
Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser
            115                 120                 125

<210> SEQ ID NO 102
<211> LENGTH: 109
<212> TYPE: PRT
<213> ORGANISM: Homo sapiens

<400> SEQUENCE: 102

Gln Ala Val Val Thr Gln Glu Pro Ser Leu Thr Val Ser Pro Gly Gly
  1               5                  10                  15

Thr Val Thr Leu Thr Cys Gly Ser Ser Thr Gly Ala Val Thr Thr Ser
                 20                  25                  30

Asn Tyr Ala Asn Trp Val Gln Gln Lys Pro Gly Lys Ser Pro Arg Gly
             35                  40                  45

Leu Ile Gly Gly Thr Asn Lys Arg Ala Pro Gly Val Pro Ala Arg Phe
 50                  55                  60

Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                 85                  90                  95

His Trp Val Phe Gly Gly Gly Thr Lys Leu Thr Val Leu
            100                 105

<210> SEQ ID NO 103
<211> LENGTH: 262
<212> TYPE: PRT
<213> ORGANISM: Homo sapiens

<400> SEQUENCE: 103

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Thr Tyr
                 20                  25                  30

Ala Met Asn Trp Val Arg Gln Ala Pro Gly Lys Gly Leu Glu Trp Val
             35                  40                  45

Gly Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Val Arg His Gly Asn Phe Gly Ala Ser Tyr Val Ser Trp Phe
            100                 105                 110

Asp Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
            130                 135                 140

Ser Gln Ala Val Val Thr Gln Glu Pro Ser Leu Thr Val Ser Pro Gly
145                 150                 155                 160
```

```
Gly Thr Val Thr Leu Thr Cys Gly Ser Ser Thr Gly Ala Val Thr Thr
            165                 170                 175
Ser Asn Tyr Ala Asn Trp Val Gln Gln Lys Pro Gly Lys Ser Pro Arg
            180                 185                 190
Gly Leu Ile Gly Gly Thr Asn Lys Arg Ala Pro Gly Val Pro Ala Arg
            195                 200                 205
Phe Ser Gly Ser Leu Leu Gly Gly Lys Ala Ala Leu Thr Ile Ser Gly
            210                 215                 220
Ala Gln Pro Glu Asp Glu Ala Asp Tyr Tyr Cys Ala Leu Trp Tyr Ser
225                 230                 235                 240
Asn His Trp Val Phe Gly Gly Gly Thr Lys Leu Thr Val Leu Gly Ser
            245                 250                 255
His His His His His His
            260
```

<210> SEQ ID NO 104
<211> LENGTH: 254
<212> TYPE: PRT
<213> ORGANISM: Homo sapiens

<400> SEQUENCE: 104

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
            20                  25                  30
Ala Met Asn Trp Val Arg Gln Ala Pro Gly Lys Gly Leu Glu Trp Val
            35                  40                  45
Gly Arg Ile Arg Ser Lys Tyr Asn Asn Tyr Ala Thr Tyr Tyr Ala Asp
        50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
            85                  90                  95
Tyr Cys Val Arg His Gly Asn Phe Gly Ala Ser Tyr Val Ser Trp Phe
            100                 105                 110
Asp Tyr Trp Gly Gln Gly Thr Leu Val Thr Val Ser Ser Gly Lys Pro
            115                 120                 125
Gly Ser Gly Lys Pro Gly Ser Gly Lys Pro Gly Ser Gly Lys Pro Gly
        130                 135                 140
Ser Gln Ala Val Val Thr Gln Glu Pro Ser Leu Thr Val Ser Pro Gly
145                 150                 155                 160
Gly Thr Val Thr Leu Thr Cys Gly Ser Ser Thr Gly Ala Val Thr Thr
            165                 170                 175
Ser Asn Tyr Ala Asn Trp Val Gln Gln Lys Pro Gly Lys Ser Pro Arg
            180                 185                 190
Gly Leu Ile Gly Gly Thr Asn Lys Arg Ala Pro Gly Val Pro Ala Arg
            195                 200                 205
Phe Ser Gly Ser Leu Leu Gly Gly Lys Ala Ala Leu Thr Ile Ser Gly
            210                 215                 220
Ala Gln Pro Glu Asp Glu Ala Asp Tyr Tyr Cys Ala Leu Trp Tyr Ser
225                 230                 235                 240
Asn His Trp Val Phe Gly Gly Gly Thr Lys Leu Thr Val Leu
            245                 250
```

<210> SEQ ID NO 105

```
<211> LENGTH: 125
<212> TYPE: PRT
<213> ORGANISM: Homo sapiens

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Ala Ser Tyr Val Ser Trp Phe
            100                 105                 110

Asp Tyr Trp Gly Gln Gly Thr Leu Val Thr Val Ser Ser
        115                 120                 125

<210> SEQ ID NO 106
<211> LENGTH: 109
<212> TYPE: PRT
<213> ORGANISM: Homo sapiens

<400> SEQUENCE: 106

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 107
<211> LENGTH: 262
<212> TYPE: PRT
<213> ORGANISM: Homo sapiens

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60
```

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Gln Ser Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 108
<211> LENGTH: 254
<212> TYPE: PRT
<213> ORGANISM: Homo sapiens

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Gln Ser Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
            195                 200                 205

Phe Ser Gly Ser Leu Leu Gly Gly Lys Ala Ala Leu Thr Ile Ser Gly
            210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Thr Lys Leu Thr Val Leu
            245                 250

<210> SEQ ID NO 109
<211> LENGTH: 125
<212> TYPE: PRT
<213> ORGANISM: Homo sapiens

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Gly Arg Ile Arg Ser Lys Tyr Asn Asn Tyr Ala Thr Tyr Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Gln Ser Tyr Val Ser Trp Phe
            100                 105                 110

Asp Tyr Trp Gly Gln Gly Thr Leu Val Thr Val Ser Ser
        115                 120                 125

<210> SEQ ID NO 110
<211> LENGTH: 109
<212> TYPE: PRT
<213> ORGANISM: Homo sapiens

<400> SEQUENCE: 110

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Gln Lys Pro Gly Lys Ser Pro Arg Gly
            35                  40                  45

Leu Ile Gly Gly Thr Asn Lys Arg Ala Pro Gly Val Pro Ala Arg Phe
        50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Thr Lys Leu Thr Val Leu
            100                 105

<210> SEQ ID NO 111

<211> LENGTH: 262
<212> TYPE: PRT
<213> ORGANISM: Homo sapiens

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Glu Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 112
<211> LENGTH: 254
<212> TYPE: PRT
<213> ORGANISM: Homo sapiens

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

```
Leu Tyr Leu Gln Met Asn Ser Leu Arg Ala Glu Asp Thr Ala Val Tyr
                85                  90                  95

Tyr Cys Val Arg His Gly Asn Phe Gly Asp Glu Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 113
<211> LENGTH: 125
<212> TYPE: PRT
<213> ORGANISM: Homo sapiens

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Glu Tyr Val Ser Trp Phe
            100                 105                 110

Asp Tyr Trp Gly Gln Gly Thr Leu Val Thr Val Ser Ser
        115                 120                 125

<210> SEQ ID NO 114
<211> LENGTH: 109
<212> TYPE: PRT
<213> ORGANISM: Homo sapiens

<400> SEQUENCE: 114

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30
```

```
Asn Tyr Ala Asn Trp Val Gln Gln Lys Pro Gly Lys Ser Pro Arg Gly
            35                  40                  45

Leu Ile Gly Gly Thr Asn Lys Arg Ala Pro Gly Val Pro Ala Arg Phe
        50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 115
<211> LENGTH: 262
<212> TYPE: PRT
<213> ORGANISM: Homo sapiens

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Asn Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 116
<211> LENGTH: 254
<212> TYPE: PRT
```

<213> ORGANISM: Homo sapiens

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Asn Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 117
<211> LENGTH: 125
<212> TYPE: PRT
<213> ORGANISM: Homo sapiens

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Asn Tyr Val Ser Trp Phe

```
                100             105             110
Asp Tyr Trp Gly Gln Gly Thr Leu Val Thr Val Ser Ser
        115             120             125
```

<210> SEQ ID NO 118
<211> LENGTH: 109
<212> TYPE: PRT
<213> ORGANISM: Homo sapiens

<400> SEQUENCE: 118

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105
```

<210> SEQ ID NO 119
<211> LENGTH: 262
<212> TYPE: PRT
<213> ORGANISM: Homo sapiens

<400> SEQUENCE: 119

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Pro Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
```

```
              195                 200                 205

Phe Ser Gly Ser Leu Leu Gly Gly Lys Ala Ala Leu Thr Ile Ser Gly
210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 120
<211> LENGTH: 254
<212> TYPE: PRT
<213> ORGANISM: Homo sapiens

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Pro Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 121
<211> LENGTH: 125
<212> TYPE: PRT
<213> ORGANISM: Homo sapiens

<400> SEQUENCE: 121

Glu Val Gln Leu Val Glu Ser Gly Gly Gly Leu Val Gln Pro Gly Gly
```

```
            1               5                   10                  15
        Ser Leu Arg Leu Ser Cys Ala Ala Ser Gly Phe Thr Phe Ser Thr Tyr
                        20                  25                  30

Ala Met Asn Trp Val Arg Gln Ala Pro Gly Lys Gly Leu Glu Trp Val
                        35                  40                  45

Gly Arg Ile Arg Ser Lys Tyr Asn Asn Tyr Ala Thr Tyr Tyr Ala Asp
                        50                  55                  60

Ser Val Lys Gly Arg Phe Thr Ile Ser Arg Asp Asp Ser Lys Asn Thr
        65                  70                  75                  80

Leu Tyr Leu Gln Met Asn Ser Leu Arg Ala Glu Asp Thr Ala Val Tyr
                        85                  90                  95

Tyr Cys Val Arg His Gly Asn Phe Gly Asp Pro Tyr Val Ser Trp Phe
                        100                 105                 110

Asp Tyr Trp Gly Gln Gly Thr Leu Val Thr Val Ser Ser
                        115                 120                 125

<210> SEQ ID NO 122
<211> LENGTH: 109
<212> TYPE: PRT
<213> ORGANISM: Homo sapiens

<400> SEQUENCE: 122

Gln Ala Val Val Thr Gln Glu Pro Ser Leu Thr Val Ser Pro Gly Gly
        1               5                   10                  15

Thr Val Thr Leu Thr Cys Gly Ser Ser Thr Gly Ala Val Thr Thr Ser
                        20                  25                  30

Asn Tyr Ala Asn Trp Val Gln Gln Lys Pro Gly Lys Ser Pro Arg Gly
                        35                  40                  45

Leu Ile Gly Gly Thr Asn Lys Arg Ala Pro Gly Val Pro Ala Arg Phe
                        50                  55                  60

Ser Gly Ser Leu Leu Gly Gly Lys Ala Ala Leu Thr Ile Ser Gly Ala
        65                  70                  75                  80

Gln Pro Glu Asp Glu Ala Asp Tyr Tyr Cys Ala Leu Trp Tyr Ser Asn
                        85                  90                  95

His Trp Val Phe Gly Gly Gly Thr Lys Leu Thr Val Leu
                        100                 105

<210> SEQ ID NO 123
<211> LENGTH: 262
<212> TYPE: PRT
<213> ORGANISM: Homo sapiens

<400> SEQUENCE: 123

Glu Val Gln Leu Val Glu Ser Gly Gly Gly Leu Val Gln Pro Gly Gly
        1               5                   10                  15

Ser Leu Arg Leu Ser Cys Ala Ala Ser Gly Phe Thr Phe Ser Thr Tyr
                        20                  25                  30

Ala Met Asn Trp Val Arg Gln Ala Pro Gly Lys Gly Leu Glu Trp Val
                        35                  40                  45

Gly Arg Ile Arg Ser Lys Tyr Asn Asn Tyr Ala Thr Tyr Tyr Ala Asp
                        50                  55                  60

Ser Val Lys Gly Arg Phe Thr Ile Ser Arg Asp Asp Ser Lys Asn Thr
        65                  70                  75                  80

Leu Tyr Leu Gln Met Asn Ser Leu Arg Ala Glu Asp Thr Ala Val Tyr
                        85                  90                  95

Tyr Cys Val Arg His Gly Asn Phe Gly Asp Gln Tyr Val Ser Trp Phe
```

```
            100                 105                 110
Asp Tyr Trp Gly Gln Gly Thr Leu Val Thr Val Ser Ser Gly Lys Pro
            115                 120                 125
Gly Ser Gly Lys Pro Gly Ser Gly Lys Pro Gly Ser Gly Lys Pro Gly
            130                 135                 140
Ser Gln Ala Val Val Thr Gln Glu Pro Ser Leu Thr Val Ser Pro Gly
145                 150                 155                 160
Gly Thr Val Thr Leu Thr Cys Gly Ser Ser Thr Gly Ala Val Thr Thr
                    165                 170                 175
Ser Asn Tyr Ala Asn Trp Val Gln Gln Lys Pro Gly Lys Ser Pro Arg
                    180                 185                 190
Gly Leu Ile Gly Gly Thr Asn Lys Arg Ala Pro Gly Val Pro Ala Arg
                    195                 200                 205
Phe Ser Gly Ser Leu Leu Gly Gly Lys Ala Ala Leu Thr Ile Ser Gly
                    210                 215                 220
Ala Gln Pro Glu Asp Glu Ala Asp Tyr Tyr Cys Ala Leu Trp Tyr Ser
225                 230                 235                 240
Asn His Trp Val Phe Gly Gly Thr Lys Leu Thr Val Leu Gly Ser
                    245                 250                 255
His His His His His His
            260
```

<210> SEQ ID NO 124
<211> LENGTH: 254
<212> TYPE: PRT
<213> ORGANISM: Homo sapiens

<400> SEQUENCE: 124

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
                20                  25                  30
Ala Met Asn Trp Val Arg Gln Ala Pro Gly Lys Gly Leu Glu Trp Val
                35                  40                  45
Gly Arg Ile Arg Ser Lys Tyr Asn Asn Tyr Ala Thr Tyr Tyr Ala Asp
            50                  55                  60
Ser Val Lys Gly Arg Phe Thr Ile Ser Arg Asp Asp Ser Lys Asn Thr
65                  70                  75                  80
Leu Tyr Leu Gln Met Asn Ser Leu Arg Ala Glu Asp Thr Ala Val Tyr
                    85                  90                  95
Tyr Cys Val Arg His Gly Asn Phe Gly Asp Gln Tyr Val Ser Trp Phe
                100                 105                 110
Asp Tyr Trp Gly Gln Gly Thr Leu Val Thr Val Ser Ser Gly Lys Pro
            115                 120                 125
Gly Ser Gly Lys Pro Gly Ser Gly Lys Pro Gly Ser Gly Lys Pro Gly
            130                 135                 140
Ser Gln Ala Val Val Thr Gln Glu Pro Ser Leu Thr Val Ser Pro Gly
145                 150                 155                 160
Gly Thr Val Thr Leu Thr Cys Gly Ser Ser Thr Gly Ala Val Thr Thr
                    165                 170                 175
Ser Asn Tyr Ala Asn Trp Val Gln Gln Lys Pro Gly Lys Ser Pro Arg
                    180                 185                 190
Gly Leu Ile Gly Gly Thr Asn Lys Arg Ala Pro Gly Val Pro Ala Arg
                    195                 200                 205
```

```
Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 125
<211> LENGTH: 125
<212> TYPE: PRT
<213> ORGANISM: Homo sapiens

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Gln Tyr Val Ser Trp Phe
            100                 105                 110

Asp Tyr Trp Gly Gln Gly Thr Leu Val Thr Val Ser Ser
        115                 120                 125

<210> SEQ ID NO 126
<211> LENGTH: 109
<212> TYPE: PRT
<213> ORGANISM: Homo sapiens

<400> SEQUENCE: 126

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 127
<211> LENGTH: 262
<212> TYPE: PRT
<213> ORGANISM: Homo sapiens

<400> SEQUENCE: 127

Glu Val Gln Leu Val Glu Ser Gly Gly Gly Leu Val Gln Pro Gly Gly
```

```
  1               5                  10                 15
Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Ala Asn Asn Tyr Ala Thr Ala Tyr Ala Asp
            50                  55                  60

Ser Val Lys Gly Arg Phe Thr Ile Ser Arg Asp Asp Ser Lys Asn Thr
 65                 70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
                100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
            130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
            195                 200                 205

Phe Ser Gly Ser Leu Leu Gly Gly Lys Ala Ala Leu Thr Ile Ser Gly
            210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 128
<211> LENGTH: 254
<212> TYPE: PRT
<213> ORGANISM: Homo sapiens

<400> SEQUENCE: 128

Glu Val Gln Leu Val Glu Ser Gly Gly Gly Leu Val Gln Pro Gly Gly
 1               5                  10                 15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
            35                  40                  45

Gly Arg Ile Arg Ser Lys Ala Asn Asn Tyr Ala Thr Ala Tyr Ala Asp
            50                  55                  60

Ser Val Lys Gly Arg Phe Thr Ile Ser Arg Asp Asp Ser Lys Asn Thr
 65                 70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
                100                 105                 110
```

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
        130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 129
<211> LENGTH: 125
<212> TYPE: PRT
<213> ORGANISM: Homo sapiens

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 130
<211> LENGTH: 109
<212> TYPE: PRT
<213> ORGANISM: Homo sapiens

<400> SEQUENCE: 130

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

```
Ser Gly Ser Leu Leu Gly Gly Lys Ala Ala Leu Thr Ile Ser Gly Ala
 65                  70                  75                  80

Gln Pro Glu Asp Glu Ala Asp Tyr Tyr Cys Ala Leu Trp Tyr Ser Asn
                 85                  90                  95

His Trp Val Phe Gly Gly Gly Thr Lys Leu Thr Val Leu
            100                 105
```

<210> SEQ ID NO 131
<211> LENGTH: 262
<212> TYPE: PRT
<213> ORGANISM: Homo sapiens

<400> SEQUENCE: 131

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
             20                  25                  30

Ala Met Asn Trp Val Arg Gln Ala Pro Gly Lys Gly Leu Glu Trp Val
         35                  40                  45

Gly Arg Ile Arg Ser Lys Ala Asn Asn Tyr Ala Thr Ala Tyr Ala Asp
 50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
             85                  90                  95

Tyr Cys Val Arg His Gly Asn Phe Gly Ala Ser Tyr Val Ser Trp Phe
        100                 105                 110

Ala Tyr Trp Gly Gln Gly Thr Leu Val Thr Val Ser Ser Gly Lys Pro
    115                 120                 125

Gly Ser Gly Lys Pro Gly Ser Gly Lys Pro Gly Ser Gly Lys Pro Gly
130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260
```

<210> SEQ ID NO 132
<211> LENGTH: 254
<212> TYPE: PRT
<213> ORGANISM: Homo sapiens

<400> SEQUENCE: 132

```
Glu Val Gln Leu Val Glu Ser Gly Gly Gly Leu Val Gln Pro Gly Gly
 1               5                  10                  15
```

```
Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Ala Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
                245                 250

<210> SEQ ID NO 133
<211> LENGTH: 125
<212> TYPE: PRT
<213> ORGANISM: Homo sapiens

<400> SEQUENCE: 133

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Ala Ser Tyr Val Ser Trp Phe
            100                 105                 110

Ala Tyr Trp Gly Gln Gly Thr Leu Val Thr Val Ser Ser
        115                 120                 125

<210> SEQ ID NO 134
```

```
<211> LENGTH: 109
<212> TYPE: PRT
<213> ORGANISM: Homo sapiens

<400> SEQUENCE: 134

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Lys Pro Gly Lys Ser Pro Arg Gly
        35                  40                  45

Leu Ile Gly Gly Thr Asn Lys Arg Ala Pro Gly Val Pro Ala Arg Phe
50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 135
<211> LENGTH: 262
<212> TYPE: PRT
<213> ORGANISM: Homo sapiens

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Gln Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240
```

```
Asn His Trp Val Phe Gly Gly Gly Thr Lys Leu Thr Val Leu Gly Ser
            245                 250                 255

His His His His His His
            260

<210> SEQ ID NO 136
<211> LENGTH: 254
<212> TYPE: PRT
<213> ORGANISM: Homo sapiens

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Gln Ser Tyr Val Ser Trp Phe
            100                 105                 110

Ala Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu
            245                 250

<210> SEQ ID NO 137
<211> LENGTH: 125
<212> TYPE: PRT
<213> ORGANISM: Homo sapiens

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45
```

Gly Arg Ile Arg Ser Lys Ala Asn Asn Tyr Ala Thr Ala Tyr Ala Asp
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Gln Ser Tyr Val Ser Trp Phe
            100                 105                 110

Ala Tyr Trp Gly Gln Gly Thr Leu Val Thr Val Ser Ser
            115                 120                 125

<210> SEQ ID NO 138
<211> LENGTH: 109
<212> TYPE: PRT
<213> ORGANISM: Homo sapiens

<400> SEQUENCE: 138

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 139
<211> LENGTH: 262
<212> TYPE: PRT
<213> ORGANISM: Homo sapiens

<400> SEQUENCE: 139

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
            130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu Gly Ser
                245                 250                 255

His His His His His His
            260

<210> SEQ ID NO 140
<211> LENGTH: 254
<212> TYPE: PRT
<213> ORGANISM: Homo sapiens

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser Gly Lys Pro
        115                 120                 125

Gly Ser Gly Lys Pro Gly Ser Gly Lys Pro Gly Ser Gly Lys Pro Gly
    130                 135                 140

Ser Gln Ala Val Val Thr Gln Glu Pro Ser Leu Thr Val Ser Pro Gly
145                 150                 155                 160

Gly Thr Val Thr Leu Thr Cys Gly Ser Ser Thr Gly Ala Val Thr Thr
                165                 170                 175

Ser Asn Tyr Ala Asn Trp Val Gln Gln Lys Pro Gly Lys Ser Pro Arg
            180                 185                 190

Gly Leu Ile Gly Gly Thr Asn Lys Arg Ala Pro Gly Val Pro Ala Arg
        195                 200                 205

Phe Ser Gly Ser Leu Leu Gly Gly Lys Ala Ala Leu Thr Ile Ser Gly
    210                 215                 220

Ala Gln Pro Glu Asp Glu Ala Asp Tyr Tyr Cys Ala Leu Trp Tyr Ser
225                 230                 235                 240

Asn His Trp Val Phe Gly Gly Gly Thr Lys Leu Thr Val Leu

-continued

<210> SEQ ID NO 141
<211> LENGTH: 125
<212> TYPE: PRT
<213> ORGANISM: Homo sapiens

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Ala Asn Asn Tyr Ala Thr Ala Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Asp Tyr Trp Gly Gln Gly Thr Leu Val Thr Val Ser Ser
        115                 120                 125

<210> SEQ ID NO 142
<211> LENGTH: 109
<212> TYPE: PRT
<213> ORGANISM: Homo sapiens

<400> SEQUENCE: 142

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 143
<211> LENGTH: 15
<212> TYPE: PRT
<213> ORGANISM: Artificial Sequence
<220> FEATURE:
<223> OTHER INFORMATION: Synthetic peptide

<400> SEQUENCE: 143

Gly Gly Gly Gly Ser Gly Gly Gly Gly Ser Gly Gly Gly Gly Ser
1               5                   10                  15

<210> SEQ ID NO 144
<211> LENGTH: 18

```
<212> TYPE: PRT
<213> ORGANISM: Artificial Sequence
<220> FEATURE:
<223> OTHER INFORMATION: Synthetic peptide

<400> SEQUENCE: 144

Gly Ser Thr Ser Gly Ser Gly Lys Pro Gly Ser Gly Glu Gly Ser Thr
1               5                   10                  15

Lys Gly

<210> SEQ ID NO 145
<211> LENGTH: 14
<212> TYPE: PRT
<213> ORGANISM: Artificial Sequence
<220> FEATURE:
<223> OTHER INFORMATION: Synthetic peptide

<400> SEQUENCE: 145

Ile Arg Pro Arg Ala Ile Gly Gly Ser Lys Pro Arg Val Ala
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Synthetic peptide

<400> SEQUENCE: 146

Gly Lys Gly Gly Ser Gly Lys Gly Gly Ser Gly Lys Gly Gly Ser
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Synthetic peptide

<400> SEQUENCE: 147

Gly Gly Lys Gly Ser Gly Gly Lys Gly Ser Gly Gly Lys Gly Ser
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Synthetic peptide

<400> SEQUENCE: 148

Gly Gly Gly Lys Ser Gly Gly Gly Lys Ser Gly Gly Gly Lys Ser
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Synthetic peptide

<400> SEQUENCE: 149

Gly Lys Gly Lys Ser Gly Lys Gly Lys Ser Gly Lys Gly Lys Ser
1               5                   10                  15

<210> SEQ ID NO 150
```

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 150

Gly Gly Gly Lys Ser Gly Gly Lys Gly Ser Gly Lys Gly Gly Ser
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Synthetic peptide

<400> SEQUENCE: 151

Gly Lys Pro Gly Ser Gly Lys Pro Gly Ser Gly Lys Pro Gly Ser
1               5                   10                  15

<210> SEQ ID NO 152
<211> LENGTH: 20
<212> TYPE: PRT
<213> ORGANISM: Artificial Sequence
<220> FEATURE:
<223> OTHER INFORMATION: Synthetic peptide

<400> SEQUENCE: 152

Gly Lys Pro Gly Ser Gly Lys Pro Gly Ser Gly Lys Pro Gly Ser Gly
1               5                   10                  15

Lys Pro Gly Ser
            20

<210> SEQ ID NO 153
<211> LENGTH: 20
<212> TYPE: PRT
<213> ORGANISM: Artificial Sequence
<220> FEATURE:
<223> OTHER INFORMATION: Synthetic peptide

<400> SEQUENCE: 153

Gly Lys Gly Lys Ser Gly Lys Gly Lys Ser Gly Lys Gly Lys Ser Gly
1               5                   10                  15

Lys Gly Lys Ser
            20

<210> SEQ ID NO 154
<211> LENGTH: 20
<212> TYPE: PRT
<213> ORGANISM: Artificial Sequence
<220> FEATURE:
<223> OTHER INFORMATION: Synthetic peptide

<400> SEQUENCE: 154

Gly Gly Gly Gly Ser Gly Gly Gly Gly Ser Gly Gly Gly Gly Ser Gly
1               5                   10                  15

Gly Gly Gly Ser
            20

<210> SEQ ID NO 155
<211> LENGTH: 14
<212> TYPE: PRT
<213> ORGANISM: Artificial Sequence
<220> FEATURE:
<223> OTHER INFORMATION: Synthetic peptide
```

<400> SEQUENCE: 155

Ser Thr Ala Gly Asp Thr His Leu Gly Gly Glu Asp Phe Asp
1               5                   10

<210> SEQ ID NO 156
<211> LENGTH: 15
<212> TYPE: PRT
<213> ORGANISM: Artificial Sequence
<220> FEATURE:
<223> OTHER INFORMATION: Synthetic peptide

<400> SEQUENCE: 156

Gly Glu Gly Gly Ser Gly Glu Gly Gly Ser Gly Glu Gly Gly Ser
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Synthetic peptide

<400> SEQUENCE: 157

Gly Gly Glu Gly Ser Gly Gly Glu Gly Ser Gly Gly Glu Gly Ser
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Synthetic peptide

<400> SEQUENCE: 158

Gly Gly Gly Glu Ser Gly Gly Gly Glu Ser Gly Gly Gly Glu Ser
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Synthetic peptide

<400> SEQUENCE: 159

Gly Glu Gly Glu Ser Gly Glu Gly Glu Ser Gly Glu Gly Glu Ser
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Synthetic peptide

<400> SEQUENCE: 160

Gly Gly Gly Glu Ser Gly Gly Glu Gly Ser Gly Glu Gly Gly Ser
1               5                   10                  15

<210> SEQ ID NO 161
<211> LENGTH: 20
<212> TYPE: PRT
<213> ORGANISM: Artificial Sequence
<220> FEATURE:
<223> OTHER INFORMATION: Synthetic peptide

```
<400> SEQUENCE: 161

Gly Glu Gly Glu Ser Gly Glu Gly Glu Ser Gly Glu Gly Glu Ser Gly
1               5                   10                  15

Glu Gly Glu Ser
            20

<210> SEQ ID NO 162
<211> LENGTH: 15
<212> TYPE: PRT
<213> ORGANISM: Artificial Sequence
<220> FEATURE:
<223> OTHER INFORMATION: Synthetic peptide

<400> SEQUENCE: 162

Gly Gly Gly Gly Ser Gly Gly Gly Gly Ser Gly Gly Gly Gly Ser
1               5                   10                  15

<210> SEQ ID NO 163
<211> LENGTH: 20
<212> TYPE: PRT
<213> ORGANISM: Artificial Sequence
<220> FEATURE:
<223> OTHER INFORMATION: Synthetic peptide

<400> SEQUENCE: 163

Gly Gly Gly Gly Ser Gly Gly Gly Gly Ser Gly Gly Gly Gly Ser Gly
1               5                   10                  15

Gly Gly Gly Ser
            20

<210> SEQ ID NO 164
<211> LENGTH: 18
<212> TYPE: PRT
<213> ORGANISM: Artificial Sequence
<220> FEATURE:
<223> OTHER INFORMATION: Synthetic peptide

<400> SEQUENCE: 164

Gly Ser Thr Ser Gly Ser Gly Lys Pro Gly Ser Gly Glu Gly Ser Thr
1               5                   10                  15

Lys Gly

<210> SEQ ID NO 165
<211> LENGTH: 19
<212> TYPE: PRT
<213> ORGANISM: Artificial Sequence
<220> FEATURE:
<223> OTHER INFORMATION: Synthetic peptide

<400> SEQUENCE: 165

Pro Arg Gly Ala Ser Lys Ser Gly Ser Ala Ser Gln Thr Gly Ser Ala
1               5                   10                  15

Pro Gly Ser

<210> SEQ ID NO 166
<211> LENGTH: 19
<212> TYPE: PRT
<213> ORGANISM: Artificial Sequence
<220> FEATURE:
<223> OTHER INFORMATION: Synthetic peptide

<400> SEQUENCE: 166

Gly Thr Ala Ala Ala Gly Ala Gly Ala Ala Gly Gly Ala Ala Ala Gly
1               5                   10                  15
```

Ala Ala Gly

<210> SEQ ID NO 167
<211> LENGTH: 19
<212> TYPE: PRT
<213> ORGANISM: Artificial Sequence
<220> FEATURE:
<223> OTHER INFORMATION: Synthetic peptide

<400> SEQUENCE: 167

Gly Thr Ser Gly Ser Ser Gly Ser Gly Ser Gly Ser Gly Ser Ser Gly
1               5                   10                  15

Gly Gly Gly

<210> SEQ ID NO 168
<211> LENGTH: 20
<212> TYPE: PRT
<213> ORGANISM: Artificial Sequence
<220> FEATURE:
<223> OTHER INFORMATION: Synthetic peptide

<400> SEQUENCE: 168

Gly Lys Pro Gly Ser Gly Lys Pro Gly Ser Gly Lys Pro Gly Ser Gly
1               5                   10                  15

Lys Pro Gly Ser
            20

<210> SEQ ID NO 169
<211> LENGTH: 125
<212> TYPE: PRT
<213> ORGANISM: Homo sapiens

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125

<210> SEQ ID NO 170
<211> LENGTH: 14
<212> TYPE: PRT
<213> ORGANISM: Homo sapiens

<400> SEQUENCE: 170

Gly Ser Ser Thr Gly Ala Val Thr Thr Ser Asn Tyr Ala Asn
1               5                   10

<210> SEQ ID NO 171

```
<211> LENGTH: 7
<212> TYPE: PRT
<213> ORGANISM: Homo sapiens

<400> SEQUENCE: 171

Gly Thr Asn Lys Arg Ala Pro
1               5

<210> SEQ ID NO 172
<211> LENGTH: 9
<212> TYPE: PRT
<213> ORGANISM: Homo sapiens

<400> SEQUENCE: 172

Ala Leu Trp Tyr Ser Asn His Trp Val
1               5

<210> SEQ ID NO 173
<211> LENGTH: 109
<212> TYPE: PRT
<213> ORGANISM: Homo sapiens

<400> SEQUENCE: 173

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Gln Lys Pro Gly Lys Ser Pro Arg Gly
            35                  40                  45

Leu Ile Gly Gly Thr Asn Lys Arg Ala Pro Gly Val Pro Ala Arg Phe
        50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 174
<211> LENGTH: 5
<212> TYPE: PRT
<213> ORGANISM: Homo sapiens

<400> SEQUENCE: 174

Thr Tyr Ala Met Asn
1               5

<210> SEQ ID NO 175
<211> LENGTH: 19
<212> TYPE: PRT
<213> ORGANISM: Homo sapiens

<400> SEQUENCE: 175

Arg Ile Arg Ser Lys Tyr Asn Asn Tyr Ala Thr Tyr Tyr Ala Asp Ser
1               5                   10                  15

Val Lys Gly

<210> SEQ ID NO 176
<211> LENGTH: 14
<212> TYPE: PRT
<213> ORGANISM: Homo sapiens
```

```
<400> SEQUENCE: 176

His Gly Asn Phe Gly Asp Ser Tyr Val Ser Trp Phe Ala Tyr
1               5                   10

<210> SEQ ID NO 177
<211> LENGTH: 490
<212> TYPE: PRT
<213> ORGANISM: Homo sapiens

<400> SEQUENCE: 177

Met Glu Ser Ile Ser Met Met Gly Ser Pro Lys Ser Leu Ser Glu Thr
1               5                   10                  15

Phe Leu Pro Asn Gly Ile Asn Gly Ile Lys Asp Ala Arg Lys Val Thr
                20                  25                  30

Val Gly Val Ile Gly Ser Gly Asp Phe Ala Lys Ser Leu Thr Ile Arg
            35                  40                  45

Leu Ile Arg Cys Gly Tyr His Val Val Ile Gly Ser Arg Asn Pro Lys
        50                  55                  60

Phe Ala Ser Glu Phe Phe Pro His Val Val Asp Val Thr His His Glu
65                  70                  75                  80

Asp Ala Leu Thr Lys Thr Asn Ile Ile Phe Val Ala Ile His Arg Glu
                85                  90                  95

His Tyr Thr Ser Leu Trp Asp Leu Arg His Leu Leu Val Gly Lys Ile
            100                 105                 110

Leu Ile Asp Val Ser Asn Asn Met Arg Ile Asn Gln Tyr Pro Glu Ser
        115                 120                 125

Asn Ala Glu Tyr Leu Ala Ser Leu Phe Pro Asp Ser Leu Ile Val Lys
130                 135                 140

Gly Phe Asn Val Val Ser Ala Trp Ala Leu Gln Leu Gly Pro Lys Asp
145                 150                 155                 160

Ala Ser Arg Gln Val Tyr Ile Cys Ser Asn Asn Ile Gln Ala Arg Gln
                165                 170                 175

Gln Val Ile Glu Leu Ala Arg Gln Leu Asn Phe Ile Pro Ile Asp Leu
            180                 185                 190

Gly Ser Leu Ser Ser Ala Arg Glu Ile Glu Asn Leu Pro Leu Arg Leu
        195                 200                 205

Phe Thr Leu Trp Arg Gly Pro Val Val Ala Ile Ser Leu Ala Thr
210                 215                 220

Phe Phe Phe Leu Tyr Ser Phe Val Arg Asp Val Ile His Pro Tyr Ala
225                 230                 235                 240

Arg Asn Gln Gln Ser Asp Phe Tyr Lys Ile Pro Ile Glu Ile Val Asn
                245                 250                 255

Lys Thr Leu Pro Ile Val Ala Ile Thr Leu Leu Ser Leu Val Tyr Leu
            260                 265                 270

Ala Gly Leu Leu Ala Ala Ala Tyr Gln Leu Tyr Tyr Gly Thr Lys Tyr
        275                 280                 285

Arg Arg Phe Pro Pro Trp Leu Glu Thr Trp Leu Gln Cys Arg Lys Gln
290                 295                 300

Leu Gly Leu Leu Ser Phe Phe Ala Met Val His Val Ala Tyr Ser
305                 310                 315                 320

Leu Cys Leu Pro Met Arg Arg Ser Glu Arg Tyr Leu Phe Leu Asn Met
                325                 330                 335

Ala Tyr Gln Gln Val His Ala Asn Ile Glu Asn Ser Trp Asn Glu Glu
            340                 345                 350
```

```
Glu Val Trp Arg Ile Glu Met Tyr Ile Ser Phe Gly Ile Met Ser Leu
            355                 360                 365
Gly Leu Leu Ser Leu Leu Ala Val Thr Ser Ile Pro Ser Val Ser Asn
        370                 375                 380
Ala Leu Asn Trp Arg Glu Phe Ser Phe Ile Gln Ser Thr Leu Gly Tyr
385                 390                 395                 400
Val Ala Leu Leu Ile Ser Thr Phe His Val Leu Ile Tyr Gly Trp Lys
                405                 410                 415
Arg Ala Phe Glu Glu Tyr Tyr Arg Phe Tyr Thr Pro Pro Asn Phe
            420                 425                 430
Val Leu Ala Leu Val Leu Pro Ser Ile Val Ile Leu Gly Lys Ile Ile
        435                 440                 445
Leu Phe Leu Pro Cys Ile Ser Arg Lys Leu Lys Arg Ile Lys Lys Gly
    450                 455                 460
Trp Glu Lys Ser Gln Phe Leu Glu Glu Gly Met Gly Gly Thr Ile Pro
465                 470                 475                 480
His Val Ser Pro Glu Arg Val Thr Val Met
                485                 490

<210> SEQ ID NO 178
<211> LENGTH: 5
<212> TYPE: PRT
<213> ORGANISM: Artificial Sequence
<220> FEATURE:
<223> OTHER INFORMATION: Synthetic Linker

<400> SEQUENCE: 178

Gly Ser Gly Gly Ser
1               5

<210> SEQ ID NO 179
<211> LENGTH: 5
<212> TYPE: PRT
<213> ORGANISM: Artificial Sequence
<220> FEATURE:
<223> OTHER INFORMATION: Synthetic Linker

<400> SEQUENCE: 179

Gly Gly Gly Gly Ser
1               5

<210> SEQ ID NO 180
<211> LENGTH: 4
<212> TYPE: PRT
<213> ORGANISM: Artificial Sequence
<220> FEATURE:
<223> OTHER INFORMATION: Syntheitc Linker

<400> SEQUENCE: 180

Gly Gly Gly Ser
1

<210> SEQ ID NO 181
<211> LENGTH: 4
<212> TYPE: PRT
<213> ORGANISM: Artificial Sequence
<220> FEATURE:
<223> OTHER INFORMATION: Sythetic Linker

<400> SEQUENCE: 181

Gly Phe Leu Gly
1
```

<210> SEQ ID NO 182
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 182

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
            20                  25                  30

Trp Ile Glu Trp Val Arg Gln Ala Pro Gly Gln Arg Leu Glu Trp Met
        35                  40                  45

Gly Glu Ile Leu Pro Gly Ser Gly Asn Thr Asp Phe Asn Glu Lys Phe
    50                  55                  60

Gln Gly Arg Val Thr Phe Thr Ala Asp Thr Ser Ser Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Gly Tyr Tyr Gly Thr Arg Gly Tyr Phe Asn Val Trp Gly
            100                 105                 110

Gln Gly Thr Leu Val Thr Val Ser Ser
        115                 120
```

<210> SEQ ID NO 183
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 183

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Arg Ser Phe Pro Tyr Thr
                85                  90                  95

Phe Gly Gln Gly Thr Lys Leu Glu Ile Lys
            100                 105
```

<210> SEQ ID NO 184
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 184

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
```

```
            20                  25                  30
Trp Ile Glu Trp Val Arg Gln Ala Pro Gly Gln Arg Leu Glu Trp Met
         35                  40                  45

Gly Glu Ile Leu Pro Gly Ser Gly Gln Thr Asp Phe Asn Glu Lys Phe
     50                  55                  60

Gln Gly Arg Val Thr Phe Thr Ala Asp Thr Ser Ser Asp Thr Ala Tyr
 65                  70                  75                  80

Met Glu Leu Ser Ser Leu Arg Ser Glu Asp Thr Ala Val Tyr Tyr Cys
                 85                  90                  95

Thr Arg Trp Gly Tyr Tyr Gly Thr Arg Gly Tyr Phe Asn Val Trp Gly
            100                 105                 110

Gln Gly Thr Leu Val Thr Val Ser Ser
        115                 120

<210> SEQ ID NO 185
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 185

Glu Ile Gln Leu Val Gln Ser Gly Ala Glu Val Lys Lys Pro Gly Ala
 1               5                  10                  15

Thr Val Lys Ile Ser Cys Lys Ala Ser Gly Tyr Thr Phe Thr Asn Tyr
            20                  25                  30

Gly Met Asn Trp Val Gln Ala Pro Gly Gln Gly Leu Glu Trp Met
         35                  40                  45

Gly Trp Met Asn Thr Tyr Thr Gly Glu Pro Thr Tyr Ala Asp Lys Phe
     50                  55                  60

Gln Gly Arg Val Thr Phe Thr Leu Asp Thr Ser Ala Arg Thr Val Tyr
 65                  70                  75                  80

Met Glu Leu Ser Ser Leu Arg Ser Glu Asp Thr Ala Val Tyr Phe Cys
                 85                  90                  95

Ala Arg Ala Gly Gly Gln Leu Arg Pro Gly Ala Met Asp Tyr Trp Gly
            100                 105                 110

Gln Gly Thr Met Val Thr Val Ser Ser
        115                 120

<210> SEQ ID NO 186
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 186

Asp Ile Val Leu Thr Gln Thr Pro Leu Ser Leu Ser Val Thr Pro Gly
 1               5                  10                  15

Gln Pro Ala Ser Ile Ser Cys Lys Ala Ser Gln Ser Val Asp Tyr Asp
            20                  25                  30

Gly Asp Ser Phe Met Asn Trp Tyr Leu Gln Lys Pro Gly Gln Pro Pro
         35                  40                  45

Gln Leu Leu Ile Tyr Val Ala Ser Asn Leu Glu Ser Gly Val Pro Asp
     50                  55                  60

Arg Phe Ser Gly Ser Gly Ser Gly Thr Asp Phe Thr Leu Lys Ile Ser
 65                  70                  75                  80
```

```
Arg Val Glu Ala Glu Asp Val Gly Val Tyr Tyr Cys Gln Gln Ser Asn
                85                  90                  95

Glu Glu Pro Pro Thr Phe Gly Gln Gly Thr Lys Leu Glu Ile Lys
            100                 105                 110

<210> SEQ ID NO 187
<211> LENGTH: 268
<212> TYPE: PRT
<213> ORGANISM: Homo sapiens

<400> SEQUENCE: 187

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265

<210> SEQ ID NO 188
<211> LENGTH: 288
<212> TYPE: PRT
<213> ORGANISM: Cynomologus Monkey

<400> SEQUENCE: 188

Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30
```

-continued

```
Asn Ala Pro Thr Phe Ser Pro Ala Leu Leu Val Thr Glu Gly Asp
         35                  40                  45

Asn Ala Thr Phe Thr Cys Ser Phe Ser Asn Ala Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
             85                  90                  95

Val Thr Arg Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
        275                 280                 285
```

<210> SEQ ID NO 189
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 189

```
Ser Tyr Asp Met Ser
1               5
```

<210> SEQ ID NO 190
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 190

```
Leu Ile Ser Gly Gly Gly Ser Gln Thr Tyr Tyr Ala Glu Ser Val Lys
1               5                   10                  15
```

<210> SEQ ID NO 191
<211> LENGTH: 11
<212> TYPE: PRT
<213> ORGANISM: Artificial Sequence

```
<220> FEATURE:
<223> OTHER INFORMATION: Synthetic Polypeptide

<400> SEQUENCE: 191

Pro Ser Gly His Tyr Phe Tyr Ala Met Asp Val
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 192

Arg Ala Ser Gln Gly Ile Ser Asn Trp Leu Ala
1               5                   10

<210> SEQ ID NO 193
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 193

Ala Ala Ser Ser Leu Gln Ser
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 194

Gln Gln Ala Glu Ser Phe Pro His Thr
1               5

<210> SEQ ID NO 195
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Leu Ile Ser Gly Gly Gly Ser Gln Thr Tyr Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Ser Pro Ser Gly His Tyr Phe Tyr Ala Met Asp Val Trp Gly Gln
            100                 105                 110

Gly Thr Thr Val Thr Val Ser Ser
        115                 120
```

```
            115                 120

<210> SEQ ID NO 196
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 196

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Glu Ser Phe Pro His
                85                  90                  95

Thr Phe Gly Gly Gly Thr Lys Val Glu Ile Lys
            100                 105

<210> SEQ ID NO 197
<211> LENGTH: 472
<212> TYPE: PRT
<213> ORGANISM: Artificial Sequence
<220> FEATURE:
<223> OTHER INFORMATION: Synthetic Polypeptide

<400> SEQUENCE: 197

Met Asp Met Arg Val Pro Ala Gln Leu Leu Gly Leu Leu Leu Leu Trp
1               5                   10                  15

Leu Arg Gly Ala Arg Cys Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Asp Met Ser Trp Val Arg Gln Ala Pro Gly
    50                  55                  60

Lys Gly Leu Glu Trp Val Ser Leu Ile Ser Gly Gly Ser Gln Thr
65                  70                  75                  80

Tyr Tyr Ala Glu Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Phe Cys Ala Ser Pro Ser Gly His Tyr Phe Tyr Ala
        115                 120                 125

Met Asp Val Trp Gly Gln Gly Thr Thr Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190
```

His Thr Phe Pro Ala Val Leu Gln Ser Ser Gly Leu Tyr Ser Leu Ser
            195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
            245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Cys Glu Glu Gln
305                 310                 315                 320

Tyr Gly Ser Thr Tyr Arg Cys Val Ser Val Leu Thr Val Leu His Gln
            325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
            450                 455                 460

Ser Leu Ser Leu Ser Pro Gly Lys
465                 470

<210> SEQ ID NO 198
<211> LENGTH: 236
<212> TYPE: PRT
<213> ORGANISM: Artificial Sequence
<220> FEATURE:
<223> OTHER INFORMATION: Synthetic Polypeptide

<400> SEQUENCE: 198

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Asn Trp Leu Ala Trp Tyr Gln Gln Lys Pro Gly Lys
    50                  55                  60

Ala Pro Lys Leu Leu Ile Phe Ala Ala Ser Ser Leu Gln Ser Gly Val
65                  70                  75                  80

```
Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Glu Ser Phe Pro His Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 199
<211> LENGTH: 472
<212> TYPE: PRT
<213> ORGANISM: Artificial Sequence
<220> FEATURE:
<223> OTHER INFORMATION: Synthetic Polypeptide

<400> SEQUENCE: 199

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Ser Thr Tyr Trp Ile Glu Trp Val Arg Gln Ala Pro Gly
        50                  55                  60

Gln Arg Leu Glu Trp Met Gly Glu Ile Leu Pro Gly Ser Gly Gln Thr
65                  70                  75                  80

Asp Phe Asn Glu Lys Phe Gln Gly Arg Val Thr Phe Thr Ala Asp Thr
                85                  90                  95

Ser Ser Asp Thr Ala Tyr Met Glu Leu Ser Ser Leu Arg Ser Glu Asp
            100                 105                 110

Thr Ala Val Tyr Tyr Cys Thr Arg Trp Gly Tyr Tyr Gly Thr Arg Gly
        115                 120                 125

Tyr Phe Asn Val Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
210                 215                 220

Ile Cys Asn Val Asn His Lys Pro Ser Asp Thr Lys Val Asp Lys Lys
225                 230                 235                 240

Val Glu Pro Lys Ser Cys Asp Lys Thr His Thr Cys Pro Pro Cys Pro
            245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Lys His Glu Asp Pro Glu Val Lys Phe Asn Trp Tyr Val
290                 295                 300

Asp Gly Val Glu Val His Asn Ala Lys Thr Lys Pro Cys Glu Glu Glu
305                 310                 315                 320

Tyr Gly Ser Thr Tyr Arg Cys Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
370                 375                 380

Lys Asn Gln Val Ser Leu Thr Cys Asp Val Ser Gly Phe Tyr Pro Ser
385                 390                 395                 400

Asp Ile Ala Val Glu Trp Glu Ser Asp Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Glu Gln Gly Asp Val Phe
            435                 440                 445

Ser Cys Ser Val Met His Glu Ala Leu His Asn His Tyr Thr Gln Lys
        450                 455                 460

Ser Leu Ser Leu Ser Pro Gly Lys
465                 470

<210> SEQ ID NO 200
<211> LENGTH: 213
<212> TYPE: PRT
<213> ORGANISM: Artificial Sequence
<220> FEATURE:
<223> OTHER INFORMATION: Synthetic Polypeptide

<400> SEQUENCE: 200

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Arg Ser Phe Pro Tyr Thr
                85                  90                  95
```

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 201
<211> LENGTH: 450
<212> TYPE: PRT
<213> ORGANISM: Artificial Sequence
<220> FEATURE:
<223> OTHER INFORMATION: Synthetic Polypeptide

<400> SEQUENCE: 201

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
            20                  25                  30

Trp Ile Glu Trp Val Arg Gln Ala Pro Gly Gln Arg Leu Glu Trp Met
        35                  40                  45

Gly Glu Ile Leu Pro Gly Ser Gly Asn Thr Asp Phe Asn Glu Lys Phe
    50                  55                  60

Gln Gly Arg Val Thr Phe Thr Ala Asp Thr Ser Ser Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Gly Tyr Tyr Gly Thr Arg Gly Tyr Phe Asn Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asp Thr Lys Val Asp Lys Lys Val Glu Pro Lys Ser Cys
    210                 215                 220

Asp Lys Thr His Thr Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Lys His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Glu Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Asp Val Ser Gly Phe Tyr Pro Ser Asp Ile Ala Val Glu Trp
    370                 375                 380

Glu Ser Asp Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asp Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 202
<211> LENGTH: 723
<212> TYPE: PRT
<213> ORGANISM: Artificial Sequence
<220> FEATURE:
<223> OTHER INFORMATION: Synthetic Polypeptide

<400> SEQUENCE: 202

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
            20                  25                  30

Trp Ile Glu Trp Val Arg Gln Ala Pro Gly Gln Arg Leu Glu Trp Met
        35                  40                  45

Gly Glu Ile Leu Pro Gly Ser Gly Asn Thr Asp Phe Asn Glu Lys Phe
    50                  55                  60

Gln Gly Arg Val Thr Phe Thr Ala Asp Thr Ser Ser Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Gly Tyr Tyr Gly Thr Arg Gly Tyr Phe Asn Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

-continued

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

Gly Gly Gly Gly Ser Gly Gly Gly Ser Glu Val Gln Leu Val Glu
225                 230                 235                 240

Ser Gly Gly Gly Leu Val Gln Pro Gly Gly Ser Leu Arg Leu Ser Cys
            245                 250                 255

Ala Ala Ser Gly Phe Thr Phe Ser Thr Tyr Ala Met Asn Trp Val Arg
            260                 265                 270

Gln Ala Pro Gly Lys Gly Leu Glu Trp Val Gly Arg Ile Arg Ser Lys
            275                 280                 285

Tyr Asn Asn Tyr Ala Thr Tyr Tyr Ala Asp Ser Val Lys Gly Arg Phe
290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
            325                 330                 335

Asn Phe Gly Asp Ser Tyr Val Ser Trp Phe Ala Tyr Trp Gly Gln Gly
            340                 345                 350

Thr Leu Val Thr Val Ser Ser Gly Lys Pro Gly Ser Gly Lys Pro Gly
            355                 360                 365

Ser Gly Lys Pro Gly Ser Gly Lys Pro Gly Ser Gln Ala Val Val Thr
            370                 375                 380

Gln Glu Pro Ser Leu Thr Val Ser Pro Gly Gly Thr Val Thr Leu Thr
385                 390                 395                 400

Cys Gly Ser Ser Thr Gly Ala Val Thr Thr Ser Asn Tyr Ala Asn Trp
            405                 410                 415

Val Gln Gln Lys Pro Gly Lys Ser Pro Arg Gly Leu Ile Gly Gly Thr
            420                 425                 430

Asn Lys Arg Ala Pro Gly Val Pro Ala Arg Phe Ser Gly Ser Leu Leu
            435                 440                 445

Gly Gly Lys Ala Ala Leu Thr Ile Ser Gly Ala Gln Pro Glu Asp Glu
            450                 455                 460

Ala Asp Tyr Tyr Cys Ala Leu Trp Tyr Ser Asn His Trp Val Phe Gly
465                 470                 475                 480

Gly Gly Thr Lys Leu Thr Val Leu Gly Gly Gly Ser Gly Gly Gly
            485                 490                 495

Gly Ser Lys Thr His Thr Cys Pro Pro Cys Pro Ala Pro Pro Val Ala
            500                 505                 510

Gly Pro Ser Val Phe Leu Phe Pro Pro Lys Pro Lys Asp Thr Leu Met
            515                 520                 525

Ile Ser Arg Thr Pro Glu Val Thr Cys Val Val Val Asp Val Lys His
            530                 535                 540

Glu Asp Pro Glu Val Lys Phe Asn Trp Tyr Val Asp Gly Val Glu Val
545                 550                 555                 560

His Asn Ala Lys Thr Lys Pro Arg Glu Glu Gln Tyr Asn Ser Thr Tyr
```

```
                        565                 570                 575
Arg Val Val Ser Val Leu Thr Val Leu His Gln Asp Trp Leu Asn Gly
            580                 585                 590

Lys Glu Tyr Lys Cys Lys Val Ser Asn Lys Ala Leu Pro Ala Pro Ile
        595                 600                 605

Glu Lys Thr Ile Ser Lys Ala Lys Gly Gln Pro Arg Glu Pro Gln Val
    610                 615                 620

Tyr Thr Leu Pro Pro Ser Arg Glu Gln Met Thr Lys Asn Gln Val Lys
625                 630                 635                 640

Leu Thr Cys Leu Val Lys Gly Phe Tyr Pro Ser Asp Ile Ala Val Glu
            645                 650                 655

Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
            675                 680                 685

Asp Lys Ser Arg Trp Gln Gln Gly Asn Val Phe Ser Cys Ser Val Met
        690                 695                 700

His Glu Ala Leu His Asn His Tyr Thr Gln Lys Ser Leu Ser Leu Ser
705                 710                 715                 720

Pro Gly Lys

<210> SEQ ID NO 203
<211> LENGTH: 450
<212> TYPE: PRT
<213> ORGANISM: Artificial Sequence
<220> FEATURE:
<223> OTHER INFORMATION: Synthetic Polypeptide

<400> SEQUENCE: 203

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
            20                  25                  30

Trp Ile Glu Trp Val Arg Gln Ala Pro Gly Gln Arg Leu Glu Trp Met
        35                  40                  45

Gly Glu Ile Leu Pro Gly Ser Gly Gln Thr Asp Phe Asn Glu Lys Phe
    50                  55                  60

Gln Gly Arg Val Thr Phe Thr Ala Asp Thr Ser Ser Asp Thr Ala Tyr
65                  70                  75                  80

Met Glu Leu Ser Ser Leu Arg Ser Glu Asp Thr Ala Val Tyr Tyr Cys
            85                  90                  95

Thr Arg Trp Gly Tyr Tyr Gly Thr Arg Gly Tyr Phe Asn Val Trp Gly
        100                 105                 110

Gln Gly Thr Leu Val Thr Val Ser Ala Ser Thr Lys Gly Pro Ser
    115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205
```

Lys Pro Ser Asp Thr Lys Val Asp Lys Val Glu Pro Lys Ser Cys
210                 215                 220

Asp Lys Thr His Thr Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Lys His Glu
        260                 265                 270

Asp Pro Glu Val Lys Phe Asn Trp Tyr Val Asp Gly Val Glu Val His
    275                 280                 285

Asn Ala Lys Thr Lys Pro Cys Glu Glu Glu Tyr Gly Ser Thr Tyr Arg
290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Asp Val Ser Gly Phe Tyr Pro Ser Asp Ile Ala Val Glu Trp
370                 375                 380

Glu Ser Asp Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Glu Gln Gly Asp Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
450

<210> SEQ ID NO 204
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 204

Asp Ile Val Leu Thr Gln Thr Pro Leu Ser Leu Ser Val Thr Pro Gly
1               5                   10                  15

Gln Pro Ala Ser Ile Ser Cys Lys Ala Ser Gln Ser Val Asp Tyr Asp
            20                  25                  30

Gly Asp Ser Phe Met Asn Trp Tyr Leu Gln Lys Pro Gly Gln Pro Pro
        35                  40                  45

Gln Leu Leu Ile Tyr Val Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Asn
            85                  90                  95

Glu Glu Pro Pro Thr Phe Gly Gln Gly Thr Lys Leu Glu Ile Lys Arg
        100                 105                 110

```
Thr Val Ala Ala Pro Ser Val Phe Ile Phe Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 205
<211> LENGTH: 448
<212> TYPE: PRT
<213> ORGANISM: Artificial Sequence
<220> FEATURE:
<223> OTHER INFORMATION: Synthetic Polypeptide

<400> SEQUENCE: 205

Gln Leu Val Gln Ser Gly Ala Glu Val Lys Lys Pro Gly Ala Thr Val
1               5                   10                  15

Lys Ile Ser Cys Lys Ala Ser Gly Tyr Thr Phe Thr Asn Tyr Gly Met
            20                  25                  30

Asn Trp Val Gln Gln Ala Pro Gly Gln Gly Leu Glu Trp Met Gly Trp
        35                  40                  45

Met Asn Thr Tyr Thr Gly Glu Pro Thr Tyr Ala Asp Lys Phe Gln Gly
    50                  55                  60

Arg Val Thr Phe Thr Leu Asp Thr Ser Ala Arg Thr Val Tyr Met Glu
65                  70                  75                  80

Leu Ser Ser Leu Arg Ser Glu Asp Thr Ala Val Tyr Phe Cys Ala Arg
                85                  90                  95

Ala Gly Gly Gln Leu Arg Pro Gly Ala Met Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asp Thr Lys Val Asp Lys Lys Val Glu Pro Lys Ser Cys Asp Lys
    210                 215                 220

Thr His Thr Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Lys His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                    325                 330                 335

Ile Ser Lys Ala Lys Gly Gln Pro Arg Glu Pro Gln Val Tyr Thr Leu
                    340                 345                 350

Pro Pro Ser Arg Glu Glu Met Thr Lys Asn Gln Val Ser Leu Thr Cys
                    355                 360                 365

Asp Val Ser Gly Phe Tyr Pro Ser Asp Ile Ala Val Glu Trp Glu Ser
            370                 375                 380

Asp Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                    405                 410                 415

Arg Trp Glu Gln Gly Asp Val Phe Ser Cys Ser Val Met His Glu Ala
                    420                 425                 430

Leu His Asn His Tyr Thr Gln Lys Ser Leu Ser Leu Ser Pro Gly Lys
                    435                 440                 445

<210> SEQ ID NO 206
<211> LENGTH: 721
<212> TYPE: PRT
<213> ORGANISM: Artificial Sequence
<220> FEATURE:
<223> OTHER INFORMATION: Synthetic Polypeptide

<400> SEQUENCE: 206

Gln Leu Val Gln Ser Gly Ala Glu Val Lys Lys Pro Gly Ala Thr Val
1               5                   10                  15

Lys Ile Ser Cys Lys Ala Ser Gly Tyr Thr Phe Thr Asn Tyr Gly Met
                20                  25                  30

Asn Trp Val Gln Gln Ala Pro Gly Gln Gly Leu Glu Trp Met Gly Trp
            35                  40                  45

Met Asn Thr Tyr Thr Gly Glu Pro Thr Tyr Ala Asp Lys Phe Gln Gly
    50                  55                  60

Arg Val Thr Phe Thr Leu Asp Thr Ser Ala Arg Thr Val Tyr Met Glu
65                  70                  75                  80

Leu Ser Ser Leu Arg Ser Glu Asp Thr Ala Val Tyr Phe Cys Ala Arg
                85                  90                  95

Ala Gly Gly Gln Leu Arg Pro Gly Ala Met Asp Tyr Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Gly Gly
    210                 215                 220

Gly Gly Ser Gly Gly Gly Ser Glu Val Gln Leu Val Glu Ser Gly
225                 230                 235                 240

Gly Gly Leu Val Gln Pro Gly Gly Ser Leu Arg Leu Ser Cys Ala Ala
            245                 250                 255

Ser Gly Phe Thr Phe Ser Thr Tyr Ala Met Asn Trp Val Arg Gln Ala
                260                 265                 270

Pro Gly Lys Gly Leu Glu Trp Val Gly Arg Ile Arg Ser Lys Tyr Asn
        275                 280                 285

Asn Tyr Ala Thr Tyr Tyr Ala Asp Ser Val Lys Gly Arg Phe Thr Ile
    290                 295                 300

Ser Arg Asp Asp Ser Lys Asn Thr Leu Tyr Leu Gln Met Asn Ser Leu
305                 310                 315                 320

Arg Ala Glu Asp Thr Ala Val Tyr Tyr Cys Val Arg His Gly Asn Phe
            325                 330                 335

Gly Asp Ser Tyr Val Ser Trp Phe Ala Tyr Trp Gly Gln Gly Thr Leu
                340                 345                 350

Val Thr Val Ser Ser Gly Lys Pro Gly Ser Gly Lys Pro Gly Ser Gly
        355                 360                 365

Lys Pro Gly Ser Gly Lys Pro Gly Ser Gln Ala Val Val Thr Gln Glu
    370                 375                 380

Pro Ser Leu Thr Val Ser Pro Gly Gly Thr Val Thr Leu Thr Cys Gly
385                 390                 395                 400

Ser Ser Thr Gly Ala Val Thr Thr Ser Asn Tyr Ala Asn Trp Val Gln
            405                 410                 415

Gln Lys Pro Gly Lys Ser Pro Arg Gly Leu Ile Gly Gly Thr Asn Lys
                420                 425                 430

Arg Ala Pro Gly Val Pro Ala Arg Phe Ser Gly Ser Leu Leu Gly Gly
        435                 440                 445

Lys Ala Ala Leu Thr Ile Ser Gly Ala Gln Pro Glu Asp Glu Ala Asp
    450                 455                 460

Tyr Tyr Cys Ala Leu Trp Tyr Ser Asn His Trp Val Phe Gly Gly Gly
465                 470                 475                 480

Thr Lys Leu Thr Val Leu Gly Gly Gly Ser Gly Gly Gly Ser
            485                 490                 495

Lys Thr His Thr Cys Pro Pro Cys Pro Ala Pro Pro Val Ala Gly Pro
                500                 505                 510

Ser Val Phe Leu Phe Pro Pro Lys Pro Lys Asp Thr Leu Met Ile Ser
        515                 520                 525

Arg Thr Pro Glu Val Thr Cys Val Val Val Asp Val Lys His Glu Asp
    530                 535                 540

Pro Glu Val Lys Phe Asn Trp Tyr Val Asp Gly Val Glu Val His Asn
545                 550                 555                 560

Ala Lys Thr Lys Pro Arg Glu Glu Gln Tyr Asn Ser Thr Tyr Arg Val
            565                 570                 575

Val Ser Val Leu Thr Val Leu His Gln Asp Trp Leu Asn Gly Lys Glu
                580                 585                 590
```

-continued

```
Tyr Lys Cys Lys Val Ser Asn Lys Ala Leu Pro Ala Pro Ile Glu Lys
            595                 600                 605

Thr Ile Ser Lys Ala Lys Gly Gln Pro Arg Glu Pro Gln Val Tyr Thr
    610                 615                 620

Leu Pro Pro Ser Arg Glu Gln Met Thr Lys Asn Gln Val Lys Leu Thr
625                 630                 635                 640

Cys Leu Val Lys Gly Phe Tyr Pro Ser Asp Ile Ala Val Glu Trp Glu
                645                 650                 655

Ser Asn Gly Gln Pro Glu Asn Asn Tyr Lys Thr Thr Pro Pro Val Leu
            660                 665                 670

Asp Ser Asp Gly Ser Phe Phe Leu Tyr Ser Lys Leu Thr Val Asp Lys
        675                 680                 685

Ser Arg Trp Gln Gln Gly Asn Val Phe Ser Cys Ser Val Met His Glu
    690                 695                 700

Ala Leu His Asn His Tyr Thr Gln Lys Ser Leu Ser Leu Ser Pro Gly
705                 710                 715                 720

Lys

<210> SEQ ID NO 207
<211> LENGTH: 723
<212> TYPE: PRT
<213> ORGANISM: Artificial Sequence
<220> FEATURE:
<223> OTHER INFORMATION: Synthetic Polypeptide

<400> SEQUENCE: 207

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
            20                  25                  30

Trp Ile Glu Trp Val Arg Gln Ala Pro Gly Gln Arg Leu Glu Trp Met
        35                  40                  45

Gly Glu Ile Leu Pro Gly Ser Gly Gln Thr Asp Phe Asn Glu Lys Phe
    50                  55                  60

Gln Gly Arg Val Thr Phe Thr Ala Asp Thr Ser Ser Asp Thr Ala Tyr
65                  70                  75                  80

Met Glu Leu Ser Ser Leu Arg Ser Glu Asp Thr Ala Val Tyr Tyr Cys
                85                  90                  95

Thr Arg Trp Gly Tyr Tyr Gly Thr Arg Gly Tyr Phe Asn Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Gly Gly Gly Gly Ser Gly Gly Gly Gly Ser Glu Val Gln Leu Val Glu
```

```
            225                 230                 235                 240
        Ser Gly Gly Gly Leu Val Gln Pro Gly Gly Ser Leu Arg Leu Ser Cys
                        245                 250                 255

Ala Ala Ser Gly Phe Thr Phe Ser Thr Tyr Ala Met Asn Trp Val Arg
                        260                 265                 270

Gln Ala Pro Gly Lys Gly Leu Glu Trp Val Gly Arg Ile Arg Ser Lys
                        275                 280                 285

Tyr Asn Asn Tyr Ala Thr Tyr Tyr Ala Asp Ser Val Lys Gly Arg Phe
                        290                 295                 300

Thr Ile Ser Arg Asp Asp Ser Lys Asn Thr Leu Tyr Leu Gln Met Asn
        305                 310                 315                 320

Ser Leu Arg Ala Glu Asp Thr Ala Val Tyr Tyr Cys Val Arg His Gly
                        325                 330                 335

Asn Phe Gly Asp Ser Tyr Val Ser Trp Phe Ala Tyr Trp Gly Gln Gly
                        340                 345                 350

Thr Leu Val Thr Val Ser Ser Gly Lys Pro Gly Ser Gly Lys Pro Gly
                        355                 360                 365

Ser Gly Lys Pro Gly Ser Gly Lys Pro Gly Ser Gln Ala Val Val Thr
        370                 375                 380

Gln Glu Pro Ser Leu Thr Val Ser Pro Gly Gly Thr Val Thr Leu Thr
        385                 390                 395                 400

Cys Gly Ser Ser Thr Gly Ala Val Thr Thr Ser Asn Tyr Ala Asn Trp
                        405                 410                 415

Val Gln Gln Lys Pro Gly Lys Ser Pro Arg Gly Leu Ile Gly Gly Thr
                        420                 425                 430

Asn Lys Arg Ala Pro Gly Val Pro Ala Arg Phe Ser Gly Ser Leu Leu
                        435                 440                 445

Gly Gly Lys Ala Ala Leu Thr Ile Ser Gly Ala Gln Pro Glu Asp Glu
                        450                 455                 460

Ala Asp Tyr Tyr Cys Ala Leu Trp Tyr Ser Asn His Trp Val Phe Gly
        465                 470                 475                 480

Gly Gly Thr Lys Leu Thr Val Leu Gly Gly Gly Gly Ser Gly Gly Gly
                        485                 490                 495

Gly Ser Lys Thr His Thr Cys Pro Pro Cys Pro Ala Pro Pro Val Ala
                        500                 505                 510

Gly Pro Ser Val Phe Leu Phe Pro Pro Lys Pro Lys Asp Thr Leu Met
                        515                 520                 525

Ile Ser Arg Thr Pro Glu Val Thr Cys Val Val Val Asp Val Lys His
        530                 535                 540

Glu Asp Pro Glu Val Lys Phe Asn Trp Tyr Val Asp Gly Val Glu Val
        545                 550                 555                 560

His Asn Ala Lys Thr Lys Pro Cys Glu Glu Gln Tyr Gly Ser Thr Tyr
                        565                 570                 575

Arg Cys Val Ser Val Leu Thr Val Leu His Gln Asp Trp Leu Asn Gly
                        580                 585                 590

Lys Glu Tyr Lys Cys Lys Val Ser Asn Lys Ala Leu Pro Ala Pro Ile
                        595                 600                 605

Glu Lys Thr Ile Ser Lys Ala Lys Gly Gln Pro Arg Glu Pro Gln Val
                        610                 615                 620

Tyr Thr Leu Pro Pro Ser Arg Glu Gln Met Thr Lys Asn Gln Val Lys
        625                 630                 635                 640

Leu Thr Cys Leu Val Lys Gly Phe Tyr Pro Ser Asp Ile Ala Val Glu
                        645                 650                 655
```

```
Trp Glu Ser Asn Gly Gln Pro Glu Asn Asn Tyr Lys Thr Thr Pro Pro
            660                 665                 670

Val Leu Asp Ser Asp Gly Ser Phe Phe Leu Tyr Ser Lys Leu Thr Val
            675                 680                 685

Asp Lys Ser Arg Trp Gln Gln Gly Asn Val Phe Ser Cys Ser Val Met
            690                 695                 700

His Glu Ala Leu His Asn His Tyr Thr Gln Lys Ser Leu Ser Leu Ser
705                 710                 715                 720

Pro Gly Lys
```

<210> SEQ ID NO 208
<211> LENGTH: 450
<212> TYPE: PRT
<213> ORGANISM: Artificial Sequence
<220> FEATURE:
<223> OTHER INFORMATION: Synthetic Polypeptide

<400> SEQUENCE: 208

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Leu Ile Ser Gly Gly Ser Gln Thr Tyr Tyr Ala Glu Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Phe Cys
                85                  90                  95

Ala Ser Pro Ser Gly His Tyr Phe Tyr Ala Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 209
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 209

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Glu Ser Phe Pro His
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 210
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 210

Lys Thr His Thr Cys Pro Pro Cys Pro
1               5

<210> SEQ ID NO 211
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 211

Glu Pro Lys Ser Ser Asp Lys Thr His Thr Cys Pro Pro Cys Pro
1               5                   10                  15

<210> SEQ ID NO 212
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 212

Gly Gly Gly Gly Ser Gly Gly Gly Ser Lys Thr His Thr Cys Pro
1               5                   10                  15

Pro Cys Pro

<210> SEQ ID NO 213
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 213

Gly Lys Pro Gly Ser Gly Lys Pro Gly Ser Lys Thr His Thr Cys Pro
1               5                   10                  15

Pro Cys Pro

<210> SEQ ID NO 214
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 214

Gly Lys Pro Gly Ser Lys Thr His Thr Cys Pro Pro Cys Pro
1               5                   10